(12) United States Patent
Hurley et al.

(10) Patent No.: US 8,999,988 B2
(45) Date of Patent: *Apr. 7, 2015

(54) PROTEIN KINASE INHIBITORS

(71) Applicants: Arizona Board of Regents on behalf of the University of Arizona, Tucson, AZ (US); Astex Pharmaceuticals, Inc., Dublin, CA (US)

(72) Inventors: Laurence H. Hurley, Tucson, AZ (US); Daruka Mahadevan, Tucson, AZ (US); David J. Bearss, Cedar Hills, UT (US); Hariprasad Vankayalapati, Draper, UT (US); Steven L. Warner, Sandy, UT (US); James Welsh, Oro Valley, AZ (US); Sridevi Bashyam, Bangalore (IN)

(73) Assignees: Arizona Board of Regents on behalf of the University of Arizona, Tucson, AZ (US); Astex Pharmaceuticals, Inc., Dublin, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/947,691

(22) Filed: Jul. 22, 2013

(65) Prior Publication Data

US 2013/0302303 A1     Nov. 14, 2013

Related U.S. Application Data

(63) Continuation of application No. 13/051,790, filed on Mar. 18, 2011, now Pat. No. 8,552,018, which is a continuation of application No. 11/735,344, filed on Apr. 13, 2007, now abandoned, which is a (Continued)

(51) Int. Cl.
    *C07D 491/14*     (2006.01)
    *A61K 31/519*     (2006.01)

(Continued)

(52) U.S. Cl.
    CPC .......... *A61K 31/519* (2013.01); *C07D 403/14* (2013.01); *C07D 405/14* (2013.01);

(Continued)

(58) Field of Classification Search
    CPC .......................... A61K 31/519; C07D 491/14
    USPC ...................................... 544/250; 514/252.16
    See application file for complete search history.

(56) References Cited

U.S. PATENT DOCUMENTS 5,679,683 A    10/1997   Bridges et al.
6,143,764 A    11/2000   Kubo et al.

(Continued)

FOREIGN PATENT DOCUMENTS

EP     0 837 063 A1    4/1998
EP     0 882 717 A1    12/1998

(Continued)

OTHER PUBLICATIONS

Mahadevan, D. et al., "Structure-Based Design of Novel Anti-Cancer Agents Targeting Aurora Kinases," Current Medicinal Chemistry—Anti-Cancer Agents 3(1):25-34, Jan. 2003.

(Continued)

*Primary Examiner* — Susanna Moore
(74) *Attorney, Agent, or Firm* — Quarles & Brady LLP; Gavin J. Milczarek-Desai

(57) ABSTRACT

Protein kinase inhibitors are disclosed having utility in the treatment of protein kinase-mediated diseases and conditions, such as cancer. The compounds of this invention have the following structure:

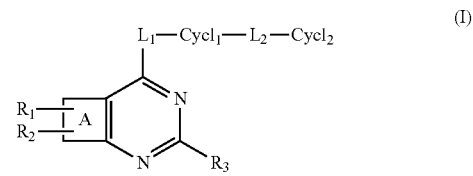

including steroisomers, prodrugs and pharmaceutically acceptable salts thereof, wherein A is a ring moiety selected from:

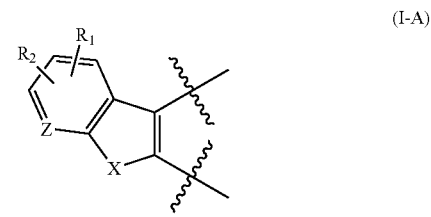

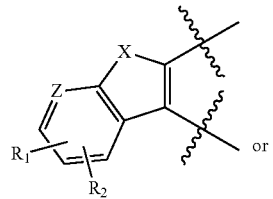

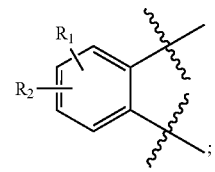

and wherein R1, R2, R3, X, Z, L1, Cycl1, L2 and Cycl2 are as defined herein. Also disclosed are compositions containing a compound of this invention, as well as methods relating to the use thereof.

12 Claims, 44 Drawing Sheets

Related U.S. Application Data continuation-in-part of application No. 11/680,921, filed on Mar. 1, 2007, now abandoned, which is a continuation-in-part of application No. 10/965,313, filed on Oct. 14, 2004, now Pat. No. 7,326,712.

(60) Provisional application No. 60/608,529, filed on Sep. 9, 2004, provisional application No. 60/511,486, filed on Oct. 14, 2003, provisional application No. 60/511,489, filed on Oct. 14, 2003.

(51) Int. Cl.
   *C07D 403/14* (2006.01)
   *C07D 405/14* (2006.01)
   *C07D 487/04* (2006.01)
   *C07D 491/048* (2006.01)
   *C07D 495/04* (2006.01)
   *C07D 495/14* (2006.01)
   *A61K 45/06* (2006.01)
   *A61N 5/00* (2006.01)
   *C07D 239/94* (2006.01)
   *C07D 487/14* (2006.01)

(52) U.S. Cl.
   CPC .......... *C07D487/04* (2013.01); *C07D 491/048* (2013.01); *C07D 495/04* (2013.01); *C07D 495/14* (2013.01); *A61K 45/06* (2013.01); *A61N 5/00* (2013.01)

(56) References Cited

U.S. PATENT DOCUMENTS

| | | | |
|---|---|---|---|
| 6,608,053 B2 | 8/2003 | Hayakawa et al. |
| 6,919,338 B2 | 7/2005 | Mortlock et al. |
| 7,312,226 B2 | 12/2007 | Hurley et al. |
| 7,326,712 B2 | 2/2008 | Hurley et al. |
| 7,326,713 B2 | 2/2008 | Hurley et al. |
| 7,335,662 B2 | 2/2008 | Hurley et al. |
| 8,552,018 B2 | 10/2013 | Hurley et al. |
| 2002/0151544 A1 | 10/2002 | Hayakawa et al. |
| 2003/0139331 A1 | 7/2003 | Martin et al. |
| 2003/0187002 A1 | 10/2003 | Mortlock et al. |

FOREIGN PATENT DOCUMENTS

| | | |
|---|---|---|
| JP | 06220059 | 8/1994 |
| JP | 06220059 A | 8/1994 |
| JP | 10175977 A | 6/1998 |
| JP | 10175977 | 10/1998 |
| WO | 96 09294 A1 | 3/1996 |
| WO | 96 33981 A1 | 10/1996 |
| WO | 00 21955 A1 | 4/2000 |
| WO | 01 21594 A1 | 3/2001 |
| WO | 01 21596 A1 | 3/2001 |
| WO | 01 21597 A1 | 3/2001 |
| WO | 03 051884 A1 | 6/2003 |
| WO | WO 03051884 | 6/2003 |
| WO | 03 055491 A1 | 7/2003 |
| WO | 2004 111052 A1 | 12/2004 |
| WO | WO 2004111052 | 12/2004 |

OTHER PUBLICATIONS

Merino et al. (IL Farmaco, 1990, 54, pp. 255-264).

Translation of JP 06220059, downloaded <http://dossier1.ipdl.inpit.go.jp/AIPN/odse_top_fwi.ipdl?N0000=7401>Mar. 1, 2010, pp. 1-69.

Translation of JP 2003183283 (WO 2003051884), downloaded <http://dossier1.ipdl.inpit.go.jp/AIPN/odse_top_fwi.ipdl?N0000=7401>Mar. 1, 2010, pp. 1-69.

FIG. 2

Scheme I

Scheme II i. BrCH$_2$COOMe, K$_2$CO$_3$, CH$_3$COCH$_3$, ii. NaH, DMSO, iii. formmide, 180 °C, iv. DMF/oxalyl chloride Scheme III i. ethyl thioglycolate, NaH, DMSO, ii. formamide, 190 °C, DMF/oxalyl chloride Scheme IV Scheme V Scheme VI

FIG. 13

PROTEIN KINASE INHIBITORS

CROSS REFERENCE TO RELATED APPLICATIONS

This application is a continuation of U.S. patent application Ser. No. 13/051,790, filed Mar. 18, 2011; which is a continuation of U.S. patent application Ser. No. 11/735,344, filed Apr. 13, 2007; which is a continuation-in-part of U.S. patent application Ser. No. 11/680,921, filed Mar. 1, 2007; which is a continuation-in-part of U.S. patent application Ser. No. 10/965,313, filed Oct. 14, 2004; now U.S. Pat. No. 7,326,712, and which claims the benefit under 35 U.S.C. §119(e) of U.S. Provisional Application No. 60/608,529, filed Sep. 9, 2004; U.S. Provisional Application No. 60/511,486, filed Oct. 14, 2003; and U.S. Provisional Application No. 60/511,489, filed Oct. 14, 2003, the disclosures of which are hereby incorporated by reference in their entireties.

STATEMENT REGARDING FEDERALLY SPONSORED RESEARCH

Certain work disclosed herein was performed under grant numbers CA95031 and CA88310 from the National Institutes of Health. The U.S. Government has certain rights in this invention.

BACKGROUND OF THE INVENTION

1. Field of the Invention

The present invention relates, in general, to compounds that inhibit protein kinase activity, and to compositions and methods related thereto.

2. Description of the Related Art

Cancer (and other hyperproliferative diseases) is characterized by uncontrolled cell proliferation. This loss of the normal control of cell proliferation often appears to occur as the result of genetic damage to cell pathways that control progress through the cell cycle. The cell cycle consists of DNA synthesis (S phase), cell division or mitosis (M phase), and non-synthetic periods referred to as gap 1 (G1) and gap 2 (G2). The M-phase is composed of mitosis and cytokinesis (separation into two cells). All steps in the cell cycle are controlled by an orderly cascade of protein phosphorylation and several families of protein kinases are involved in carrying out these phosphorylation steps. In addition, the activity of many protein kinases increases in human tumors compared to normal tissue and this increased activity can be due to many factors, including increased levels of a kinase or changes in expression of co-activators or inhibitory proteins.

Cells have proteins that govern the transition from one phase of the cell cycle to another. For example, the cyclins are a family of proteins whose concentrations increase and decrease throughout the cell cycle. The cyclins turn on, at the appropriate time, different cyclin-dependent protein kinases (CDKs) that phosphorylate substrates essential for progression through the cell cycle. Activity of specific CDKs at specific times is essential for both initiation and coordinated progress through the cell cycle. For example, CDK1 is the most prominent cell cycle regulator that orchestrates M-phase activities. However, a number of other mitotic protein kinases that participate in M-phase have been identified, which include members of the polo, aurora, and NIMA (Never-In-Mitosis-A) families and kinases implicated in mitotic checkpoints, mitotic exit, and cytokinesis.

Aurora kinases are a family of oncogenic serine/threonine kinases that localize to the mitotic apparatus (centrosome, poles of the bipolar spindle, or midbody) and regulate completion of centrosome separation, bipolar spindle assembly and chromosome segregation. Three human homologs of aurora kinases have been identified (aurora-1, aurora-2 and aurora-3). They all share a highly conserved catalytic domain located in the carboxyl terminus, but their amino terminal extensions are of variable lengths with no sequence similarity. The human aurora kinases are expressed in proliferating cells and are also overexpressed in numerous tumor cell lines including breast, ovary, prostate, pancreas, and colon. Aurora-2 kinase acts as an oncogene and transforms both Rat1 fibroblasts and mouse NIH3T3 cells in vitro, and aurora-2 transforms NIH 3T3 cells grown as tumors in nude mice. Excess aurora-2 may drive cells to aneuploidy (abnormal numbers of chromosomes) by accelerating the loss of tumor suppressor genes and/or amplifying oncogenes, events known to contribute to cellular transformation. Cells with excess aurora-2 may escape mitotic check points, which in turn can activate proto-oncogenes inappropriately. Up-regulation of aurora-2 has been demonstrated in a number of pancreatic cancer cell lines. In additional, aurora-2 kinase antisense oligonucleotide treatment has been shown to cause cell cycle arrest and increased apoptosis. Therefore, aurora-2 kinase is an attractive target for rational design of novel small molecule inhibitors for the treatment of cancer and other conditions.

C-kit is a transmembrane receptor belonging to the type 3 subgroup of receptor tyrosine kinases that also includes platelet-derived growth factor receptor (PDGFR), colony-stimulating factor 1 receptor (CSF-1), and FMS-like tyrosine kinase (Flt-3). Gastrointestinal stromal tumors (GIST), which are the most common mesenchymal tumors of the gastrointestinal tract, have been demonstrated to frequently over-express c-kit. GISTs are thought to originate from the Interstitial Cells of Cajal (ICCs) that play a role in the control of gut motility. ICCs express the c-kit proto-oncogene. When c-kit binds to its ligand stem cell factor (SCF) and dimerizes with another c-kit receptor, trans-autophosphorylation on tyrosines occurs and activates a number of downstream signaling pathways that lead to a proliferative response. These events are believed to contribute to the induction of GIST.

Other GISTs are associated with excess activity of platelet-derived growth factor receptor A (PDGFR-A), which is considered a key player in the new blood vessel formation necessary for tumors to grow beyond more than a few millimeters. PDGFR-A is found in stroma and pericytes (support cells for blood vessels). PDGFR-A levels have been found to be increased in a number of other tumor types.

Researchers have explored cancer treatment approaches that inhibit tyrosine kinases and other proteins involved in uncontrolled signal transduction. For example, the signal transduction inhibitors STI571, SU5614, CT52923 (herein HPK15) and PD1739 are known to inhibit the activity of Bcr-Abl, c-kit and PDGFR tyrosine kinases. STI571 (Gleevec®; a phenylaminopyrimidine) is a small molecule inhibitor currently used in the clinic, which selectively blocks the BCR-ABL tyrosine kinase dimer in chronic myelogenous leukemia. However, Gleevec® also has been shown to inhibit the c-kit and PDGFR tyrosine kinases and therefore may also be useful in tumors that over-express these receptors. Recent studies on patients with metastatic GISTs treated with STI571 have shown decreased tumor size on computed tomography and MRI and metabolic response measured with 19-fluoro-desoxyglucose positron emission tomography (FDG-PET). However, two Phase I trials with STI571 at dose levels of 400 mg or 600 mg per day showed a partial response in 54%, stable disease in 34% and progressive disease in 12% of patients assessed at 1-3 months. These initial trials indicate that although a very good partial response was initially obtained, complete responses were quite rare, and patients eventually developed progressive disease. Recent studies showed that a particular mutant (V560G) of c-kit is more sensitive to STI571, and a mutant in the c-kit kinase domain (D816V) was resistant. Therefore, the design and development of novel inhibitors of mutant c-kit and/or of PDGFR are needed for the treatment of GIST and other conditions associated with excess c-kit and/or PDGFR activity.

Quinazoline derivatives have been proposed for inhibiting protein kinase activity. For example, WO 96/09294, WO 96/33981 and EP 0837 063 describe the use of certain quinazoline compounds as receptor tyrosine kinase inhibitors. In addition, WO 01/21596 proposes the use of quinazoline derivatives to inhibit aurora-2 kinase.

What remains needed, however, are additional and improved inhibitors of protein kinase activity, particularly inhibitors of aurora-2 kinase, c-kit and/or PDGFR-A kinase activity. The present invention fulfills these needs and offers other related advantages.

BRIEF SUMMARY OF THE INVENTION

The present invention is generally directed to compounds having the following general structure (I):

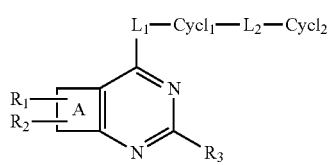

including stereoisomers, prodrugs and pharmaceutically acceptable salts thereof, wherein A is a ring moiety selected from:

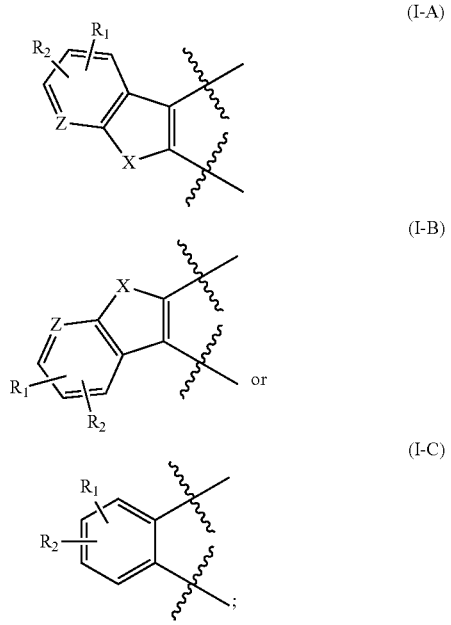

and wherein $R_1$, $R_2$, $R_3$, X, Z, $L_1$, $Cycl_1$, $L_2$ and $Cycl_2$ are as defined herein.

These compounds of the present invention have utility over a broad range of therapeutic applications, and may be used to treat diseases, such as cancer, that are mediated at least in part by protein kinase activity. Accordingly, in one aspect of the invention, the compounds described herein are formulated as pharmaceutically acceptable compositions for administration to a subject in need thereof.

In another aspect, the invention provides methods for treating or preventing a protein kinase-mediated disease, such as cancer, which method comprises administering to a patient in need of such a treatment a therapeutically effective amount of a compound described herein or a pharmaceutically acceptable composition comprising said compound. In certain embodiments, the protein kinase-mediated disease is an aurora-2 kinase-mediated disease or a c-kit-mediated disease.

Another aspect of the invention relates to inhibiting protein kinase activity in a biological sample, which method comprises contacting the biological sample with a compound described herein, or a pharmaceutically acceptable composition comprising said compound. In certain embodiments, the protein kinase is aurora-2 kinase, PDGFR-a or c-kit kinase.

Another aspect of this invention relates to a method of inhibiting protein kinase activity in a patient, which method comprises administering to the patient a compound described herein or a pharmaceutically acceptable composition comprising said compound. In certain embodiments, the protein kinase is aurora-2 kinase or c-kit kinase.

These and other aspects of the invention will be apparent upon reference to the following detailed description and attached figures. To that end, certain patent and other documents are cited herein to more specifically set forth various aspects of this invention. Each of these documents is hereby incorporated by reference in its entirety.

BRIEF DESCRIPTION OF THE DRAWINGS

FIG. 2 displays structure-based sequence alignments in the Clustal X program (multiple alignment program, EMBL-EBI, UK) of the catalytic protein kinase domains of aurora-2 (ARK1); SEQ ID NO. 1, aurora-1 (ARK2); SEQ ID NO. 2, bovine cAMP-dependent PK (1CDK); SEQ ID NO. 3, murine cAMP-dependent PK (1APM); SEQ ID NO. 4, and *C. elegans* twitchin kinase (1KOA); SEQ ID NO. 5. Black bars: α-helices (α1-α11); gray bars: β-sheets (β1-β11); shaded and *: identical residues; :: highly conserved residues; and •: similar residues.

FIG. 13 displays structure-based sequence alignments in the Clustal X program (multiple alignment program, EMBL-EBI, UK) of the catalytic protein kinase domains of c-kit; SEQ ID NO. 6, PDGDR-α; SEQ ID NO. 7, PDGFR-β; SEQ ID NO. 8, FGFr1; SEQ ID NO. 9, VEGFR2; SEQ ID NO. 10, and BCR-ABL; SEQ ID NO. 11. Shaded and * are identical residues; "::" are highly conserved residues; and • are similar residues. The N-terminal and C-terminal extensions of c-kit are not included in the modeling.

FIGS. 26A and 26B and 26C show the effects of compound (II-2-6) on in vitro cytotoxicity of colon, breast, ovarian and pancreatic cancer cell lines.

DETAILED DESCRIPTION OF THE INVENTION

Figure 1:
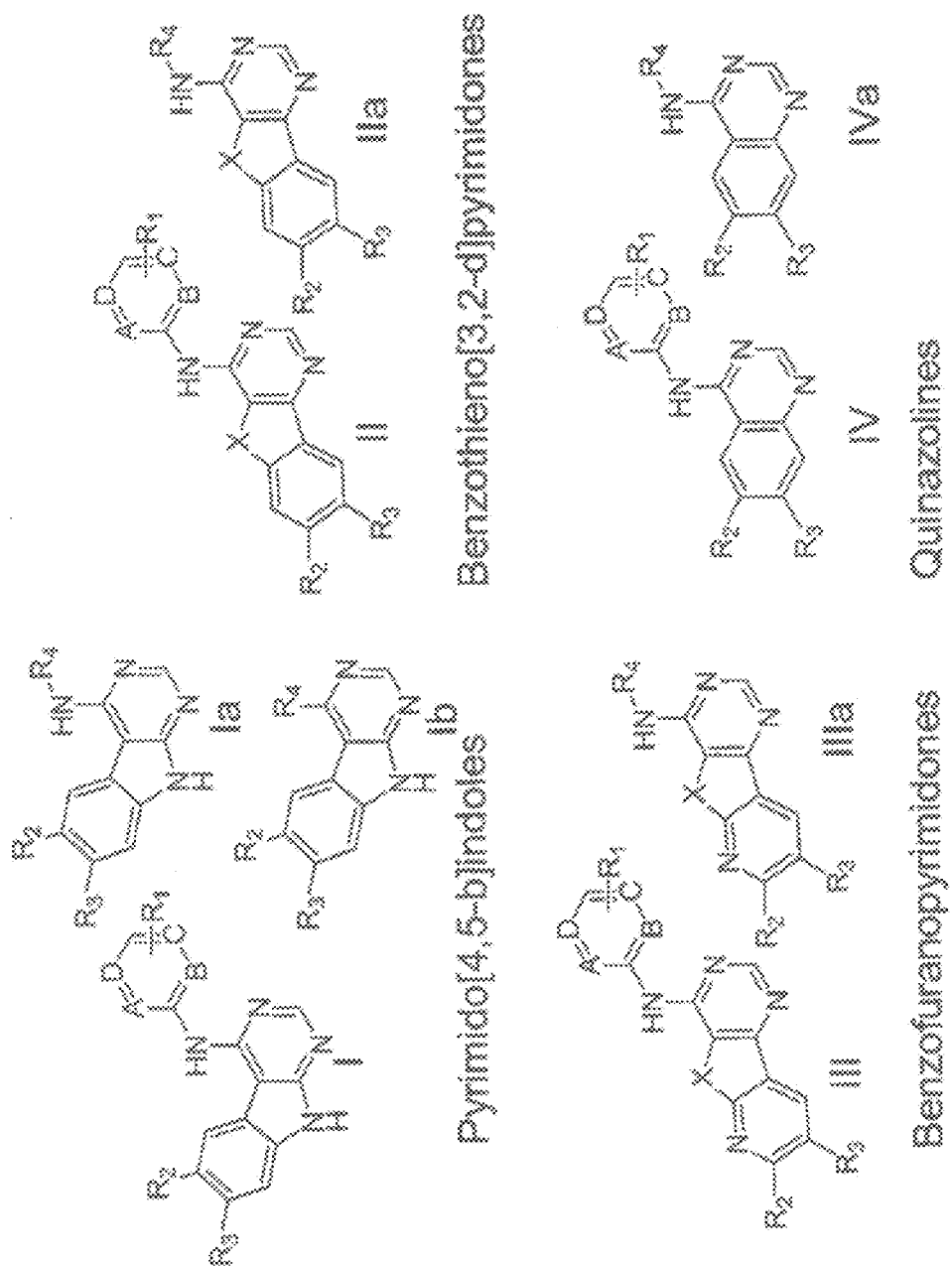
FIG. 1 displays the general structures of illustrative compounds of the present invention.

The present invention is generally directed to compounds useful as protein kinase inhibitors and to compositions and methods relating thereto. Such compounds of the invention have the following structure (I):

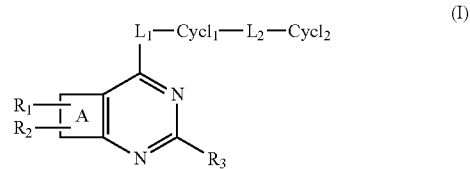

including steroisomers, prodrugs and pharmaceutically acceptable salts thereof, wherein A is a ring moiety selected from:

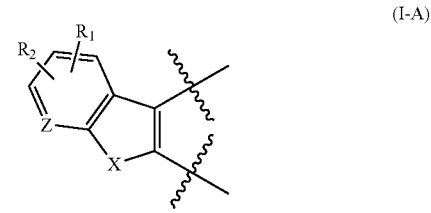

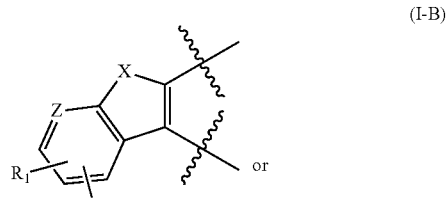

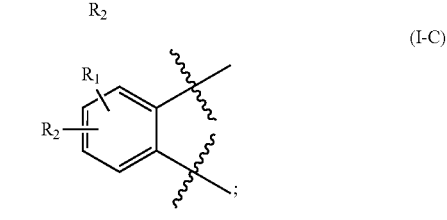

and wherein:
X is NH, S or O;
Z is CH or N;

$R_1$ and $R_2$ are the same or different and are independently hydrogen, hydroxyl, halo, —CN, —NO$_2$, —NH$_2$, —R, —OR, —SCH$_3$, —CF$_3$, —C(=O)OR or —OC(=O)R, where R is alkyl or substituted alkyl;

$R_3$ is hydrogen, —NH$_2$, alkyl, —CN, or —NO$_2$, or $R_3$ is -L$_3$-Cycl$_3$ wherein L$_3$ is a direct bond, —S— or —NH—, and Cycl$_3$ is a carbocycle, substituted carbocycle, heterocycle or substituted heterocycle;

$L_1$ is a direct bond, —NR'—, —OC(=S)NH— or —NHC (=S)O—; wherein R' is H or alkyl;

Cycl$_1$ is optional and, when present, is a carbocycle, substituted carbocycle, heterocycle or substituted heterocycle;

$L_2$ is a direct bond or —C(=S)NH—, —NHC(=S)—, —NHC(=S)NH—, —C(=O)NH—, —NHC(=O)—, —NHC(=O)NH—, —(CH$_2$)$_n$—, —NH(CH$_2$)$_n$—, —(CH$_2$)$_n$ NH—, —NH(CH$_2$)$_n$NH—, —C(=S)NH (CH$_2$)$_n$—, —NHC(=S)(CH$_2$)$_n$—, —(CH$_2$)$_n$C(=S)NH (CH$_2$)$_n$—, —(CH$_2$)$_n$—, —NHC(=S)(CH$_2$)$_n$—, —NHC (=O)—S(=O)$_2$—, —S(=O)$_2$NH—, —NHS(=O)$_2$—, wherein n is, at each occurrence the same or different and independently 1, 2, 3 or 4; and Cycl$_2$ is a carbocycle, substituted carbocycle, heterocycle or substituted heterocycle.

Unless otherwise stated the following terms used in the specification and claims have the meanings discussed below:

"Alkyl" refers to a saturated straight or branched hydrocarbon radical of one to six carbon atoms, preferably one to four carbon atoms, e.g., methyl, ethyl, propyl, 2-propyl, n-butyl, iso-butyl, tert-butyl, pentyl, hexyl, and the like, preferably methyl, ethyl, propyl, or 2-propyl. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, —CH$_2$-cyclohexyl, and the like; while unsaturated cyclic alkyls include cyclopentenyl, cyclohexenyl, —CH$_2$-cyclohexenyl, and the like. Cyclic alkyls are also referred to herein as a "cycloalkyl." Unsaturated alkyls contain at least one double or triple bond between adjacent carbon atoms (referred to as an "alkenyl" or "alkynyl", respectively.) Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like, preferably methylene, ethylene, or propylene.

"Cycloalkyl" refers to a saturated cyclic hydrocarbon radical of three to eight carbon atoms, e.g., cyclopropyl, cyclobutyl, cyclopentyl or cyclohexyl.

"Alkoxy" means a radical —OR$_a$ where R$_a$ is an alkyl as defined above, e.g., methoxy, ethoxy, propoxy, butoxy and the like.

"Halo" means fluoro, chloro, bromo, or iodo, preferably fluoro and chloro.

"Haloalkyl" means alkyl substituted with one or more, preferably one, two or three, same or different halo atoms, e.g., —CH$_2$Cl, —CF$_3$, —CH$_2$CF$_3$, —CH$_2$CCl$_3$, and the like.

"Haloalkoxy" means a radical —OR$_b$ where R$_b$ is an haloalkyl as defined above, e.g., trifluoromethoxy, trichloroethoxy, 2,2-dichloropropoxy, and the like.

"Acyl" means a radical —C(O)R$_b$ where R$_b$ is hydrogen, alkyl, or haloalkyl as defined herein, e.g., formyl, acetyl, trifluoroacetyl, butanoyl, and the like.

"Aryl" refers to an all-carbon monocyclic or fused-ring polycyclic (i.e., rings which share adjacent pairs of carbon atoms) groups of 6 to 12 carbon atoms having a completely conjugated pi-electron system. Examples, without limitation, of aryl groups are phenyl, naphthyl and anthracenyl. The aryl group may be substituted or unsubstituted. When substituted, the aryl group is substituted with one or more, more preferably one, two or three, even more preferably one or two substituents independently selected from the group consisting of alkyl, haloalkyl, halo, hydroxy, alkoxy, mercapto, alkylthio, cyano, acyl, nitro, phenoxy, heteroaryl, heteroaryloxy, haloalkyl, haloalkoxy, carboxy, alkoxycarbonyl, amino, alkylamino or dialkylamino.

"Heteroaryl" refers to a monocyclic or fused ring (i.e., rings which share an adjacent pair of atoms) group of 5 to 12 ring atoms containing one, two, three or four ring heteroatoms selected from N, O, or S, the remaining ring atoms being C, and, in addition, having a completely conjugated pi-electron system. Examples, without limitation, of unsubstituted heteroaryl groups are pyrrole, furan, thiophene, imidazole, oxazole, thiazole, pyrazole, pyridine, pyrimidine, quinoline, isoquinoline, purine, triazole, tetrazole, triazine, and carbazole. The heteroaryl group may be substituted or unsubstituted. When substituted, the heteroaryl group is substituted with one or more, more preferably one, two or three, even more preferably one or two substituents independently selected from the group consisting of alkyl, haloalkyl, halo, hydroxy, alkoxy, mercapto, alkylthio, cyano, acyl, nitro, haloalkyl, haloalkoxy, carboxy, alkoxycarbonyl, amino, alkylamino or dialkylamino.

"Carbocycle" refers to an aliphatic ring system having 3 to 14 ring atoms. The term "carbocycle", whether saturated or partially unsaturated, also refers to rings that are optionally substituted. The term "carbocycle" also includes aliphatic rings that are fused to one or more aromatic or nonaromatic rings, such as in a decahydronaphthyl or tetrahydronaphthyl, where the radical or point of attachment is on the aliphatic ring.

"Heterocycle" refers to a saturated cyclic ring system having 3 to 14 ring atoms in which one, two or three ring atoms are heteroatoms selected from N, O, or S(O)$_m$ (where m is an integer from 0 to 2), the remaining ring atoms being C, where one or two C atoms may optionally be replaced by a carbonyl group. The heterocyclyl ring may be optionally substituted independently with one or more, preferably one, two, or three substituents selected from alkyl (wherein the alkyl may be optionally substituted with one or two substituents independently selected from carboxy or ester group), haloalkyl, cycloalkylamino, cycloalkylalkyl, cycloalkylaminoalkyl, cycloalkylalkylaminoalkyl, cyanoalkyl, halo, nitro, cyano, hydroxy, alkoxy, amino, alkylamino, dialkylamino, hydroxyalkyl, carboxyalkyl, aminoalkyl, alkylaminoalkyl, dialkylaminoalkyl, aralkyl, heteroaralkyl, aryl, heteroaryl, aralkyl, heteroaralkyl, saturated or unsaturated heterocycloamino, saturated or unsaturated heterocycloaminoalkyl, and —COR$_d$ (where R$_d$ is alkyl). More specifically the term heterocyclyl includes, but is not limited to, tetrahydropyranyl, 2,2-dimethyl-1,3-dioxolane, piperidino, N-methylpiperidin-3-yl, piperazino, N-methylpyrrolidin-3-yl, pyrrolidino, morpholino, 4-cyclopropylmethylpiperazino, thiomorpholino, thiomorpholino-1-oxide, thiomorpholino-1,1-dioxide, 4-ethyloxycarbonylpiperazino, 3-oxopiperazino, 2-imidazolidone, 2-pyrrolidinone, 2-oxohomopiperazino, tetrahydropyrimidin-2-one, and the derivatives thereof. In certain embodiments, the heterocycle group is optionally substituted with one or two substituents independently selected from halo, alkyl, alkyl substituted with carboxy, ester, hydroxy, alkylamino, saturated or unsaturated heterocycloamino, saturated or unsaturated heterocycloaminoalkyl, or dialkylamino.

"Optional" or "optionally" means that the subsequently described event or circumstance may but need not occur, and that the description includes instances where the event or circumstance occurs and instances in which it does not. For example, "heterocyclic group optionally substituted with an alkyl group" means that the alkyl may but need not be present, and the description includes situations where the heterocycle group is substituted with an alkyl group and situations where the heterocycle group is not substituted with the alkyl group.

Lastly, the term "substituted" as used herein means any of the above groups (e.g., alkyl, aryl, heteroaryl, carbocycle, heterocycle, etc.) wherein at least one hydrogen atom is replaced with a substituent. In the case of an oxo substituent ("=O") two hydrogen atoms are replaced. "Substituents" within the context of this invention include halogen, hydroxy, oxo, cyano, nitro, amino, alkylamino, dialkylamino, alkyl, alkoxy, thioalkyl, haloalkyl, hydroxyalkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl, substituted heterocyclealkyl, —$NR_eR_f$, —$NR_eC(=O)R_f$, —$NR_eC(=O)NR_eR_f$, —$NR_eC(=O)OR_f$, —$NR_eSO_2R_f$, —$OR_e$, —$C(=O)R_e$, —$C(=O)OR_e$, —$C(=O)NR_eR_f$, —$OC(=O)NR_eR_f$, —SH, —$SR_e$, —$SOR_e$, —$S(=O)_2R_e$, —$OS(=O)_2R_e$, —$S(=O)_2OR_e$, wherein $R_e$ and $R_f$ are the same or different and independently hydrogen, alkyl, haloalkyl, substituted alkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl or substituted heterocyclealkyl.

In one embodiment of the invention, ring moiety A of structure (I) is as shown above in (I-A), and the compounds have the following structure (II):

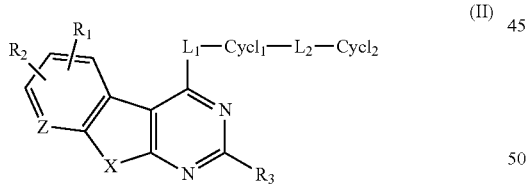

(II)

In another embodiment, the present invention provides more specific compounds of structure (II) wherein $L_1$ is a direct bond, and the compounds have the following structure (II-1):

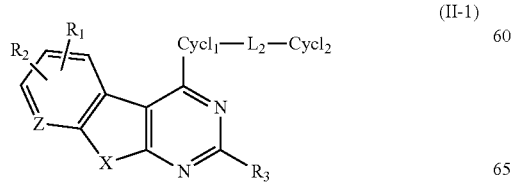

(II-1)

In a more specific aspect of structure II-1 above, $Cycl_1$ is a heterocycle or substituted heterocycle.

In a more specific aspect of structure II-1 above, $Cycl_1$ is a heterocycle or substituted heterocycle, and the compounds have the following structures (II-2) to (II-5):

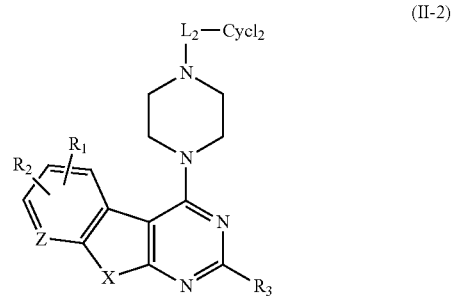

(II-2)

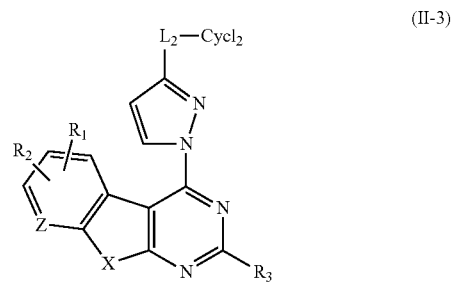

(II-3)

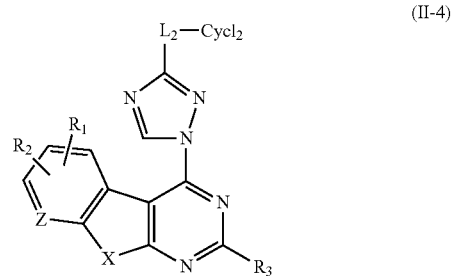

(II-4)

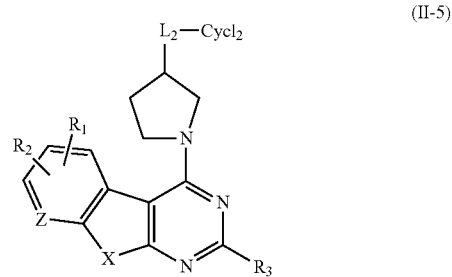

(II-5)

In a more specific aspect of structure (II-2), $L_2$ is either —C(=S)NH— or —C(=S)NHCH$_2$—, and the compounds have the structures (II-2-1) and (II-2-2), respectively:

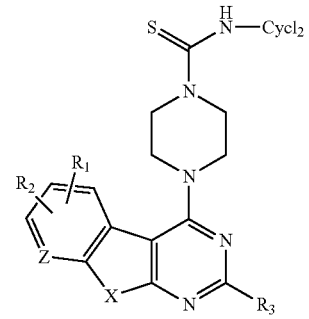
(II-2-1)

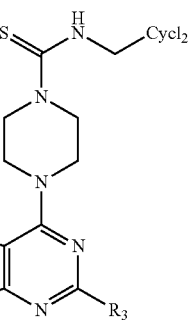
(II-2-2)

In more specific aspects of structure (II-2-1) and (II-2-2) above, X is NH and Z is CH.

In more specific aspects of structure (II-2-1) and (II-2-2) above, $L_2$ is either —C(=S)NH— or —C(=S)NHCH$_2$—.

In more specific aspects of structure (II-2-1) and (II-2-2) above, X is NH, Z is CH, $L_2$ is either —C(=S)NH— or —C(=S)NHCH$_2$—, and the compounds have the following structures (II-2-3) and (II-2-4), respectively:

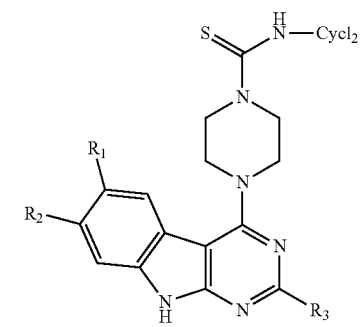
(II-2-3)

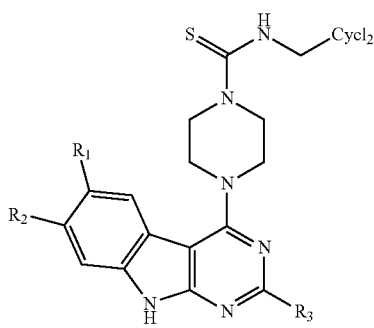
(II-2-4)

In more specific aspects of structures (II-2-3) and (II-2-4) above, Cycl$_2$ is selected from:

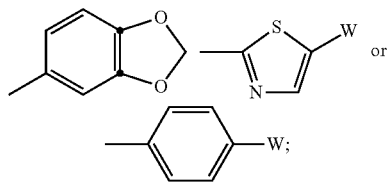

where w is

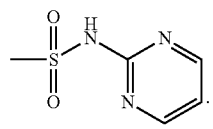

In more specific aspects of structure (II-2-3) and (II-2-4), $R_1$ and $R_2$ are selected from —OCH$_3$, —OH, —Cl, —CF$_3$, or —OC(=O)CH$_3$, and $R_3$ is selected from hydrogen or —NH$_2$.

In a more specific aspect of structure (II-2-3), Cycl$_2$ is a substituted carbocyle.

In a more specific aspect of structure (II-2-3), Cycl$_2$ is a substituted carbocyle, and the compounds have the following structure (II-2-5) below:

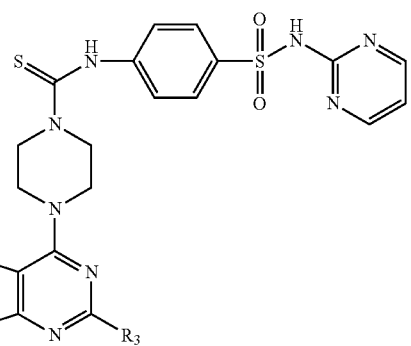
(II-2-5)

In a more specific aspect of structure (II-2-5), $R_1$ and $R_2$ are methoxy, $R_3$ is H, and the compound has the following structure (II-2-6):

(II-2-6)

In a more specific aspect of structure (II-2-4) above, $R_1$ and $R_2$ are methoxy and $R_3$ is hydrogen.

In a more specific aspect of structure (II-2-4) above, $R_1$ and $R_2$ are methoxy, $R_3$ is hydrogen, and $Cycl_2$ is:

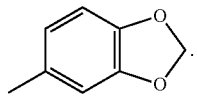

and the compound has the following structure (II-2-7):

(II-2-7)

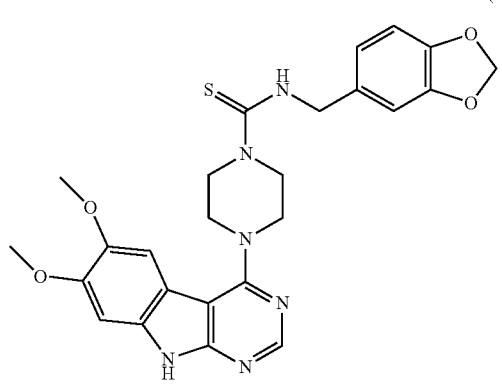

In more specific aspects of structure (II-3), Z is CH and X is NH, and the compounds have the following structure (II-3-1):

(II-3-1)

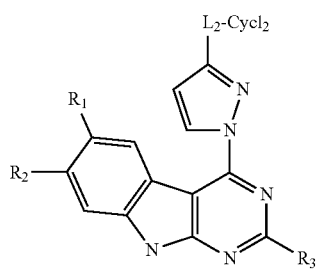

In more specific aspects of structure (II-3-1), $R_1$ and $R_2$ are methoxy and $R_3$ is hydrogen, and the compounds have the following structure (II-3-2):

(II-3-2)

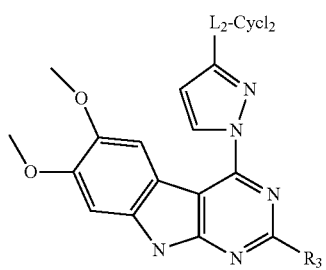

In a more specific aspect of structure (II-3-2), $L_2$ is —NHC(=S)NH— or —NHC(=O)— and $Cycl_2$ is:

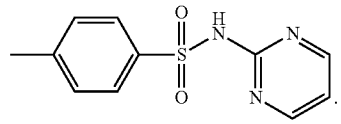 [SMILES: Cc1ccc(S(=O)(=O)Nc2ncccn2)cc1]

In a more specific aspect of structure (II-1) above, $Cycl_1$ is not present, $L_2$ is a direct bond, and $Cycl_2$ is a heterocycle or substituted heterocycle.

In a more specific aspect of structure (II-1) above, $Cycl_1$ is not present, $L_2$ is a direct bond, $Cycl_2$ is a substituted heterocycle, and the compounds have the following structure (II-3-3) below:

(II-3-3)

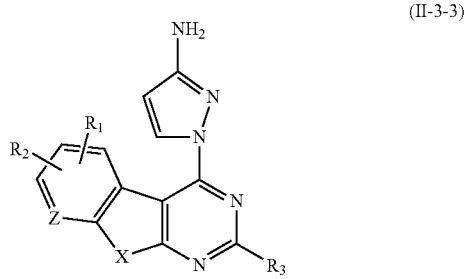

In a more specific aspect structure (II-4) above, Z is CH and X is NH, and the compounds have the following structure (II-4-1):

(II-4-1)

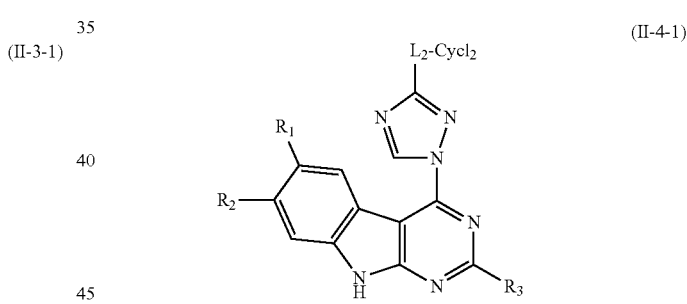

In a more specific aspect structure (II-4-1) above, $R_1$ and $R_2$ are methoxy and $R_3$ is hydrogen, and the compounds have the following structure (II-4-2):

(II-4-2)

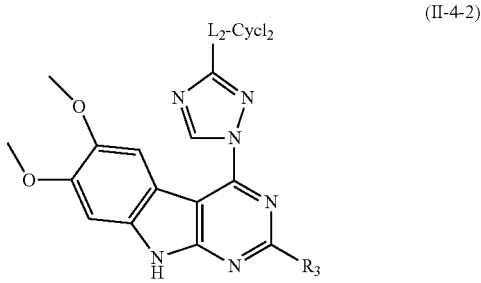

In more specific aspects of structure (II-4-2) above, $L_2$ is —NHC(=O)NH—, —NHC(=O)— or —HNC(=S)NH—, and $Cycl_2$ is selected from:

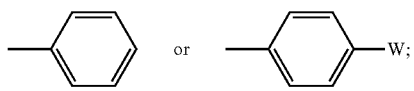

where w is

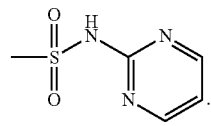

In a more specific aspect of structure (II-I) above, $Cycl_1$ is not present, $L_2$ is a direct bond, and $Cycl_2$ is a heterocycle or substituted heterocycle.

In a more specific aspect of structure (II-I) above, Z is CH, X is NH, $Cycl_1$ is not present, L2 is a direct bond and $Cycl_2$ is a heterocycle or substituted heterocycle.

In a more specific aspect of structure (II-I) above, Z is CH, X is NH, $Cycl_1$ is not present, L2 is a direct bond and $Cycl_2$ is a heterocycle or substituted heterocycle, and the compounds have the following structure (II-4-3) below:

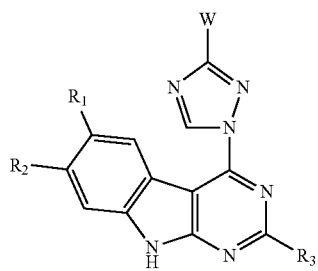

(II-4-3)

In a more specific aspect of structure (II-4-3) above, w is —$NO_2$.

In a more specific aspect of structure (II-5) above, Z is CH and X is NH, and the compounds have the following structure (II-5-1):

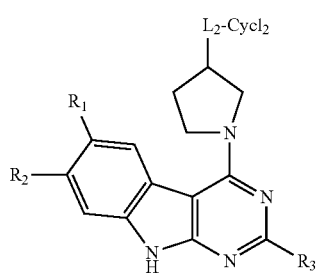

(II-5-1)

In a more specific aspect of structure (II-5-1) above, $R_1$ and $R_2$ are methoxy and $R_3$ is hydrogen, and the compounds have the following structure (II-5-2):

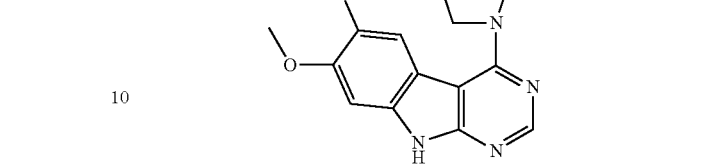

(II-5-2)

In a more specific aspect of structure (II-5-2) above, $L_2$ is —NHC(=O)— and $Cycl_2$ is a carbocycle.

In a more specific aspect of structure (II-5-2) above, $L_2$ is —NHC(=O)— and $Cycl_2$ is phenyl.

In another embodiment, the present invention provides compounds of structure (II) above wherein $L_1$ is —NH— or —OC(=S)NH—, and the compounds have the following structures (II-6) and (II-7), respectively:

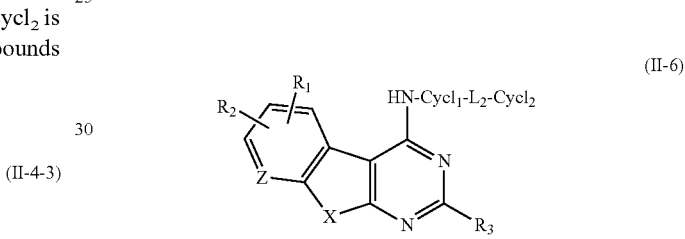

(II-6)

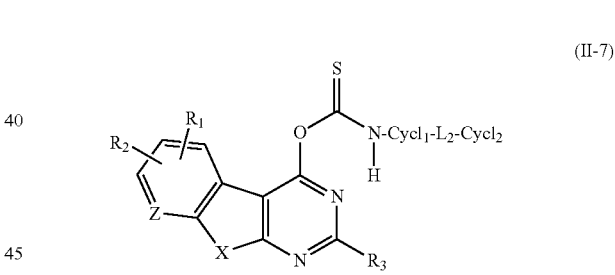

(II-7)

In a more specific aspect of structure (II-6), $Cycl_1$ is a carbocycle or heterocycle, and the compounds have the following structures (II-6-1) to (II-6-6):

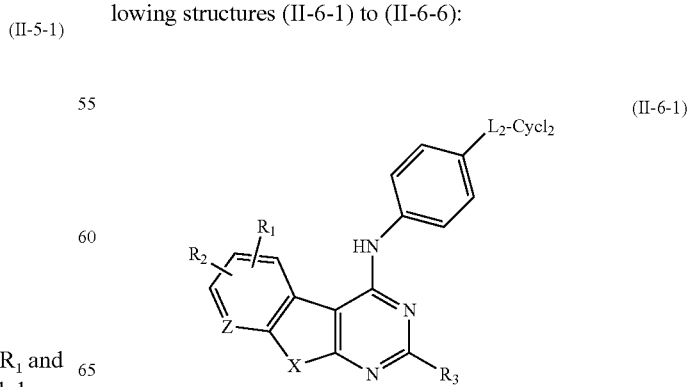

(II-6-1)

-continued
(II-6-2)
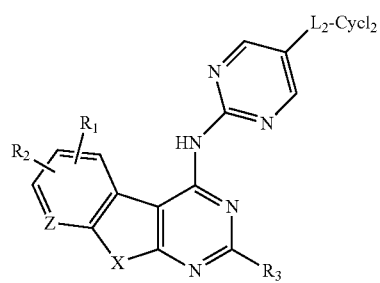
(II-6-3)
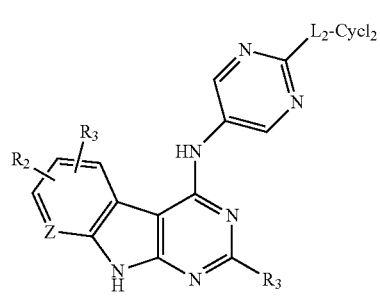
(II-6-4)
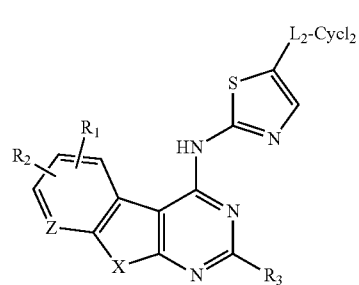
(II-6-5)
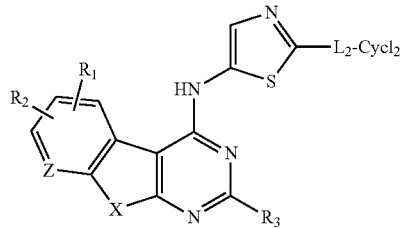
(II-6-6)
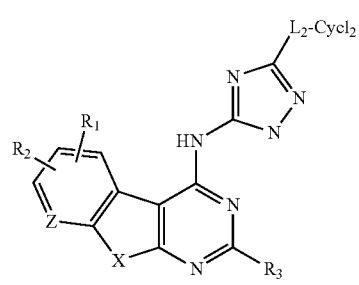
In more specific aspects of structure (II-6-1) to (II-6-6), Z is CH, X is NH and the compounds have the following structures (II-6-7) to (II-6-12):
(II-6-7)
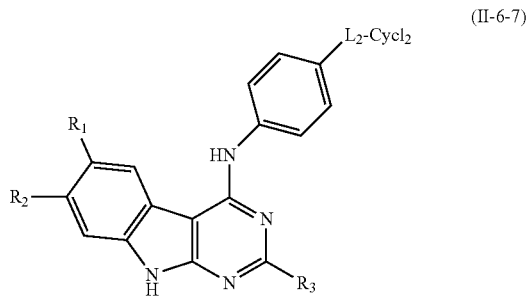
(II-6-8)
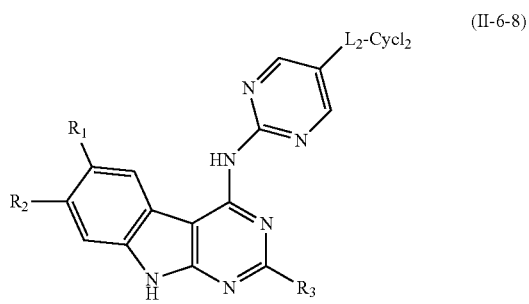
(II-6-9)
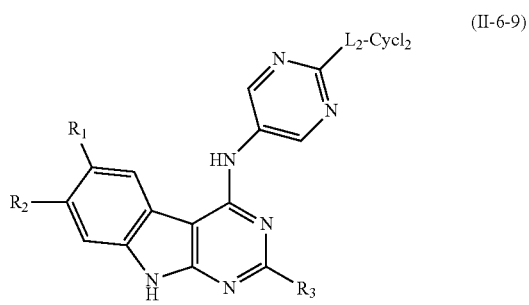
(II-6-10)
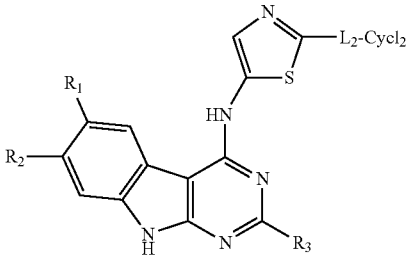
(II-6-11)

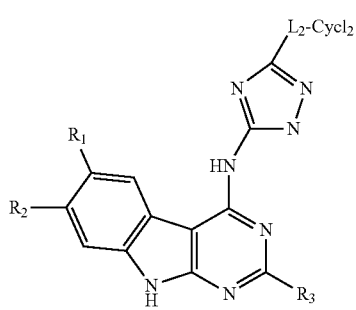

(II-6-12)

In a more specific aspect of structure (II-6-7) above, $R_1$ and $R_2$ are both methoxy, and $R_3$ is hydrogen.

In a more specific aspect of structure (II-6-7) above, $R_1$ and $R_2$ are both methoxy, $R_3$ is hydrogen, and $L_2$ is —NHCH$_2$—, —NHC(=O)— or —NH—.

In a more specific aspect of structure (II-6-7) above, $R_1$ and $R_2$ are both methoxy, $R_3$ is hydrogen, $L_2$ is —NHCH$_2$—, —NHC(=O)— or —NH—, and Cycl$_2$ is:

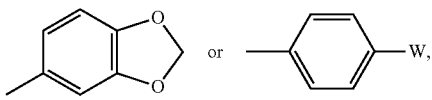

where w is

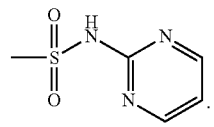

In a more specific aspect of structure (II-6-8) above, $R_1$ and $R_2$ are both methoxy, and $R_3$ is hydrogen.

In a more specific aspect of structure (II-6-8) above, $R_1$ and $R_2$ are both methoxy, $R_3$ is hydrogen, and $L_2$ is —NHCH$_2$—, —NHC(=S)NH—, —NHC(=O)— or —NH—.

In a more specific aspect of structure (II-6-8) above, $R_1$ and $R_2$ are both methoxy, $R_3$ is hydrogen, $L_2$ is —NHCH$_2$—, —NHC(=S)NH—, —NHC(=O)— or —NH—, and Cycl$_2$ is:

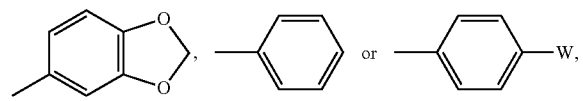

where w is

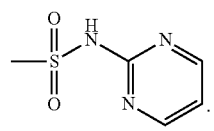

In a more specific aspect of structure (II-6-9) above, $R_1$ and $R_2$ are both methoxy, and $R_3$ is hydrogen.

In a more specific aspect of structure (II-6-9) above, $L_2$ is —NHC(=O)—.

In a more specific aspect of structure (II-6-9) above, $R_1$ and $R_2$ are both methoxy, $R_3$ is hydrogen, and $L_2$ is —NHC(=O)—.

In a more specific aspect of structure (II-6-9) above, Cycl$_2$ is phenyl.

In a more specific aspect of structure (II-6-9) above, $R_1$ and $R_2$ are both methoxy, $R_3$ is hydrogen, $L_2$ is —NHC(=O)—, and Cycl$_2$ is phenyl.

In more specific aspects of structures (II-6-10), (II-6-11) and (II-6-12) above, $R_1$ and $R_2$ are both methoxy, and $R_3$ is hydrogen or —NH$_2$.

In more specific aspects of structures (II-6-10), (II-6-11) and (II-6-12) above, $L_2$ is —NHC(=S)NH—, —NHC(=S)— or —S(=O)$_2$—.

In more specific aspects of structures (II-6-10), (II-6-11) and (II-6-12) above, Cycl$_2$ is:

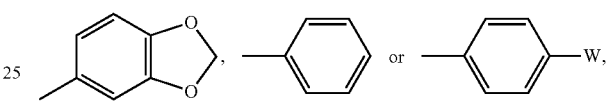

wherein w is —NH$_2$, —NO$_2$ or:

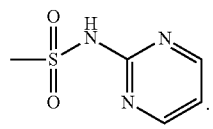

In more specific aspects of structures (II-6-10), (II-6-11) and (II-6-12) above, $R_1$ and $R_2$ are both methoxy, $R_3$ is hydrogen or —NH$_2$, and $L_2$ is —NHC(=S)NH—, —NHC(=S)— or —S(=O)$_2$—.

In more specific aspects of structure (II-6-10), (II-6-11) and (II-6-12) above, $R_1$ and $R_2$ are both methoxy, $R_3$ is hydrogen or —NH$_2$, $L_2$ is —NHC(=S)NH—, —NHC(=S)— or —S(=O)$_2$—, and Cycl$_2$ is:

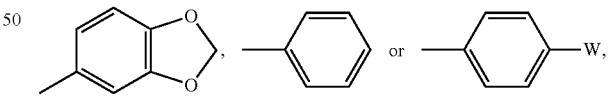

wherein w is —NH$_2$, —NO$_2$ or:

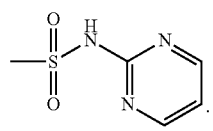

In another embodiment relating to structure (I) of the invention, ring moiety A is as shown above in (I-B), and the compounds having the following structure (III):

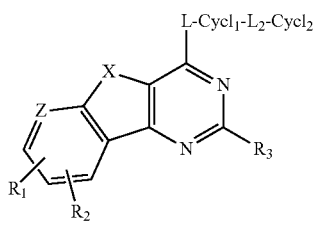
(III)

In another embodiment, the present invention provides compounds of structure (III) in which $L_1$ is a direct bond and having structure (III-1) below:

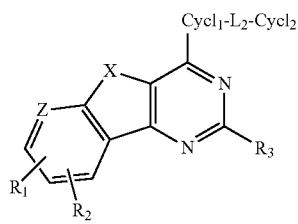
(III-1)

In a more specific aspect of structure (III-1) above, $Cycl_1$ is a heterocycle.

In a more specific aspect of structure (III-1) above, $Cycl_1$ is a heterocycle, and the compounds have the structure (III-1-1) below:

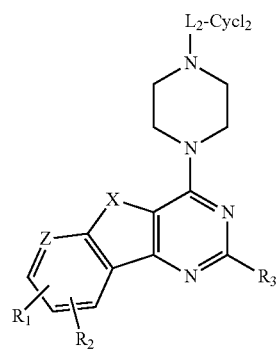
(III-1-1)

In a more specific aspect of structure (III-1-1), $R_1$ and $R_2$ are selected from hydrogen, methoxy or hydroxyl, and $R_3$ is selected from hydrogen or —$NH_2$, and the compounds have the following structure (III-1-2) below:

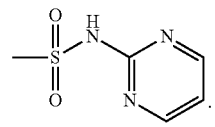
(III-1-2)

In a more specific aspect of structure (III-1-2) above, X is S, O or NH, Z is CH or N.

In a more specific aspect of structure (III-1-2) above, $R_1$, $R_2$ and $R_3$ are hydrogen.

In a more specific aspect of structure (III-1-2) above, X is S, O or NH, Z is CH or N, and $R_1$, $R_2$ and $R_3$ are hydrogen.

In a more specific aspect of structure (III-1-2) above, $L_2$ is selected from —C(=S)NH—, —C(=S)—, —C(=S)NHCH$_2$— or —CH$_2$—.

In a more specific aspect of structure (III-1-2) $Cycl_2$ is selected from:

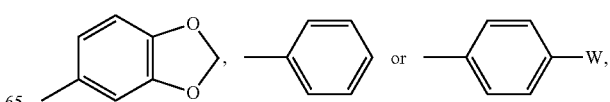

where w is

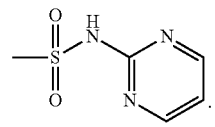

In a more specific aspect of structure (III-1-2), X is S, O or NH, Z is CH or N, $R_1$, $R_2$ and $R_3$ are hydrogen, and $L_2$ is selected from —C(=S)NH—, —C(=S)—, —C(=S)NHCH$_2$— or —CH$_2$—.

In a more specific aspect of structure (III-1-2), X is S, O or NH, Z is CH or N, $R_1$, $R_2$ and $R_3$ are hydrogen, $L_2$ is selected from —C(=S)NH—, —C(=S)—, —C(=S)NHCH$_2$— or —CH$_2$—, and $Cycl_2$ is selected from:

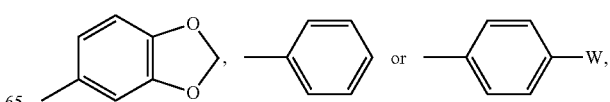

where w is

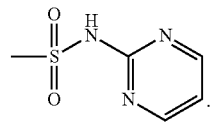

In a more specific aspect of structure (III-1-2) above, Z is CH and X is O.

In a more specific aspect of structure (III-1-2) above, Z is CH, X is O, and $L_2$ is —C(=S)NHCH$_2$—.

In a more specific aspect of structure (III-1-2) above, Z is CH, X is O, $L_2$ is —C(=S)NHCH$_2$—, and Cycl$_2$ is:

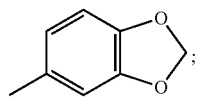

and the compound has the following structure (III-1-3):

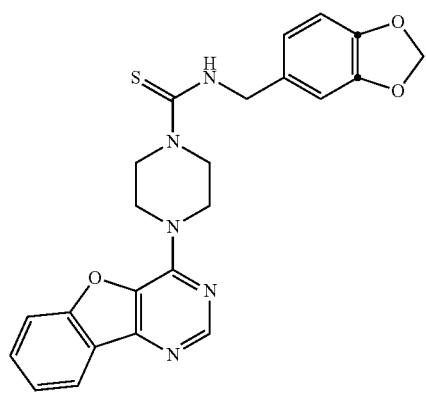
(III-1-3)

In a more specific aspect of structure (III-1-2) above, Z is N and X is S.

In a more specific aspect of structure (III-1-2) above, Z is N, X is S and $R_1$, $R_2$ and $R_3$ are hydrogen.

In a more specific aspect of structure (III-1-2) above, Z is N, X is S, $R_1$, $R_2$ and $R_3$ are hydrogen, and $L_2$ is —C(=S)NHCH$_2$—.

In a more specific aspect of structure (III-1-2) above, Z is N, X is S, $R_1$, $R_2$ and $R_3$ are hydrogen, $L_2$ is —C(=S)NHCH$_2$—, and Cycl$_2$ is:

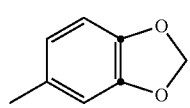

and the compound has the following structure (III-1-4):

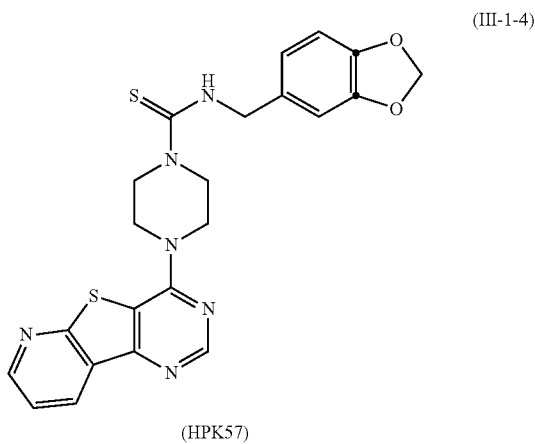
(III-1-4)

(HPK57)

In a more specific aspect of structure (III-1-2) above, Z is CH and X is O.

In a more specific aspect of structure (III-1-2) above, Z is CH and X is O, and $R_1$, $R_2$ and $R_3$ are hydrogen.

In a more specific aspect of structure (III-1-2) above, Z is CH and X is O, $R_1$, $R_2$ and $R_3$ are hydrogen, and $L_2$ is —C(=S)NH—.

In a more specific aspect of structure (III-1-2) above, Z is CH, X is O, $R_1$, $R_2$ and $R_3$ are hydrogen, $L_2$ is —C(=S)NH—, and Cycl$_2$ is:

where w is

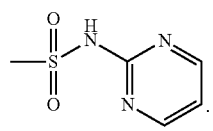

and the compound has the following structure (III-1-5):

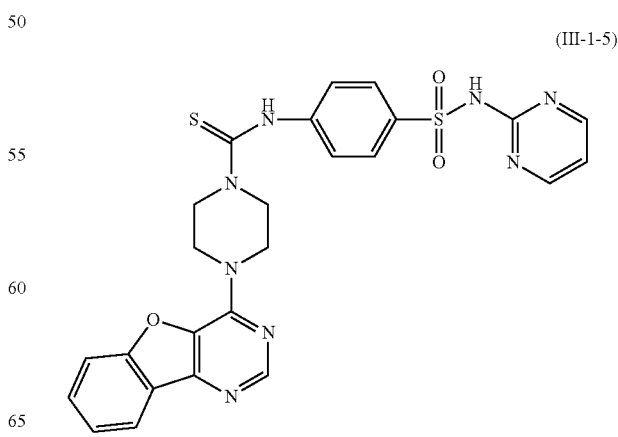
(III-1-5)

In another embodiment relating to compounds of structure (III) above, $L_1$ is —NH— or —OC(=S)NH—, and the compounds have structures (III-2) and (III-3) below:

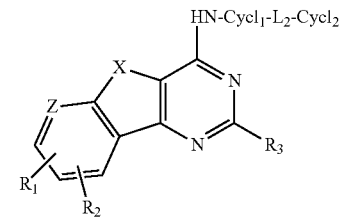
(III-2)

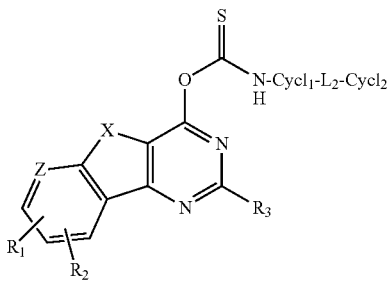
(III-3)

In a more specific aspect of structure (III-2), $R_1$, $R_2$ and $R_3$ are hydrogen, and the compounds have structures (III-2-1) and (III-2-2) below:

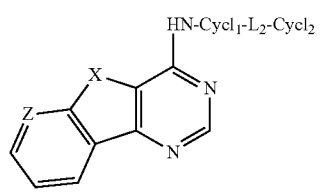
(III-2-1)

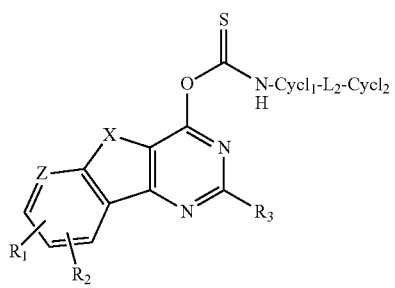
(III-2-2)

In more specific aspects of structures (III-2-1) and (III-2-2) above, $Cycl_1$ is selected from:

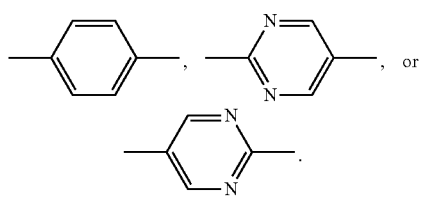

In more specific aspects of structures (III-2-1) and (III-2-2) above, $L_2$ is selected from —NHC(=S)NH—, —NHC(=O)—, —NH—, or —NHCH$_2$—.

In more specific aspects of structures (III-2-1) and (III-2-2) above, $L_2$ is selected from —NHC(=S)NH—, —NHC(=O)—, —NH—, or —NHCH$_2$—, and $Cycl_2$ is selected from a carbocycle or substituted carbocycle.

In more specific aspects of structures (III-2-1) and (III-2-2) above, $L_2$ is selected from —NHC(=S)NH—, —NHC(=O)—, —NH—, or —NHCH$_2$—, and $Cycl_2$ is selected from:

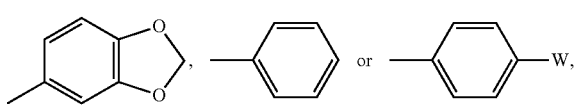

where w is

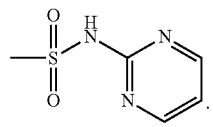

In another embodiment relating to structure (I), ring moiety A is as shown above in (I-C), and the compounds have the following structure (IV):

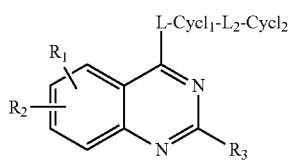
(IV)

In another embodiment, the present invention provides compounds of structure (IV) wherein $L_1$ is a direct bond, and the compounds have the following structure (IV-1):

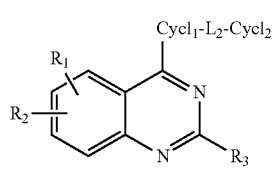
(IV-1)

In another embodiment relating to structure (IV-1), $Cycl_1$ is a heterocycle or substituted heterocycle.

In another embodiment relating to structure (IV-1), $Cycl_1$ is a heterocycle, and the compounds have the structure (IV-1-1) below:

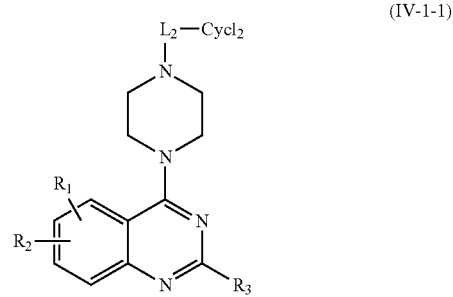
(IV-1-1)

In a more specific aspect of structure (IV-1-1), $R_1$ and $R_2$ are both methoxy, and $R_3$ is hydrogen.

In a more specific aspect of structure (IV-1-1), $R_1$ and $R_2$ are both methoxy, $R_3$ is hydrogen, and the compounds have the structure (IV-1-2) below:

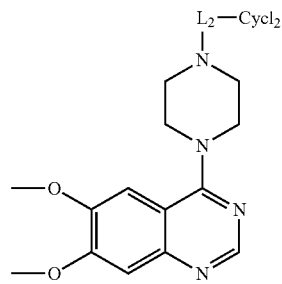
(IV-1-2)

In a more specific aspect of structures (IV-1-2), $L_2$ is —C(=S)NH—.

In a more specific aspect of structure (IV-1-2), $L_2$ is —C(=S)NH— and Cycl$_2$ is

where w is

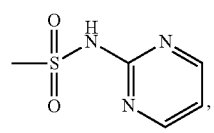

and the compound has the following structure (IV-1-3):

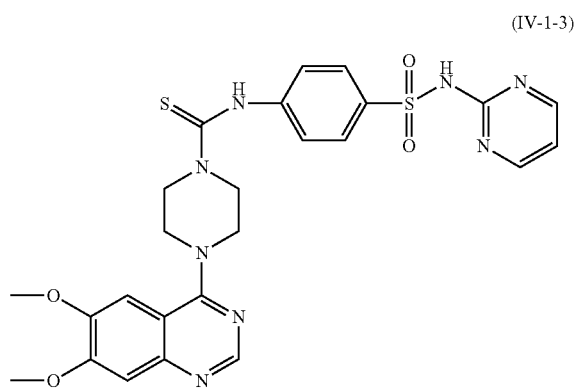 [SMILES: COc1cc2ncnc(N3CCN(C(=S)Nc4ccc(S(=O)(=O)Nc5ncccn5)cc4)CC3)c2cc1OC]
(IV-1-3)

In another embodiment relating to compounds of structure (IV) above, $L_1$ is —NH—, and these compounds of the invention have the structures IV-2 below:

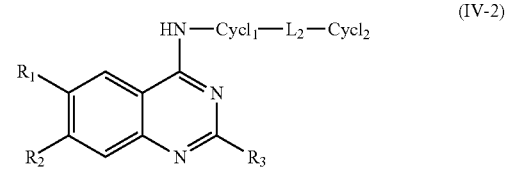
(IV-2)

In a more specific aspect of structure (IV-2), $R_1$ and $R_2$ are both from methoxy and $R_3$ is hydrogen.

In a more specific aspect of structure (IV-2), $R_1$ and $R_2$ are both methoxy, $R_3$ is hydrogen, and Cycl$_1$ is a heterocycle or substituted heterocycle.

In a more specific aspect of structure (IV-2), $R_1$ and $R_2$ are both methoxy, $R_3$ is hydrogen, and Cycl$_1$ is a heterocycle, and the compounds have the structure (IV-2-1) below:

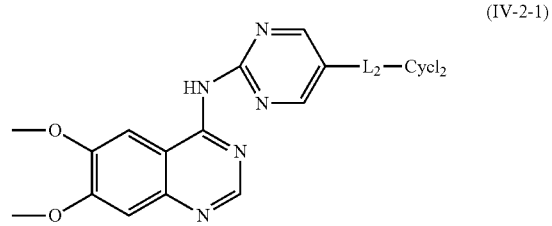
(IV-2-1)

In a more specific aspect of structures (IV-2-1), $L_2$ is selected from —NHC(=S)NH—, —NH— or —NHCH$_2$—.

In a more specific aspect of structures (IV-2-1), $L_2$ is not —NHC(=O)—.

In a more specific aspect of structures (IV-2-1), $L_2$ is selected from —NHC(=S)NH—, —NH— or —NHCH$_2$— and Cycl$_2$ is selected from:

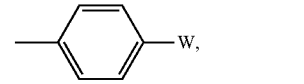

wherein w is L$_4$-Cycl$_4$, wherein L$_4$ is selected from —S(=O)$_2$NH—, —NHC(=S)NHCH$_2$—, —NHCH$_2$— or —NHC(=S)NH—, and wherein Cycl$_4$ is:

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog (Cahn, R., Ingold, C., and Prelog, V. Angew. Chem. 78:413-47, 1966; Angew. Chem. Internat. Ed. Eng. 5:385-415, 511, 1966), or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Ch. 4 of ADVANCED ORGANIC CHEMISTRY, 4$^{th}$ edition, March, J., John Wiley and Sons, New York City, 1992).

The compounds of the present invention may exhibit the phenomena of tautomerism and structural isomerism. For example, the compounds described herein may adopt an E or a Z configuration about the double bond connecting the 2-indolinone moiety to the pyrrole moiety or they may be a mixture of E and Z. This invention encompasses any tautomeric or structural isomeric form and mixtures thereof which possess the ability to modulate aurora-2 kinase activity and is not limited to, any one tautomeric or structural isomeric form.

It is contemplated that a compound of the present invention would be metabolized by enzymes in the body of the organism such as human being to generate a metabolite that can modulate the activity of the protein kinases. Such metabolites are within the scope of the present invention.

The compounds of this invention may be made by one skilled in this field according to the following general reaction schemes, as well as by the more detailed procedures set forth in the Examples.

Substituted tricyclic pyrimido[5,4-b]indole compounds (having structure (I) above where ring moiety A is (I-A)), benzothieno[3,2-d, benzofurano-pyrimidine compounds (having structure (I) above where ring moiety A is (I-B)) and quinazoline compounds (having structure (I) above where ring moiety A is (I-C)) can be prepared as outlined generally in Scheme 1 below.

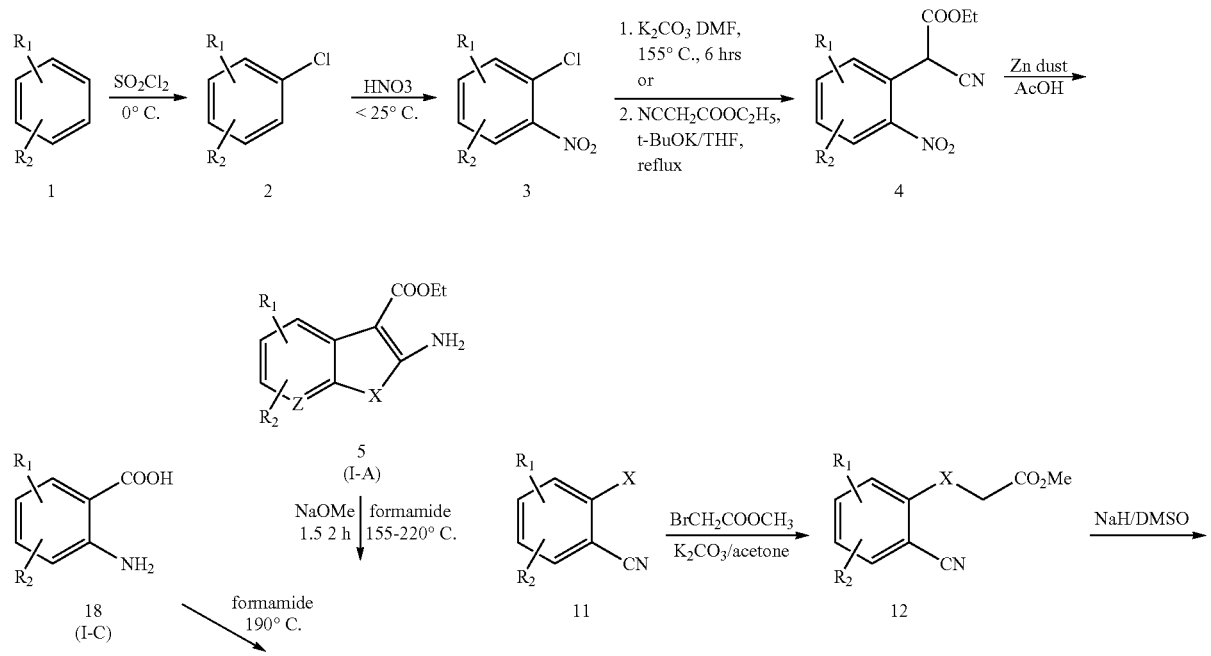

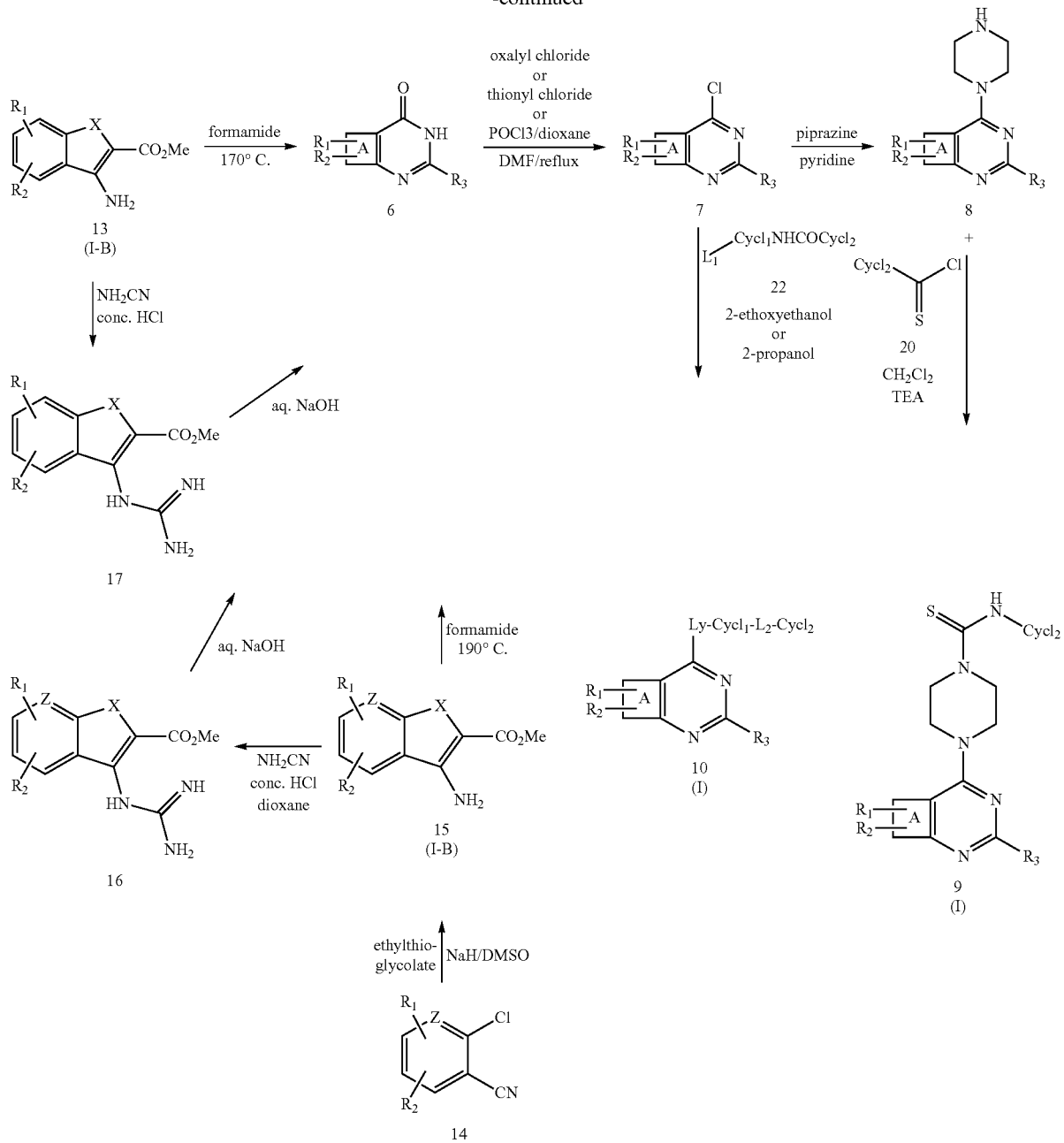

Chlorination of (un)substituted 6-membered aromatic moieties can be carried out in the presence of sulfuryl chloride at about 0° C. The 4-chloro-(un)substituted benzene (2) can be nitrated to obtain 1-chloro-(un)substituted-2-nitrobenzene (3) with fuming nitric acid, preferably without the temperature exceeding about 25° C. Ethyl 2-cyano-2-(un)substituted-2-nitrophenyl)acetate (4) can be prepared by reacting compound 3 with ethylcyanoacetate in the presence of potassium-tert-butoxide in THF (yielded compound 4 at 23%). Further the yields can be optimized at this stage by reacting compound 3 in the presence of $K_2CO_3$ in DMF at a temperature of about 155° C. for 6 hours to give the ethylcyano ester in high yield. Reduction of ester 4, can be carried out with excess of Zn dust (4-6 eq) using known conditions to give an ethyl 2-amino-5,6-dimethoxy-1H-indole-3-carboxylate (5) without an N-hydroxy side product.

Both the benzofuranopyrimidine and the benzothieno[3,2-d]pyrimidones (I-B) can be prepared by alkylation of (un)substituted-2-cyanophenol (11) with methyl bromoacetate followed by cyclization in the presence of NaH and DMSO, to give the benzofuran (13) in quantitative yields. Similarly, treatment of 2-chloronicotinonitrile (14) with ethyl thioglycolate in the presence of NaH/DMSO gives the cyclic methyl ester (15) in good yields. Cyclization to known dihydro-4H-pyrimido[4,5-b]indoles or the congeners; 3H-Benzofurano[3,2-d]pyrimid-4-one and 3H-thieno[3,2-d]pyrimid-4-one to the corresponding pyrimido[4,5-b]indol-4-ones respectively, can be performed by heating at about 155 to 220° C. in formamide and catalytic sodium methoxide.

The dihydro-pyrimidines can be converted to 4-chlorides (7) in good yields with Vilsmeier's reagent (oxalyl chloride/DMF) or thionylchloride and/or POCl₃ in dioxane solvent. The 4-chlorides can be utilized in preparing either 4-amino or 4-piprazine substituted tricyclic analogues as outlined in Scheme 1. Condensation of 4-chlorides can then be carried out with substituted aromatic amines to provide various compounds of the invention. The reaction can be carried out in refluxing lower alcohol or DMA with a catalytic amount of dry HCl gas. Similarly the 4-chlorides can be reacted with piprazine in the presence of pyridine at reflux temperature to give compound 8 in good yields. The quinazolines of formula I-C can be prepared by reacting (un)substituted anthranilic acid and formamide at 190° C. to give the dihydro-quinazolines. Under similar conditions to that of tricyclic-dihydropyrimido-indoles, the 4-chloride analogues of quinazolines can be prepared. The substitutent at the R₃ position can be obtained by reacting either cyclic ethyl or methyl esters in presence of cyanoacetamide and dry HCl to give the guanidine analogues 16 and 17. These compounds can be cyclized to 3-substituted tricyclic pyrimidine in presence of aqueous NaOH.

Certain intermediates that can be utilized in the preparation of target compounds are outlined in Scheme 2. The variously substituted aromatic amines can be treated with thiophosgene in CH₂Cl₂/TEA to give thiourea analogue 20 in moderate yields. The compounds of formula I having 4-substituted piprazine analogues can be prepared by reacting compound 20 in the presence of TEA or pyridine. Similarly, 4-substituted aryl analogues can be prepared by utilizing the starting materials as outlined in Scheme 1. The variously substituted aryl chlorides can be reacted with 1,4-diamino or 1-amino-4-nitrobenzene building blocks (with 1,2-heteroatoms in the ring) in presence of TEA to give compound 22.

Scheme 2

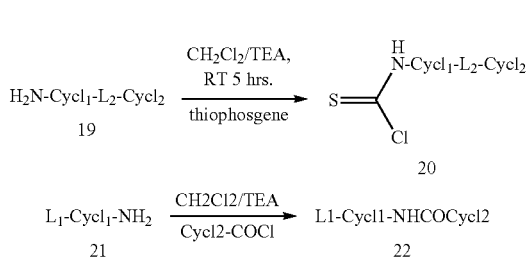

A compound of the present invention or a pharmaceutically acceptable salt thereof, can be administered as such to a human patient or can be administered in pharmaceutical compositions in which the foregoing materials are mixed with suitable carriers or excipient(s). Techniques for formulation and administration of drugs may be found, for example, in REMINGTON'S PHARMACOLOGICAL SCIENCES, Mack Publishing Co., Easton, Pa., latest edition.

A "pharmaceutical composition" refers to a mixture of one or more of the compounds described herein, or pharmaceutically acceptable salts or prodrugs thereof, with other chemical components, such as pharmaceutically acceptable excipients. The purpose of a pharmaceutical composition is to facilitate administration of a compound to an organism.

"Pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

"Pharmaceutically acceptable salt" refers to those salts which retain the biological effectiveness and properties of the parent compound. Such salts may include: (1) acid addition salt which is obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D)- or (L)-malic acid, maleic acid, methanesulfonic acid, ethanesulfonic acid, p-toluenesulfonic acid, salicylic acid, tartaric acid, citric acid, succinic acid or malonic acid and the like, preferably hydrochloric acid or (L)-malic acid; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The compound of the present invention may also act, or be designed to act, as a prodrug. A "prodrug" refers to an agent, which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. An example, without limitation, of a prodrug would be a compound of the present invention, which is, administered as an ester (the "prodrug"), phosphate, amide, carbamate or urea.

"Therapeutically effective amount" refers to that amount of the compound being administered which will relieve to some extent one or more of the symptoms of the disorder being treated. In reference to the treatment of cancer, a therapeutically effective amount refers to that amount which has the effect of: (1) reducing the size of the tumor; (2) inhibiting tumor metastasis; (3) inhibiting tumor growth; and/or (4) relieving one or more symptoms associated with the cancer.

The term "protein kinase-mediated condition" or "disease", as used herein, means any disease or other deleterious condition in which a protein kinase is known to play a role. The term "protein kinase-mediated condition" or "disease" also means those diseases or conditions that are alleviated by treatment with a protein kinase inhibitor. Such conditions include, without limitation, cancer and other hyperproliferative disorders. In certain embodiments, the cancer is a cancer of colon, breast, stomach, prostate, pancreas, or ovarian tissue. Illustrative protein kinases in this respect include, for example, aurora-2 kinase, c-kit kinase, PDGFR-a, c-met and c-ret.

The term "Aurora-2 kinase-mediated condition" or "disease", as used herein, means any disease or other deleterious condition in which Aurora is known to play a role. The term "Aurora-2 kinase-mediated condition" or "disease" also means those diseases or conditions that are alleviated by treatment with an Aurora-2 inhibitor.

The term "c-kit-mediated condition" or "disease", as used herein, means any disease or other deleterious condition in which c-kit is known to play a role. The term "c-kit-mediated condition" or "disease" also means those diseases or conditions that are alleviated by treatment with a c-kit inhibitor. Such conditions include, without limitation, cancer.

The term "PDGFR-a-mediated condition" or "disease", as used herein, means any disease or other deleterious condition in which PDGFR-a is known to play a role. The term "PDGFR-a-mediated condition" or "disease" also means those diseases or conditions that are alleviated by treatment with a PDGFR-a inhibitor. Such conditions include, without limitation, cancer.

As used herein, "administer" or "administration" refers to the delivery of an inventive compound or of a pharmaceutically acceptable salt thereof or of a pharmaceutical composition containing an inventive compound or a pharmaceutically acceptable salt thereof of this invention to an organism for the purpose of prevention or treatment of a protein kinase-related disorder.

Suitable routes of administration may include, without limitation, oral, rectal, transmucosal or intestinal administration or intramuscular, subcutaneous, intramedullary, intrathecal, direct intraventricular, intravenous, intravitreal, intraperitoneal, intranasal, or intraocular injections. In certain embodiments, the preferred routes of administration are oral and intravenous.

Alternatively, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. In this way, the liposomes may be targeted to and taken up selectively by the tumor.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in any conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, or liquid polyethylene glycols. Stabilizers may be added in these formulations, also. Pharmaceutical compositions which may also be used include hard gelatin capsules. The capsules or pills may be packaged into brown glass or plastic bottles to protect the active compound from light. The containers containing the active compound capsule formulation are preferably stored at controlled room temperature (15-30° C.).

For administration by inhalation, the compounds for use according to the present invention may be conveniently delivered in the form of an aerosol spray using a pressurized pack or a nebulizer and a suitable propellant, e.g., without limitation, dichlorodifluoromethane, trichlorofluoromethane, dichlorotetra-fluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

A non-limiting example of a pharmaceutical carrier for the hydrophobic compounds of the invention is a cosolvent system comprising benzyl alcohol, a nonpolar surfactant, a water-miscible organic polymer and an aqueous phase such as the VPD cosolvent system. VPD is a solution of 3% w/v benzyl alcohol, 8% w/v of the nonpolar surfactant polysorbate 80, and 65% w/v polyethylene glycol 300, made up to volume in absolute ethanol. The VPD cosolvent system (VPD:D5W) consists of VPD diluted 1:1 with a 5% dextrose in water solution. This cosolvent system dissolves hydrophobic compounds well, and itself produces low toxicity upon systemic administration. Naturally, the proportions of such a cosolvent system may be varied considerably without destroying its solubility and toxicity characteristics. Furthermore, the identity of the cosolvent components may be varied: for example, other low-toxicity nonpolar surfactants may be used instead of polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. In addition, certain organic solvents such as dimethylsulfoxide also may be employed, although often at the cost of greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the protein kinase-modulating compounds of the invention may be provided as physiologically acceptable salts wherein the claimed compound may form the negatively or the positively charged species. Examples of salts in which the compound forms the positively charged moiety include, without limitation, quaternary ammonium (defined elsewhere herein), salts such as the hydrochloride, sulfate, carbonate, lactate, tartrate, malate, maleate, succinate wherein the nitrogen atom of the quaternary ammonium group is a nitrogen of the selected compound of this invention which has reacted with the appropriate acid. Salts in which a compound of this invention forms the negatively charged species include, without limitation, the sodium, potassium, calcium and magnesium salts formed by the reaction of a carboxylic acid group in the compound with an appropriate base (e.g. sodium hydroxide (NaOH), potassium hydroxide (KOH), calcium hydroxide ($Ca(OH)_2$), etc.).

Pharmaceutical compositions suitable for use in the present invention include compositions wherein the active ingredients are contained in an amount sufficient to achieve the intended purpose, e.g., the modulation of protein kinase activity and/or the treatment or prevention of a protein kinase-related disorder.

More specifically, a therapeutically effective amount means an amount of compound effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from cell culture assays. Then, the dosage can be formulated for use in animal models so as to achieve a circulating concentration range that includes the $IC_{50}$ as determined in cell culture (i.e., the concentration of the test compound which achieves a half-maximal inhibition of the protein kinase activity). Such information can then be used to more accurately determine useful doses in humans.

Toxicity and therapeutic efficacy of the compounds described herein can be determined by standard pharmaceutical procedures in cell cultures or experimental animals, e.g., by determining the $IC_{50}$ and the $LD_{50}$ (both of which are discussed elsewhere herein) for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See, e.g., GOODMAN & GILMAN'S THE PHARMACOLOGICAL BASIS OF THERAPEUTICS, Ch. 3, 9th ed., Ed. by Hardman, J., and Limbard, L., McGraw-Hill, New York City, 1996, p. 46.)

Dosage amount and interval may be adjusted individually to provide plasma levels of the active species which are sufficient to maintain the kinase modulating effects. These plasma levels are referred to as minimal effective concentrations (MECs). The MEC will vary for each compound but can be estimated from in vitro data, e.g., the concentration necessary to achieve 50-90% inhibition of a kinase may be ascertained using the assays described herein. Dosages necessary to achieve the MEC will depend on individual characteristics and route of administration. HPLC assays or bioassays can be used to determine plasma concentrations.

Dosage intervals can also be determined using MEC value. Compounds should be administered using a regimen that maintains plasma levels above the MEC for 10-90% of the time, preferably between 30-90% and most preferably between 50-90%.

At present, the therapeutically effective amounts of compounds of the present invention may range from approximately 2.5 mg/m$^2$ to 1500 mg/m$^2$ per day. Additional illustrative amounts range from 0.2-1000 mg/qid, 2-500 mg/qid, and 20-250 mg/qid.

In cases of local administration or selective uptake, the effective local concentration of the drug may not be related to plasma concentration, and other procedures known in the art may be employed to determine the correct dosage amount and interval.

The amount of a composition administered will, of course, be dependent on the subject being treated, the severity of the affliction, the manner of administration, the judgment of the prescribing physician, etc.

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

As mentioned above, the compounds and compositions of the invention will find utility in a broad range of diseases and conditions mediated by protein kinases, including diseases and conditions mediated by aurora-2 kinase, c-kit and/or PDGFR-a. Such diseases may include by way of example and not limitation, cancers such as lung cancer, NSCLC (non small cell lung cancer), oat-cell cancer, bone cancer, pancreatic cancer, skin cancer, dermatofibrosarcoma protuberans, cancer of the head and neck, cutaneous or intraocular melanoma, uterine cancer, ovarian cancer, colo-rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, hepatocellular cancer, cancer of the esophagus, cancer of the small intestine, cancer of the endocrine system (e.g., cancer of the thyroid, pancreas, parathyroid or adrenal glands), sarcomas of soft tissues, cancer of the urethra, cancer of the penis, prostate cancer (particularly hormone-refractory), chronic or acute leukemia, solid tumors of childhood, hypereosinophilia, lymphocytic lymphomas, cancer of the bladder, cancer of the kidney or ureter (e.g., renal cell carcinoma, carcinoma of the renal pelvis), pediatric malignancy, neoplasms of the central nervous system (e.g., primary CNS lymphoma, spinal axis tumors, medulloblastoma, brain stem gliomas or pituitary adenomas), Barrett's esophagus (pre-malignant syndrome), neoplastic cutaneous disease, psoriasis, mycoses fungoides, and benign prostatic hypertrophy, diabetes related diseases such as diabetic retinopathy, retinal ischemia, and retinal neovascularization, hepatic cirrhosis, angiogenesis, cardiovascular disease such as atherosclerosis, immunological disease such as autoimmune disease and renal disease.

The inventive compound can be used in combination with one or more other chemotherapeutic agents. The dosage of the inventive compounds may be adjusted for any drug-drug reaction. In one embodiment, the chemotherapeutic agent is selected from the group consisting of mitotic inhibitors, alkylating agents, anti-metabolites, cell cycle inhibitors, enzymes, topoisomerase inhibitors such as CAMPTOSAR (irinotecan), biological response modifiers, anti-hormones, antiangiogenic agents such as MMP-2, MMP-9 and COX-2 inhibitors, anti-androgens, platinum coordination complexes (cisplatin, etc.), substituted ureas such as hydroxyurea; methylhydrazine derivatives, e.g., procarbazine; adrenocortical suppressants, e.g., mitotane, aminoglutethimide, hormone and hormone antagonists such as the adrenocorticosteriods (e.g., prednisone), progestins (e.g., hydroxyprogesterone caproate), estrogens (e.g., diethylstilbesterol), antiestrogens such as tamoxifen, androgens, e.g., testosterone propionate, and aromatase inhibitors, such as anastrozole, and AROMASIN (exemestane).

Examples of alkylating agents that the above method can be carried out in combination with include, without limitation, fluorouracil (5-FU) alone or in further combination with leukovorin; other pyrimidine analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

Examples of antimetabolite chemotherapeutic agents that the above method can be carried out in combination with include, without limitation, folic acid analogs, e.g., methotrexate (used in the treatment of acute lymphocytic leukemia, choriocarcinoma, mycosis fungiodes, breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

Examples of natural product-based chemotherapeutic agents that the above method can be carried out in combination with include, without limitation, the vinca alkaloids, e.g., vinblastine (used in the treatment of breast and testicular cancer), vincristine and vindesine; the epipodophyllotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

Examples of useful COX-II inhibitors include Vioxx, CELEBREX (celecoxib), valdecoxib, paracoxib, rofecoxib, and Cox 189.

Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred are those that selectively inhibit MMP-2 and/or MMP-9 relative to the other matrix-metalloproteinases (i.e., MMP-1, MMP-3, MMP-4, MMP-5, MMP-6, MMP-7, MMP-8, MMP-10, MMP-11, MMP-12, and MMP-13).

Some specific examples of MMP inhibitors useful in the present invention are AG-3340, RO 32-3555, RS 13-0830, and compounds selected from: 3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R,3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R,3R) 1-[4-(4-fluoro-2-methylbenzyloxy)-benzenesulfonyl]-3-hydroxy-3-methyl-piperidine-2-carboxylic acid hydroxyamide; 3-[[(4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxa-bicyclo[3.2.1]octane-3-carboxylic acid hydroxyamide; 3-endo-3-[4-(4-fluoro-phenoxy)-benzenesulfonylamino]-8-oxa-bicyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide; and pharmaceutically acceptable salts and solvates of these compounds.

Other anti-angiogenesis agents, other COX-II inhibitors and other MMP inhibitors, can also be used in the present invention.

An inventive compound can also be used with other signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, such as HERCEPTIN (Genentech, Inc., South San Francisco, Calif.). EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein.

EGFR-inhibiting agents include, but are not limited to, the monoclonal antibodies C225 and anti-EGFR 22Mab (ImClone Systems, Inc., New York, N.Y.), the compounds ZD-1839 (AstraZeneca), BIBX-1382 (Boehringer Ingelheim), MDX-447 (Medarex Inc., Annandale, N.J.), and OLX-103 (Merck & Co., Whitehouse Station, N.J.), and EGF fusion toxin (Seragen Inc., Hopkinton, Mass.).

These and other EGFR-inhibiting agents can be used in the present invention. VEGF inhibitors, for example SU-5416 and SU-6668 (Sugen Inc., South San Francisco, Calif.), can also be combined with an inventive compound. VEGF inhibitors are described in, for example, WO 01/60814 A3 (published Aug. 23, 2001), WO 99/24440 (published May 20, 1999), PCT International Application PCT/IB99/00797 (filed May 3, 1999), WO 95/21613 (published Aug. 17, 1995), WO 99/61422 (published Dec. 2, 1999), U.S. Pat. No. 5,834,504 (issued Nov. 10, 1998), WO 01/60814, WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc., Kirkland, Wash.); anti-VEGF monoclonal antibody of Genentech, Inc.; and angiozyme, a synthetic ribozyme from Ribozyme (Boulder, Colo.) and Chiron (Emeryville, Calif.). These and other VEGF inhibitors can be used in the present invention as described herein. pErbB2 receptor inhibitors, such as GW-282974 (Glaxo Wellcome plc), and the monoclonal antibodies AR-209 (Aronex Pharmaceuticals Inc., The Woodlands, Tex.) and 2B-1 (Chiron), can furthermore be combined with an inventive compound, for example, those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Pat. No. 6,284,764 (issued Sep. 4, 2001), incorporated in its entirety herein by reference. The erbB2 receptor inhibitor compounds and substance described in the aforementioned PCT applications, U.S. patents, and U.S. provisional applications, as well as other compounds and substances that inhibit the erbB2 receptor, can be used with an inventive compound, in accordance with the present invention.

An inventive compound can also be used with other agents useful in treating cancer, including, but not limited to, agents capable of enhancing antitumor immune responses, such as CTLA4 (cytotoxic lymphocite antigen 4) antibodies, and other agents capable of blocking CTLA4; and anti-proliferative agents such as other farnesyl protein transferase inhibitors, for example the farnesyl protein transferase inhibitors described in the references cited in the "Background" section, of U.S. Pat. No. 6,258,824 B1.

The above method can be also be carried out in combination with radiation therapy, wherein the amount of an inventive compound in combination with the radiation therapy is effective in treating the above diseases.

Techniques for administering radiation therapy are known in the art, and these techniques can be used in the combination therapy described herein. The administration of the compound of the invention in this combination therapy can be determined as described herein.

Agents and therapies that induce damage to DNA are commonly used in the treatment of cancer. For example, ionizing radiation (IR) and platinum-based chemotherapeutic drugs have mechanisms of action that are known to involve the induction of DNA damage, with IR causing double-stranded DNA (dsDNA) breaks and platinum agents causing DNA adduct formation. DNA repair pathways initiated in response to these forms of DNA damage are mediated in part by a protein known as Rad51. Rad51 protein plays an essential role in homologous recombination by catalyzing strand transfer between a broken sequence and its undamaged homologue. Although Rad51 is important in the repair of DNA damage in normal, non-cancerous cells, it can also mediate resistance of tumor cells to cancer treatments which rely upon DNA damage as their mechanisms of action. Indeed, correlations have observed between the expression levels of Rad51 and resistance to chemotherapeutic drugs in cancer cells. Additionally, reducing levels of Rad51 in cells increases the sensitivity of those cells to radiation.

As further demonstrated herein, it has been found that the anti-tumor activity of compounds of the present invention is mediated at least in part by their ability to modulate the Rad51 protein. Therefore, in other embodiments of the invention, there are provided methods for modulating Rad51 levels and/or activity in cells using compounds described herein. As Rad51 plays a known role in the repair of DNA damage caused by DNA-damaging chemotherapeutic agents and therapies, combination therapies employing compounds of the invention in conjunction with DNA-damaging agents can improve the sensitivity of cancer cells to these therapies and thereby improve treatment efficacy. In addition, Rad51 represents an effective biomarker (along with other biomarkers such as CTC, FDG-PET and pERK) for assessing the sensitivity of cells to treatment with a compound of the invention.

In one embodiment, a compound of the invention used in these methods is a compound of class (I-B) as described herein. In a particular embodiment, the compound is a compound as set forth in structure (III) herein, and sub-structures thereof. In a more particular embodiment, the compound is a compound as set forth in structure (III-1-3) herein.

The invention will be better understood upon consideration of the following non-limiting Examples.

EXAMPLES

A structure-based design approach was used employing three-dimensional structural modeling of protein kinase catalytic sites and their binding relationship with inhibitor compounds to design the inventive compounds described herein. Homology modeling of protein kinases has been used to predict and analyze the three-dimensional structures of these proteins. A suite of programs that employs PSI-BLAST (NCBI), THREADER (HGMP Resource Center, Hinxton, Cambs, CB10 1SA, UK), 3D-PSSM (three-dimensional position scoring matrix) (HGMP) and SAP programs was used to determine the optimal template for homology modeling of aurora-1 and aurora-2 kinases, c-kit tyrosine kinase receptor and PDGFR-A. The crystal structure of the activated form of bovine cAMP-dependent protein kinase was identified as the best template and subsequently used for aurora kinase homology modeling using molecular dynamics (MD) simulations in INSIGHT II (version 2000, Accelrys Inc.) running on an Indigo2 workstation (Silicon Graphics, Inc.). The modeled aurora-2 structure was docked with known S/T kinase and aurora-2 kinase inhibitors using the binary complex of cAMP-dependent PK-$Mn^{2+}$-adenylyl imidodiphosphate (AMP-PNP). The calculated binding energies from the docking analysis are in agreement with experimental $IC_{50}$ values obtained from an in vitro kinase assay, which uses histone H1 or myelin basic protein (MBP) phosphorylation to assess inhibitory activity. The aurora-2 structural model provided a rational basis for site-directed mutagenesis studies of the active site and in silico screening of chemical databases, thereby allowing the design of novel aurora-2 kinase inhibitors described herein, e.g., pyrimido[4,5-b]indoles, benzothieno[3,2-d]pyrimidones, benzofuranopyrimidines and 6,7-quinazolines.

The crystal structures of the activated forms of VEGFR2 and FGFR1 protein kinase receptors were identified as the best templates and subsequently used for c-kit homology modeling using molecular dynamics (MD) simulations in INSIGHT II (version 2000, Accelrys Inc.) running on an Indigo2 workstation (Silicon Graphics, Inc.). Then the modeled c-kit binding site structure was docked with known c-kit inhibitors (STI571, CT52923, PD173955 and SU5614).

Figure 12:
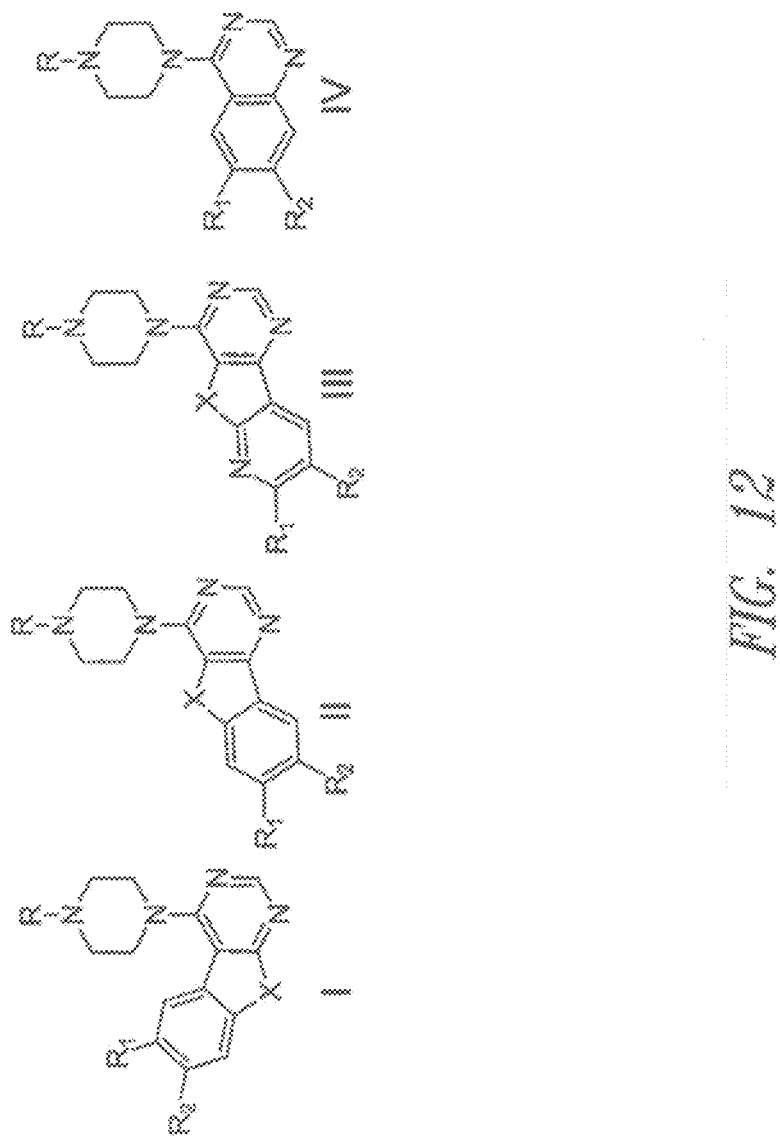
FIG. 12 displays the general structures of further illustrative inventive compounds.

The c-kit structural model provided a basis for electronically mutating the active site and using another computer program to screen chemical databases, thereby allowing the design of novel c-kit kinase inhibitors. For example, on the basis of docking chemicals in the active site, it was determined that certain compound classes (4-piprazinylpyrimido [4,5-b]indoles, benzothieno[3,2-d], benzofuranopyrimidines and quinazolines containing analogs, see FIG. 12) could replace the 6,7-dimethoxy quinazoline and the adenine base of ATP, thereby allowing new hydrogen bonding and hydrophobic interactions within the ATP binding pocket.

Example 1

Aurora Sequence and Structure Analysis

Figure 2:
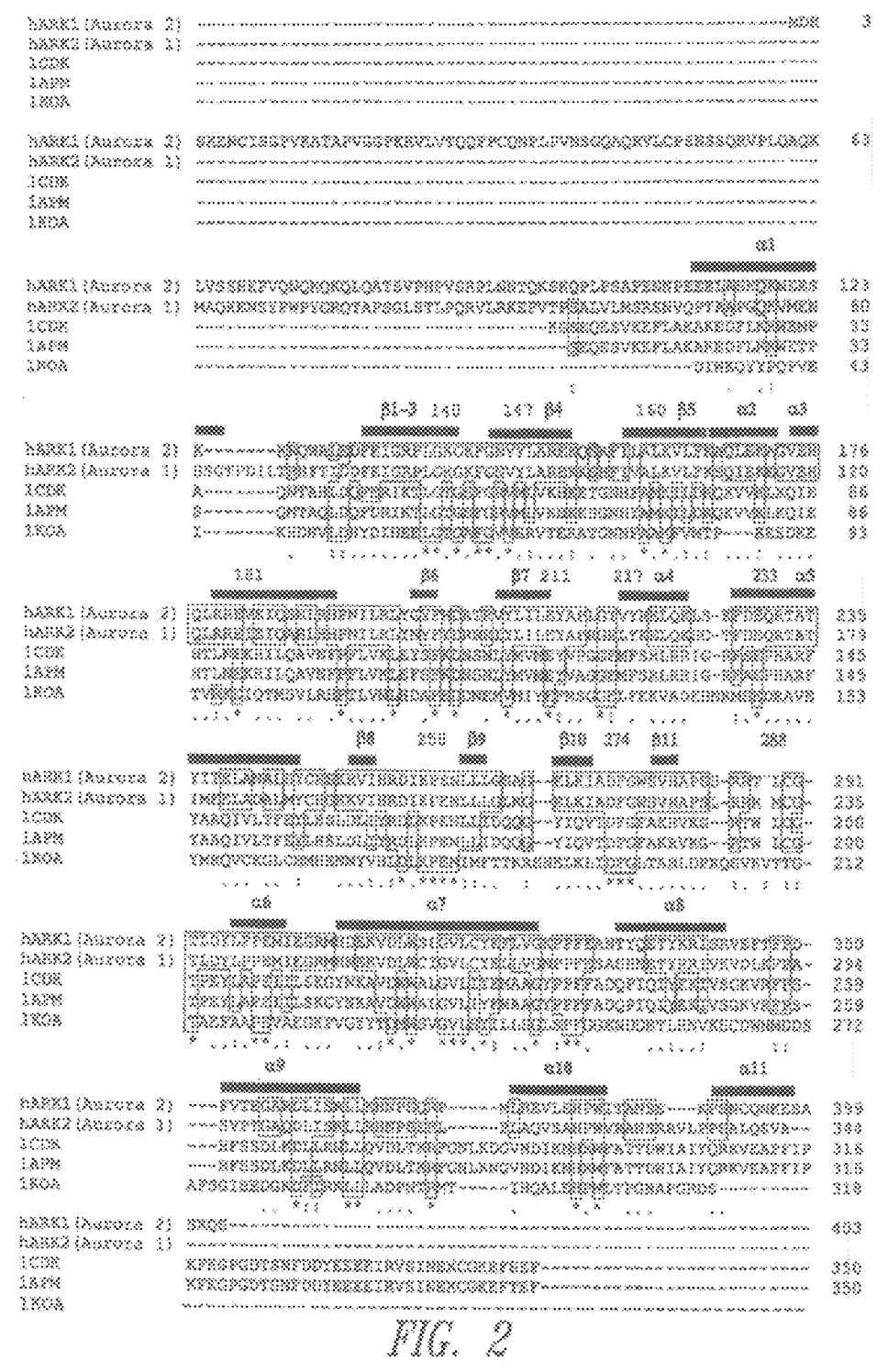

A PSI-BLAST search (NCBI) was performed with the sequence of the kinase portion of human aurora-1 and aurora-2 kinases and high sequence similarities were found to porcine heart bovine cAMP-dependent kinase (PDB code 1CDK), murine cAMP-dependent kinase (1APM), and *C. elegans* twitchin kinase (1KOA), whose three-dimensional structures have been solved. The three manually aligned S/T kinase domain sequences with their respective secondary structures were viewed in Clustal X (FIG. 2).

The aurora-1 or aurora-2 sequences were inputted into the tertiary structure prediction programs THREADER and 3D-PSSM, which compare primary sequences with all of the known three-dimensional structures in the Brookhaven Protein Data Bank. The output is composed of the optimally aligned, lowest-energy, three-dimensional structures that are similar to the aurora kinases. The top structural matches were bovine 1CDK, murine 1APM and 1KOA, confirming that the aurora kinase proteins are structurally conserved.

Example 2

Aurora Homology Modeling

The 1CDK, 1APM and 1KOA tertiary structures provided the three-dimensional templates for the homology modeling of aurora-1 and aurora-2 kinases. The crystal structure coordinates for the above serine/tyrosine kinase domains were obtained from the Protein Data Bank. These domains were pair-wise superimposed onto each other using the program SAP. The structural alignments produced by the SAP program were fine-tuned manually to better match residues within the regular secondary structural elements.

Figure 3:
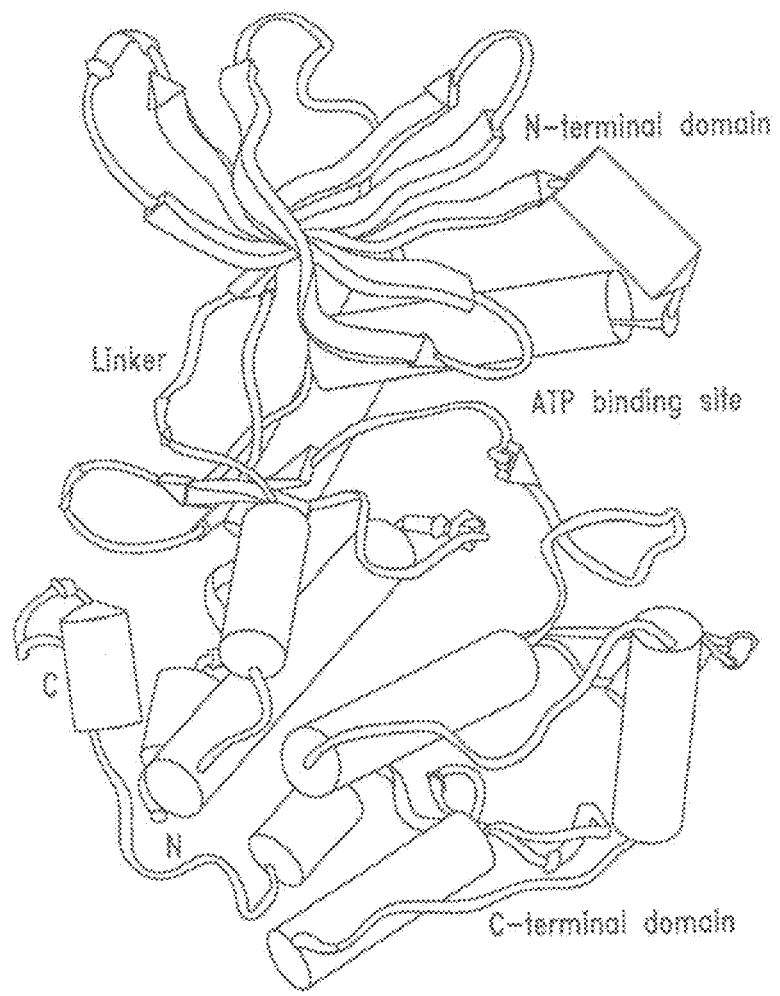
FIG. 3 displays the homology model of aurora-2 kinase. Secondary structural elements include α-helix, β-sheet, coil, and turns.

Structural models were built of aurora-1 and 2 using 1CDK as the template structure. The final aurora-2 model (FIG. 3) was analyzed using Profile-3D. The Profile-3D and 3D-1 D score plots of the model were positive over the entire length of protein in a moving-window scan to the template structure.

Additionally, the PROCHECK program was used to verify the correct geometry of the dihedral angles and the handedness of the aurora-2 model.

Example 3

Aurora Molecular Dynamics (MD) and Docking Analysis

MD simulations were performed in the canonical ensemble (NVT) at 300° K using the CFF force field implemented in the Discover_3 program (version 2.9.5). Dynamics were equilibrated for 10 picoseconds with time steps of 1 femtosecond and continued for 10-picosecond simulations. A nonbonded cutoff distance of 8 Å and a distance-dependent dielectric constant ($\in$=5rij) for water were used to simulate the aqueous media. All of the bonds to hydrogen were constrained. Dynamic trajectories were recorded every 0.5 picoseconds for analysis. The resulting low energy structure was extracted and energy-minimized to 0.001 kcal/mol/Å. To examine the conformational changes that occur during MD, the root mean square (rms) deviations were calculated from trajectories at 0.5-picosecond intervals and compared to the Cα backbone of cAMP-dependent PK. The rms deviation for the two superimposed structures was 0.42 Å. Furthermore, the rms deviations were calculated for the protein backbone (0.37 Å) and the active-site pocket (0.41 Å) and were compared with crystal structure before the docking experiments. The resulting aurora-2 structure served as the starting model for docking studies.

Figure 4:
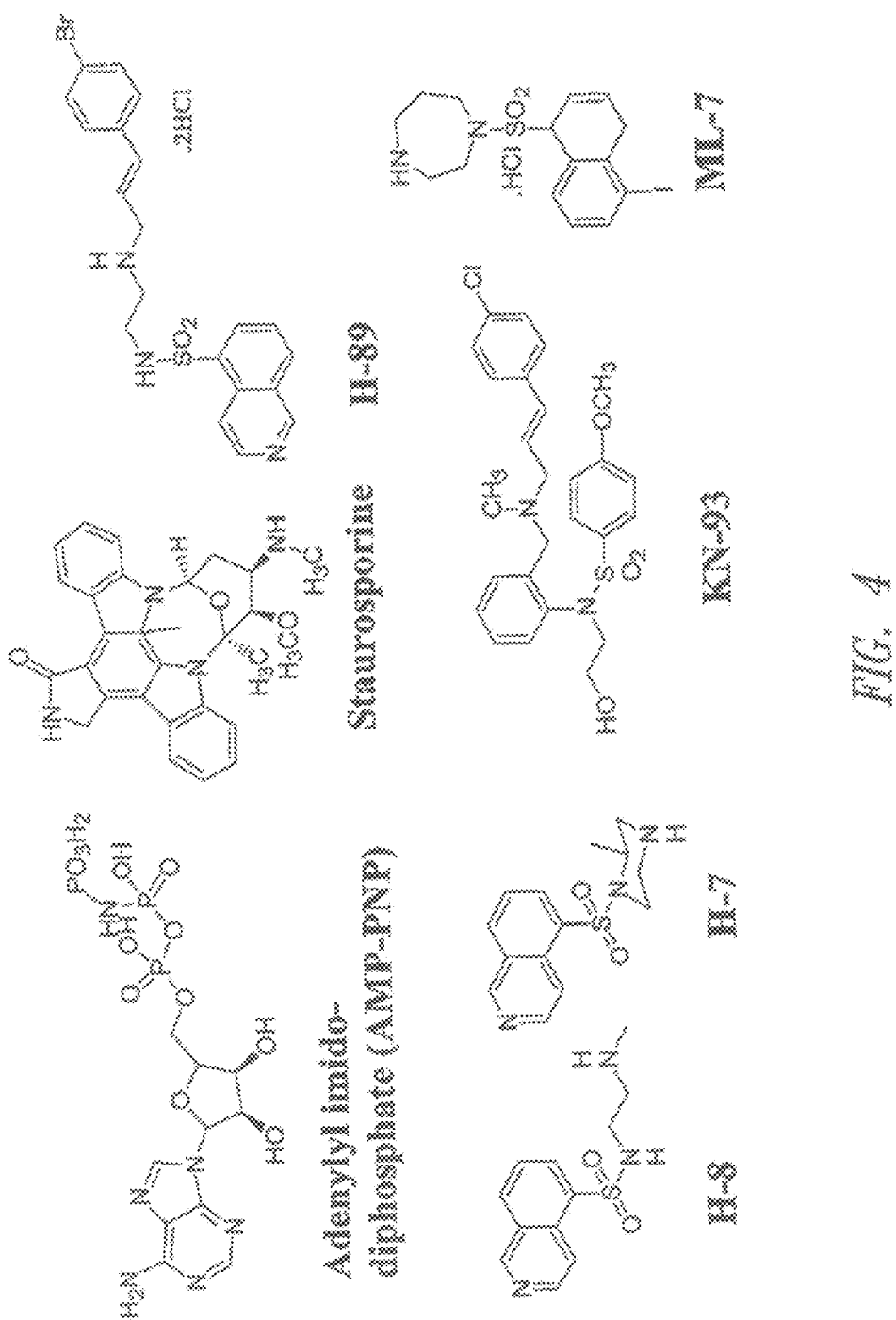
FIG. 4 displays the structures of the ATP analog (AMP-PNP) and S/T kinase inhibitors (staurosporine, H-89, H-8, H-7, KN-93, ML-7, and 6,7-dimethoxyquinazoline) evaluated for inhibitory activities against aurora-2 kinase.

For docking analysis, the ligand structures were obtained from five crystal structure complexes of cAMP-dependent PK bound with AMP-PNP, staurosporine, H-89, H-7, or H-8 and from structures that were empirically built and energy minimized (KN-93, ML-7, and 6,7-dimethoxyquinazoline) (FIG. 4) in the INSIGHT II program. The heavy atoms from AMP-PNP were used as sphere centers for the docking procedures. Docking simulations were performed at 500° K with 100 femtosecond/stage (total of 50 stages), quenching the system to a final temperature of 300° K. The whole complex structure was energy minimized using 1000 steps. This provided 10 structures from the simulated annealing (SA) docking, and their generated conformers were clustered according to rms deviation. The lowest global structure complexes were used to calculate intermolecular binding energies.

Example 4

Design Strategy for Aurora-2 Kinase Inhibitors

Figure 5:
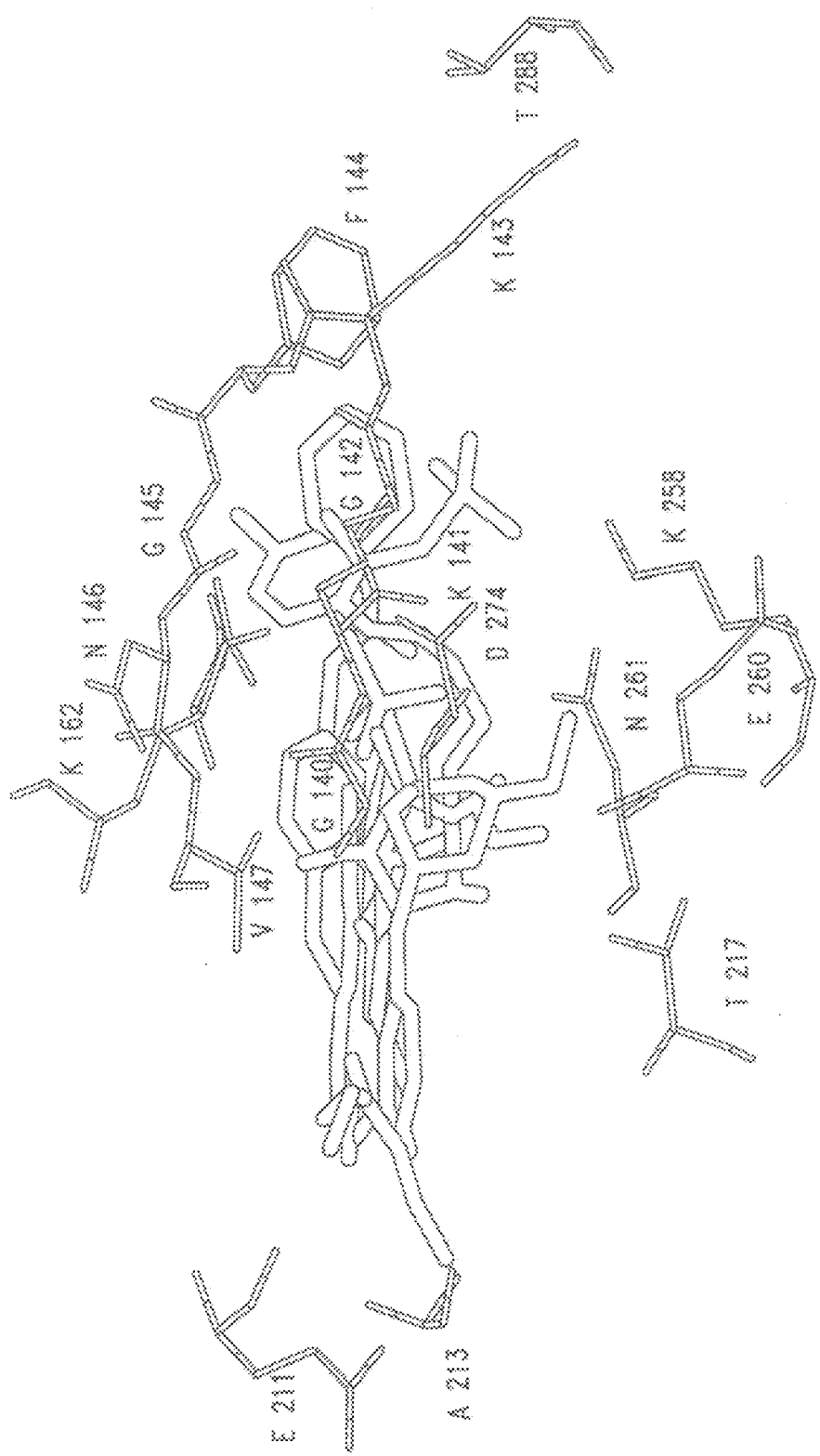
FIG. 5 shows the superposed structures of staurosporine, 6,7-dimethoxyquinazoline, H-89, and AMP-PNP docked into the ATP-binding pocket of aurora-2. The enzyme active site is clipped.

Based on the binding mode of several competitive inhibitors of aurora-2 kinase depicted in FIG. 5, we explored the structural moieties required for aurora-2 kinase inhibition. The structures are shown superimposed. The enzyme active site has been clipped. We evaluated the functional relationship among the known serine/threonine kinase inhibitors by structure-based design and molecular modeling approaches. In aurora-2 kinase, the NH and C=O groups in Glu211 and Ala213 and the Gly-rich pocket residues appear to be most important in inhibitor binding. These structures are hydrogen-bond donors/acceptors and are in all reported S/T kinase structures. Residues Asp274 and Lys141 are also very important in hydrogen bonding. Additionally, our modeling indicated that the flat aromatic rings of the aurora-2 inhibitors occupy the ATP binding pocket around Glu211 and are surrounded by residues Val147 and Ala213. Also, structural alignments of known S/T kinase inhibitors show two shared structural motifs with similarly placed nitrogens and six-membered aromatic rings, suggesting that these compounds have similar binding patterns.

Figure 6:
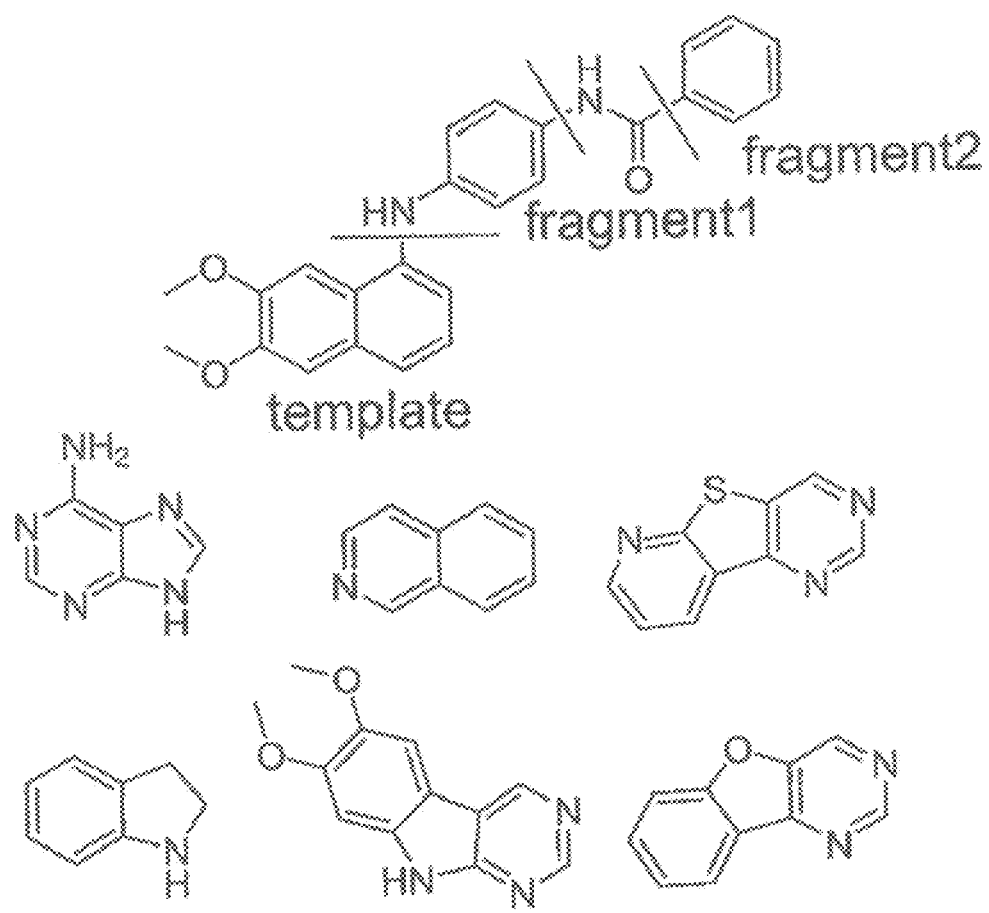
FIG. 6 shows the purine, quinazoline, isoquinazoline and indole ring templates used in LUDI search.
Figure 7A:
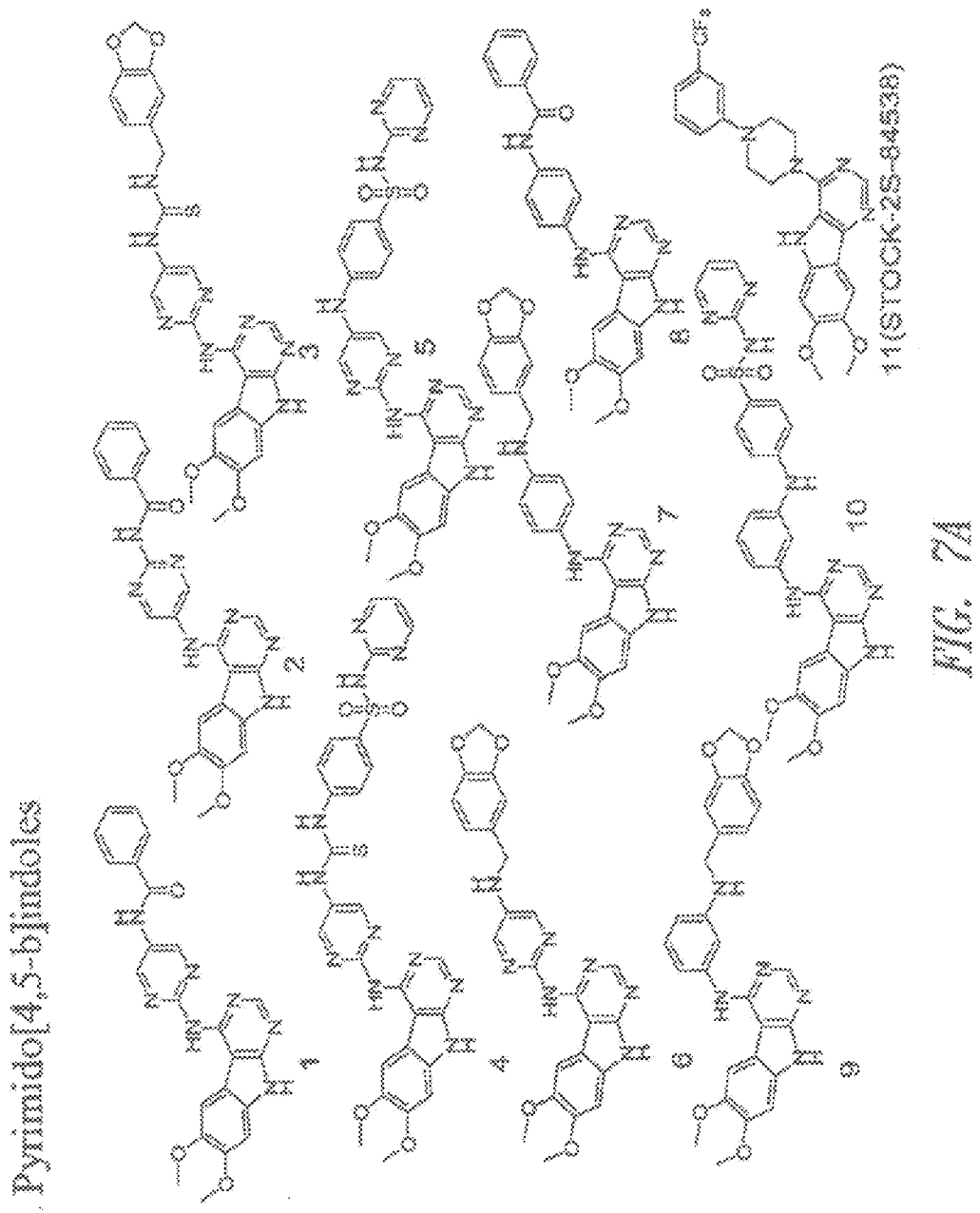
FIG. 7A displays structures of illustrative pyrimido[4,5-b] indoles.
Figure 7B:
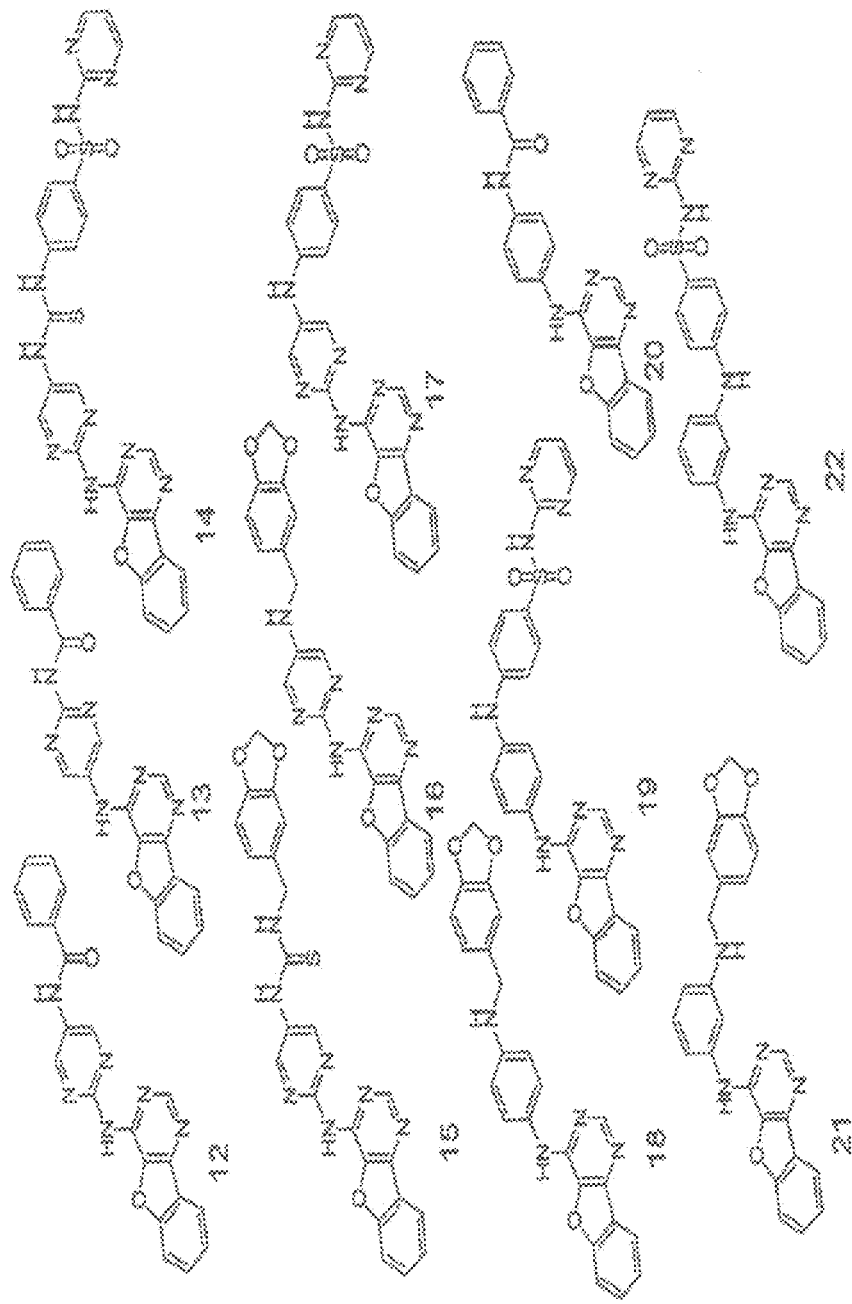
FIG. 7B displays structures of illustrative benzofuranopyrimidines.
Figure 7C:
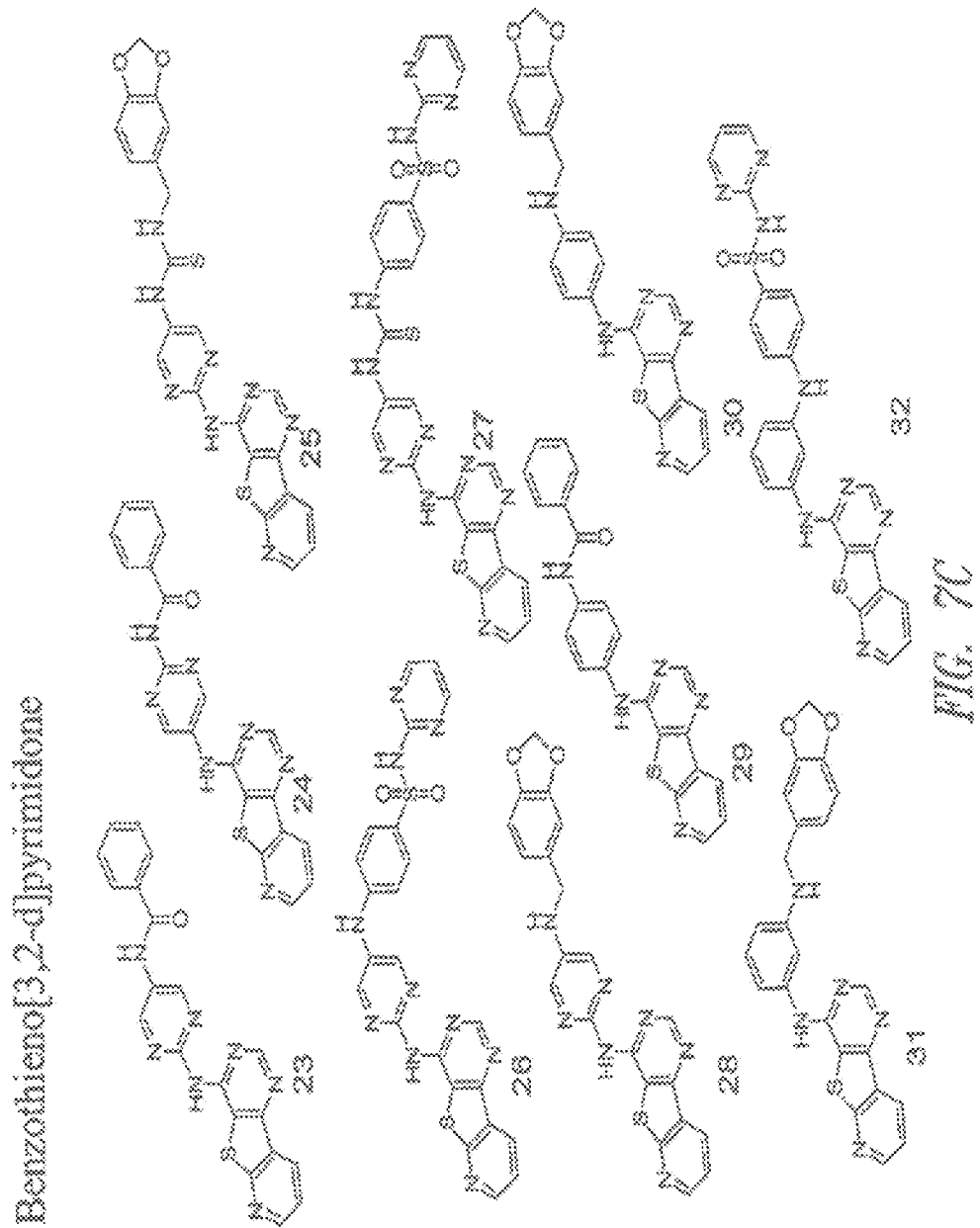
FIG. 7C displays structures of illustrative benzothieno[3,2-d]pyrimidone.
Figure 7D:
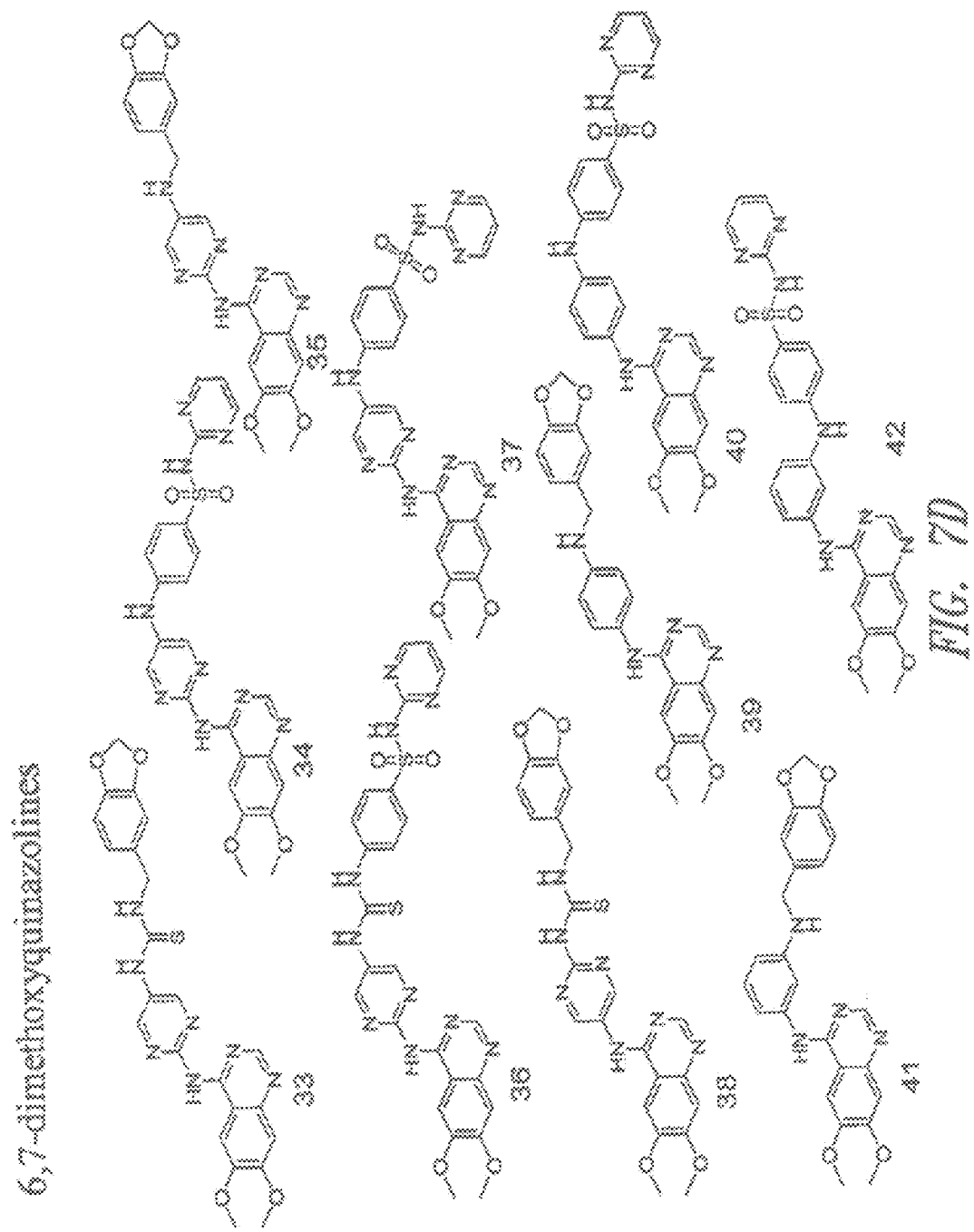
FIG. 7D displays structures of illustrative 6,7-dimethoxyquinazolines.

To identify new chemicals that satisfy these structural requirements, a de novo design approach was employed using the graphical chemical modeling program LUDI (Accelrys). Initially, lead structures (purine base, quinazoline, isoquinazoline and indole rings) were dissected into core templates and two additional fragments (FIG. 6), which formed the basis of a built-in compound library. Then template structures were obtained from the Available Chemical Directory (ACD). The compounds with molecular weight >350 were selected, and chemical skeletons or functional groups that were unacceptable for the development of lead compounds were omitted from the library. An in-house compound library containing the identified templates was built and utilized in LUDI search procedures. Additionally, three tricyclic quinazoline type templates were identified apart from the isoquinolines and quinazolines. From the LUDI fragment library, structurally similar fragments were obtained for fragments 1 and 2 (FIG. 6). Fragment selection was based on the following criteria: (1) molecular weight <350, (2) at least two hydrogen bond donor/acceptor groups, (3) at least three rings, and (4) correct position and orientation with respect to lead compounds within the ATP binding pocket. The template and fragments were linked in LUDI link mode to confirm their binding mode for the newly built structures. Several combinations of structures were designed by keeping the required pharmacophores identified from ACD and LUDI fragment searches. More than 90 compounds were built using this structure-based scaffold approach. Further, these compounds were screened to exclude molecules that were not complementary to the ATP binding pocket by the FlexX docking method (Tripos, St. Louis, Mo.). Forty-two compounds (FIGS. 7A-7D) were found to have the optimal number of H-bonds, position and orientation within the ATP binding pocket and FlexX scoring.

Example 5

Chemical Synthesis of Kinase Inhibitors

General Methods. $^1$HNMR was run on a Unity 300-MHz NMR Spectrophotometer (Varian, Palo Alto, Calif.). The chemical shifts are relative to the trace proton signals of the deuterated solvent. Coupling constants, J, are reported in Hz and refer to apparent peak multiplicity rather than coupling constants. Fast atom bombardment (FAB) measurements have been carried out on a mass spectrometer HX-110 instrument (JEOL, Akishima, Japan) equipped with a conventional Xe gun. A mixture matrix of glycerol:thioglycerol:mNBA (meta-nitrobenzyl alcohol) 50:25:25 containing 0.1% of trifluoroacetic acid (TFA) was used as the matrix for fast atom bombardment (FAB). For accurate mass measurements, polyethylene glycol (PEG) was used as the internal standard. Flash column chromatography was performed on silica gel 60, purchased from Spectrum. Combustion analysis (CHNS) was performed by Desert Analytics Laboratory, Tucson, Ariz. Synthesis of 4-chloro-6,7-dimethoxyquinazoline, 4-chlorobenzothieno[3,2-d]pyrimidone, 4-chloro-benzofuranopyrimidone and 4-chloropyrimido[4,5-b]indole is carried out by reaction with various dihydro-quinazolines using formamide HCl/formaide at 180-190° C. followed by the addition of Vilsmeier's reagent to obtain 4-chloro-quinazolines. General methods for synthesizing these building blocks are illustrated in FIG. 8.

Figure 8:
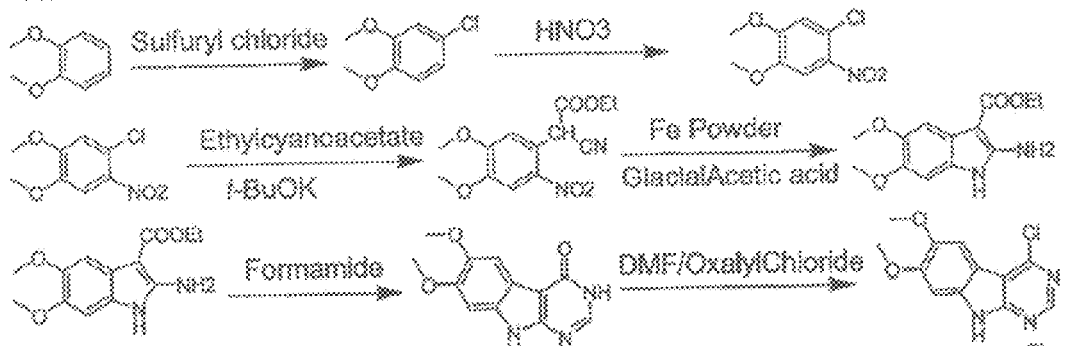
FIG. 8 shows schematic synthetic methods for making illustrative compounds of the invention.
Figure 8:
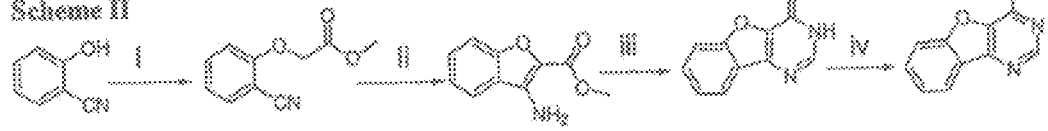
Figure 8:
Figure 8:
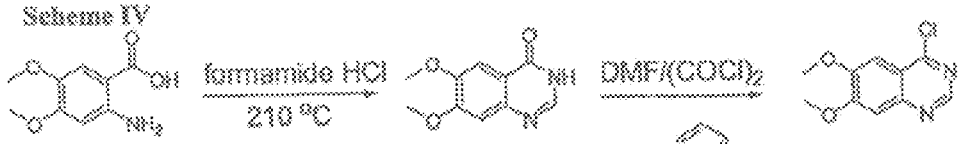
Figure 8:
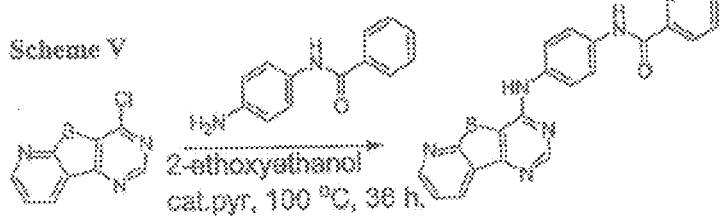
Figure 8:
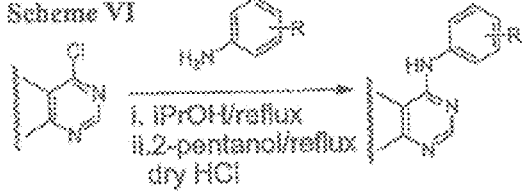

The 4-chloro-quinazoline building blocks are reacted with 2-amino-5-nitropyrimidines, and various unsubstituted o-, m- or p-6-membered aromatic rings, or containing a direct bond, NHCO, NHCSNH, SO$_2$NH, NHSO$_2$, NHCH$_2$Ph, aminopyrazoles, amino-substituted oxadiazoles, thiadiazoles or triazoles, to give the 4-substituted tricyclic and quinazoline series of compounds (e.g., FIG. 8).

The synthesis of the thiourea-containing compounds was carried out using the following general procedure. Piprenolamine, sulfadiazine and/or substituted aromatic amines were slowly added to a solution of thiophosgene in dichloromethane, followed by the addition of triethylamine on an ice bath. After the reaction mixture was stirred for 4 hours, 4-chloro-quinazolines or tricyclic building blocks were added and the resulting mixture was stirred overnight at room temperature. Methanol was added to quench the excess thiophosgene, and the residue was purified by silica gel column chromatography after removal of solvent.

Example 6

4-Chloro-Tricyclic and Quinazoline Building Blocks

Figure 9:
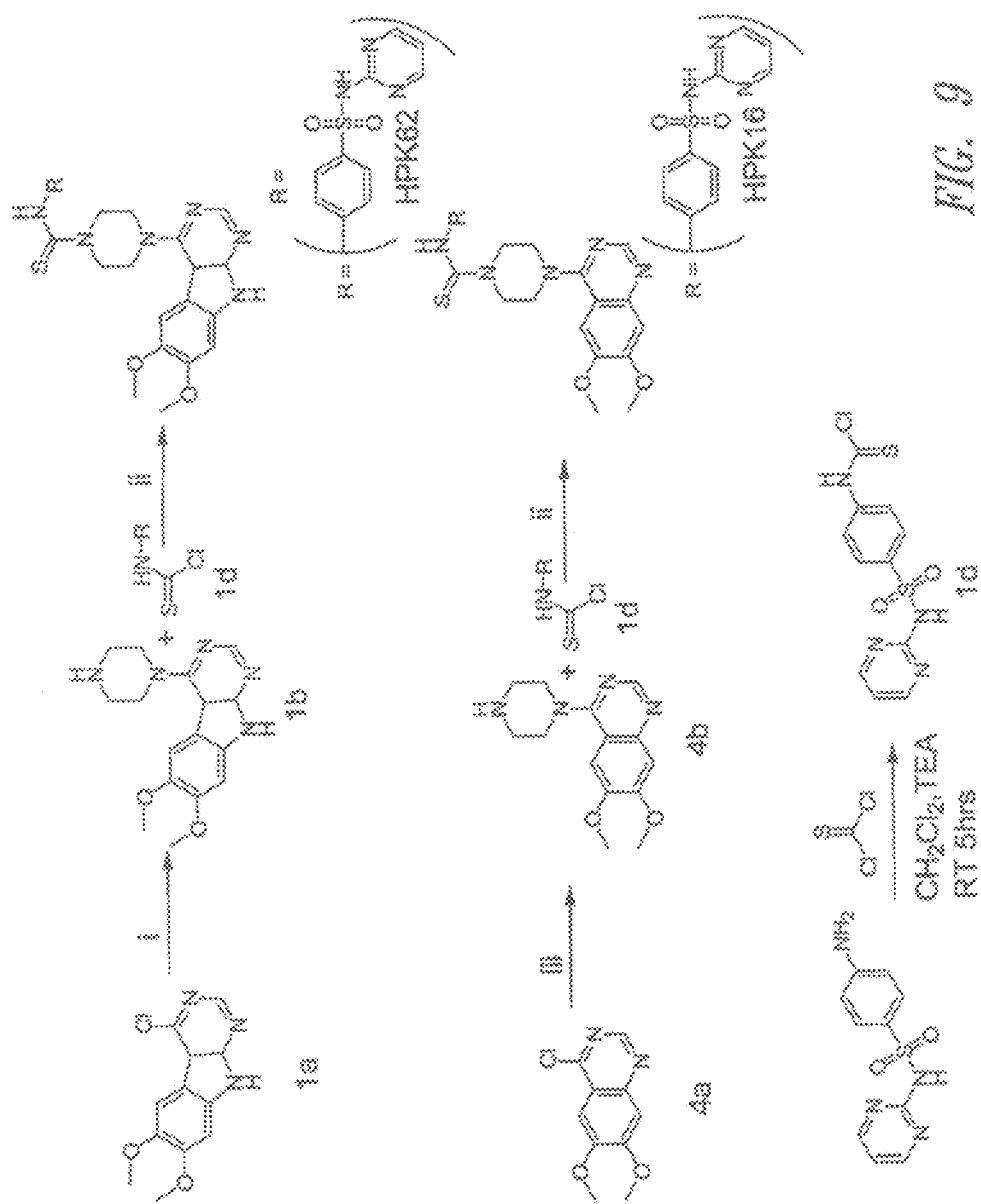
FIG. 9 shows the schematic synthesis of compounds HPK 16 and HPK 62.

The 4-chloro-tricyclic and quinazoline building blocks were synthesized using literature methods (Pandey, A., et al., J. Med. Chem. 2002, 45:3772-93; Matsuno, K., et al., J. Med. Chem. 2002, 45:3057-66; Matsuno, K., et al., J. Med. Chem. 2002, 45:4513-23; and Venugopalan, B., et al., J. Heterocycl. Chem. 1988, 25:1633-39). As shown in FIG. 9, these were converted to the corresponding 4-piperazine derivatives by refluxing with piperazine in pyridine or dioxane.

Example 7

N-Pyrimidin-2-yl-4-thioformylamino-benzene-sulfonamide chloride (1d)

To a stirred solution of sulfadiazine (192 mg, 0.77 mmol) in dichloromethane (20 mL) were slowly added thiophosgene (0.06 mL, 0.83 mmol) and triethylamine (0.05 mL, 0.32 mmol) under cooling with an ice bath. After the reaction mixture was stirred for 5 hours at room temperature, it was washed with water and brine, dried over anhydrous sodium sulfate, filtered, evaporated and dried under vacuum; and the product was used immediately for the next reaction.

Example 8

4-(6,7-Dimethoxy-quinazolin-4-yl)-piperazine-1-carbothioic acid [4-(pyrimidin-2-ylsulfamoyl)-phenyl]-amide (HPK16)

To a solution of 4-(l-piperazinyl)-6,7-dimethoxy quinazoline (200 mg, 0.73 mmol) and pyridine (0.5 mL, 6.4 mmol) in dichloromethane (20 mL) was added a solution of product 1d in dichloromethane (20 mL) and stirred overnight. Methanol was added for quenching excess thiophosgene, and the residue after removal of solvent was purified by silica gel column chromatography eluting with 5% methanol/dichloromethane and further recrystallized from dichloromethane/hexane to give 80 mg (20%).

$^1$H NMR (CDCl$_3$, 300 MHZ) δ 3.85 (s, 4H), 3.98 (s, 3H), 4.02 (s, 3H), 4.11 (s, 4H), 6.98 (m, 1H), 7.08 (s, 1H), 7.32 (d, 2H), 7.88 (s, 1H), 8.00 (d, J=6.7 Hz, 2H), 8.62 (d, 2H), 8.66 (s, 1H).

FAB HRMS [M+H]$^+$ calcd for C$_{26}$H$_{26}$N$_8$O$_4$S$_2$: 566.1518. found 567.1597.

Combustion Analysis: C$_{26}$H$_{26}$N$_8$O$_4$S$_2$ Requires C 52.99%, H 4.62%, N 19.77%, O 11.29%, S 11.32%. Found C 53.27%, H 4.94%, N 19.99%, O 11.57%, S 11.64%

Example 9

4-(6,7-Dimethoxy-9H-1,3,9-triaza-fluoren-4-yl)-piperazine-1-carbothioic acid [4-(pyrimidin-2-ylsulfamoyl)-phenyl]-amide (HPK62/MP-235)

To a solution of 6,7-dimethoxy-4-piperazino-9H-pyrimido[4,5-b]indole (200 mg, 0.64 mmol) and pyridine (0.5 mL, 6.4 mmol) in dichloromethane (20 mL) was added a solution of product 1d in dichloromethane (20 mL) and the mixture was stirred overnight. Methanol was added to quench excess thiophosgene, and the residue after removal of solvent was purified by silica gel column chromatography, eluting with 5% methanol/dichloromethane and was further recrystallized from dichloromethane/hexane to give 50 mg (16%).

$^1$HNMR (DMSO-d$_6$, 300 MHZ) δ 3.75 (s, 4H), 3.87 (s, 3H), 3.88 (s, 3H), 4.19 (s, 4H), 7.04-7.06 (m, 1H), 7.07 (s, 1H), 7.24 (s, 1H), 7.53 (d, J=8.4 Hz, 2H), 7.90 (d, J=8.4 Hz, 2H), 8.44 (s, 1H), 8.51 (d, J=4.8 HZ, 2H), 9.72 (s, 1H, —NH), 12.01 (s, 1H, —NH).

FAB HRMS [M+H]$^+$ calcd for C$_{27}$H$_{27}$N$_9$O$_4$S$_2$: 605.1627. found 606.1699.

Combustion Analysis: Requires C$_{27}$H$_{27}$N$_9$O$_4$S$_2$ Requires C 53.54%, H 4.49%, N 20.81%, O 10.57%, S 10.59%; Found C 53.84%, H 4.91%, N 21.21%, O 11.87%, S 8.17%.

Example 10

Aurora-2 Kinase Inhibition Assay

In this assay kinase activity is determined by quantifying the amount of ATP remaining in solution following the kinase reaction by measuring the light units (LU) produced by luciferase using a luminometer. Percent inhibition was determined for individual compounds by comparing luminometer readings of drug-treated reactions to controls containing no drug (DMSO control) and no Aurora-2 enzyme (ATP control) in the following equation:

$$\text{Percent Inhibition} = \frac{LU_{drug} - LU_{DMSO}}{LU_{ATP} - LU_{DMSO}} \times 100$$

Figure 10:
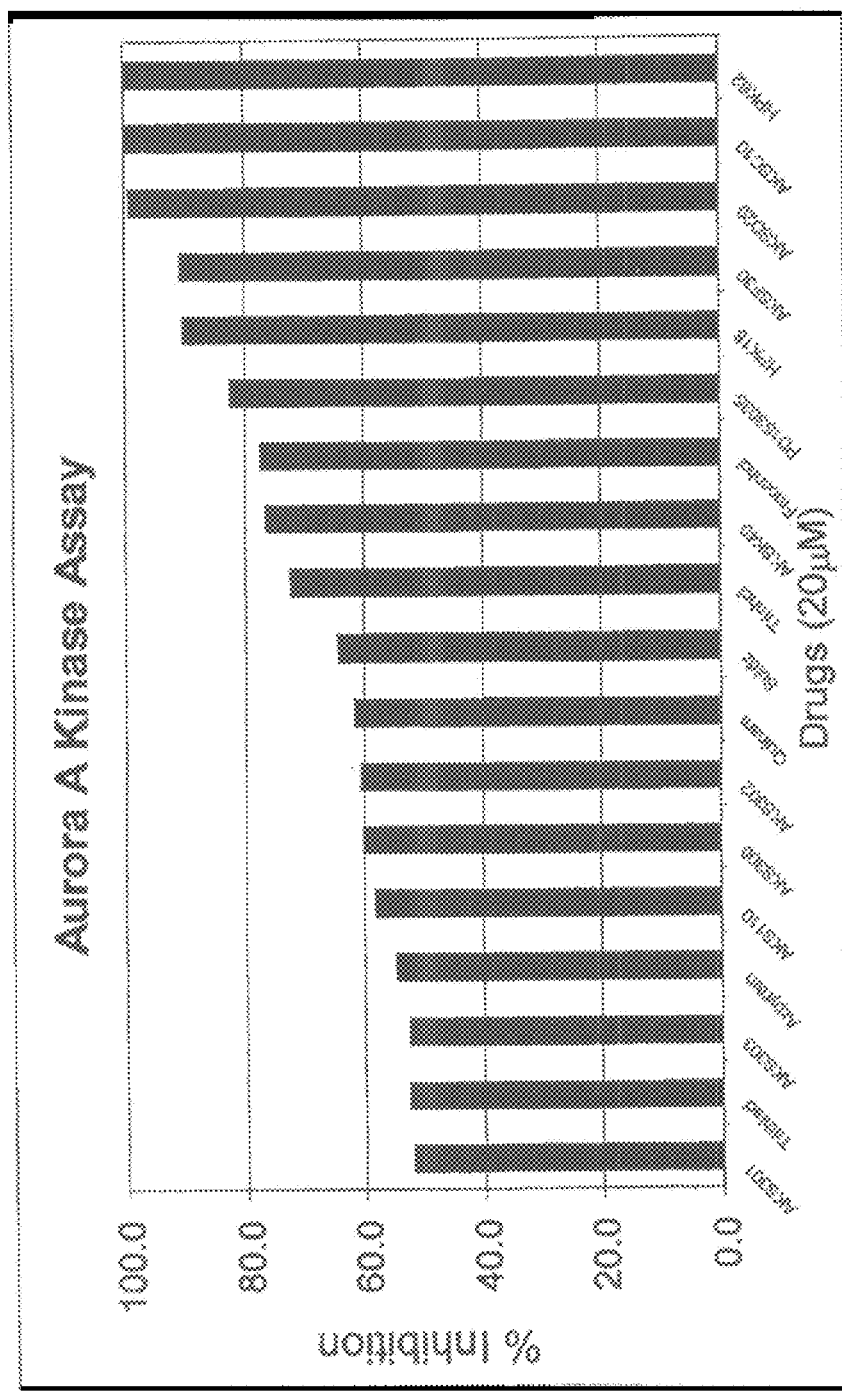
FIG. 10 is a bar graph showing inhibition of aurora-2 kinase by illustrative compounds (20 μM) in an in vitro assay.

In a 50 μl reaction, recombinant aurora-2 kinase produced in sf9 cells (Imgenex, San Diego, Calif.) was incubated at 30° C. for two hours with 62.5 μM Kemptide (Calbiochem, San Diego, Calif.), 3 μM ATP (Invitrogen, Carlsbad, Calif.) and kinase reaction buffer (40 mM Tris-HCl, 10 mM MgCl$_2$ and 0.1 μg/μl bovine serum albumin (BSA)). This reaction was carried out in the presence of drug substances, which had been previously diluted to desired concentrations in DMSO. After incubation, 50 μl of Kinase-Glo® (Promega, Inc., Madison, Wis.) solution was added to each reaction mixture and allowed to equilibrate for 10 minutes at room temperature. Kinase-Glo solution contains luciferase enzyme and luciferin, which react with ATP to produce light. Kinase activity is determined by quantifying the amount of ATP remaining in solution following the kinase reaction by measuring the light units (LU) produced by luciferase using a luminometer (PerkinElmer, Boston, Mass.). FIG. 10 shows the degree of inhibition of aurora-2 kinase activity by illustrative compounds of the invention, including HPK56 (Structure III-1-3), HPK61 (Structure II-2-7), HPK60 (Table 4; Structure 34-4), HPK59 (Structure III-1-5), AKS301 (Table 6; Structure 38-16), AKS110 (Table 6, Structure 38-14), AKS300 (Table 6, Structure 38-15), AKS302 (Table 6, Structure 38-17), HPK16 (Structure IV-1-3) and HPK62 (Structure II-2-6), in addition to several precursors and known kinase inhibitors (e.g., HMN-176, Quincl, trioxd, trithiad, azpyram, Quinam, Suldz, Gmocnhcl and trinhcl). The synthesized compound HPK62 had the highest inhibition, and compound HPK16 had the second highest inhibition of the tested compounds.

Figure 11:
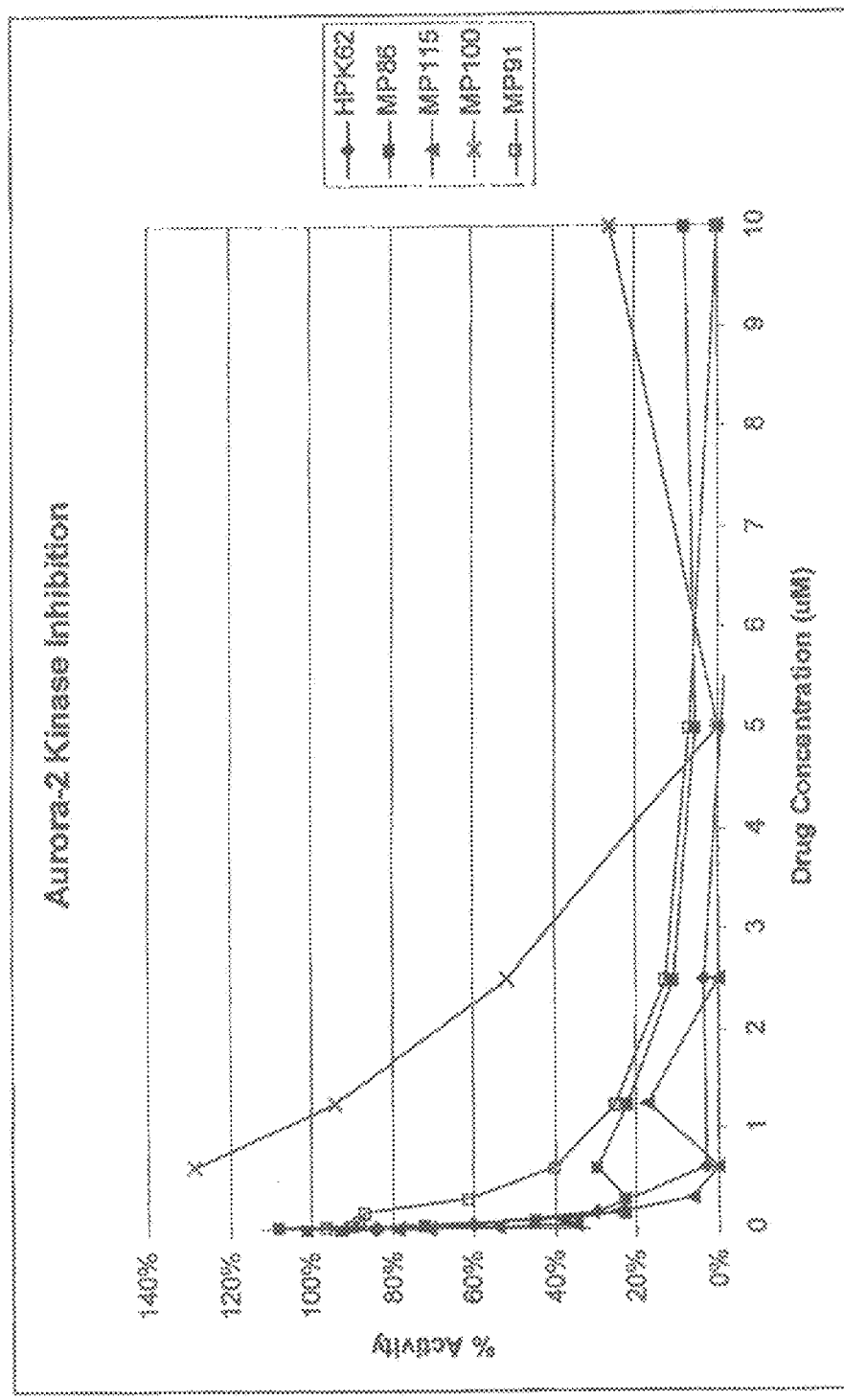
FIG. 11 graphs aurora-2 kinase inhibition by five compounds at different concentrations to determine the concentration providing 50% inhibition ($IC_{50}$).

The drug concentration at which 50% of aurora-2 kinase activity was inhibited ($IC_{50}$) was determined for illustrative compounds and the results shown in FIG. 11. HPK16 (Structure IV-1-3) and HPK62 (Structure II-2-6) were particularly effective inhibitors. A range of chemical doses was tested, and graphed, as shown in FIG. 11. The $IC_{50}$ values for the compounds are shown below in Table 1.

TABLE 1

| Compound Designation | Structure | $IC_{50}$ |
|---|---|---|
| HPK16 | IV-1-3 | 4.7 µM |
| HPK62 | II-2-6 | 0.9 µM |
| AKS110 | 38-14 | 36 µM |

Example 11 c-Kit Sequence and Structure Analysis

Figure 13:
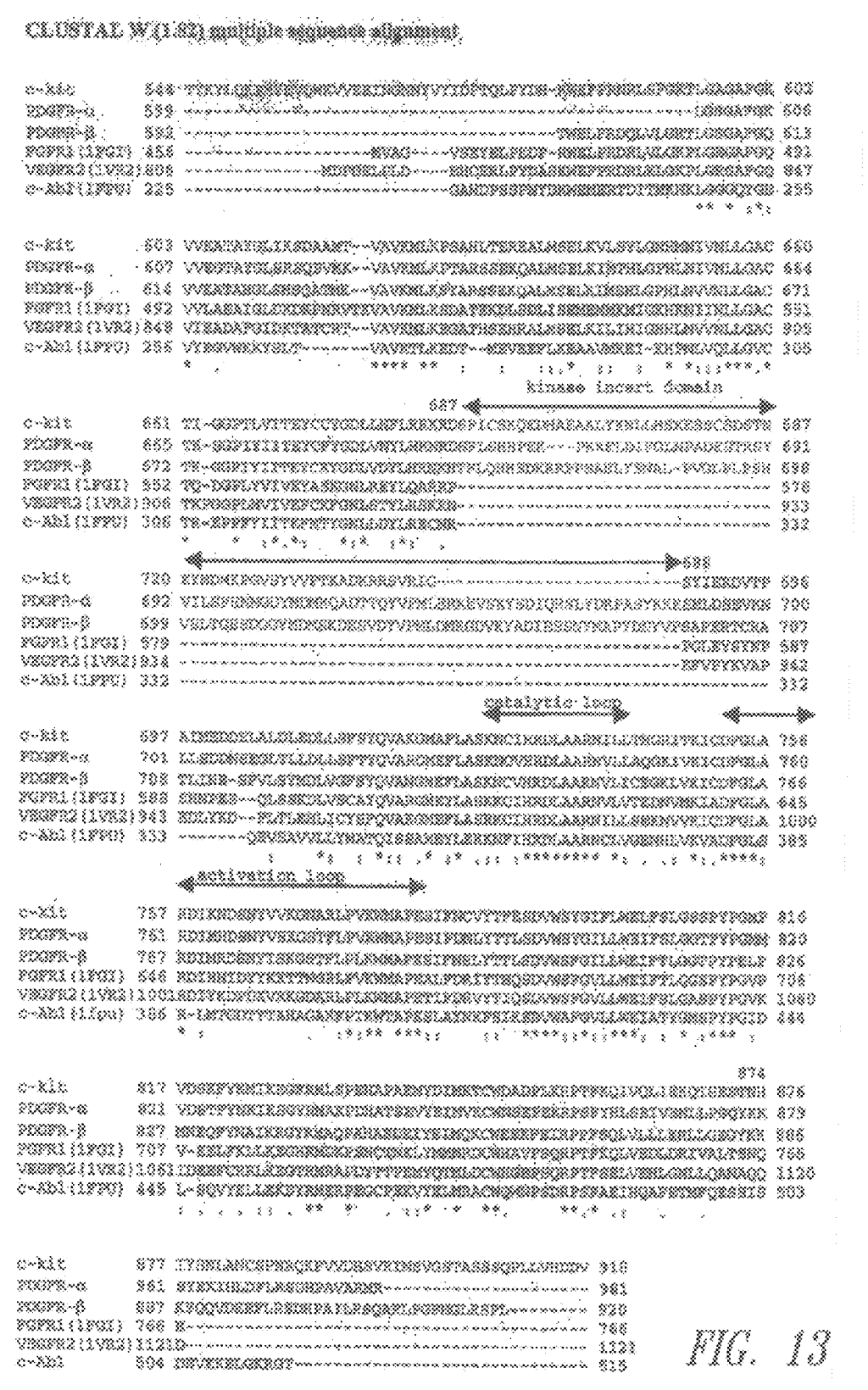

The known sequence of the c-kit tyrosine kinase active domain was used in a PSI-BLAST search (NCBI) of non-redundant database of sequences. Top-ranked sequences for which three-dimensional structures of tyrosine kinase (TK) domains also were available were the vascular endothelial growth factor receptor (VEGFR2, or 1VR2) and fibroblast growth factor receptor 1 (FGFr1, or 1FGI). These sequences, along with those of PDGFR-α, PDGFR-β and c-Abl, were manually aligned by their kinase domain sequences and their respective secondary structures and viewed in Clustal X (FIG. 13).

The c-kit TK domain sequence was inputted into the tertiary structure prediction programs THREADER and 3D-PSSM, which compare primary sequences with all of the known three-dimensional structures in the Brookhaven Protein Data Bank. The output was composed of the optimally aligned, lowest-energy, three-dimensional structures that were similar to c-kit. The top structural matches were VEGFR2 and FGFr1, confirming that these proteins are structurally conserved.

Example 12 c-Kit Homology Modeling

Figure 14:
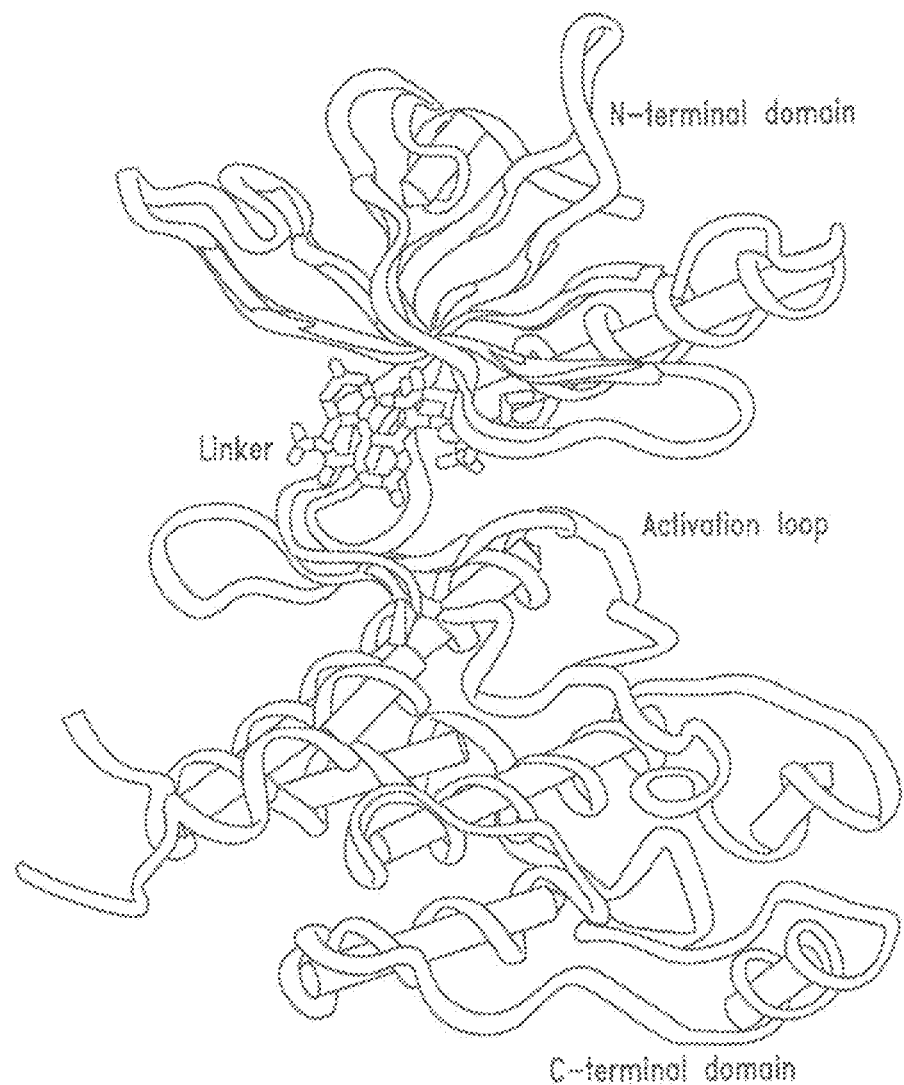
FIG. 14 displays the homology model of c-kit bound compound 1 docked into the ATP binding site.

VEGFR2 and FGFr1 structures provided the three-dimensional templates for the homology modeling of c-kit. The crystal structure coordinates for the above TK domains were obtained from the Protein Data Bank. These domains were pair-wise superimposed onto each other using the SAP program. The structural alignments from SAP were fine-tuned manually to better match residues within the regular secondary structural elements. The modeling software used was Insight II (version 2000, Accelrys Inc.), running on a Silicon Graphics Indigo2 workstation under the Unix operating system. After the model building processes were complete, a series of minimizations were performed to relax the structure. The final c-kit model (FIG. 14) was examined using 3D-profile. Additionally, PROCHECK was used to verify the correct geometry of the dihedral angles and the handedness of the model-built structure.

Example 13 c-Kit Molecular Dynamics (MD) and Docking Analysis

The 3D c-kit model served as the starting point for docking studies of CT662923 and STI571 (Gleevec®). MD simulations were performed in the canonical ensemble (NVT) at 300° K using the CFF force field implemented in Discover_3 (version 2.9.5; Accelrys). Dynamics were equilibrated for 10 picoseconds with time steps of 1 femtosecond and continued for 10-picosecond simulations. The nonbonded cutoff distance of 8 Å and a distance-dependent dielectric constant ($\in=5rij$) for water were used to simulate the aqueous media. All of the bonds to hydrogen were constrained. Dynamic trajectories were recorded every 0.5 picoseconds for analysis. The resulting low energy structure was extracted and energy-minimized to 0.001 kcal/mol/Å. To examine the conformational changes that occur during MD, the root mean square (rms) deviations were calculated from trajectories at 0.5-picosecond intervals and compared to the Cα backbones of VDGFR and FDFr TK. The resulting c-kit structure served as the starting model for docking studies.

For docking studies, the starting model structures of ligands were from the known c-kit tyrosine kinase inhibitors of CT52923 (FIG. 15A) and STI571 (Gleevec®) (FIG. 15B) and were empirically built and energy minimized. The heavy atoms from FGFr kinase domain were used as sphere centers for the docking procedures. Docking simulations were performed at 500° K with 100 femtosecond/stage (total of 50 stages), quenching the system to a final temperature of 300° K. The whole complex structure was energy minimized using 1000 steps. This provided 10 structures from the simulated annealing (SA) docking, and their generated conformers were clustered according to rms deviation. The lowest energy global structure complexes were used to calculate intermolecular binding energies.

Example 14 c-Kit FlexX Docking

FlexX docking was performed in the Sybyl 6.8 program (Tripos, St. Louis, Mo.). The structures of ligands used for docking were the crystal structure of STI571 with the Abl tyrosine kinase and the CT52923 which was empirically built and energy-minimized in Insight II. Systematic conformational searches were performed on each of the minimized ligands using 10-picosecond MD simulations at 300° K. For docking with CT 52923 and STI571, the position of the SU5402, an indolinone analog was retained from its crystal structure of 1 FGI in which the indolinone served as a template for field-fit alignments with the quinazoline and pyrimidoindole-containing compounds. The indolinone analog was then removed from the field-fit alignment, and each of the other ligands was docked into the active site pocket with a similar position and orientation to that of CT52923 (FIG. 15A) and STI571 (FIG. 15B) using FlexX multiple molecule docking methodology.

Figure 15A:
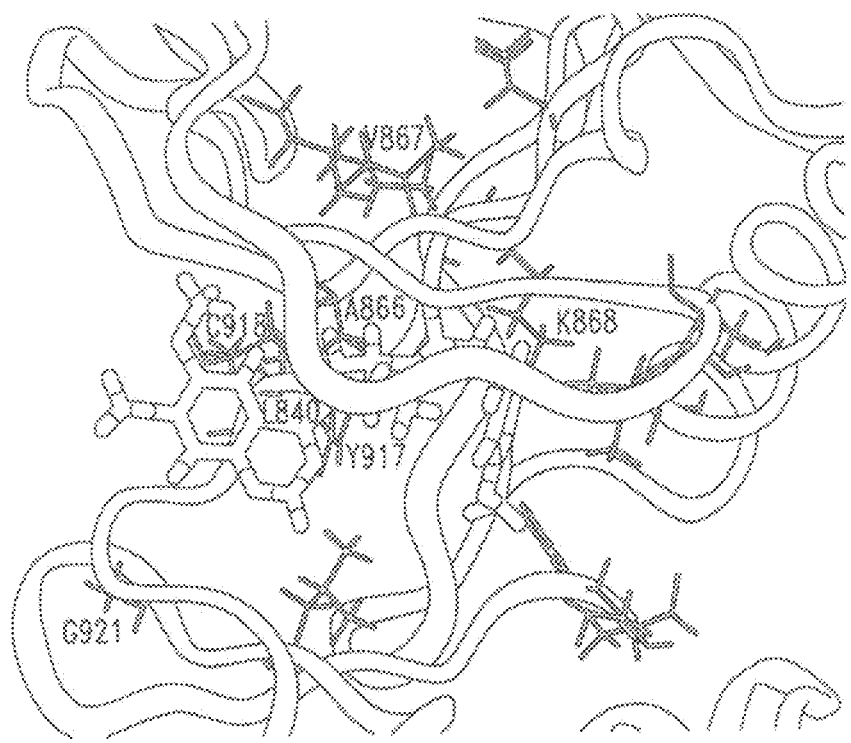
FIGS. 15A and 15B are molecular models of the c-kit binding site with two different prior art compounds, CT52923 and STI571, respectively.
Figure 15B:
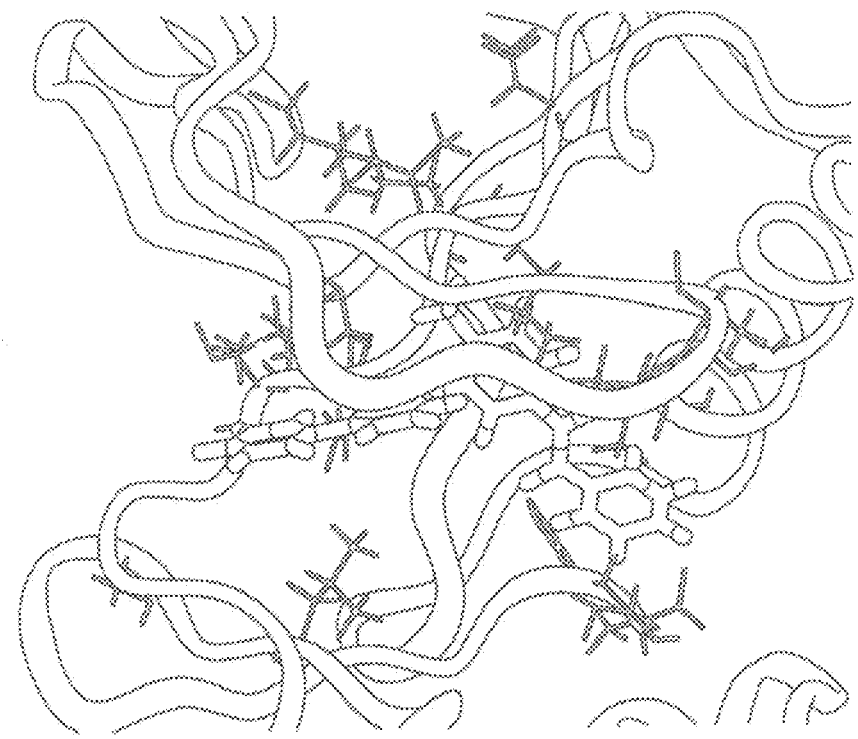

Based on our analysis of the binding mode of CT52923 and STI571 depicted in FIGS. 15A and 15B, respectively, the presence of two shared structural motifs of similarly placed hydrogen bond acceptors and six-membered aromatic rings suggested that these compounds may be exhibiting some common binding regions. Based on these two sets of alignments, a phenylamine-pyrimidine moiety was introduced at position 4 of CT52923 and the position of this substitution was further rationalized by FlexX docking and molecular dynamics simulation.

Example 15

Design Strategy

Figure 16:
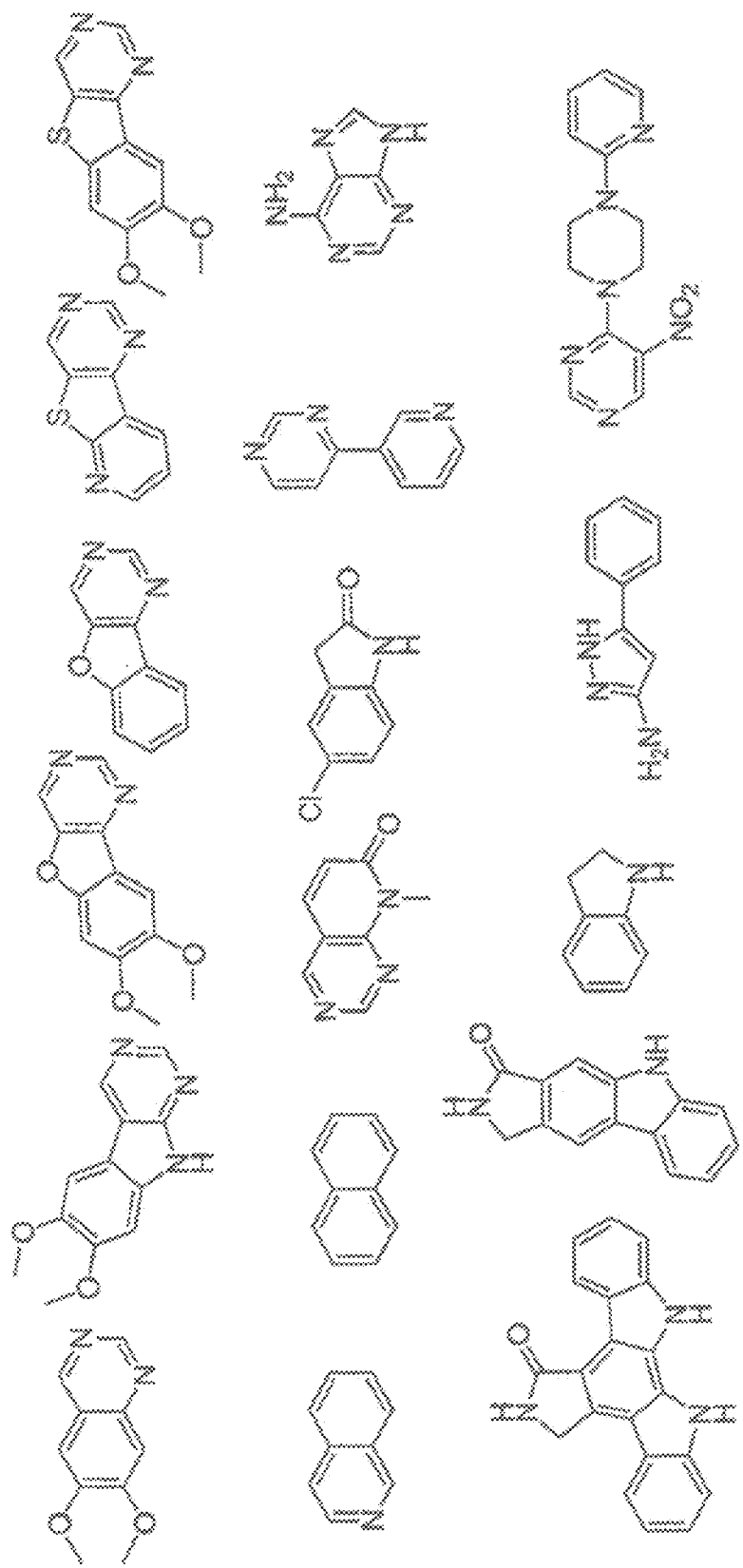
FIG. 16 shows the purine, quinazoline, isoquinazoline, pyrimido[4,5-b]indoles, benzothieno[3,2-d], benzofuranopyrimidines and indole ring structures used in the LUDI search.

To identify new chemicals that satisfy the above-identified structural requirements, a de novo design approach was employed using the graphical chemical modeling program LUDI (Accelrys). Initially, the lead structures (purine base, phenylamino pyrimidines, pyrimido[4,5-b]indoles, benzofurano and benzothieno[3,2-d]pyrimidenes, pyrido[3,2-d]pyrimidenes, quinazolines, and indole rings) were dissected into core templates and two additional fragments (FIG. 16), which formed the basis of our built-in compound library. This built-in library, containing the identified templates, together with the LUDI/ACD databases, was used in the search procedures within the Insight II program (Accelrys). In addition to the known quinazoline and phenylamino-pyrimidine moieties, which are the tricyclic pyrimido[4,5-b]indoles, benzofuranopyrimidines, and benzothieno[3,2-d]pyrimidines (Scheme 1), three novel hits were identified from the LUDI search. Further, fragment searches were performed for the replacement of the sugar and α-, β-, and γ-phosphate binding regions (e.g., Mohammedi, M., et al., Science, 1997, 276: 955-960). The piperazine, thiourea, and piperonylamine fragments of CT52923 were bonded in the LUDI link mode at the 4-position of the new tricyclic moieties. The position and orientation of this substitution were further rationalized by LUDI FlexX. docking (Tripos, St. Louis, Mo.) within the Sybyl software, and molecular dynamics simulations. Finally, 4-amino-N-(2-pyrimidinyl)benzene sulfonamide (sulphadiazine) fragments were identified from the LUDI/ACD databases. These fragments were also linked at the 4-position of the tricyclic structural moieties. The fragment selection was based on hydrogen bond donor/acceptor groups and correct position and orientation with respect to the lead compounds (FIG. 12) within the ATP binding pocket.

Figure 17:
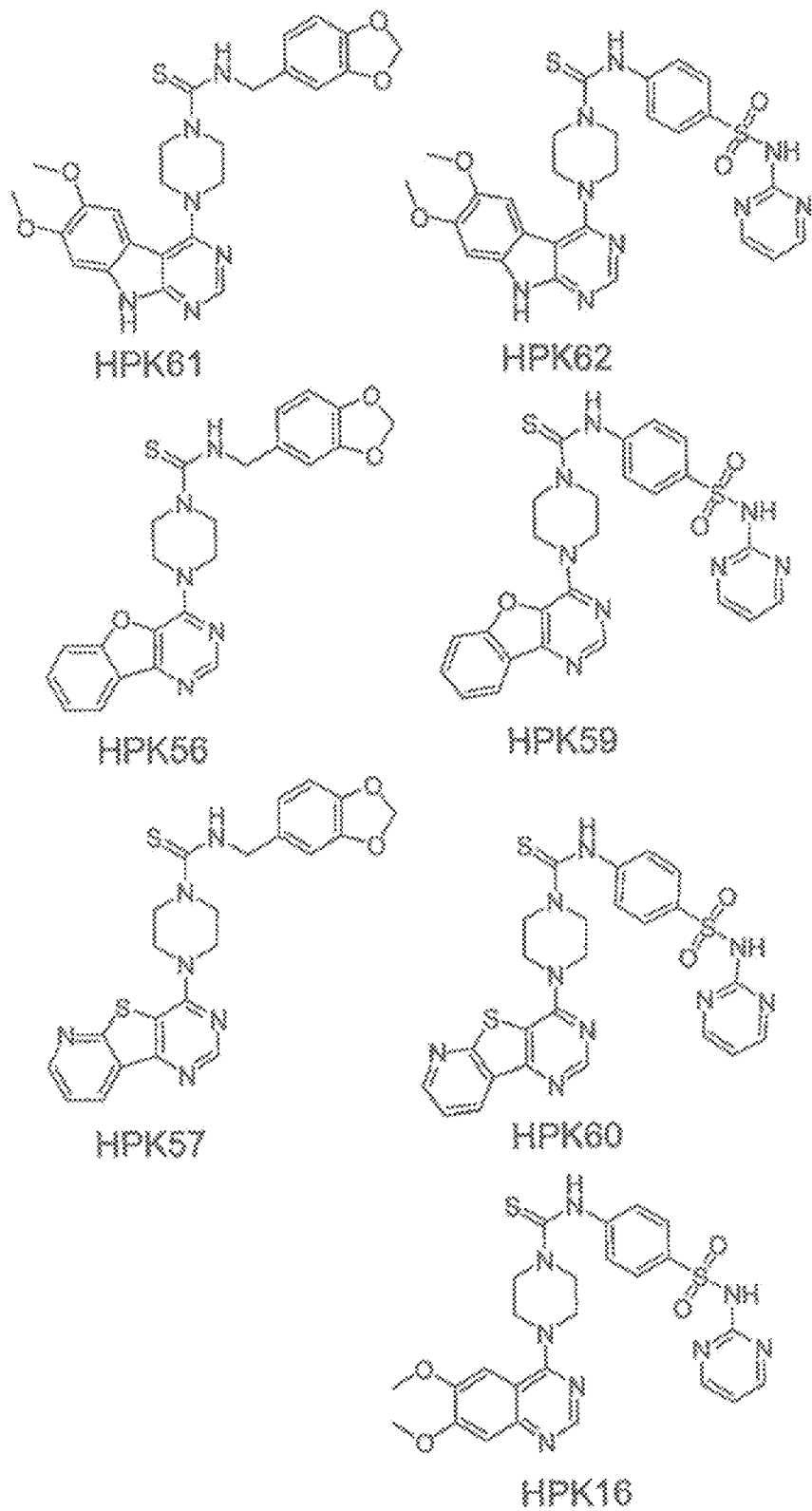
FIG. 17 shows the structures of novel 4-piprazinylpyrimido[4,5-b]indoles, benzothieno[3,2-d], benzofuranopyrimidines and quinazoline inhibitors designed as c-kit tyrosine kinase inhibitors.
Figure 18A:
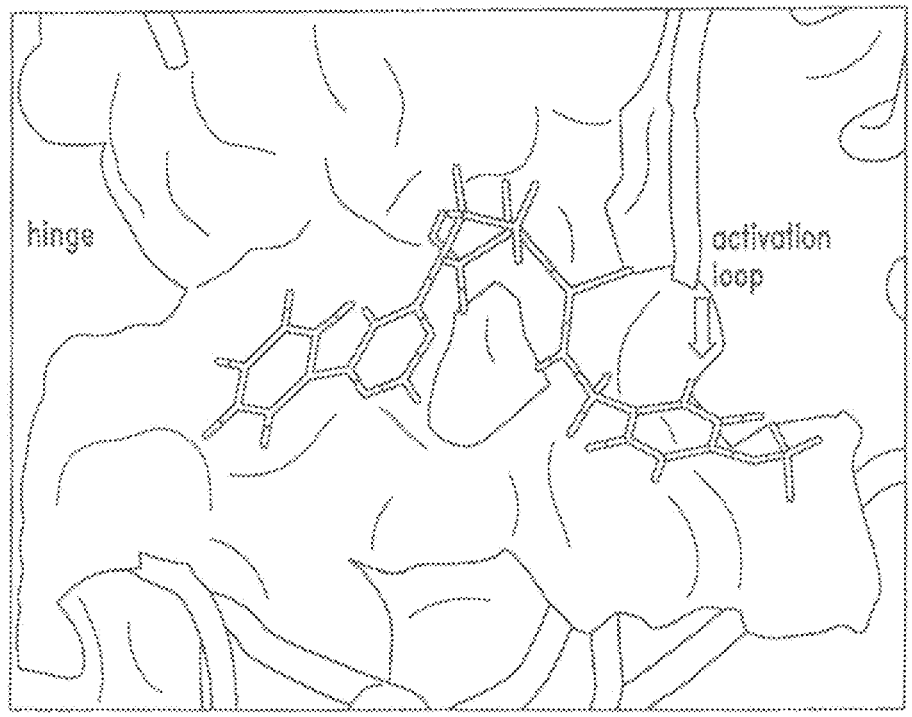
FIGS. 18A and 18B show molecular models of the c-kit kinase active site pocket containing compounds 3 and 1, respectively.
Figure 18B:
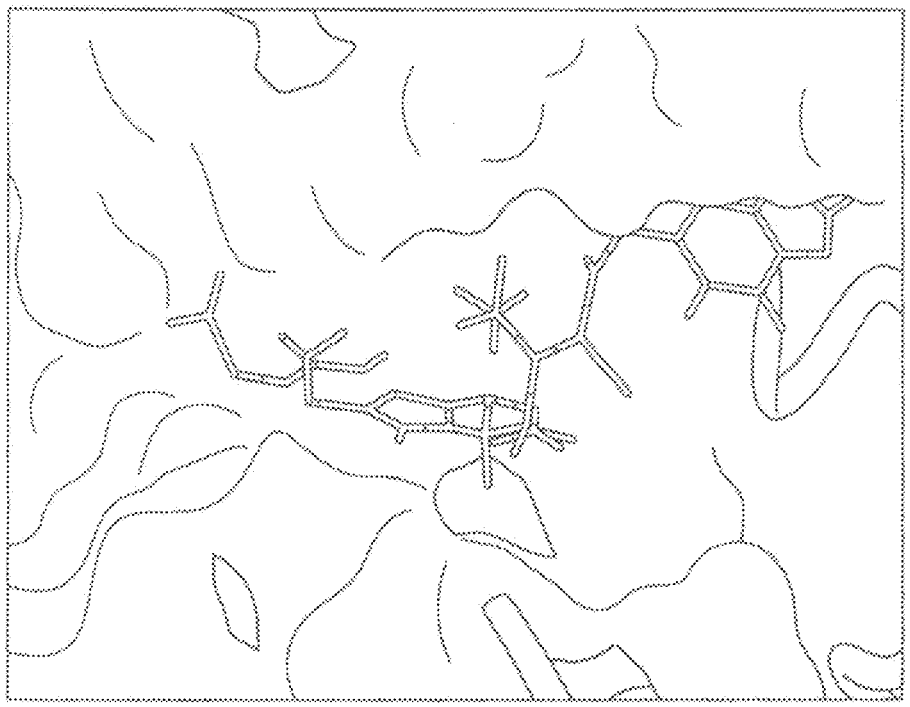
Figure 19:
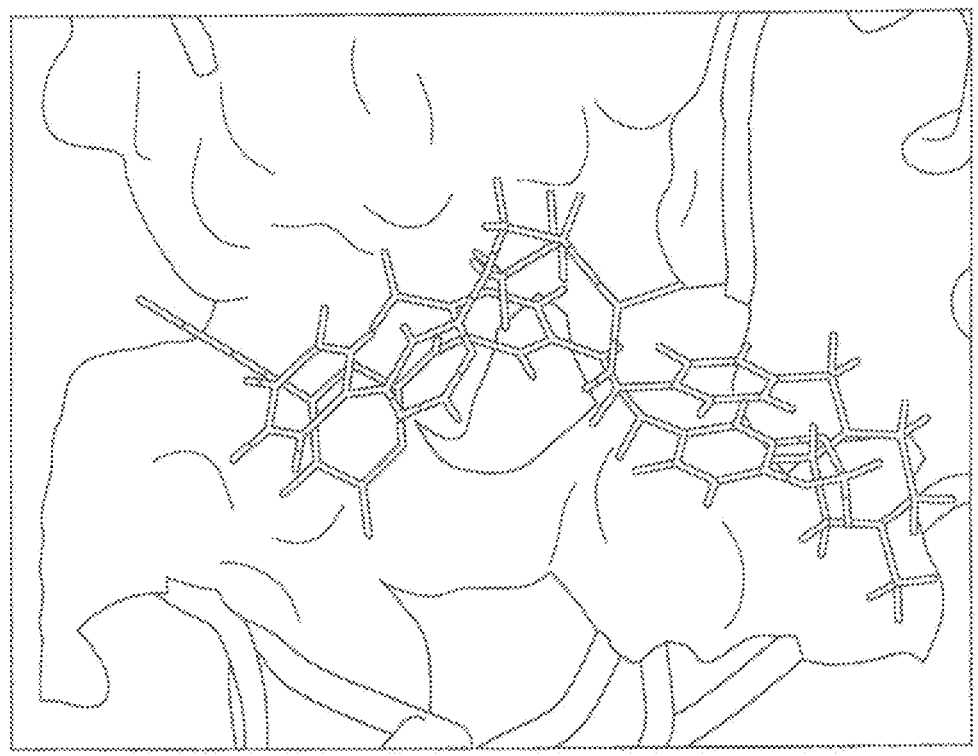
FIG. 19 shows a molecular model developed with FlexX software. It shows docking and overlay of compound 3 and STI571 within the c-kit kinase active site pocket.

Several combinations of structures were designed by keeping the required core structures identified from ACD and LUDI fragment searches. More than 60 compounds were built using this structure-based scaffold approach. Further, these compounds were screened to exclude molecules that were not complementary to the ATP binding pocket (Leu595, Phe600, Val603, Ala621, Val654, Thr670, Glu671, Tyr672, Cys673, Gly676, Asp677, Asn739, Leu741, and Asp752) by the FlexX docking method. Compounds I-7 of FIG. 17 (HPK61 (II-2-7), HPK62 (II-2-6), HPK56 (III-1-3), HPK59 (III-1-5), HPK57 (III-1-4), HPK60 (34-4) and HPK16 (IV-1-3), respectively) were found to have the optimal number of hydrogen bonds, positions and orientations within the ATP binding pocket and the optimal FlexX scoring (kJ/mol). These seven compounds were synthesized and evaluated for c-kit and PDGFR tyrosine kinase inhibitory activity.

Example 16

Chemical Synthesis

General Methods. $^1$HNMR was run on a Unity 300-MHz NMR Spectrophotometer (Varian, Palo Alto, Calif.). The chemical shifts are relative to the trace proton signals of the deuterated solvent. Coupling constants, J, are reported in Hz and refer to apparent peak multiplicity rather than coupling constants. Fast atom bombardment (FAB) measurements have been carried out on a mass spectrometer HX-110 instrument (JEOL, Akishima, Japan) equipped with a conventional Xe gun. A mixture matrix of glycerol:thioglycerol:mNBA (meta-nitrobenzyl alcohol) 50:25:25 containing 0.1% of trifluoroacetic acid (TFA) was used as the fast atom bombardment (FAB) matrix. For accurate mass measurements, polyethylene glycol (PEG) was used as the internal standard. Flash column chromatography was performed on silica gel 60, purchased from Spectrum. Combustion analysis (CHNS) was performed by Desert Analytics Laboratory, Tucson, Ariz.

Figure 20:
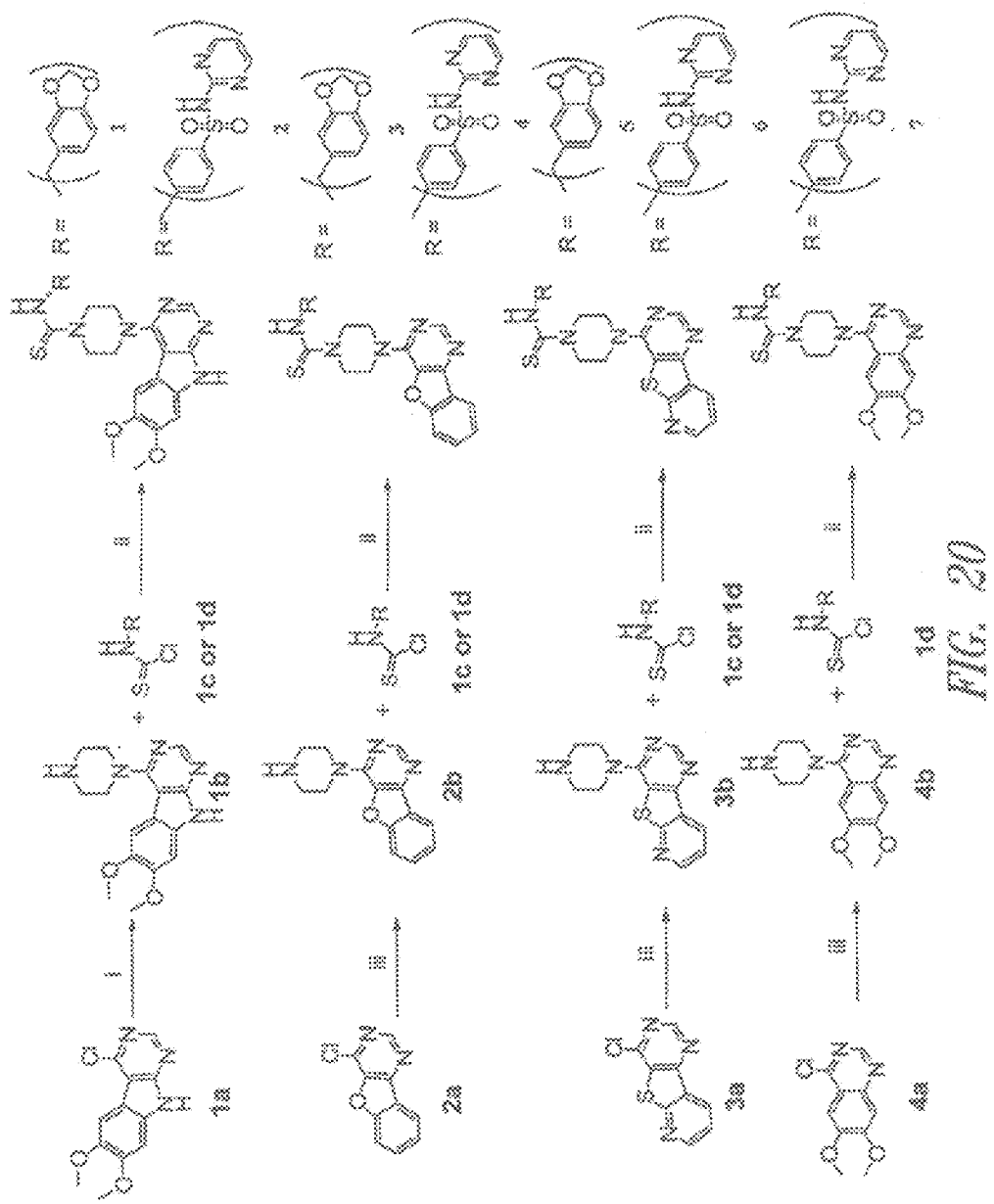
FIG. 20 depicts the synthesis of seven illustrative compounds.
Figure 21:
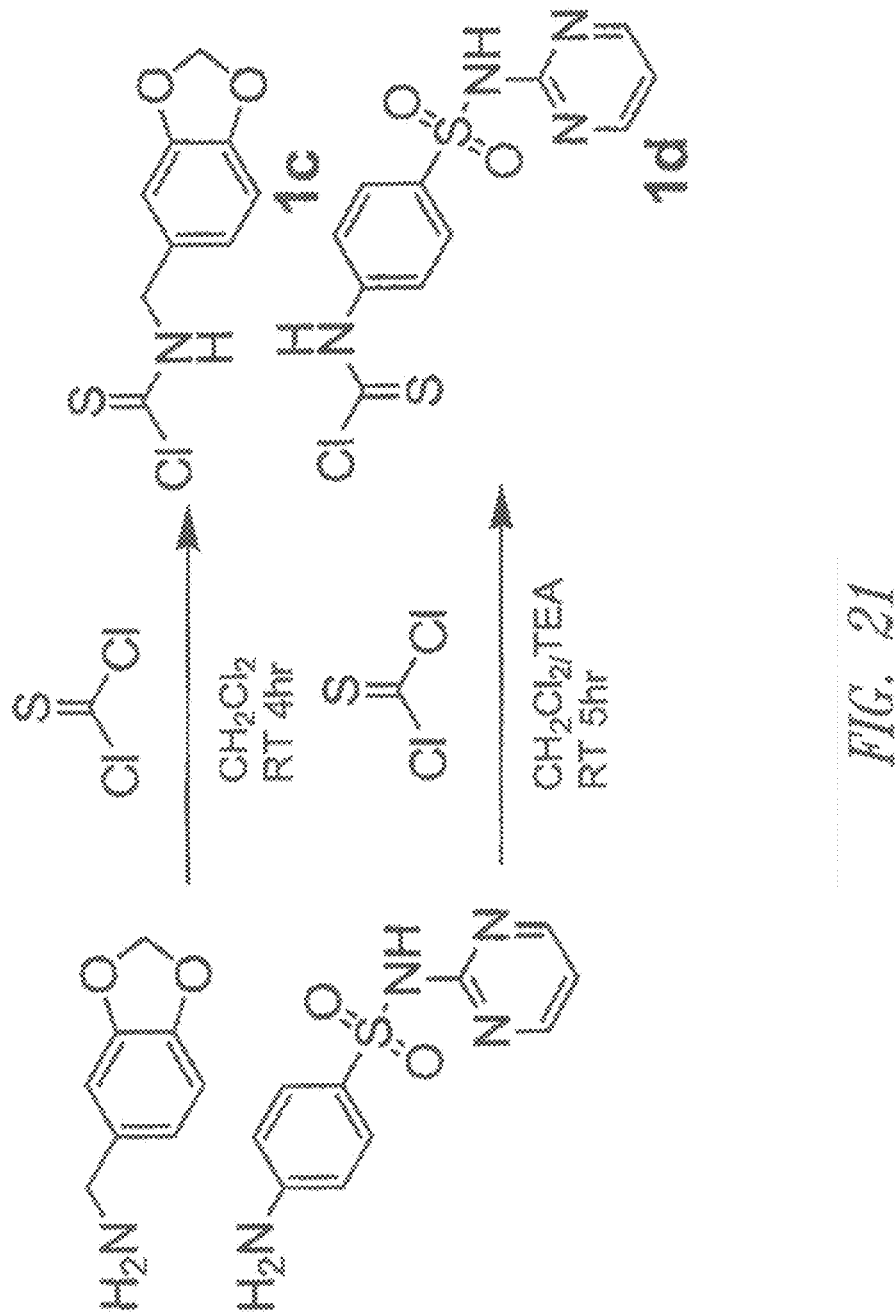
FIG. 21 summarizes the preparation of intermediates 1c and 1d.

The synthesis of 4-piperazinylpyrimido[4,5-b]indoles (1b), benzofuranopyrimidines (2b), benzothieno[3,2-d]pyrimidines (3b), and quinazoline (4b) derivatives is depicted in FIG. 20. 4-Chloro-tricyclic and quinazoline building blocks (1a-4-a) were synthesized using literature methods. (Pandey, A., et al., J. Med. Chem. 2002, 45:3772-93; Matsuno, K., et al., J. Med. Chem. 2002, 45:3057-66; Matsuno, K., et al., J. Med. Chem. 2002, 45:4513-23; and Venugopalan, B., et al., J. Heterocycl. Chem. 1988, 25:1633-39.) These were converted to the corresponding 4-piperazine derivatives by refluxing with piperazine in pyridine or dioxane. Piperonylamine or sulfadiazine were slowly added to a solution of thiophosgene in dichloromethane while cooling with an ice bath. The resulting mixture was stirred for four hours at room temperature, which gave 1c or 1d, as shown in FIG. 21. Compounds Ic or 1d were further reacted with 4-piperazine-substituted tricyclic or quinazoline derivatives in dichloromethane and stirred overnight at room temperature. To quench excess isothiocyanate, methanol was added, and after removal of solvent, the residue was purified by silica gel chromatography to give compounds I-7 of FIG. 17 in approximately 20-40% yields.

Example 17

N-Benzo[1,3]-dioxol-5-ylmethyl-thioformamide chloride (1c)

To a stirred solution of piperonylamine (0.1 mL, 0.77 mmol) in dichloromethane (20 mL) was slowly added thiophosgene (0.06 mL, 0.83 mmol) under cooling with an ice bath. After the reaction mixture was stirred for four hours at room temperature, it was washed with water and brine, dried over anhydrous sodium sulfate, filtered, evaporated and dried under vacuum; and the product was used immediately for the next reaction.

Example 18

N-Pyrimidin-2-yl-4-thioformylamino-benzene-sulfonamide chloride (1d)

To a stirred solution of sulfadiazine (192 mg, 0.77 mmol) in dichloromethane (20 mL) were slowly added thiophosgene (0.06 mL, 0.83 mmol) and triethylamine (0.05 mL, 0.32 mmol) under cooling with an ice bath. After the reaction mixture was stirred for five hours at room temperature, it was washed with water and brine, dried over anhydrous sodium sulfate, filtered, evaporated and dried under vacuum. The product was used immediately for the next reaction.

Example 19

4-(6,7-Dimethoxy-9H-1,3,9-triaza-fluoren-4-yl)-piperazine-1-carbothioic acid (benzo[1,3]-dioxol-5-ylmethyl)-amide (1)

To a solution of 6,7-dimethoxy-4-piperazino-9H-pyrimido[4,5-b]indole (200 mg, 0.64 mmol) and pyridine (0.5 mL, 6.4 mmol) in dichloromethane (20 mL) was added the solution of product 1c in dichloromethane (20 mL) and the mixture was stirred overnight. Methanol was added to quench excess thiophosgene, and the residue after removal of solvent was purified by silica gel column chromatography eluting with 5% methanol/dichloromethane and further recrystallized from dichloromethane/hexane to give 130 mg (40%).

$^1$HNMR (CDCl$_3$, 300 MHZ) δ 3.79 (s, 4H), 3.96 (s, 3H), 3.97 (s, 3H), 4.07 (s, 4H), 4.79 (s, 2H), 5.92 (s, 2H), 6.75 (d, J=7.9 Hz, 1H), 6.81 (d, J=7.9 Hz, 1H), 6.87 (s, 1H), 7.04 (s, 1H), 7.18 (s, 1H), 8.40 (s, 1H).

FAB HRMS [M+H]$^+$ calcd for C$_{25}$H$_{26}$N$_6$O$_4$S: 506.1736. found 507.1820.

Combustion Analysis: C$_{25}$H$_{26}$N$_6$O$_4$S Requires C 59.27%, H 5.17%, N 16.59%, O 12.63%, S 6.33%; Found C 59.89%, H 5.65%, N 16.99%, O 12.83%, S 6.83%.

Example 20

4-(6,7-Dimethoxy-9H-1,3,9-triaza-fluoren-4-yl)-piperazine-1-carbothioic acid [4-(pyrimidin-2-ylsulfamoyl)-phenyl]-amide (2)

To a solution of 6,7-dimethoxy-4-piperazino-9H-pyrimido[4,5-b]indole (200 mg, 0.64 mmol) and pyridine (0.5 mL, 6.4 mmol) in dichloromethane (20 mL) was added a solution of product 1d in dichloromethane (20 mL) and this was stirred overnight. Methanol was added to quench excess thiophosgene, and the residue after removal of solvent was purified by silica gel column chromatography and eluted with 5% methanol/dichloromethane and further recrystallized from dichloromethane/hexane to give 50 mg (16%).

$^1$HNMR (DMSO-d$_6$, 300 MHZ) δ 3.75 (s, 4H), 3.87 (s, 3H), 3.88 (s, 3H), 4.19 (s, 4H), 7.04-7.06 (m, 1H), 7.07 (s, 1H), 7.24 (s, 1H), 7.53 (d, J=8.4 Hz, 2H), 7.90 (d, J=8.4 Hz, 2H), 8.44 (s, 1H), 8.51 (d, J=4.8 HZ, 2H), 9.72 (s, 1H, —NH), 12.01 (s, 1H, —NH).

FAB HRMS [M+H]$^+$ calcd for C$_{27}$H$_{27}$N$_9$O$_4$S$_2$: 605.1627. found 606.1699

Combustion Analysis: Requires C$_{27}$H$_{27}$N$_9$O$_4$S$_2$ Requires C 53.54%, H 4.49%, N 20.81%, O 10.57%, S 10.59%; Found C 53.84%, H 4.91%, N 21.21%, O 11.87%, S 8.17%.

Example 21

4-Benzo[4,5]furo[3,2-d]pyrimidin-4-yl-piperazine-1-carbothioic acid (benzo[1,3]-dioxol-5-ylmethyl)-amide (3)

To a solution of 4-piperazinobenzofurano[3,2-d]pyrimidine (200 mg, 0.79 mmol) and pyridine (0.5 mL, 7.9 mmol) in dichloromethane (20 mL) was added a solution of product 1c in dichloromethane (20 mL) and this was stirred overnight. Methanol was added to quench excess thiophosgene, and the residue after removal of solvent was purified by silica gel column chromatography eluting with 5% methanol/dichloromethane and further recrystallized from dichloromethane/hexane to give 150 mg (37%).

$^1$HNMR (CDCl$_3$, 300 MHZ) δ 4.09 (s, 4H), 4.27 (s, 4H), 4.82 (d, J=4.7 Hz, 2H), 5.99 (s, 2H), 6.77-6.79 (m, 1H), 6.80-6.83 (m, 1H), 6.89 (s, 1H), 7.47-7.52 (m, 1H), 7.61-7.65 (m, 1H), 7.66-7.70 (m, 1H), 8.33 (d, J=7.0 Hz, 1H).

FAB HRMS [M+H]$^+$ calcd for C$_{23}$H$_{21}$N$_5$O$_3$S: 447.1365. found 448.1443.

Combustion Analysis: C$_{23}$H$_{21}$N$_5$O$_3$S Requires C 61.73%, H 4.73%, N 15.65%, O 10.73%, S 7.17%; Found C 61.95%, H 4.99%, N 15.93%, O 11.13%, S 7.55%.

Example 22

4-Benzo[4,5]furo[3,2-d]pyrimidin-4-yl-piperazine-1-carbothioic acid [4-(pyrimidin-2-ylsulfamoyl)-phenyl]-amide (4)

To a solution of 4-piperazinobenzofurano[3,2-d]pyrimidine (200 mg, 0.79 mmol) and pyridine (0.5 mL, 7.9 mmol) in dichloromethane (20 mL) was added a solution of product 1d in dichloromethane (20 mL) and this was stirred overnight. Methanol was added to quench excess thiophosgene; and the residue after removal of solvent was purified by silica gel column chromatography eluting with 5% methanol/dichloromethane and further recrystallized from dichloromethane/hexane to give 150 mg (37%).

$^1$HNMR (DMSO-d$_6$, 300 MHZ) δ 4.17 (s, 8H), 7.04-7.08 (m, 1H), 7.49-7.52 (m, 1H), 7.56-7.59 (m, 1H), 7.70-7.75 (m, 1H), 7.84 (d, J=8.2 Hz, 1H), 7.91 (d, J=8.6 Hz, 2H), 8.12 (d, J=7.6 Hz, 2H), 8.52 (d, J=4.8 Hz, 2H), 8.58 (s, 1H), 9.82 (s, 1H, NH).

FAB HRMS [M+H]$^+$ calcd for C$_{25}$H$_{22}$N$_8$O$_3$S$_2$: 546.1256. found 547.1325.

Combustion Analysis: C$_{25}$H$_{22}$N$_8$O$_3$S$_2$ Requires C 54.93%, H 4.06%, N 20.50%, O 8.78%, S 11.73%; Found 55.35%, H 4.44%, N 20.83%, O 8.96%, S 11.89%

Example 23

4-(9-Thia-1,5,7-triaza-fluoren-8-yl)-piperazine-1-carbothioic acid (benzo[1,3]-dioxol-5-ylmethyl)-amide (5)

To a solution of 4-piperazinopyrido[3',2';4,5]thieno[3,2-d]pyrimidine (200 mg, 0.74 mmol) and pyridine (0.5 mL, 7.9 mmol) in dichloromethane (20 mL) was added a solution of product 1c in dichloromethane (20 mL) and this was stirred overnight. Methanol was added to quench excess thiophosgene, and the residue after removal of solvent was purified by silica gel column chromatography eluting with 5% methanol/dichloromethane and further recrystallized from dichloromethane/hexane to give 110 mg (32%).

$^1$HNMR (CDCl$_3$, 300 MHZ) δ 4.07 (s, 4H), 4.17 (s, 4H), 4.72 (d, J=4.5 Hz, 2H), 5.88 (s, 2H), 6.69 (d, 1H), 6.75 (d, 1H), 6.80 (s, 1H), 7.43-7.47 (m, 1H), 8.65 (s, 1H), 8.75 (d, J=3.8 Hz, 2H).

FAB HRMS [M+H]$^+$ calcd for C$_{22}$H$_{20}$N$_6$O$_2$S$_2$: 464.1089. found 465.1167.

Combustion Analysis: C$_{22}$H$_{20}$N$_6$O$_2$S$_2$ Requires C 56.88%, H 4.34%, N 18.09%, O 6.80%, S 13.80%; Found C 57.16%, H 4.94%, N 18.53%, O 6.97%, S 14.30%

Example 24

4-(9-Thia-1,5,7-triaza-fluoren-8-yl)-piperazine-1-carbothioic acid [4-(pyrimidin-2-ylsulfamoyl)-phenyl]-amide (6)

To a solution of 4-piperazinopyrido[3',2';4,5]thieno[3,2-d]pyrimidine (200 mg, 0.74 mmol) and pyridine (0.5 mL, 7.9 mmol) in dichloromethane (20 mL) was added a solution of product 1d in dichloromethane (20 mL) and this was stirred overnight. Methanol was added to quench excess thiophosgene, and the residue after removal of solvent was purified by silica gel column chromatography eluting with 5% methanol/dichloromethane and further recrystallized from dichloromethane/hexane to give 60 mg (15%).

$^1$HNMR (DMSO-$d_6$, 300 MHZ) δ 4.07 (s, 8H), 6.96-6.99 (m, 1H), 7.47-7.50 (m, 1H), 7.58-7.62 (m, 1H), 7.82 (d, J=8.6 Hz, 2H), 8.43 (d, J=4.9 Hz, 2H), 8.63 (d, J=8.02 Hz, 2H), 8.70 (s, 1H), 8.80 (d, J=4.0 Hz, 1H).

FAB HRMS [M+H]$^+$ calcd for $C_{24}H_{21}N_9O_2S_3$: 563.0980. found 564.1059.

Combustion Analysis: $C_{24}H_{21}N_9O_2S_3$ Requires C 51.14%, H 3.76%, N 22.36%, O 5.68%, S17.07%; Found 51.44%, H 3.98%, N 22.84%, O 5.96, S 17.45

Example 25

4-(6,7-Dimethoxy-quinazolin-4-yl)-piperazine-1-carbothioic acid [4-(pyrimidin-2-ylsulfamoyl)-phenyl]-amide (7)

To a solution of 4-(I-piperazinyl)-6,7-dimethoxy quinazoline (200 mg, 0.73 mmol) and pyridine (0.5 mL, 6.4 mmol) in dichloromethane (20 mL) was added a solution of product 1d in dichloromethane (20 mL) and this was stirred overnight. Methanol was added to quench excess thiophosgene, and the residue after removal of solvent was purified by silica gel column chromatography eluting with 5% methanol/dichloromethane and further recrystallized from dichloromethane/hexane to give 80 mg (20%).

$^1$HNMR (CDCl$_3$, 300 MHZ) δ 3.85 (s, 4H), 3.98 (s, 3H), 4.02 (s, 3H), 4.11 (s, 4H), 6.98 (m, 1H), 7.08 (s, 1H), 7.32 (d, 2H), 7.88 (s, 1H), 8.00 (d, J=6.7 Hz, 2H), 8.62 (d, 2H), 8.66 (s, 1H).

FAB HRMS [M+H]$^+$ calcd for $C_{26}H_{26}N_8O_4S_2$: 566.1518. found 567.1597.

Combustion Analysis: $C_{26}H_{26}N_8O_4S_2$ Requires C 52.99%, H 4.62%, N 19.77%, O 11.29%, S11.32%; Found C 53.27%, H 4.94%, N 19.99%, O 11.57%, S11.64%

Example 26

Cancer Cell Cytotoxicity Assay

To validate the hypothesis that the designed c-kit/PDGFR tyrosine kinase inhibitors mediate GIST882 cell killing and PDGFR-mediated cell killing of pancreatic cancer cell lines (CFPAC-1, PANC-1 and MIA PaCa-2), an in vitro cytotoxicity assay was performed. The GIST882 cell line used in this study has a c-kit gain-of-function mutation (K642E). The assay utilized the Cell Titer 965 Non-Radioactive Cell Proliferation Assay (Promega Corp., Madison, Wis.). First the cells were cultured. GIST882 cells were provided by Dr. Jonathan A. Fletcher (Dana-Farber Cancer Institute, Boston, Mass.). PANC-1 and MIAPaCa-2 cells were provided by Dr. Daniel Von Hoff (Arizona Cancer Center, Tucson, Ariz.). GIST882 cells were cultured in RPMI 1640 medium (Cat#21870-076, Invitrogen Corporation) supplemented with 300 mg/L L-glutamine, 100 unit/ml penicillin, 100 µg/ml streptomycin and 15% fetal bovine serum. PANC-1 and MIAPaCa-2 cells were maintained in RPMI 1640 medium (cat#10-040, Mediatech, Inc.) supplemented with 100 unit/ml penicillin, 100 µg/ml streptomycin and 10% fetal bovine serum. All the cell lines were incubated in a humidified incubator at 37° C. with 5% $CO_2$ atmosphere.

Cells were plated at a density of 2000 to 10000 cells per well, depending on their growth rate, in 0.1 mL medium on day 0 in 96-well Falcon microtiter plates (#3072, Becton-Dickinson Labware, Lincoln Park, N.J.). On day 1, 10 µL of serial dilutions of the individual compounds were added to the plates in replicates of 4. After incubation for 4 days at 37° C. in a humidified incubator, the cells were fixed with 10% Trichloroacetic acid solution (Catalog No. 490-10, Sigma). Subsequently, they were labeled with 0.04% Sulforhodamine B (S9012, Sigma) in 1% acetic acid. After multiple washes to remove excess dye, 100 µl of 50 mM Tris solution was added to each well in order to dissolve the dye. The absorbance of each well was read on a plate reader (Wallac Vector$^2$, PerkinElmer) at the wavelength of 570 nm. Data were expressed as the percentage of survival of control calculated from the absorbance corrected for background absorbance. The surviving percent of cells was determined by dividing the mean absorbance values of the monoclonal antibody by the mean absorbance values of the control and multiplying by 100.

The calculated FlexX scoring and IC$_{50}$ values for these novel and prior art c-kit inhibitors are shown in Table 2 below. Not all of the novel compounds evaluated exhibited cytotoxicity against GIST882 cells. Moreover, in an in vitro assay of aurora 2 kinase, a serine/threonine kinase, these compounds showed no activity (data not shown). Taken together, these results validate compounds of the invention, such as HPK61 (II-2-7) and HPK56 (III-1-3), as potent, specific c-kit and PDGFR tyrosine kinase inhibitors.

Figure 22A:
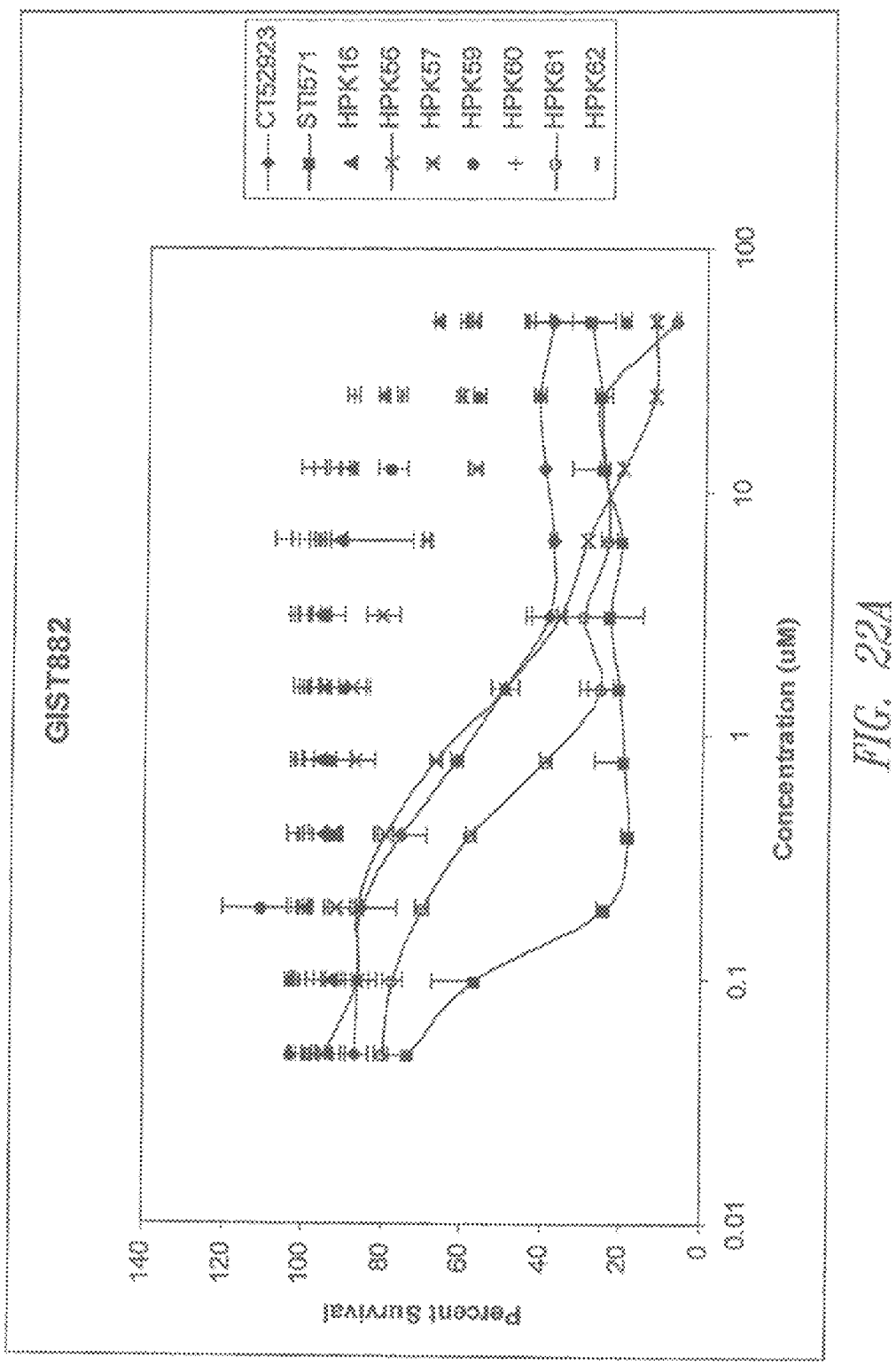
FIGS. 22A, 22B, and 22C display graphically the results of in vitro cytotoxicity testing of GIST882, MIAPaCa-2 and PANC-1 cell lines, respectively.
Figure 22B:
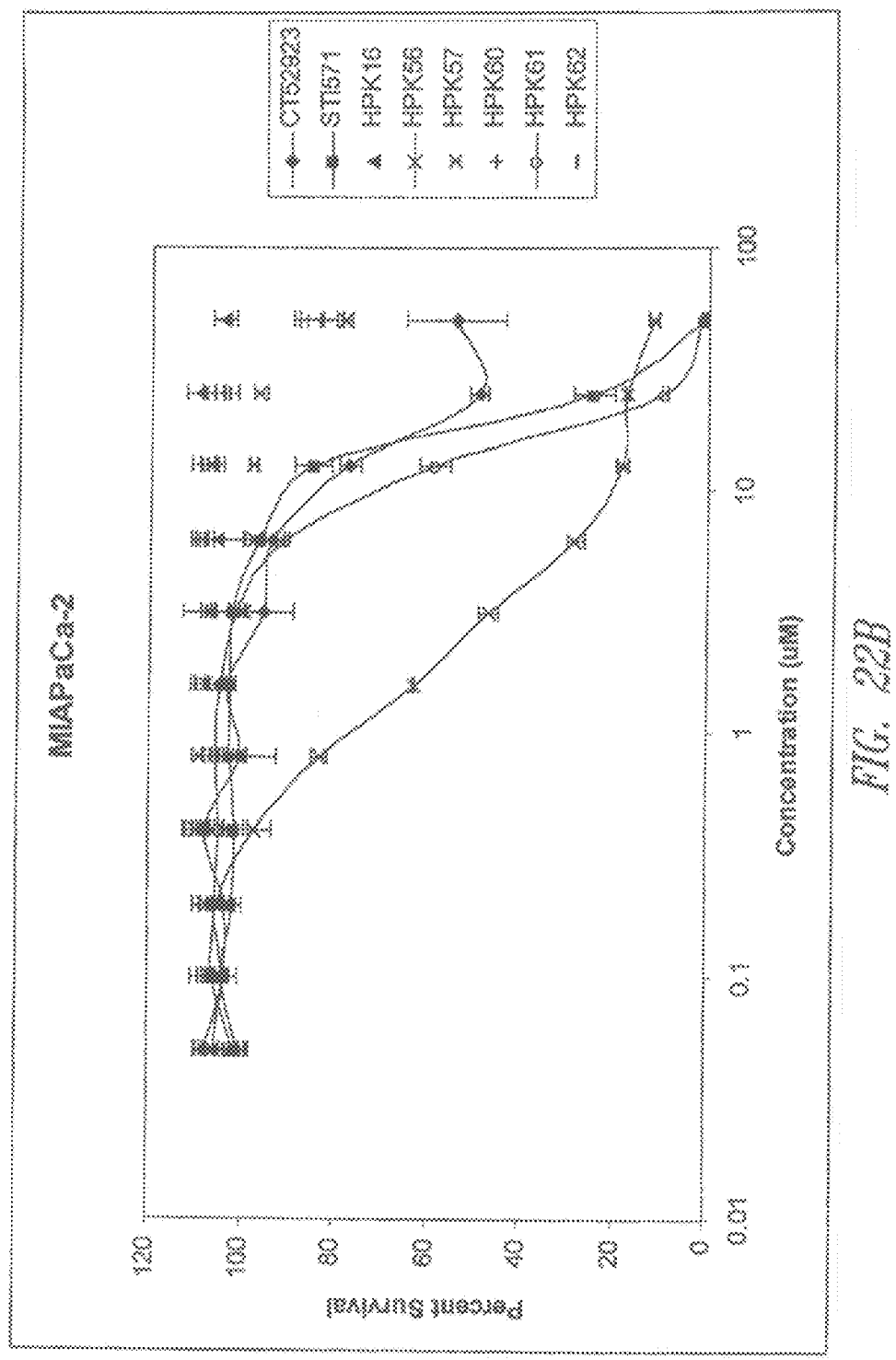
Figure 22C:
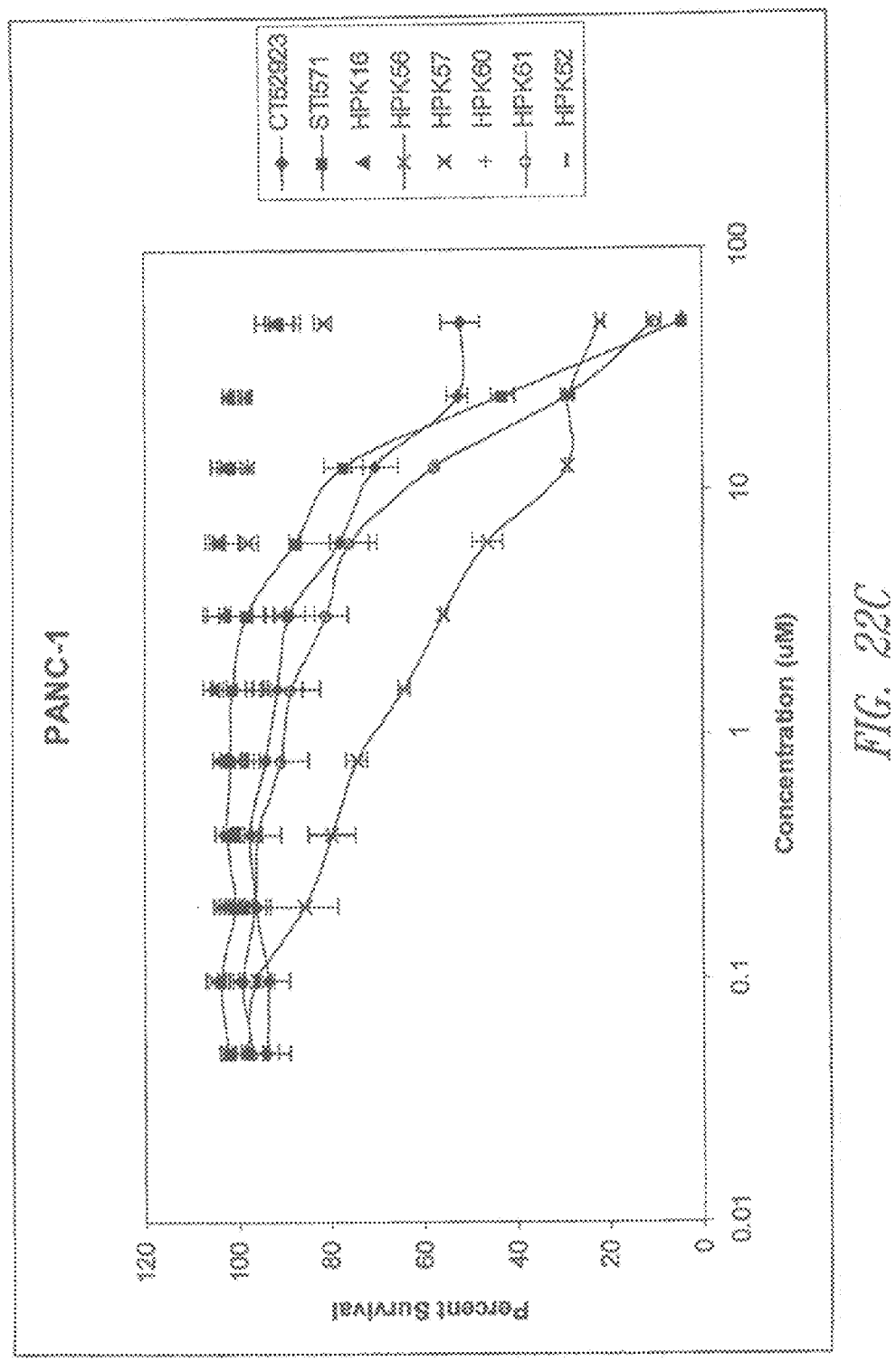

A comparison of the cytotoxicity profiles of the designed and synthesized compounds 1-7 (FIG. 17), as well as known kinase inhibitors STI571 and CT52923, is shown in FIGS. 22A, 22B and 22C, and the calculated IC$_{50}$ values are shown below in Table 2. For the GIST882 cell line, HPK61 (II-2-7), HPK56 (III-1-3), STI571, and CT52923 were similarly potent, with IC$_{50}$ values ranging from 0.1 to 1.8 µM and with a potency order of STI571 (0.1 µM)>HPK61 (II-2-7) (0.45 µM)>HPK56 (III-1-3) (1.60 µM)>CT52923 (1.80 µM). Although STI571 killed cells early, 25% of cells exposed to STI571 were alive at day 4. In contrast, HPK61 (II-2-7) and HPK56 (III-1-3) had a more prolonged effect, with 5% of cells alive at day 4. For the pancreatic cancer cell lines MIA-PaCa-2 and PANC-1, HPK56 (III-1-3) was the most potent, with IC$_{50}$ values of 2.10 and 3.00 µM, respectively, and a potency order of HPK56 (III-1-3) (2.1-3.0 µM)>HPK61 (II-2-7) (15.5-16.0 µM)>STI571 (20.0-24.0 µM)>CT52923 (25.0-26.6 µM).

TABLE 2

Activity (IC$_{50}$ µM) and FlexX (kJ/mol) results of lead compounds and tricyclic and quinazoline inhibitors against c-kit and PDGFR tyrosine kinases.

| Compound | Structure | c-kit GIST882 | PDGFR MIAPaCa | PANC-1 | FlexX$^a$ FlexX score | Drug score |
|---|---|---|---|---|---|---|
| 1 (HPK61) | II-2-7 | 0.45 | 15.5 | 16.0 | −34.8 | −66.9 |
| 2 (HPK62) | II-2-6 | 28.0 | >50 | >50 | −19.3 | −44.5 |

TABLE 2-continued

Activity (IC$_{50}$ µM) and FlexX (kJ/mol) results of lead compounds and tricyclic and quinazoline inhibitors against c-kit and PDGFR tyrosine kinases.

| | | c-kit | PDGFR | PANC- | FlexX | Drug |
|---|---|---|---|---|---|---|
| Compound | Structure | GIST882 | MIAPaCa | 1 | score | score |
| 3 (HPK56) | III-1-3 | 1.60 | 2.10 | 3.00 | −28.4 | −62.4 |
| 4 (HPK59) | III-1-5 | 27.5 | ND[b] | ND | −27.9 | −59.3 |
| 5 (HPK57) | III-1-4 | 28.0 | >50 | >50 | −22.2 | −54.3 |
| 6 (HPK60) | 34-4 (Table 4) | 50.0 | >50 | >50 | −21.1 | −57.2 |
| 7 (HPK16) | IV-1-3 | 50.0 | >50 | >50 | −21.2 | −50.6 |

[a]FlexX score for c-kit tyrosine kinase. FlexX belongs to the category of empirical free energy scoring function (energy decomposition into various scores to which a coefficient has been assigned). The drug score combines drug likeness, cLogP, molecular weight, and toxicity risks in one handy value than may be used to judge the compound's overall potential to qualify for a drug.
[b]ND: not determined
[c]NA: not available.

Furthermore, a recent study reported that approximately 35% of GIST samples lacked c-kit mutations and had activation mutations in PDGFR-A (Heinrich, M., et al., Science 299(5607):708-10, 2003). Docking studies demonstrated that HPK61 (II-2-7) and HPK56 (III-1-3) interact equally with the tyrosine kinase domains of c-kit and PDGFR. Cellular cytotoxicity assays demonstrated that HPK61 (II-2-7) and HPK56 (III-1-3) are highly selective for c-kit and PDGFR tyrosine kinases and are superior to STI571 and CT52923 in pancreatic cancer cell lines. Therefore, it is expected that HPK61 (II-2-7) and HPK56 (III-1-3), as well as other related compounds of the invention, will be effective in treating both c-kit- and PDGFR-mediated GIST.

Example 27

Kinase Inhibition Assay

This example describes the inhibitory activity of compound (II-2-6), also referred to herein as HPK62), against various kinase proteins, including Aurora-A, cAMP-PK, MKK6 and CDK1.

In vitro

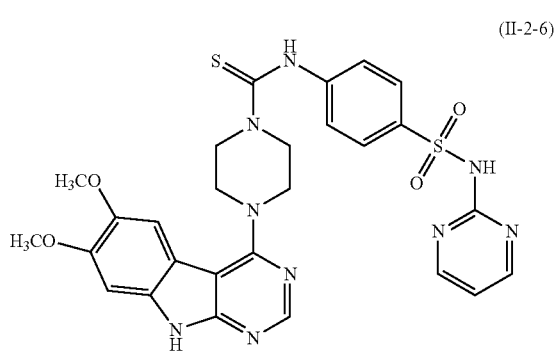 [SMILES: COc1cc2[nH]c3ncnc(N4CCN(C(=S)Nc5ccc(S(=O)(=O)Nc6ncccn6)cc5)CC4)c3c2cc1OC]

(II-2-6)

enzyme assays were performed using the Kinase-Glo™ Luminescent Kinase Assay from Promega Corporation (Madison, Wis.). The following conditions were used:

| Kinase | Enzyme | [ATP] (µM) | Substrate | [Substrate] (µM) |
|---|---|---|---|---|
| Aurora-A | 20 ng | 0.1 | Kemptide | 30 |
| cAMP-PK | 0.5 units | 0.1 | Kemptide | 30 |
| MKK6 | 1.0 µg | 0.1 | Kemptide | 30 |
| CDK1 | 10 units | 0.1 | Kemptide | 30 |

Enzymatic reactions were allowed to progress for 2 hours at 30° C., then assayed for kinase activity according to manufacturer protocol. The following IC$_{50}$ values were determined for the compound, using the above kinases:

| Kinase | IC$_{50}$ (µM) |
|---|---|
| Aurora-A | 0.9 |
| cAMP-PK | >100 |
| MKK6 | 6.2 |
| CDK1 | 22.3 |

Example 28

Effects of Compound (II-2-6) on Cell Cycle Distribution

Figure 23:
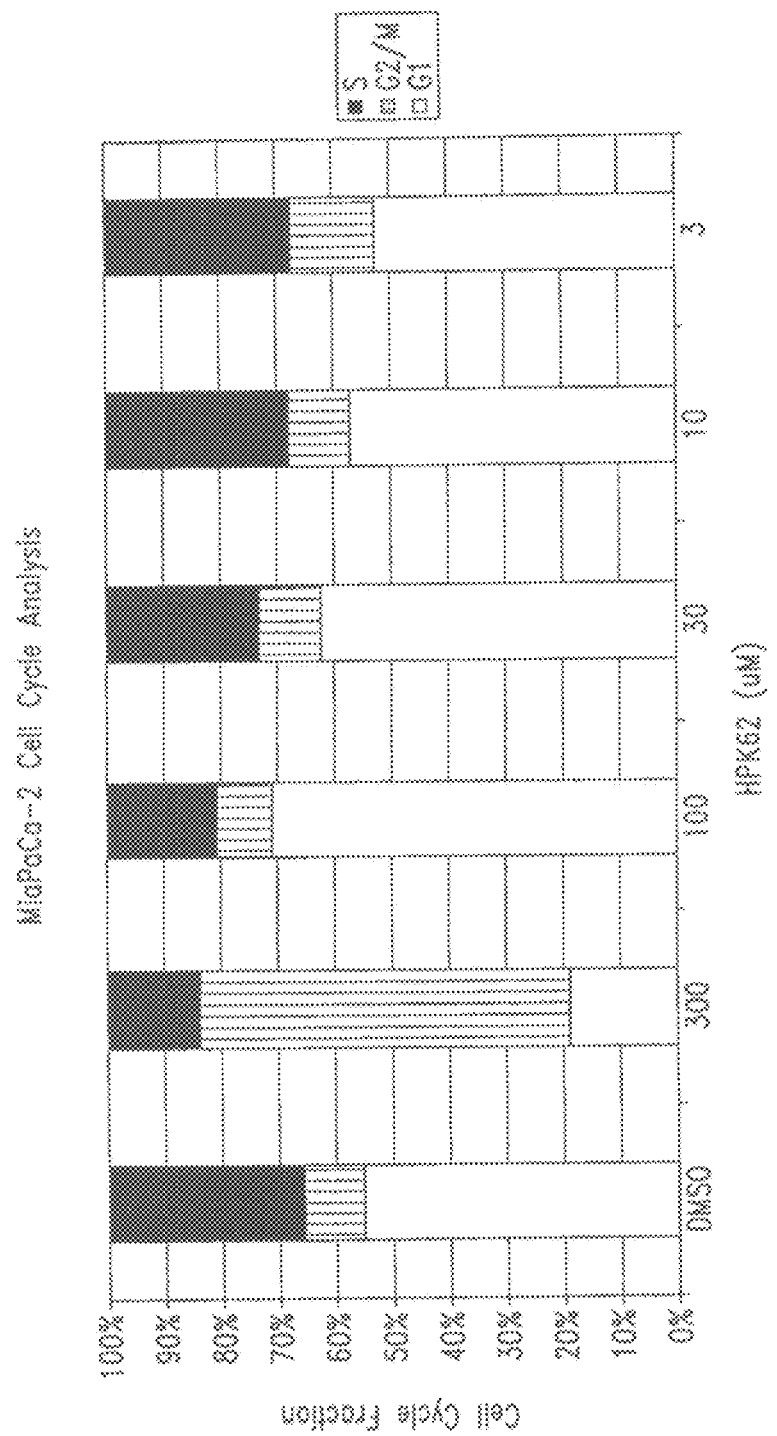
FIG. 23 shows the effects of compound (II-2-6) on cell cycle distribution of the MIA PaCa-2 pancreatic cancer cell line.

The effects of Structure (II-2-6) on cell cycle distribution were assayed using flow cytometry, using the following procedure: MIA PaCa-2 cells (American Type Culture Collection, Manassas, Va.) were grown to ~40% confluency. At this point, MP-235 at various concentrations, or an equal volume of DMSO (drug diluent) was added. Cells were grown in the presence of drug for 48 hours, and harvested using trypsin. 1 million cells were washed in 1 mL of Modified Krishan's Buffer (0.1% sodium citrate, 0.3% NP-40, 0.05 mg/ml propidium iodide, 0.02 mg/ml RNase A), and resuspended in 1 mL of fresh Modified Krishan's Buffer. Cell pellets were kept at 4° C. for no more than 24 hours before flow cytometric analysis was performed by the University of Arizona Flow Cytometry Core Facility. The cell cycle profile obtained from this analysis is illustrated in FIG. 23.

Example 29

Effects of Compound (II-2-6) on Cell Proliferation

Figure 24:
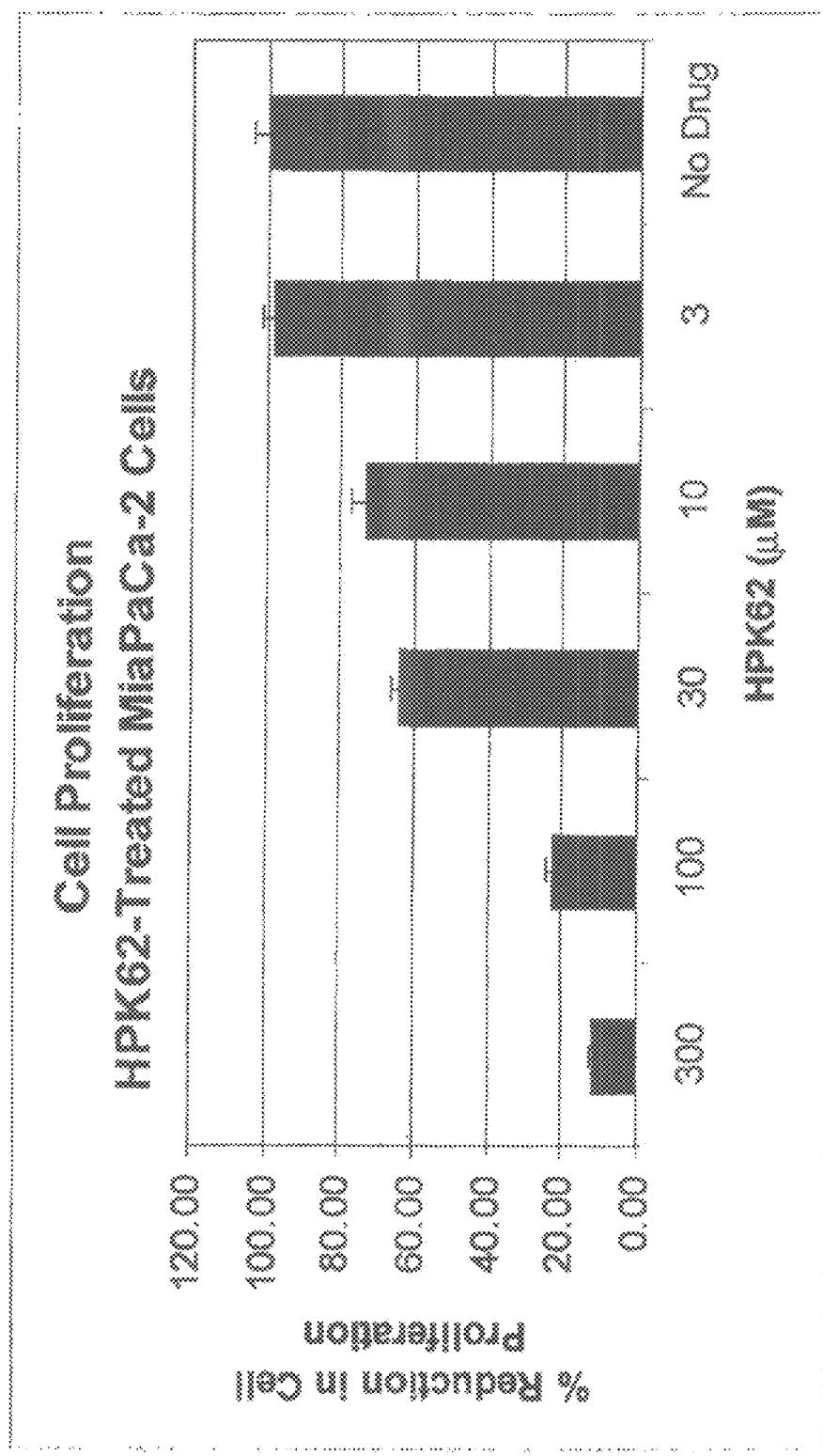
FIG. 24 shows the effects of compound (II-2-6) on cell proliferation of the MIA PaCa-2 pancreatic cancer cell line.

The ability of compound (II-2-6) at various concentrations to inhibit cell proliferation was also tested, using the MIA PaCa-2 cell line. 200,000 MIA PaCa-2 cells were plated into each well of a six-well plate and incubated overnight. At this point, MP-235 at various concentrations, or an equal volume of DMSO (drug diluent) was added. Cells were grown in the presence of drug for 48 hours, and harvested using trypsin. The number of cells in each well was determined by a cell counting assay using a hematocytometer. Each drug concentration was tested in triplicate and each well was counted in triplicate. Reduction in cell proliferation was determined by dividing the number of cells in drug-treated wells by the number in equivalent DMSO-treated wells. Results from this analysis are illustrated in FIG. 24.

Example 30

Effects of Structure (II-2-6) on Cytotoxicity of Pancreatic Cancer Cell Lines

Figure 25A:
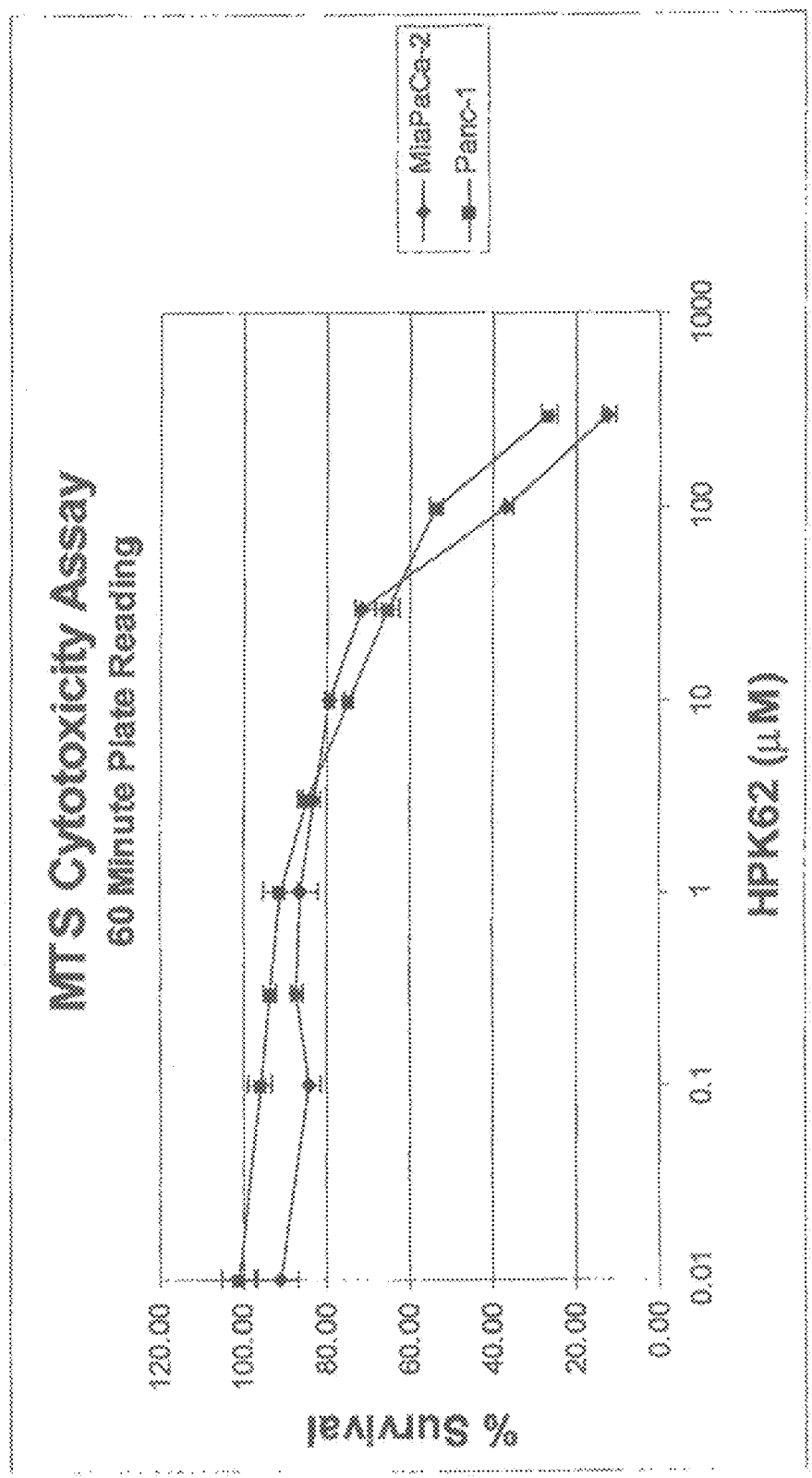
FIGS. 25A and 25B show the effects of compound (II-2-6) on in vitro cytotoxicity of the MIA PaCa-2 pancreatic cancer cell line.
Figure 25B:
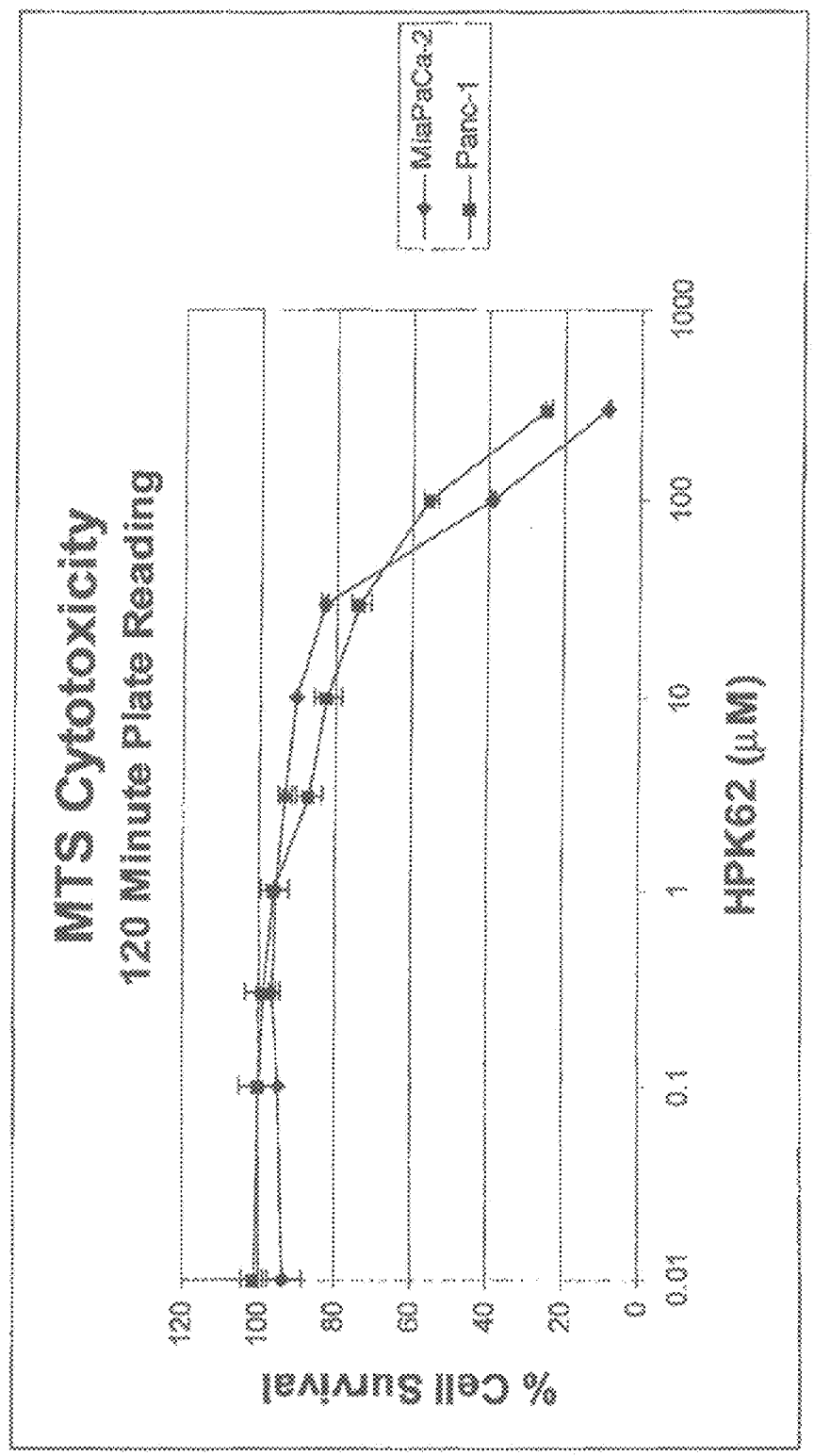

To determine if the reduction in cell number was due to slowing of cell growth or outright cell killing, the cytotoxicity of Structure (II-2-6) was determined, using an MTS-based assay in cultured MIA PaCa-2 and Panc-1 pancreatic cancer cells. In vitro cytotoxicity assays were performed using the CellTiter 96 Non-Radioactive Cell Proliferation Assay (Promega Corp., Madison, Wis.). Cells were plated in 0.1 ml medium on day 0 in 96-well microtiter plates (Falcon, #3072). On day 1, 10 μL of serial dilutions of the test agent were added in replicates of 4 to the plates. After incubation for 4 days at 37° C. in a humidified incubator, 20 μl of a 20:1 mixture of [3-(4,5-dimethyl-2-yl)-5-(3-carboxymethoxyphenyl)-2-(4-sulfophenyl)-2H-tetrazolium, inner salt; MTS], 2 mg/ml, and an electron coupling reagent, phenazine methosulfate (PMS, 0.92 mg/ml in DPBS), was added to each well and incubated for 1 or 2 hours at 37° C. Absorbance was measured using Model 7520 microplate reader (Cambridge Technology, Inc.) at 490 nm. Data were expressed as the percentage of survival of control calculated from the absorbance corrected for background absorbance. The surviving fraction of cells was determined by dividing the mean absorbance values of the test agents by the mean absorbance values of untreated control. Plate readings at 490 nm were taken after 60 and 120 minutes of incubation with the MTS substrate, and the results are illustrated in FIGS. 25A-B, respectively.

Example 31

Figure 26A:
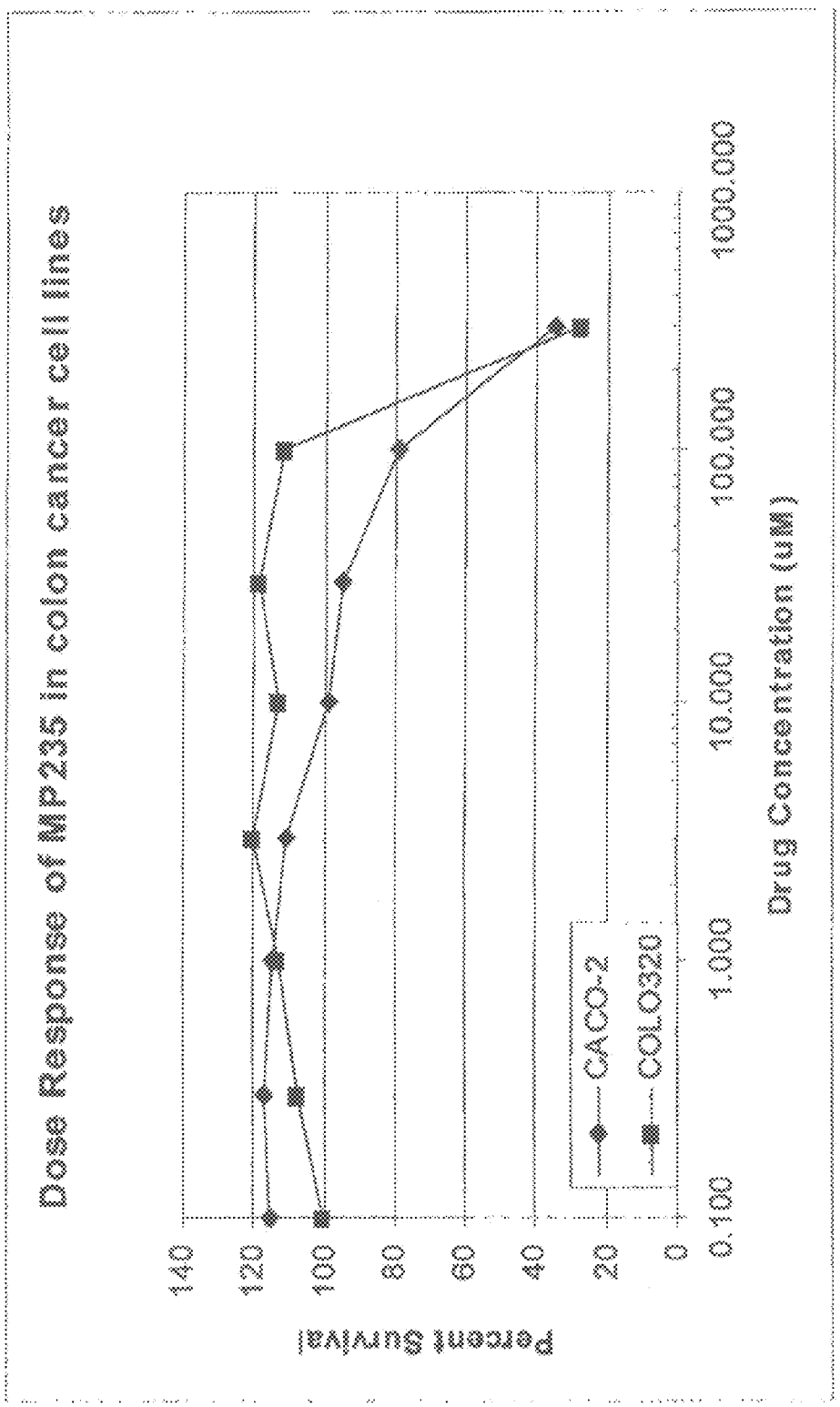
Figure 20B:
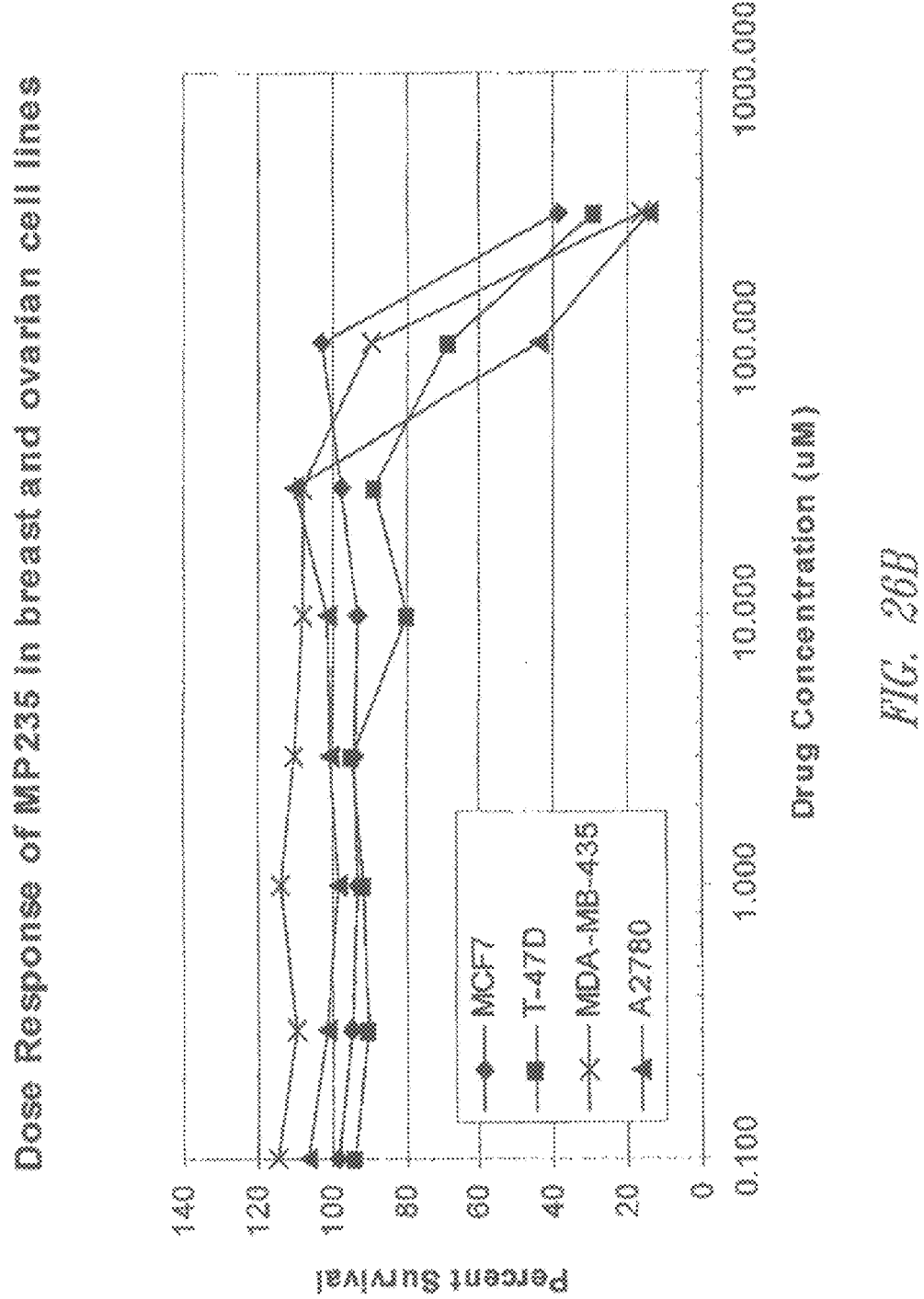
Figure 26C:
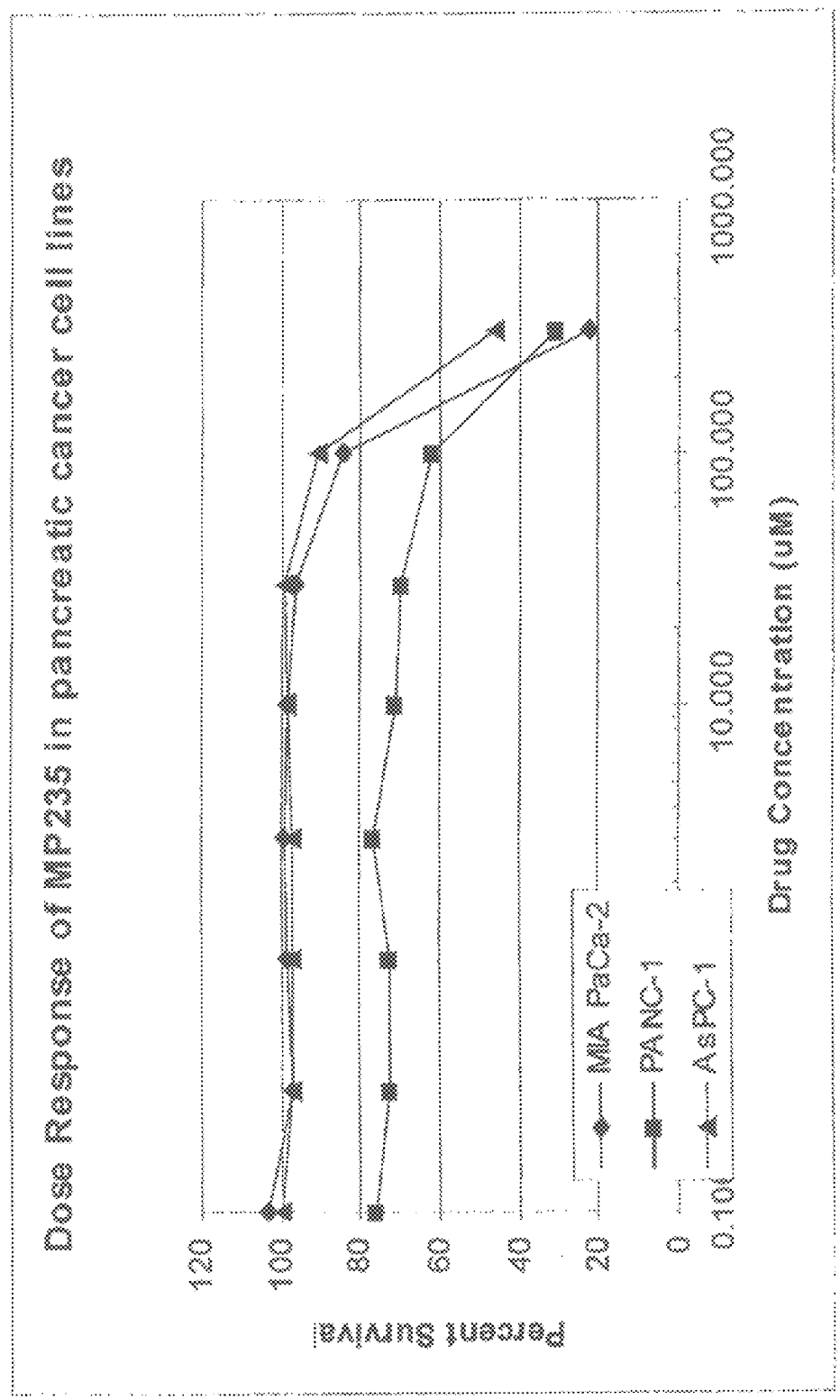

Effects of Compound (II-2-6) on Cytotoxicity of Colon, Breast, Ovarian and Pancreatic Cancer Cell Lines These cytotoxicity data were further complemented by performing the same MTS assay described above in a number of different cell lines from various sources. The results obtained from these experiments are illustrated in FIGS. 26A-C.

Example 32

Further Illustrative Inhibitory Compounds

Compound (II-2-6) is an illustrative kinase inhibitory compound of the invention belonging to a class of 4-Piprazinylpyrimido[4,5-b]indoles. This series of compounds was designed as inhibitors of both aurora-2 and c-kit kinases and Structure (II-2-6) was confirmed to have low nanomolar inhibitory activity against Aurora-2 kinase and to have low μM inhibitory activity against c-kit kinase.

(II-2-6)

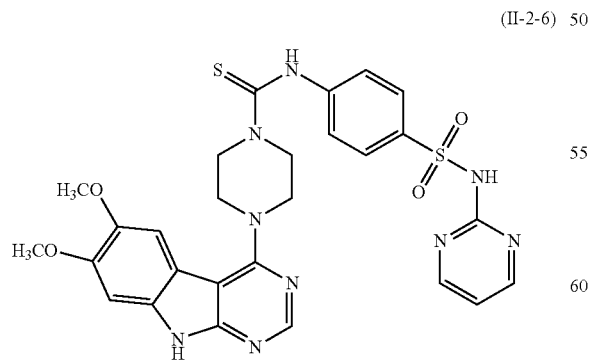

Compound (II-2-6) analogues were designed and synthesized according to Schemes 3-5 below in order to evaluate and optimize aurora-2 kinase activity, aqueous solubility and pharmacokinetic/pharmacodynamic profiles. The compounds belong to the class of pyrimido[4,5-b]indoles (Ia to Id) and quinazolines (IIa to IId below). Detailed structural information of illustrative compounds is provided in Table 3 below. Analogues were made in which $R_1$, $R_2$, $R_3$ and $R_4$ (1)-4-Piprazinylpyrimido[4,5-b]indoles, pyrimido[4,5-b]indoles of formula Ia-Id and $R_1$, $R_2$, $R_3$ and $R_4$ (1)-4-piperazin-1-yl-quinazolines and substituted quinazoline compounds of IIa-IId were synthesized.

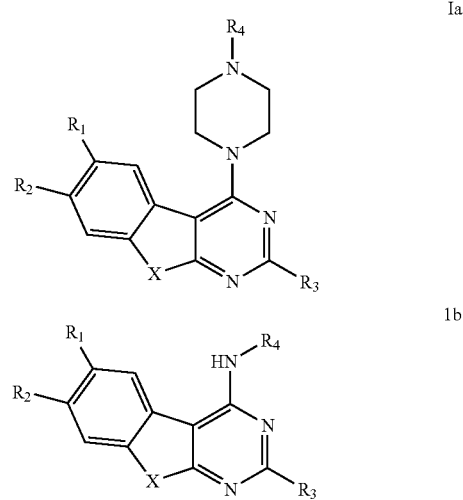

Ia

Ib

Ic

Id

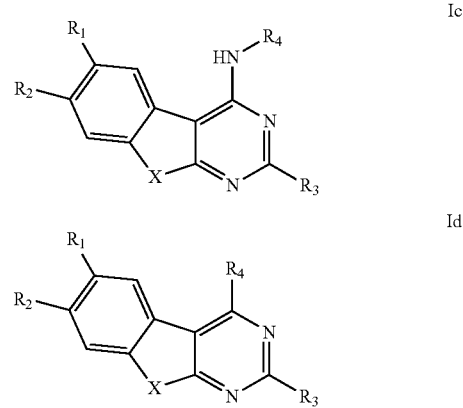

IIa

IIb

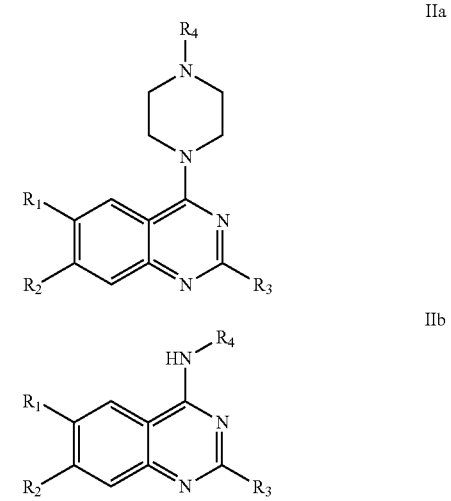

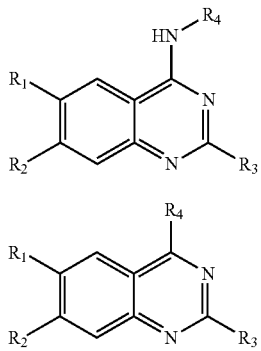

Based on the docking results, (II-2-6) binds to the ATP-binding pocket and is involved in several Van der Waals contacts and hydrogen bonding interactions with the active site pocket. The 6,7-dimethoxy pyrimido[4,5-b]indole moiety positioned into the adenine binding pocket, the 6,7-substituents of the pyrimido[4,5-b]indole orients from the hinge region into the solvent pocket and the benzenesulfonamide group is involved in interactions with the β and γ phosphate regions, whereas the piprazine group occupies the sugar binding pocket. Structure (II-2-6) had strong hydrogen bonding interactions with Pro214, Arg220 and is in close contact with Glu211 and Ala213 residues. The sulfonamide —S=O group forms hydrogen bonds with Lys258. In terms of hydrophobicity, areas deep in the ATP pocket around Phe144 are occupied by the flat aromatic ring and pyrimidine ring of (II-2-6).

Several analogues of (II-2-6) were studied using virtual docking to predict their binding mode. The compounds developed based on the mode of binding of (II-2-6) were undertaken for synthesis. Synthetic approaches for generating substitutions at $R_1$, $R_2$, $R_3$, $R_4$, $R_5$, $R_6$ and X are set forth in the following Schemes 3 to 7, and illustrative compounds are depicted in Table 3.

Scheme 3

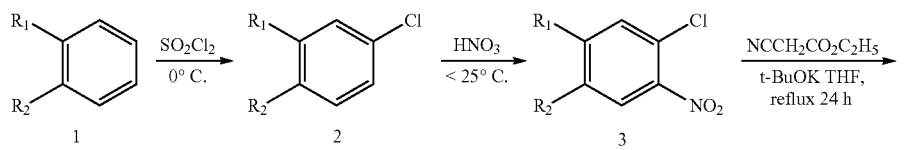

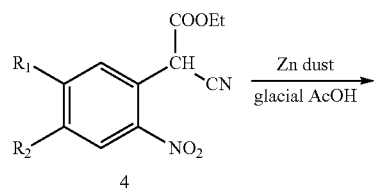

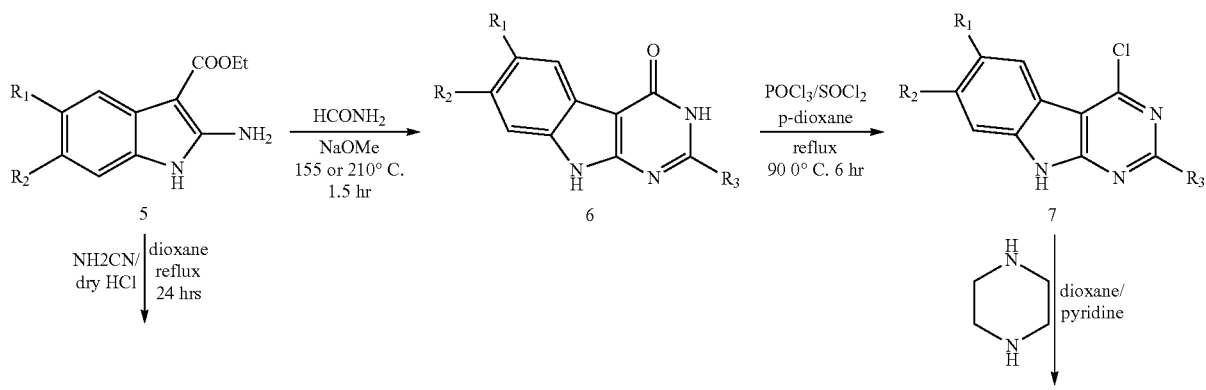

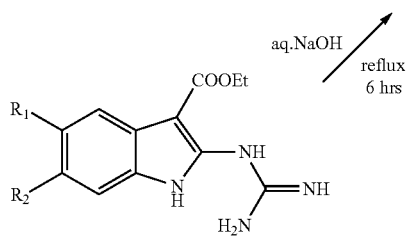

-continued
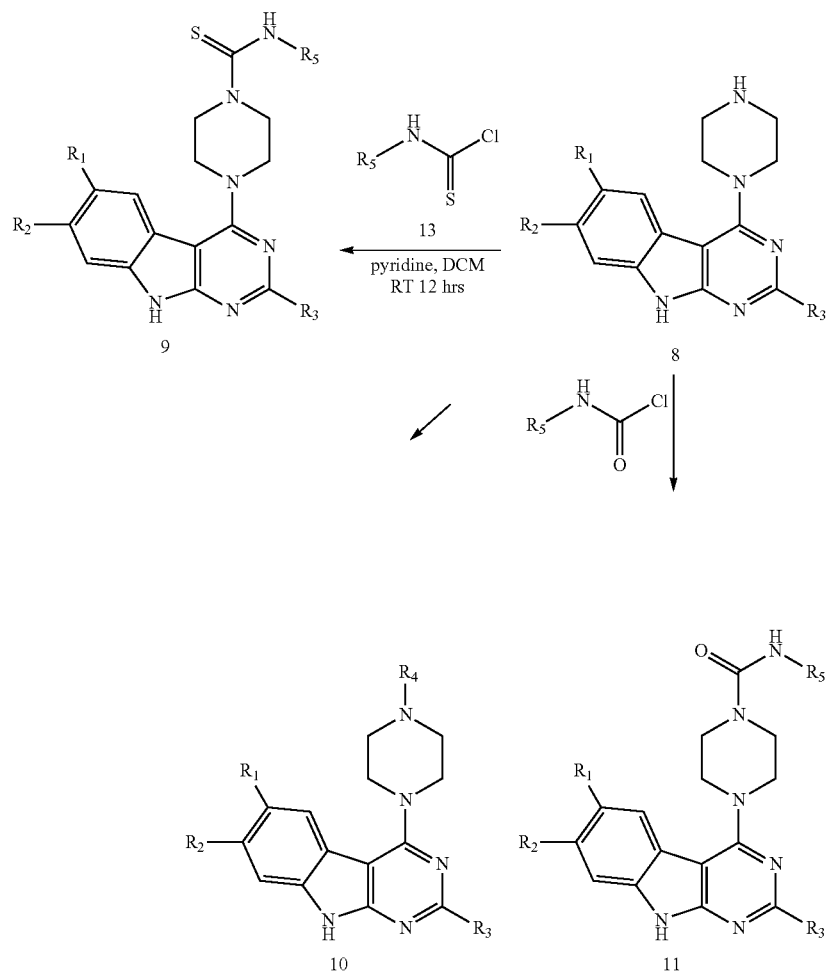
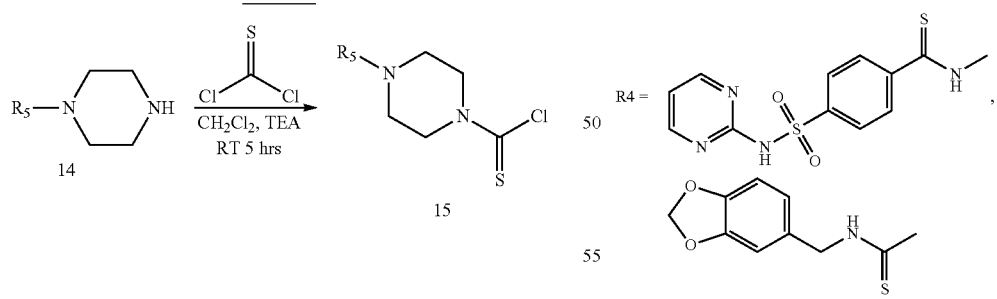
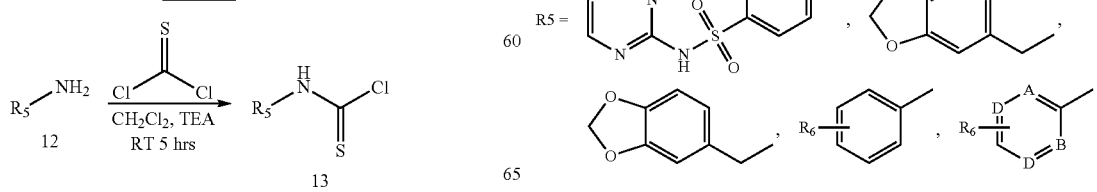

Scheme 6
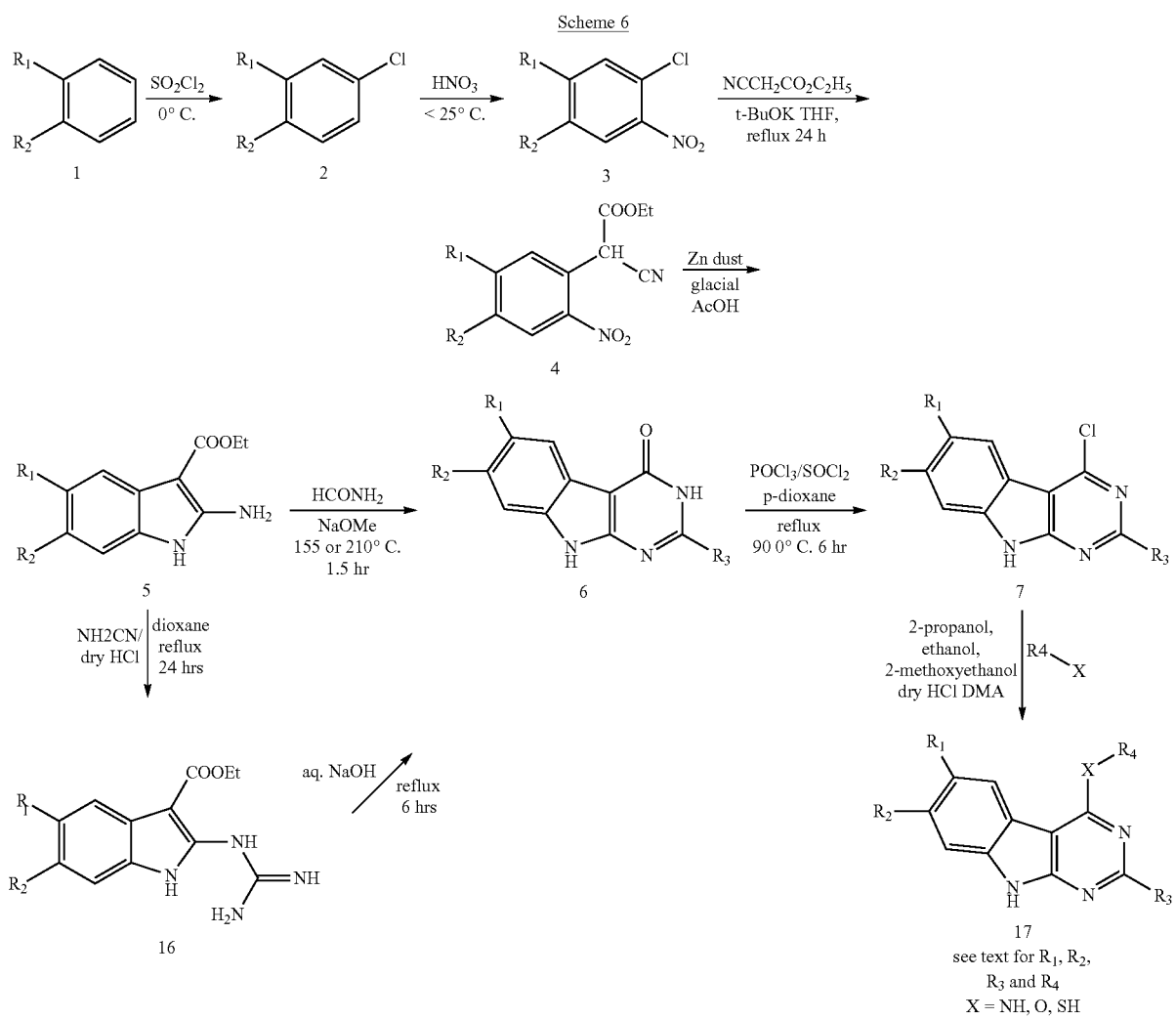
Scheme 7
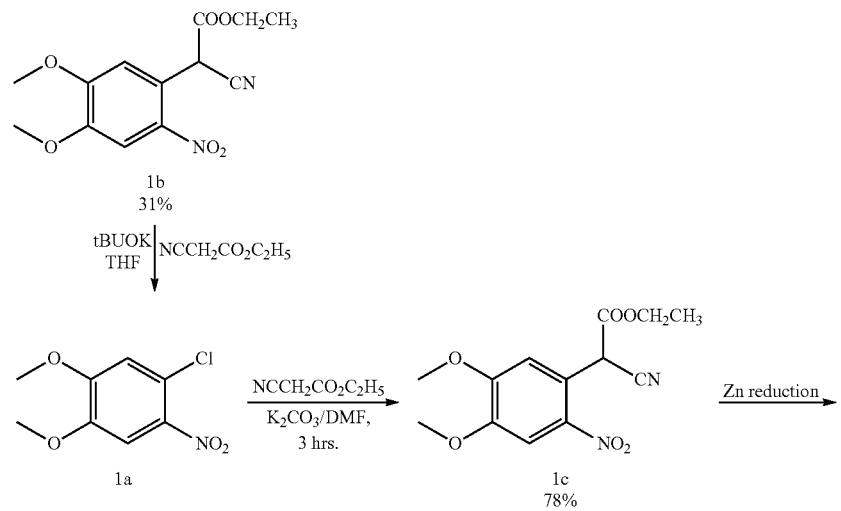

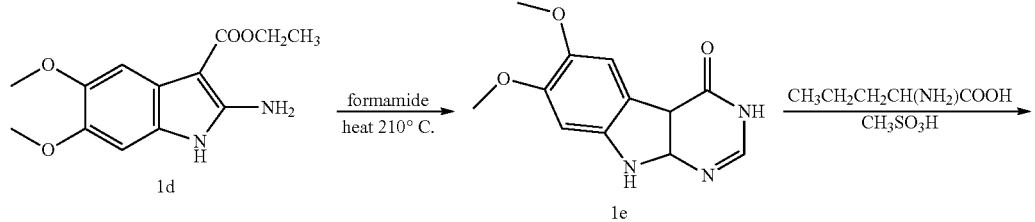
-continued
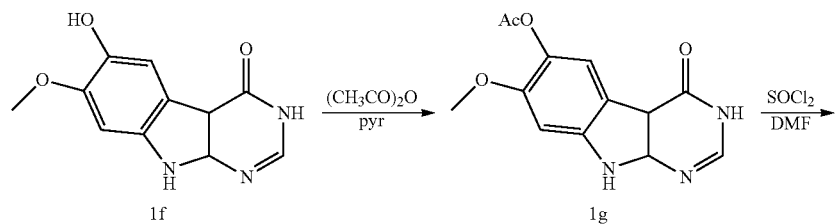
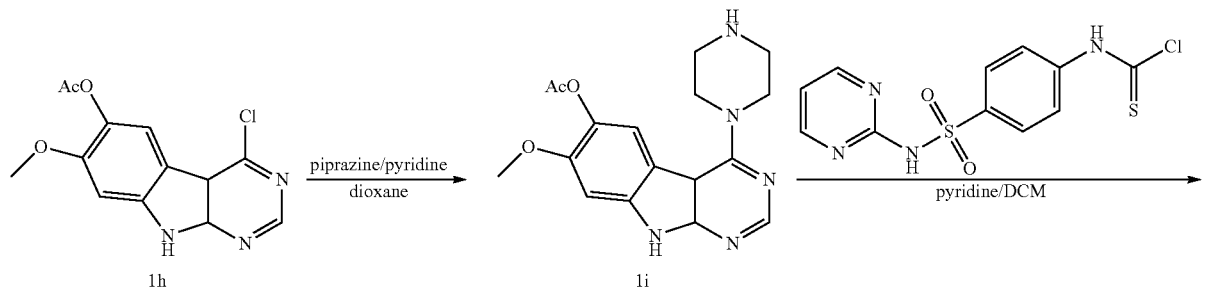
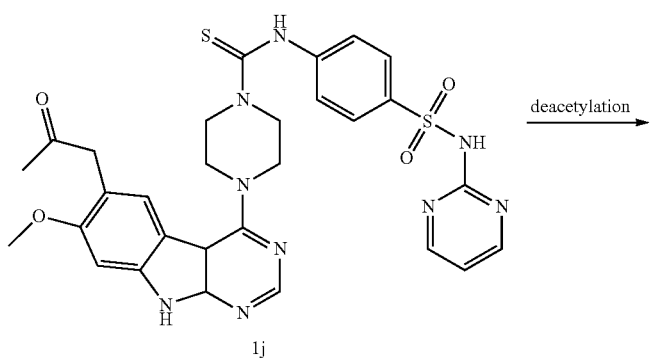
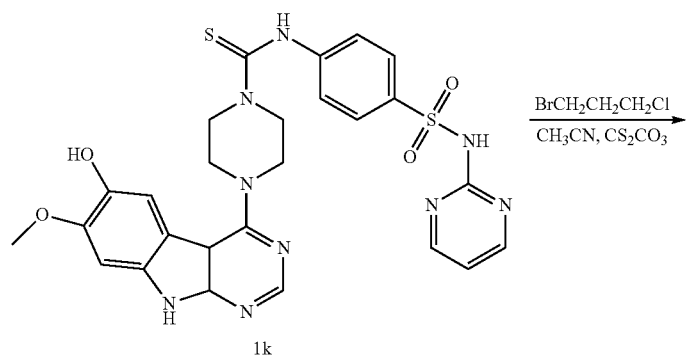

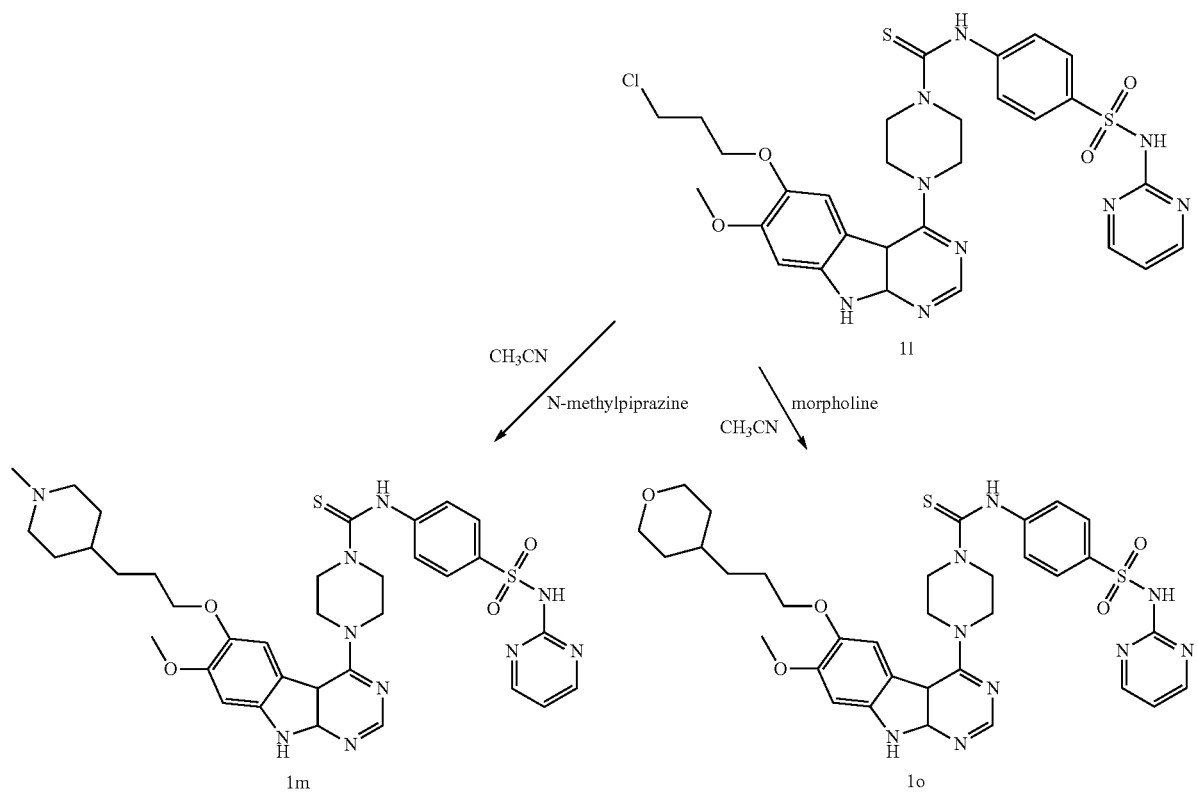
TABLE 3
| No | Structure* |
|---|---|
| 32-1 | 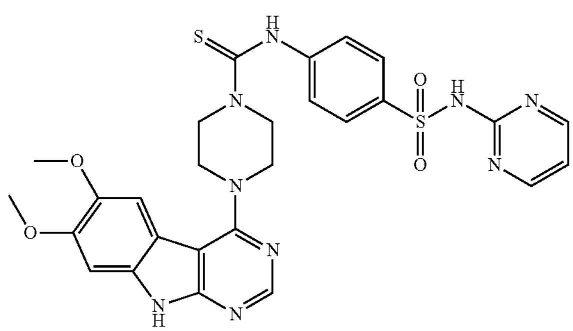 [SMILES: COc1cc2[nH]c3ncnc(N4CCN(C(=S)Nc5ccc(S(=O)(=O)Nc6ncccn6)cc5)CC4)c3c2cc1OC] |
| 32-2 | 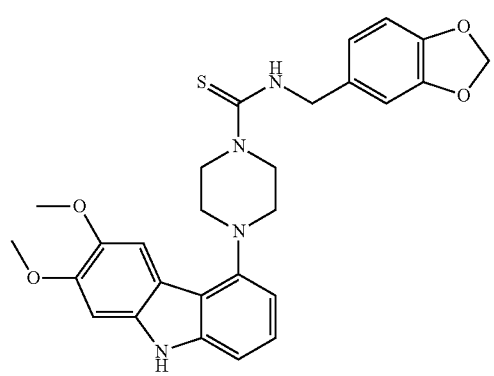 [SMILES: COc1cc2[nH]c3cccc(N4CCN(C(=S)NCc5ccc6c(c5)OCO6)CC4)c3c2cc1OC] |

TABLE 3-continued
| No | Structure* |
|---|---|
| 32-3 | 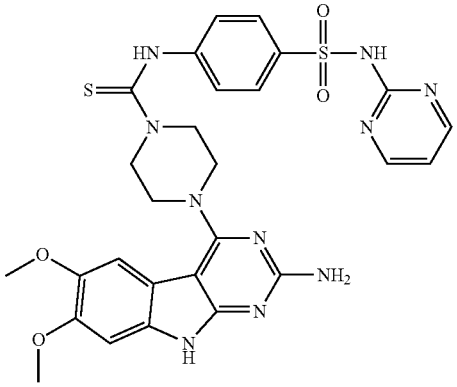 [SMILES: COc1cc2[nH]c3nc(N)nc(N4CCN(C(=S)Nc5ccc(S(=O)(=O)Nc6ncccn6)cc5)CC4)c3c2cc1OC] |
| 32-4 | 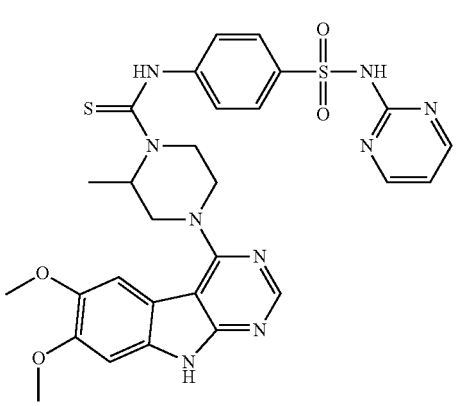 [SMILES: COc1cc2[nH]c3ncnc(N4CCN(C(=S)Nc5ccc(S(=O)(=O)Nc6ncccn6)cc5)C(C)C4)c3c2cc1OC] |
| 32-5 | 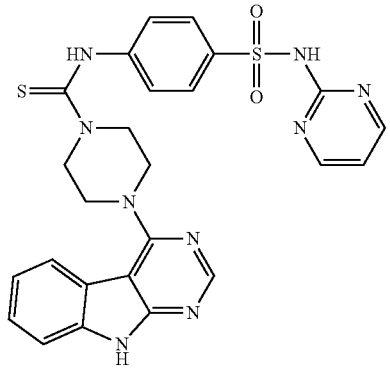 [SMILES: O=S(=O)(Nc1ncccn1)c1ccc(NC(=S)N2CCN(c3ncnc4[nH]c5ccccc5c34)CC2)cc1] |
| 32-6 | 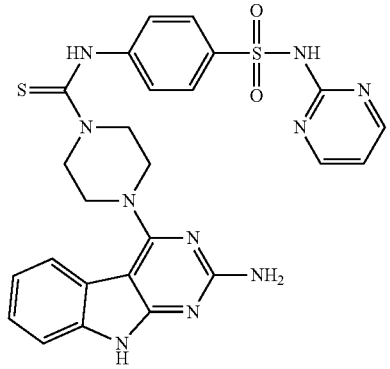 [SMILES: Nc1nc(N2CCN(C(=S)Nc3ccc(S(=O)(=O)Nc4ncccn4)cc3)CC2)c2c(n1)[nH]c1ccccc12] |

TABLE 3-continued
| No | Structure* |
|---|---|
| 32-7 | 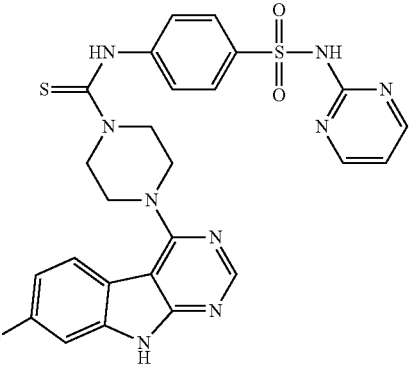 |
| 32-8 | 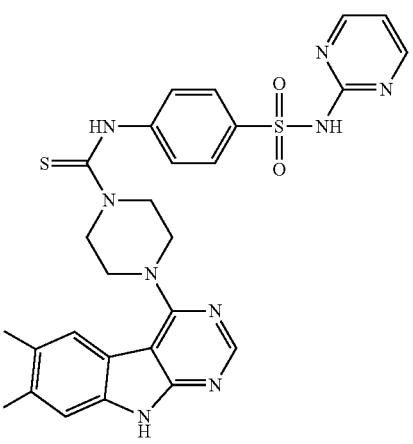 |
| 32-9 | 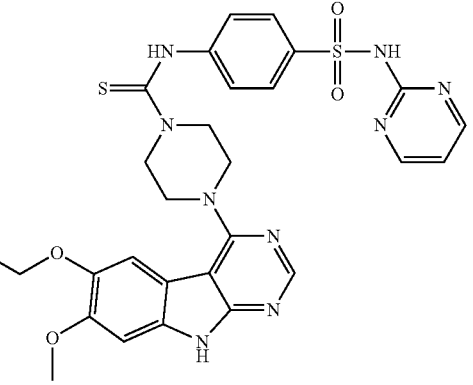 |
| 32-10 | 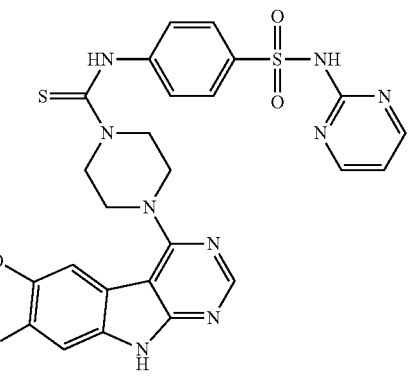 |

TABLE 3-continued
| No | Structure* |
|---|---|
| 32-11 | 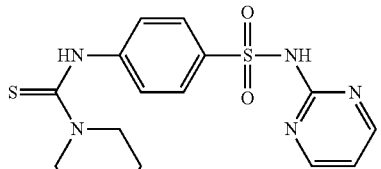 |
| 32-12 | 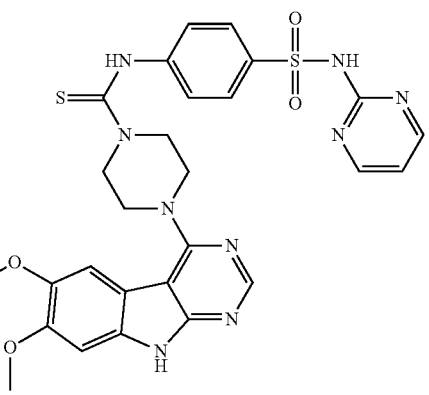 |
| 32-13 | 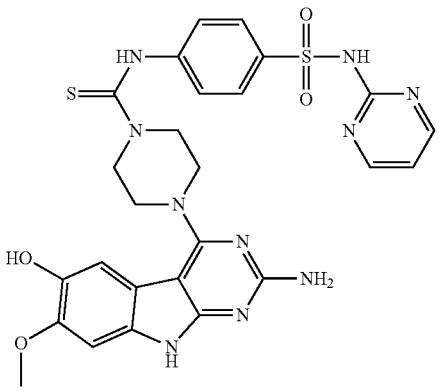 [SMILES: COc1cc2[nH]c3nc(N)nc(N4CCN(C(=S)Nc5ccc(S(=O)(=O)Nc6ncccn6)cc5)CC4)c3c2cc1O] |
| 32-14 | 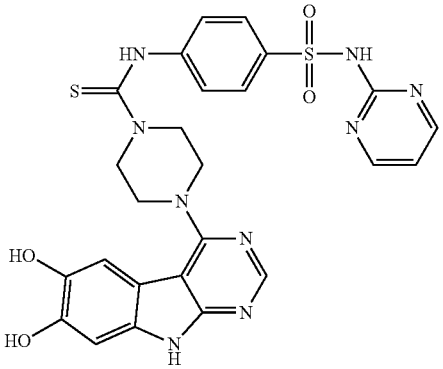 [SMILES: O=S(=O)(Nc1ncccn1)c1ccc(NC(=S)N2CCN(c3ncnc4[nH]c5cc(O)c(O)cc5c34)CC2)cc1] |

TABLE 3-continued
| No | Structure* |
|---|---|
| 32-15 | 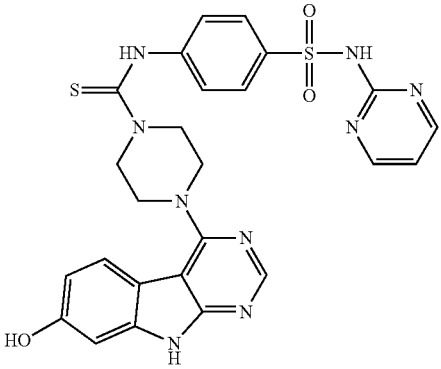 [SMILES: O=S(=O)(Nc1ncccn1)c1ccc(NC(=S)N2CCN(c3ncnc4[nH]c5cc(O)ccc5c34)CC2)cc1] |
| 32-16 | 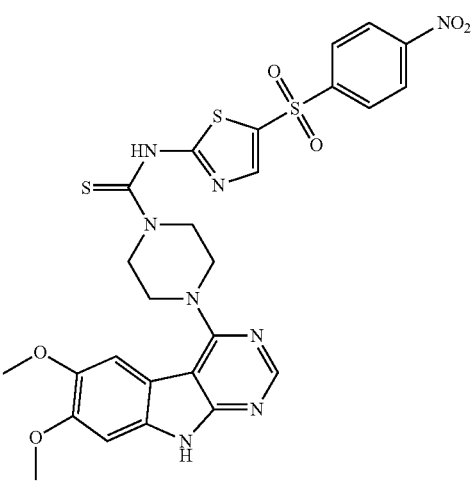 [SMILES: COc1cc2[nH]c3ncnc(N4CCN(C(=S)Nc5ncc(S(=O)(=O)c6ccc(N)cc6)s5)CC4)c3c2cc1OC] |
| 32-17 | 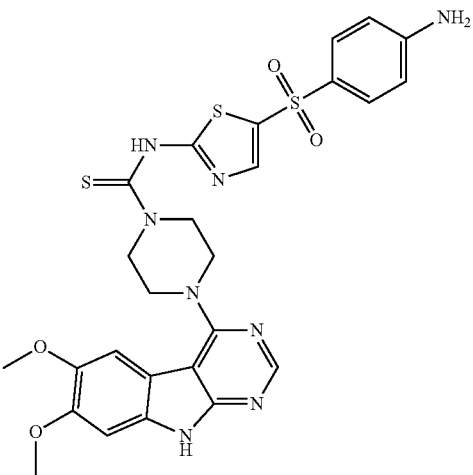 |

TABLE 3-continued

| No | Structure* |
|---|---|
| 32-18 | 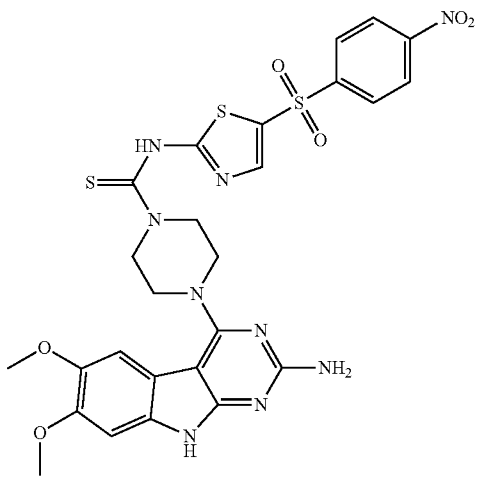 [SMILES: COc1cc2[nH]c3nc(N)nc(N4CCN(C(=S)Nc5ncc(S(=O)(=O)c6ccc([N+](=O)[O-])cc6)s5)CC4)c3c2cc1OC] |
| 32-19 | 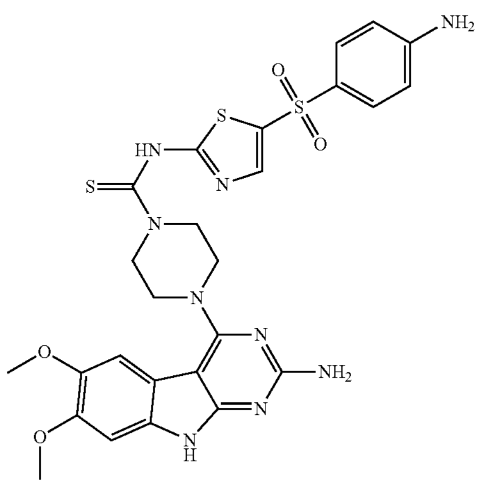 |
| 32-20 | 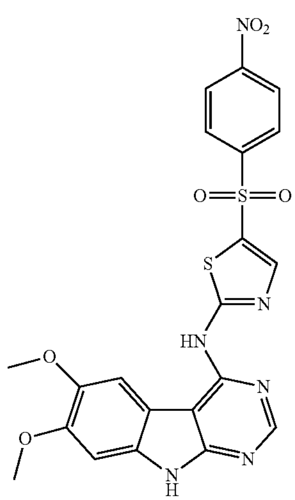 [SMILES: COc1cc2[nH]c3ncnc(Nc4ncc(S(=O)(=O)c5ccc([N+](=O)[O-])cc5)s4)c3c2cc1OC] |

TABLE 3-continued

| No | Structure* |
|---|---|
| 32-21 | 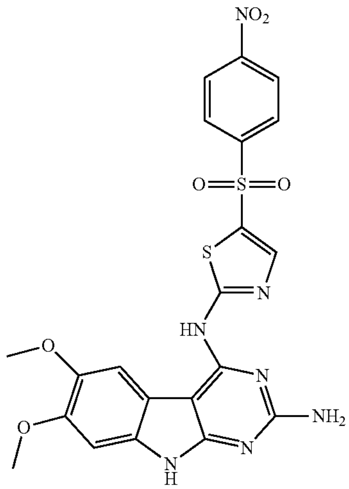 |
| 32-22 | 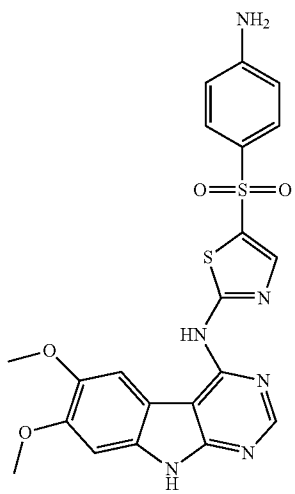 |
| 32-23 | 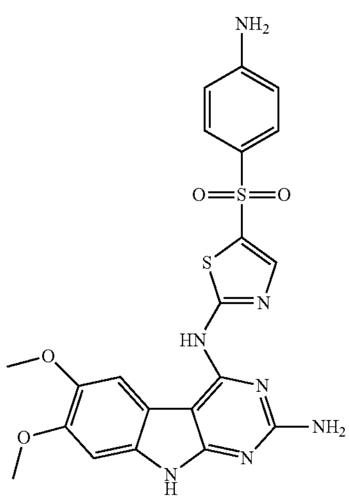 [SMILES: COc1cc2[nH]c3nc(N)nc(Nc4ncc(S(=O)(=O)c5ccc(N)cc5)s4)c3c2cc1OC] |

TABLE 3-continued

| No | Structure* |
|---|---|
| 32-24 | 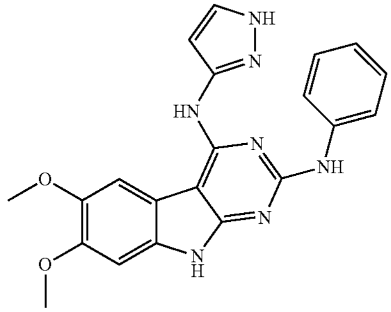 [SMILES: COc1cc2[nH]c3nc(Nc4ccccc4)nc(Nc4cc[nH]n4)c3c2cc1OC] |
| 32-25 | 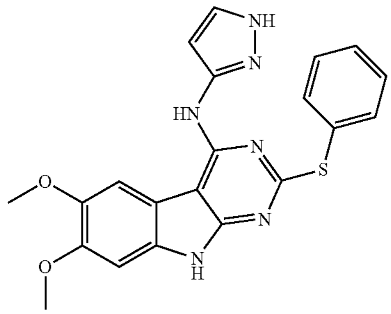 [SMILES: COc1cc2[nH]c3nc(Sc4ccccc4)nc(Nc4cc[nH]n4)c3c2cc1OC] |
| 32-26 | 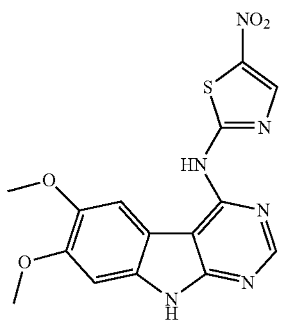 [SMILES: COc1cc2[nH]c3ncnc(Nc4ncc([N+](=O)[O-])s4)c3c2cc1OC] |
| 32-27 | 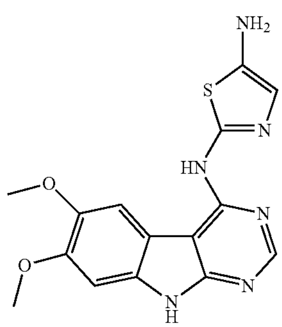 |
| 32-28 | 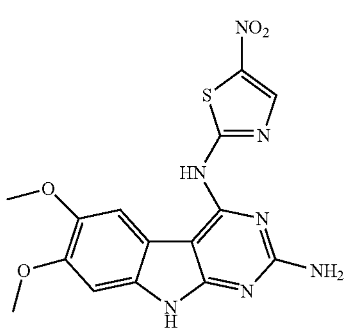 [SMILES: COc1cc2[nH]c3nc(N)nc(Nc4ncc([N+](=O)[O-])s4)c3c2cc1OC] |

TABLE 3-continued
| No | Structure* |
|---|---|
| 32-29 | 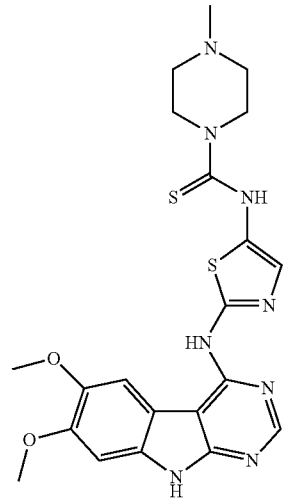 [SMILES: COc1cc2[nH]c3ncnc(Nc4ncc(NC(=S)N5CCN(C)CC5)s4)c3c2cc1OC] |
| 32-30 | 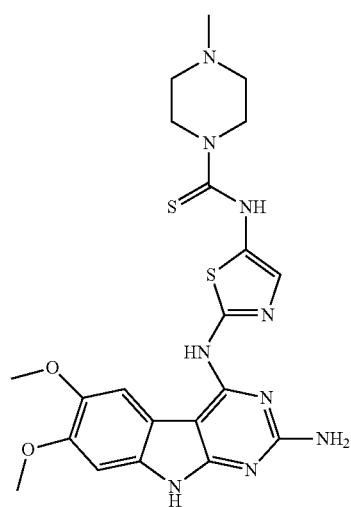 [SMILES: COc1cc2[nH]c3nc(N)nc(Nc4ncc(NC(=S)N5CCN(C)CC5)s4)c3c2cc1OC] |

TABLE 3-continued

| No | Structure* |
|---|---|
| 32-31 | 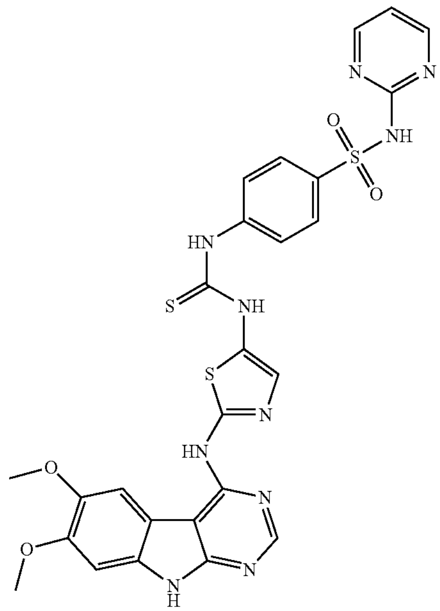 [SMILES: COc1cc2[nH]c3ncnc(Nc4ncc(NC(=S)Nc5ccc(S(=O)(=O)Nc6ncccn6)cc5)s4)c3c2cc1OC] |
| 32-32 | 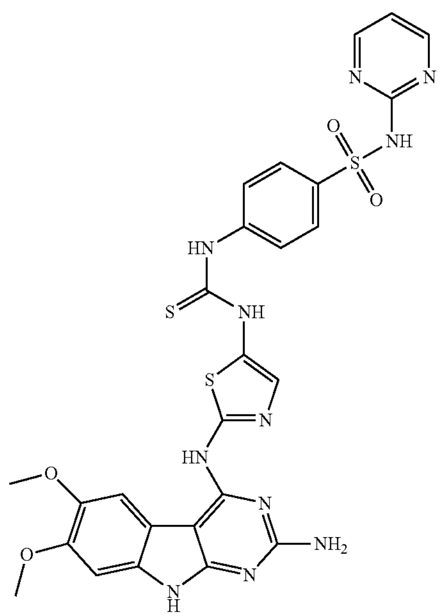 [SMILES: COc1cc2[nH]c3nc(N)nc(Nc4ncc(NC(=S)Nc5ccc(S(=O)(=O)Nc6ncccn6)cc5)s4)c3c2cc1OC] |
| 32-33 | 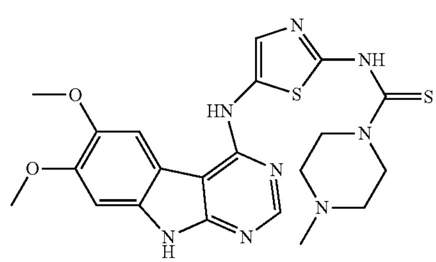 [SMILES: COc1cc2[nH]c3ncnc(Nc4cnc(NC(=S)N5CCN(C)CC5)s4)c3c2cc1OC] |

TABLE 3-continued

| No | Structure* |
|---|---|
| 32-34 | 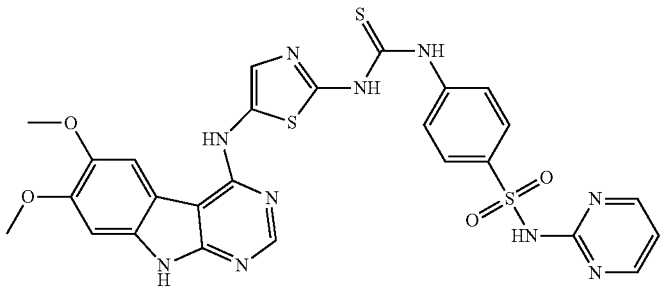 [SMILES: COc1cc2[nH]c3ncnc(Nc4cnc(NC(=S)Nc5ccc(S(=O)(=O)Nc6ncccn6)cc5)s4)c3c2cc1OC] |
| 32-35 | 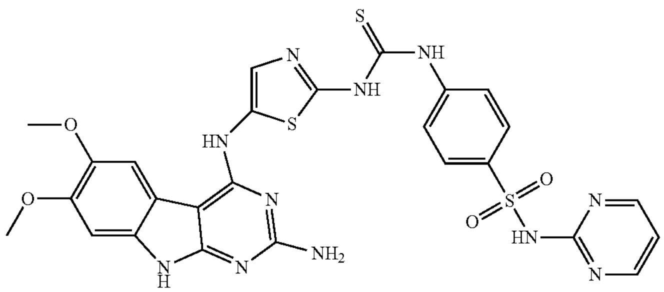 [SMILES: COc1cc2[nH]c3nc(N)nc(Nc4cnc(NC(=S)Nc5ccc(S(=O)(=O)Nc6ncccn6)cc5)s4)c3c2cc1OC] |
| 32-36 | 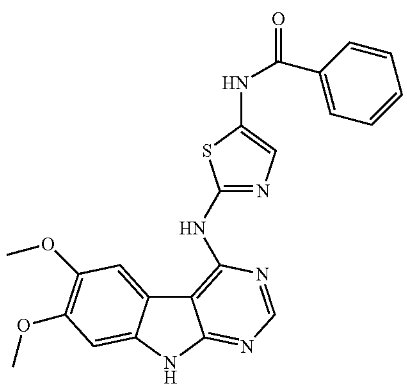 [SMILES: COc1cc2[nH]c3ncnc(Nc4ncc(NC(=O)c5ccccc5)s4)c3c2cc1OC] |
| 32-37 | 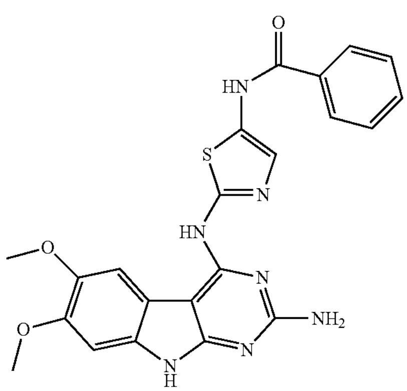 [SMILES: COc1cc2[nH]c3nc(N)nc(Nc4ncc(NC(=O)c5ccccc5)s4)c3c2cc1OC] |
| 32-38 | 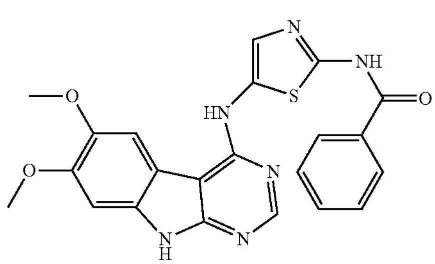 [SMILES: COc1cc2[nH]c3ncnc(Nc4cnc(NC(=O)c5ccccc5)s4)c3c2cc1OC] |

TABLE 3-continued

| No | Structure* |
|---|---|
| 32-39 | 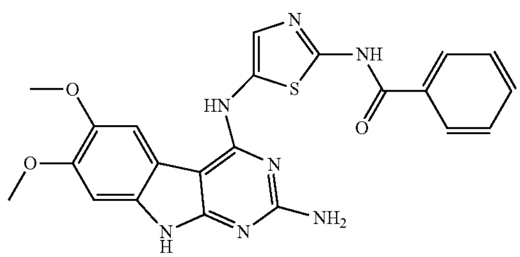 [SMILES: COc1cc2[nH]c3nc(N)nc(Nc4cnc(NC(=O)c5ccccc5)s4)c3c2cc1OC] |
| 32-40 | 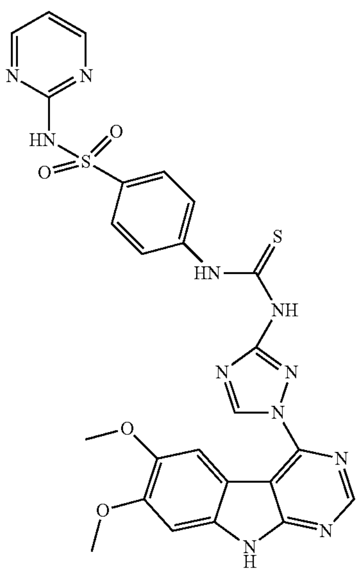 [SMILES: COc1cc2[nH]c3ncnc(-n4cnc(NC(=S)Nc5ccc(S(=O)(=O)Nc6ncccn6)cc5)n4)c3c2cc1OC] |
| 32-41 | 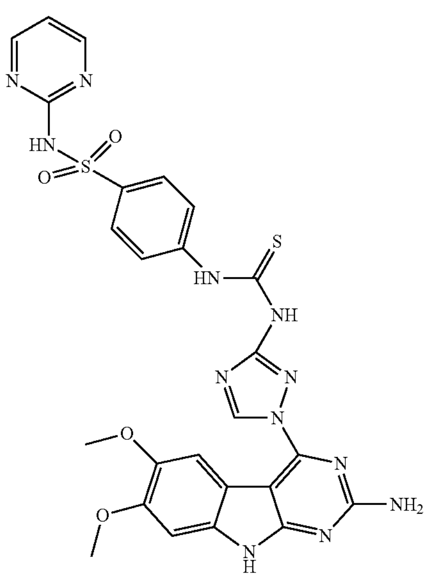 [SMILES: COc1cc2[nH]c3nc(N)nc(-n4cnc(NC(=S)Nc5ccc(S(=O)(=O)Nc6ncccn6)cc5)n4)c3c2cc1OC] |

TABLE 3-continued
| No | Structure* |
|---|---|
| 32-42 | 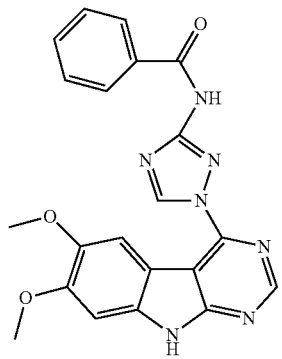 [SMILES: COc1cc2[nH]c3ncnc(-n4cnc(NC(=O)c5ccccc5)n4)c3c2cc1OC] |
| 32-43 | 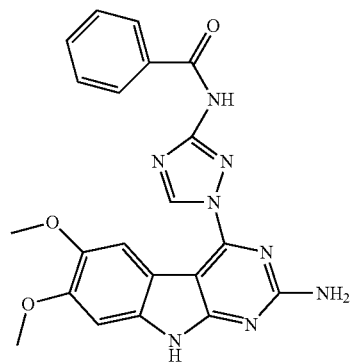 [SMILES: COc1cc2[nH]c3nc(N)nc(-n4cnc(NC(=O)c5ccccc5)n4)c3c2cc1OC] |
| 32-44 | 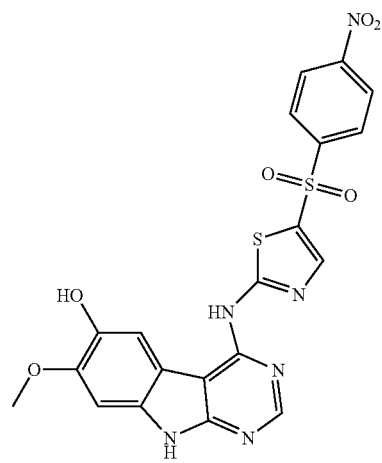 [SMILES: COc1cc2[nH]c3ncnc(Nc4ncc(S(=O)(=O)c5ccc([N+](=O)[O-])cc5)s4)c3c2cc1O] |

TABLE 3-continued
| No | Structure* |
|---|---|
| 32-45 | 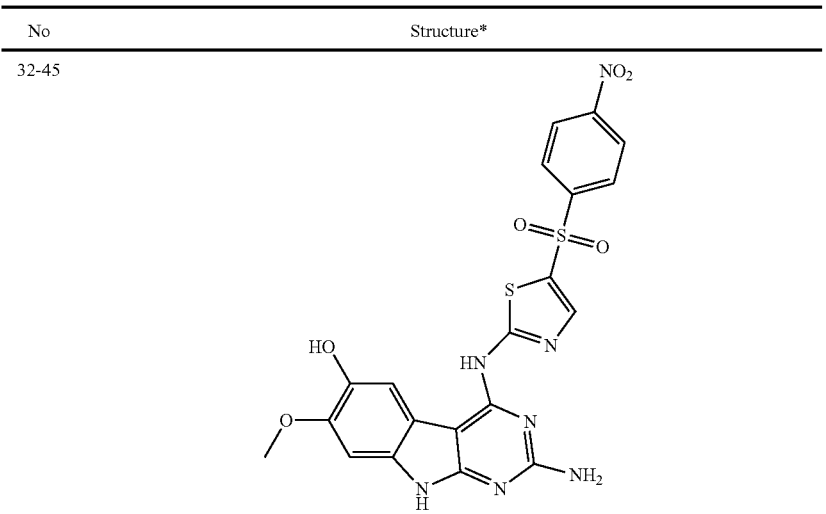 |
| 32-46 | 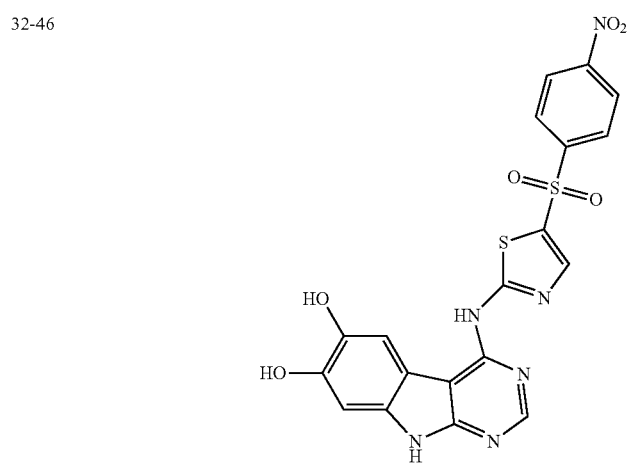 |
| 32-47 | 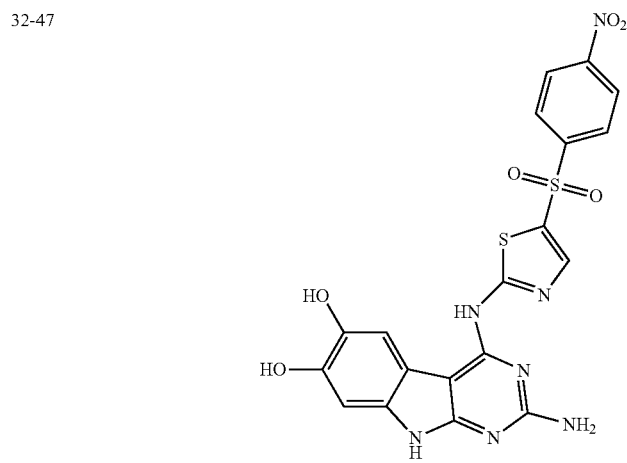 |

TABLE 3-continued
| No | Structure* |
|---|---|
| 32-48 | 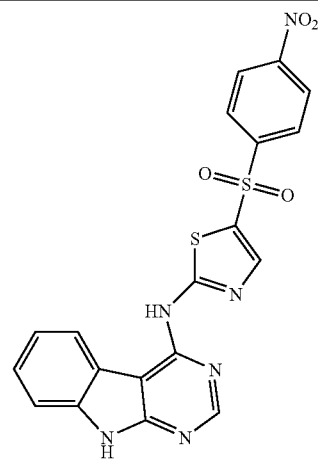 |
| 32-49 | 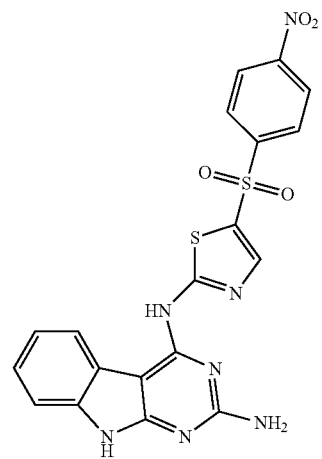 [SMILES: Nc1nc(Nc2ncc(S(=O)(=O)c3ccc([N+](=O)[O-])cc3)s2)c2c(n1)[nH]c1ccccc12] |
| 32-50 | 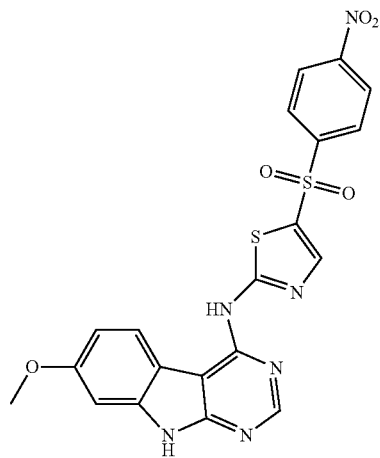 [SMILES: COc1ccc2c(c1)[nH]c1ncnc(Nc3ncc(S(=O)(=O)c4ccc([N+](=O)[O-])cc4)s3)c12] |

TABLE 3-continued
| No | Structure* |
|---|---|
| 32-51 | 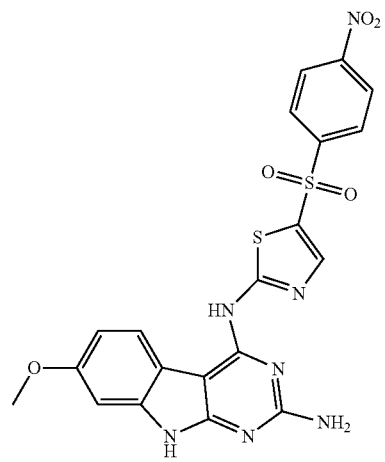 [SMILES: COc1ccc2c(c1)[nH]c1nc(N)nc(Nc3ncc(S(=O)(=O)c4ccc([N+](=O)[O-])cc4)s3)c12] |
| 32-52 | 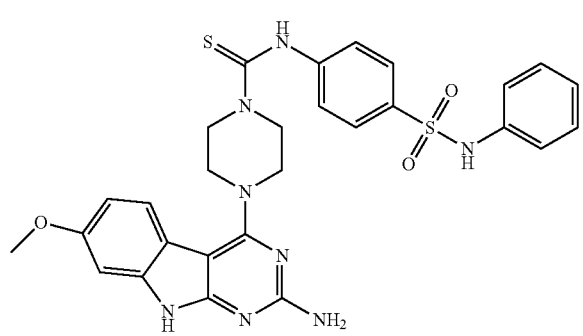 [SMILES: COc1ccc2c(c1)[nH]c1nc(N)nc(N3CCN(C(=S)Nc4ccc(S(=O)(=O)Nc5ccccc5)cc4)CC3)c12] |
| 32-53 | 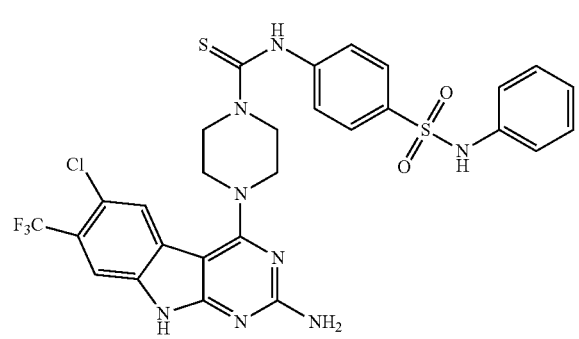 [SMILES: Nc1nc(N2CCN(C(=S)Nc3ccc(S(=O)(=O)Nc4ccccc4)cc3)CC2)c2c(n1)[nH]c1cc(C(F)(F)F)c(Cl)cc12] |
| 32-54 | 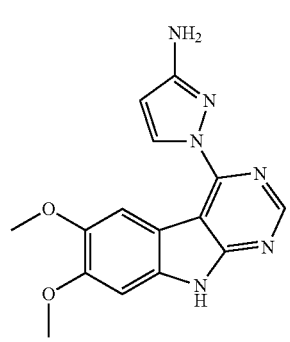 [SMILES: COc1cc2[nH]c3ncnc(-n4ccc(N)n4)c3c2cc1OC] |

TABLE 3-continued
| No | Structure* |
|---|---|
| 32-55 | 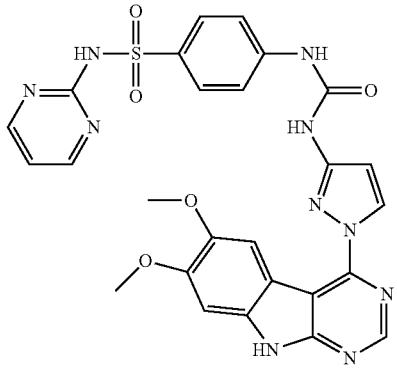 [SMILES: COc1cc2[nH]c3ncnc(-n4ccc(NC(=O)Nc5ccc(S(=O)(=O)Nc6ncccn6)cc5)n4)c3c2cc1OC] |
| 32-56 | 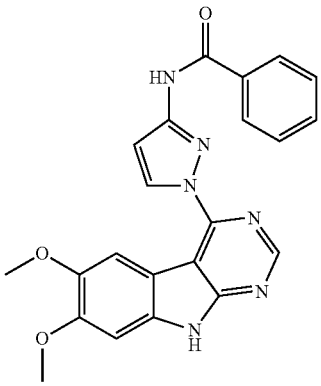 [SMILES: COc1cc2[nH]c3ncnc(-n4ccc(NC(=O)c5ccccc5)n4)c3c2cc1OC] |
| 32-57 | 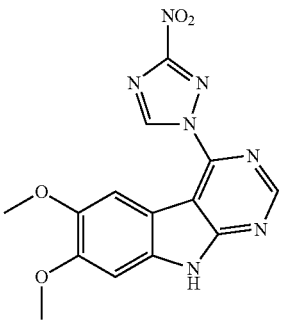 |
| 32-58 | 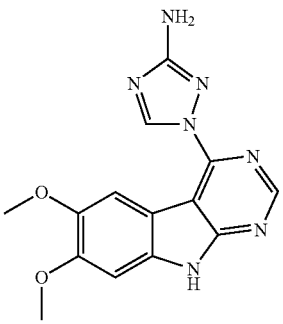 [SMILES: COc1cc2[nH]c3ncnc(-n4cnc(N)n4)c3c2cc1OC] |

TABLE 3-continued

| No | Structure* |
|---|---|
| 32-59 | 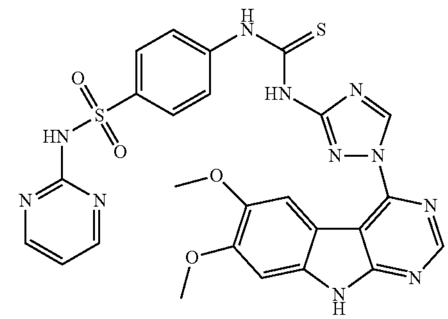 [SMILES: COc1cc2[nH]c3ncnc(-n4cnc(NC(=S)Nc5ccc(S(=O)(=O)Nc6ncccn6)cc5)n4)c3c2cc1OC] |
| 32-60 | 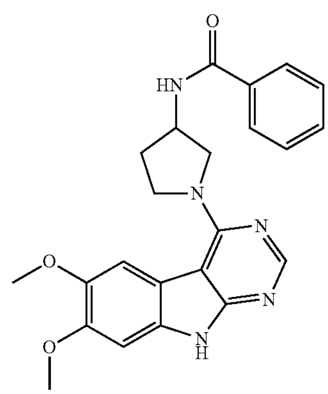 [SMILES: COc1cc2[nH]c3ncnc(N4CCC(NC(=O)c5ccccc5)C4)c3c2cc1OC] |
| 32-61 | 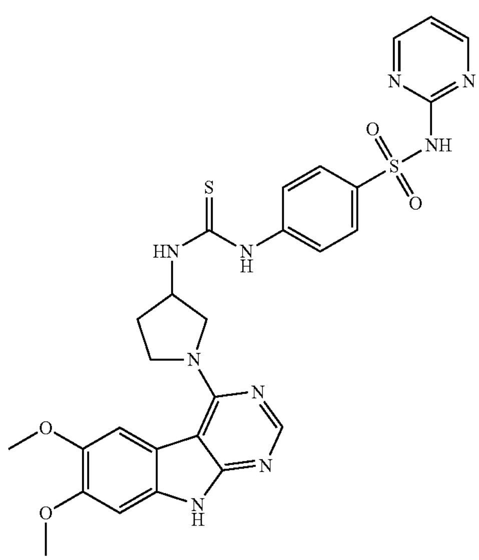 [SMILES: COc1cc2[nH]c3ncnc(N4CCC(NC(=S)Nc5ccc(S(=O)(=O)Nc6ncccn6)cc5)C4)c3c2cc1OC] |

TABLE 3-continued
| No | Structure* |
|---|---|
| 32-62 | 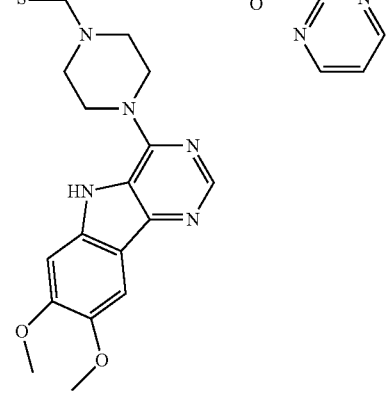 |
| 32-63 | 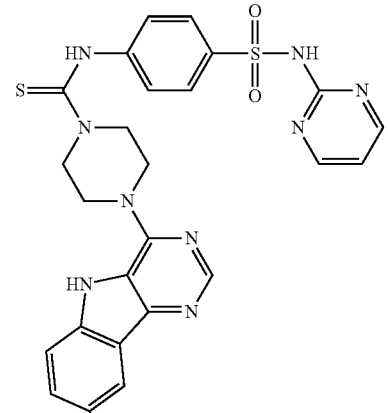 [SMILES: Nc1nc(N2CCN(C(=S)Nc3ccc(S(=O)(=O)Nc4ncccn4)cc3)CC2)c2[nH]c3ccccc3c2n1] |
| 32-64 | 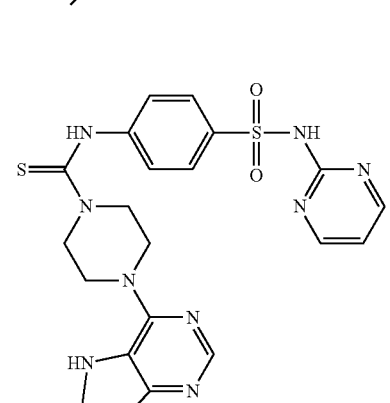 |

TABLE 3-continued

| No | Structure* |
|---|---|
| 32-65 | 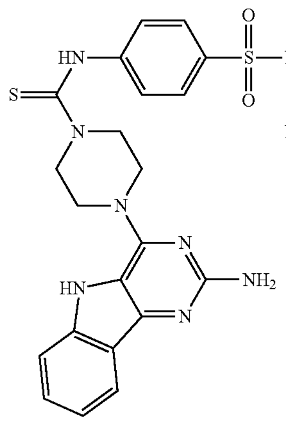 |
| 32-66 | 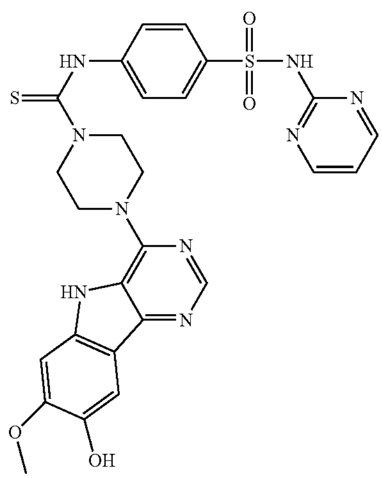 [SMILES: COc1cc2[nH]c3c(N4CCN(C(=S)Nc5ccc(S(=O)(=O)Nc6ncccn6)cc5)CC4)ncnc3c2cc1O] |
| 32-67 | 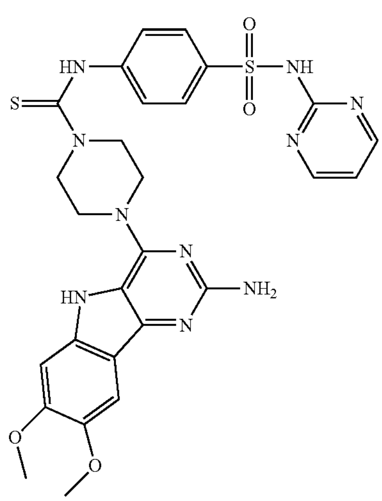 [SMILES: COc1cc2[nH]c3c(N4CCN(C(=S)Nc5ccc(S(=O)(=O)Nc6ncccn6)cc5)CC4)nc(N)nc3c2cc1OC] |

TABLE 3-continued

| No | Structure* |
|---|---|
| 32-68 | 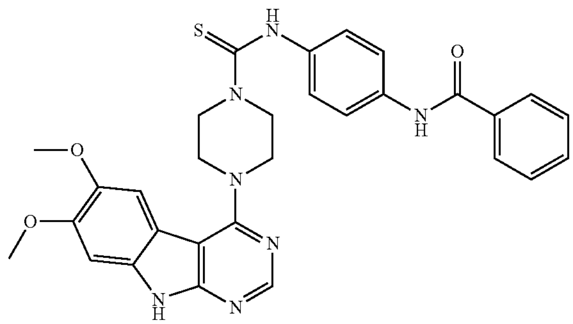 [SMILES: COc1cc2[nH]c3ncnc(N4CCN(C(=S)Nc5ccc(NC(=O)c6ccccc6)cc5)CC4)c3c2cc1OC] |
| 32-69 | 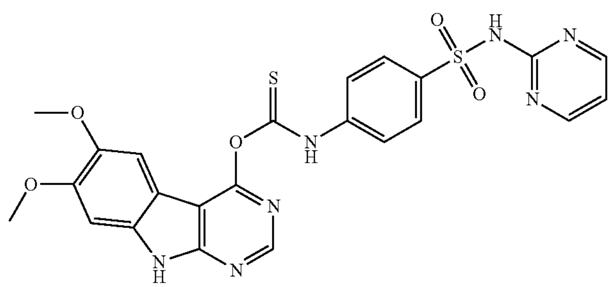 [SMILES: COc1cc2[nH]c3ncnc(OC(=S)Nc4ccc(S(=O)(=O)Nc5ncccn5)cc4)c3c2cc1OC] |
| 32-70 | 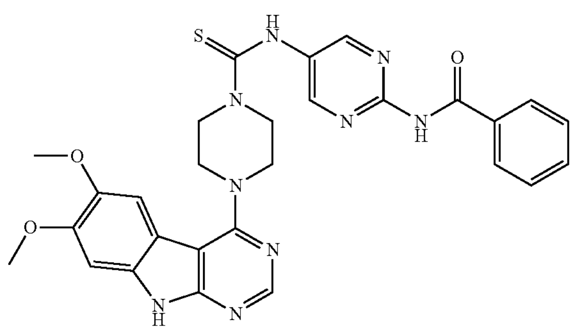 [SMILES: COc1cc2[nH]c3ncnc(N4CCN(C(=S)Nc5cnc(NC(=O)c6ccccc6)nc5)CC4)c3c2cc1OC] |
| 32-71 | 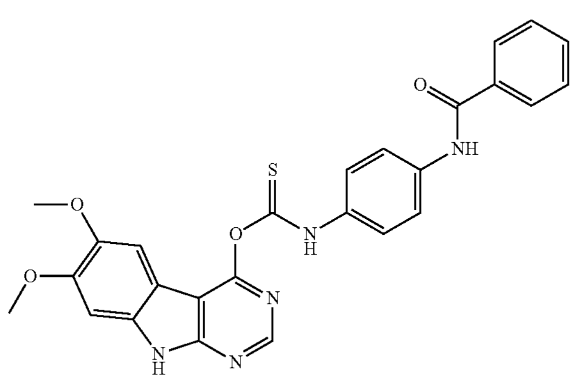 [SMILES: COc1cc2[nH]c3ncnc(OC(=S)Nc4ccc(NC(=O)c5ccccc5)cc4)c3c2cc1OC] |

TABLE 3-continued
| No | Structure* |
|---|---|
| 32-72 | 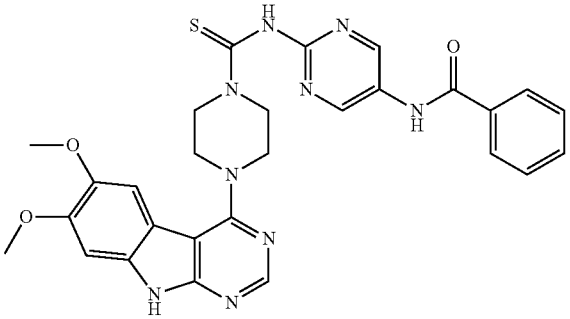 [SMILES: COc1cc2[nH]c3ncnc(N4CCN(C(=S)Nc5ncc(NC(=O)c6ccccc6)cn5)CC4)c3c2cc1OC] |
| 32-73 | 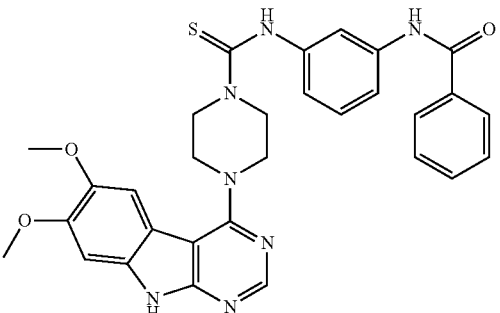 |
| 32-74 | 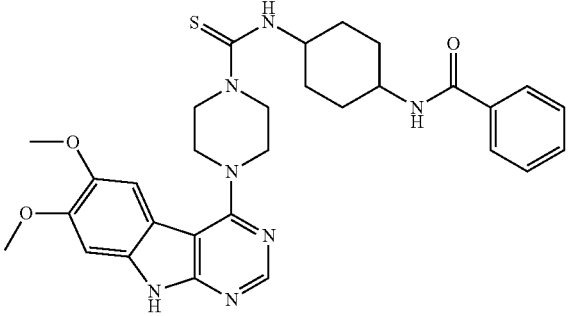 [SMILES: COc1cc2[nH]c3ncnc(N4CCN(C(=S)NC5CCC(NC(=O)c6ccccc6)CC5)CC4)c3c2cc1OC] |
| 32-75 | 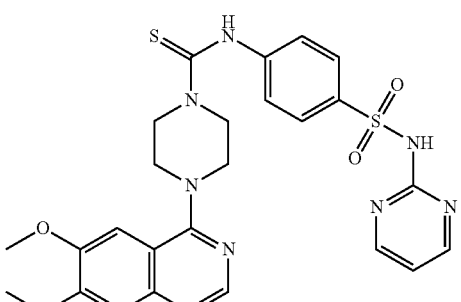 |
| 32-76 | 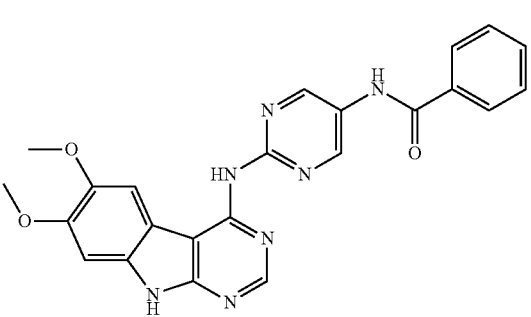 [SMILES: COc1cc2[nH]c3ncnc(Nc4ncc(NC(=O)c5ccccc5)cn4)c3c2cc1OC] |

TABLE 3-continued

| No | Structure* |
|---|---|
| 32-77 | 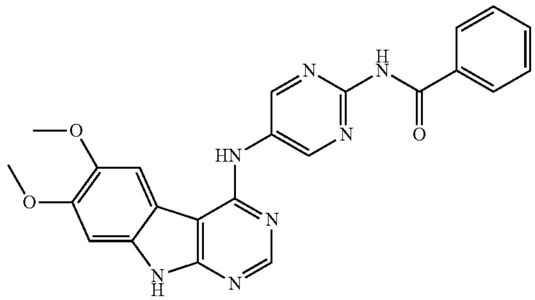 [SMILES: COc1cc2[nH]c3ncnc(Nc4cnc(NC(=O)c5ccccc5)nc4)c3c2cc1OC] |
| 32-78 | 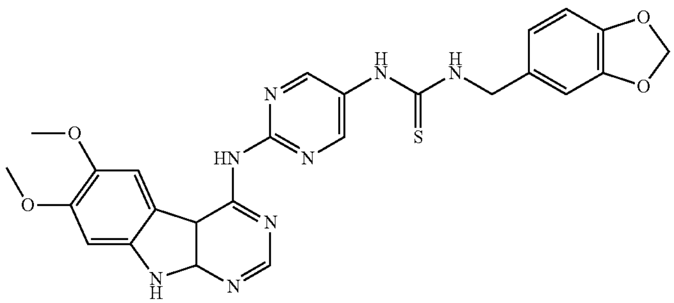 [SMILES: COc1cc2c(cc1OC)C1C(Nc3ncc(NC(=S)NCc4ccc5c(c4)OCO5)cn3)=NC=NC1N2] |
| 32-79 | 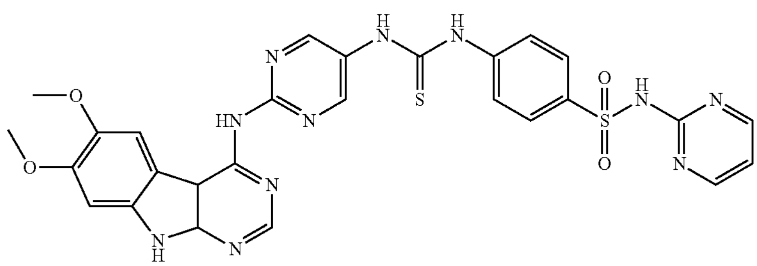 [SMILES: COc1cc2c(cc1OC)C1C(Nc3ncc(NC(=S)Nc4ccc(S(=O)(=O)Nc5ncccn5)cc4)cn3)=NC=NC1N2] |
| 32-80 | 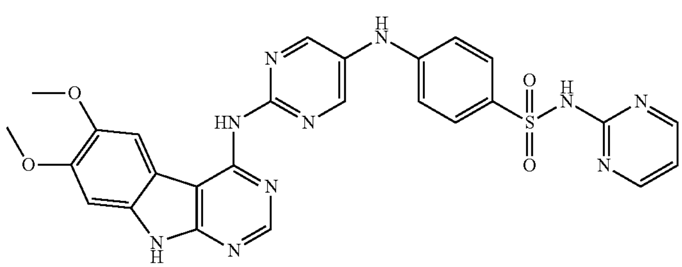 [SMILES: COc1cc2[nH]c3ncnc(Nc4ncc(Nc5ccc(S(=O)(=O)Nc6ncccn6)cc5)cn4)c3c2cc1OC] |
| 32-81 | 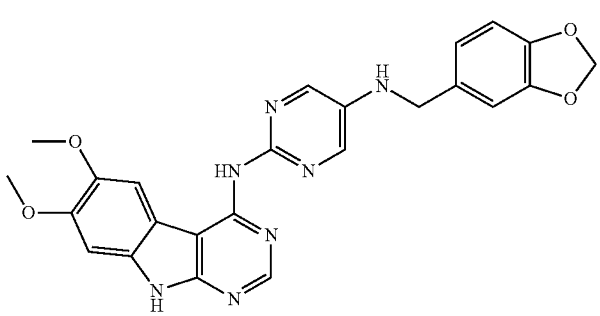 [SMILES: COc1cc2[nH]c3ncnc(Nc4ncc(NCc5ccc6c(c5)OCO6)cn4)c3c2cc1OC] |

TABLE 3-continued
| No | Structure* |
|---|---|
| 32-82 | 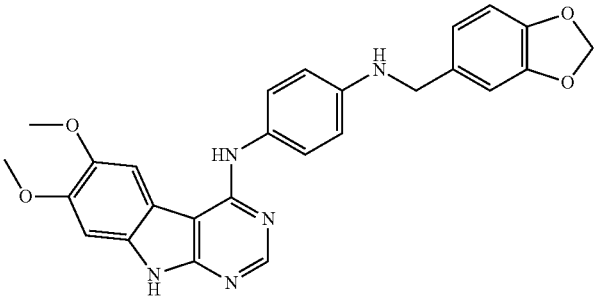 [SMILES: COc1cc2[nH]c3ncnc(Nc4ccc(NCc5ccc6c(c5)OCO6)cc4)c3c2cc1OC] |
| 32-83 | 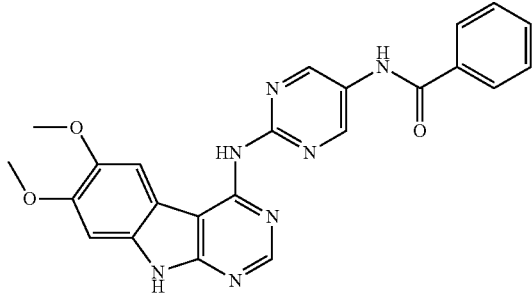 [SMILES: COc1cc2[nH]c3ncnc(Nc4ncc(NC(=O)c5ccccc5)cn4)c3c2cc1OC] |
| 32-84 | 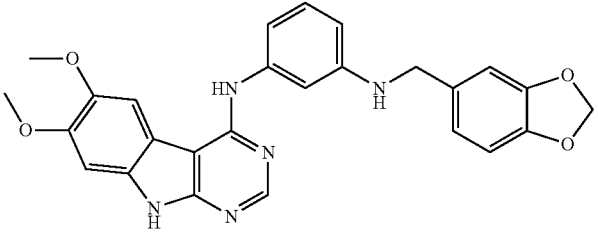 [SMILES: COc1cc2[nH]c3ncnc(Nc4cccc(NCc5ccc6c(c5)OCO6)c4)c3c2cc1OC] |
| 32-85 | 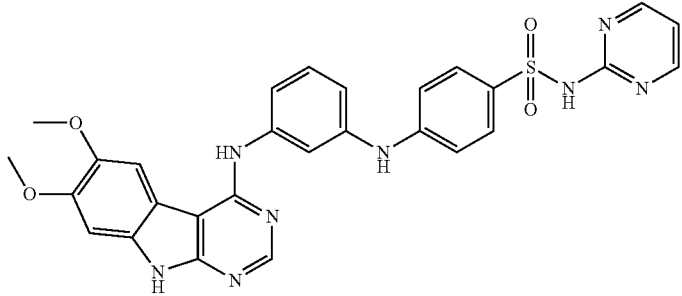 [SMILES: COc1cc2[nH]c3ncnc(Nc4cccc(Nc5ccc(S(=O)(=O)Nc6ncccn6)cc5)c4)c3c2cc1OC] |
| 32-86 | 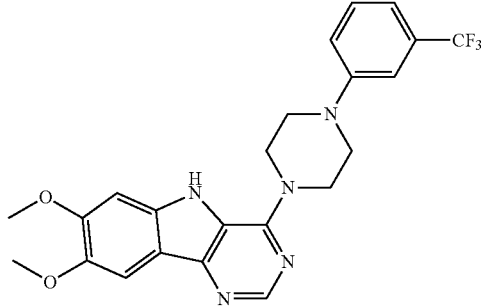 [SMILES: COc1cc2[nH]c3c(N4CCN(c5cccc(C(F)(F)F)c5)CC4)ncnc3c2cc1OC] |

TABLE 3-continued

| No | Structure* |
|---|---|
| 32-87 | 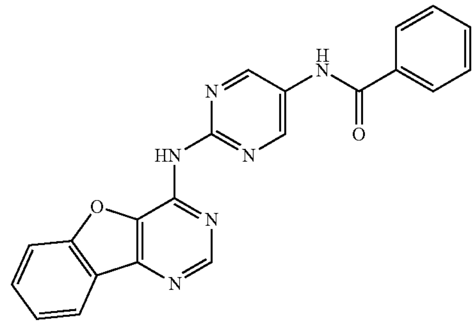 [SMILES: O=C(Nc1cnc(Nc2ncnc3c2oc2ccccc23)nc1)c1ccccc1] |
| 32-88 | 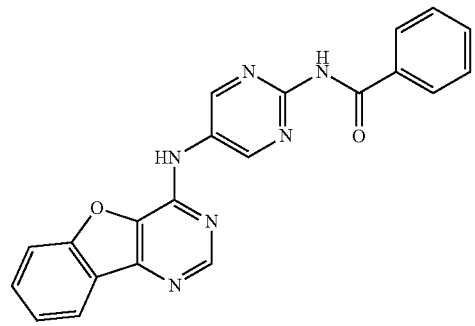 [SMILES: O=C(Nc1ncc(Nc2ncnc3c2oc2ccccc23)cn1)c1ccccc1] |
| 32-89 | 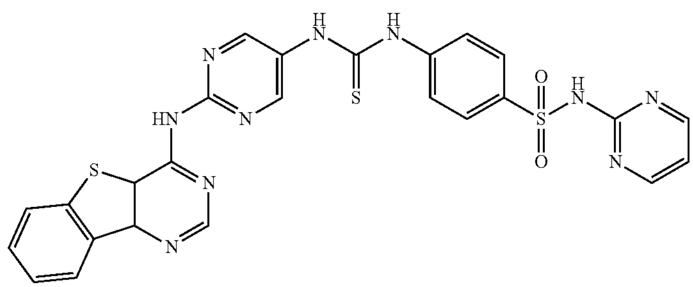 [SMILES: O=S(=O)(Nc1ncccn1)c1ccc(NC(=S)Nc2cnc(NC3=NC=NC4c5ccccc5SC34)nc2)cc1] |
| 32-90 | 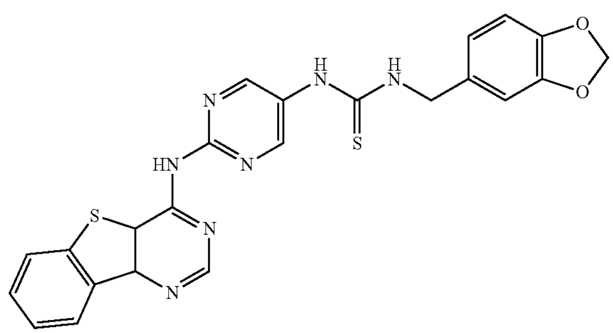 [SMILES: S=C(NCc1ccc2c(c1)OCO2)Nc1cnc(NC2=NC=NC3c4ccccc4SC23)nc1] |
| 32-91 | 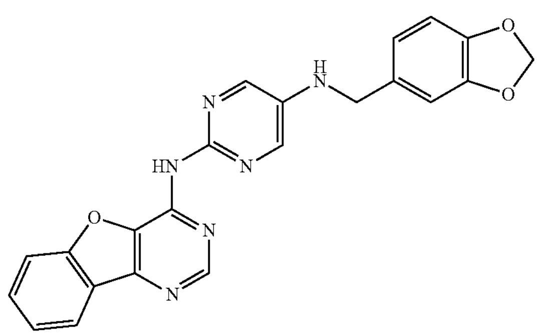 |

TABLE 3-continued
| No | Structure* |
|---|---|
| 32-92 | 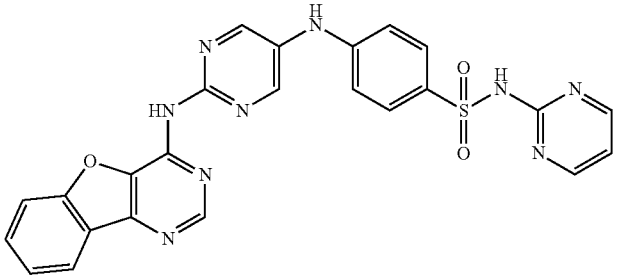 [SMILES: O=S(=O)(Nc1ncccn1)c1ccc(Nc2cnc(Nc3ncnc4c3oc3ccccc34)nc2)cc1] |
| 32-93 | 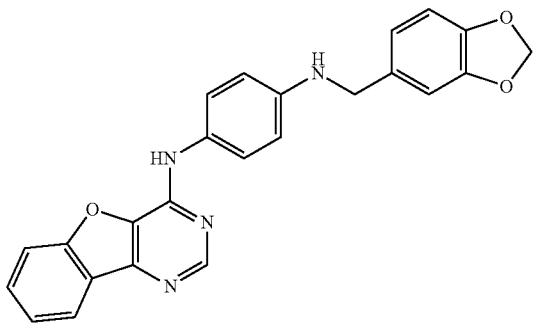 |
| 32-94 | 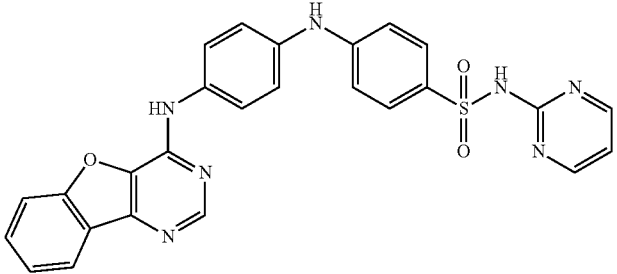 [SMILES: O=S(=O)(Nc1ncccn1)c1ccc(Nc2ccc(Nc3ncnc4c3oc3ccccc34)cc2)cc1] |
| 32-95 | 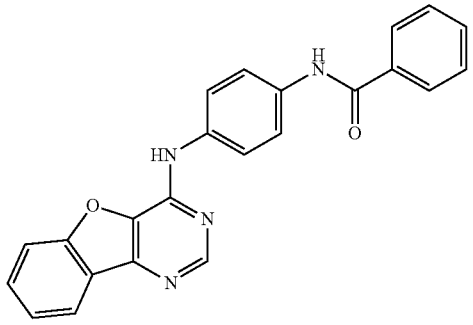 [SMILES: O=C(Nc1ccc(Nc2ncnc3c2oc2ccccc23)cc1)c1ccccc1] |
| 32-96 | 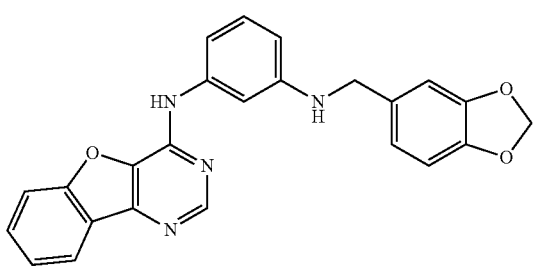 [SMILES: c1cc(NCc2ccc3c(c2)OCO3)cc(Nc2ncnc3c2oc2ccccc23)c1] |

| No | Structure* |
|---|---|
| 32-97 | 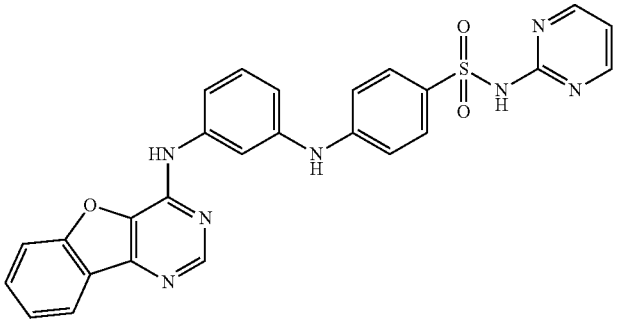 [SMILES: O=S(=O)(Nc1ncccn1)c1ccc(Nc2cccc(Nc3ncnc4c3oc3ccccc34)c2)cc1] |
| 32-98 | 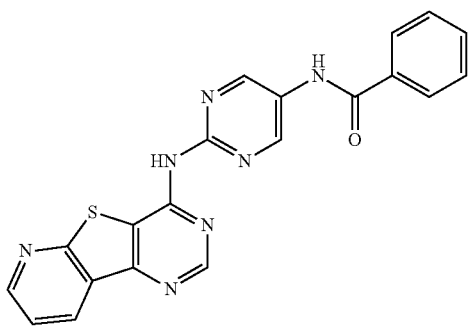 [SMILES: O=C(Nc1cnc(Nc2ncnc3c2sc2ncccc23)nc1)c1ccccc1] |
| 32-99 | 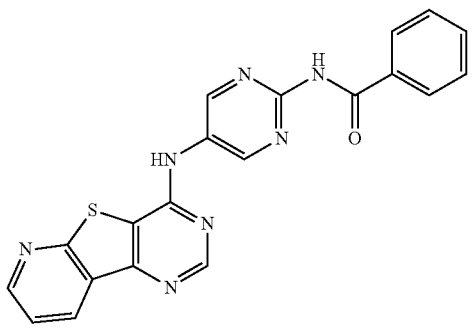 [SMILES: O=C(Nc1ncc(Nc2ncnc3c2sc2ncccc23)cn1)c1ccccc1] |
| 32-100 | 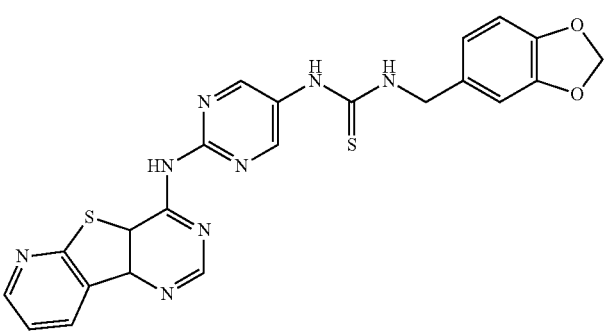 [SMILES: S=C(NCc1ccc2c(c1)OCO2)Nc1cnc(NC2=NC=NC3c4cccnc4SC23)nc1] |
| 32-101 | 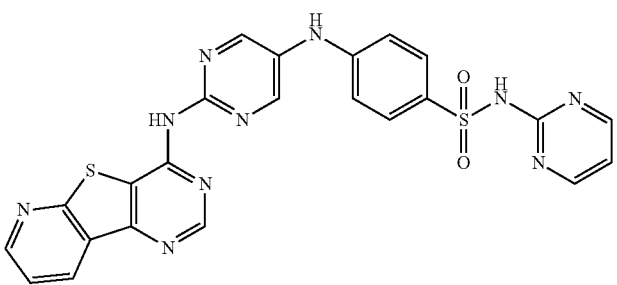 [SMILES: O=S(=O)(Nc1ncccn1)c1ccc(Nc2cnc(Nc3ncnc4c3sc3ncccc34)nc2)cc1] |

TABLE 3-continued

| No | Structure* |
|---|---|
| 32-102 | 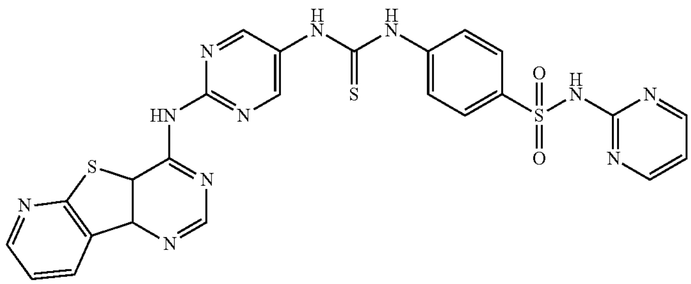 [SMILES: O=S(=O)(Nc1ncccn1)c1ccc(NC(=S)Nc2cnc(NC3=NC=NC4c5cccnc5SC34)nc2)cc1] |
| 32-103 | 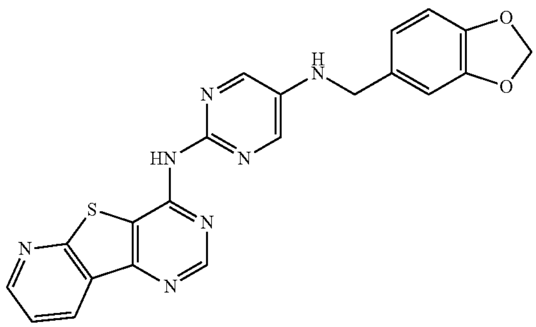 [SMILES: c1cnc2sc3c(Nc4ncc(NCc5ccc6c(c5)OCO6)cn4)ncnc3c2c1] |
| 32-104 | 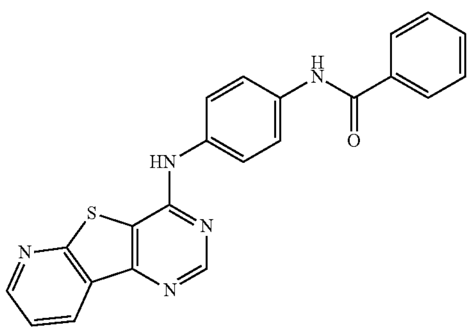 [SMILES: O=C(Nc1ccc(Nc2ncnc3c2sc2ncccc23)cc1)c1ccccc1] |
| 32-105 | 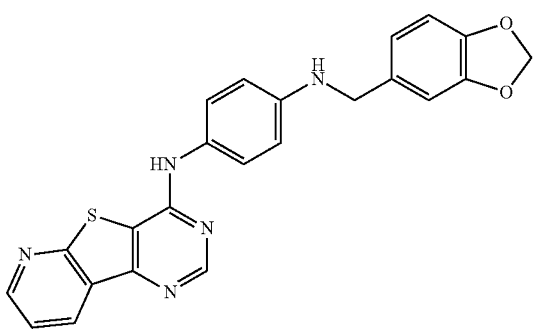 [SMILES: c1cnc2sc3c(Nc4ccc(NCc5ccc6c(c5)OCO6)cc4)ncnc3c2c1] |
| 32-106 | 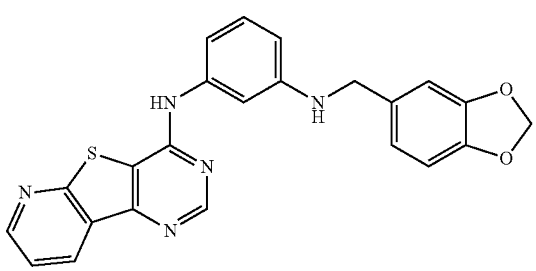 [SMILES: c1cc(NCc2ccc3c(c2)OCO3)cc(Nc2ncnc3c2sc2ncccc23)c1] |

TABLE 3-continued
| No | Structure* |
|---|---|
| 32-107 | 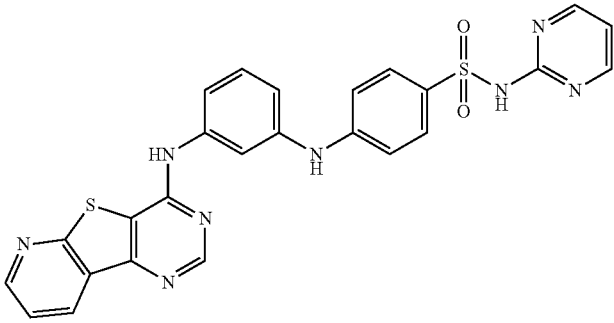 [SMILES: O=S(=O)(Nc1ncccn1)c1ccc(Nc2cccc(Nc3ncnc4c3sc3ncccc34)c2)cc1] |
| 32-108 | 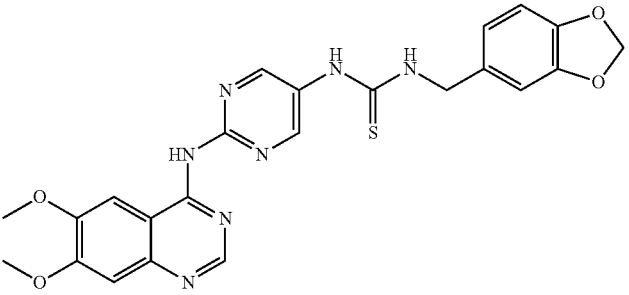 [SMILES: COc1cc2ncnc(Nc3ncc(NC(=S)NCc4ccc5c(c4)OCO5)cn3)c2cc1OC] |
| 32-109 | 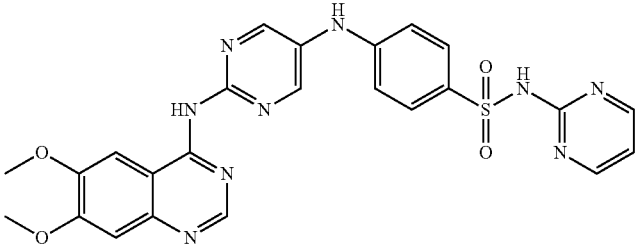 [SMILES: COc1cc2ncnc(Nc3ncc(Nc4ccc(S(=O)(=O)Nc5ncccn5)cc4)cn3)c2cc1OC] |
| 32-110 | 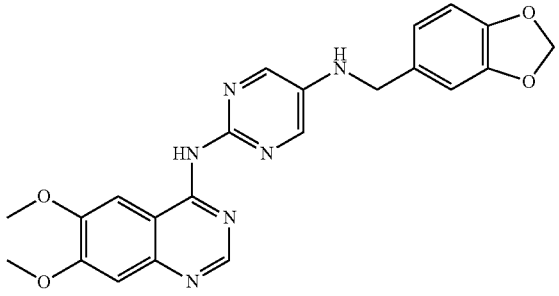 [SMILES: COc1cc2ncnc(Nc3ncc(NCc4ccc5c(c4)OCO5)cn3)c2cc1OC] |
| 32-111 | 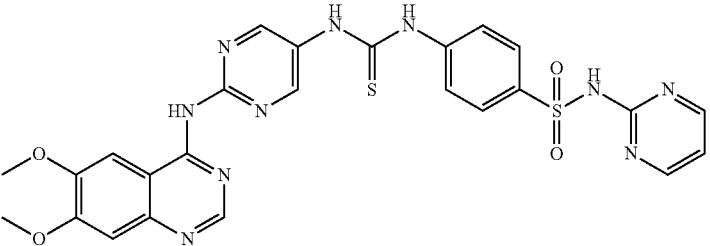 [SMILES: COc1cc2ncnc(Nc3ncc(NC(=S)Nc4ccc(S(=O)(=O)Nc5ncccn5)cc4)cn3)c2cc1OC] |

TABLE 3-continued
| No | Structure* |
|---|---|
| 32-112 | 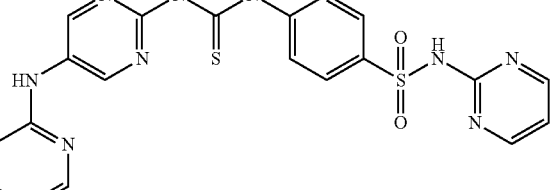 |
| 32-113 | 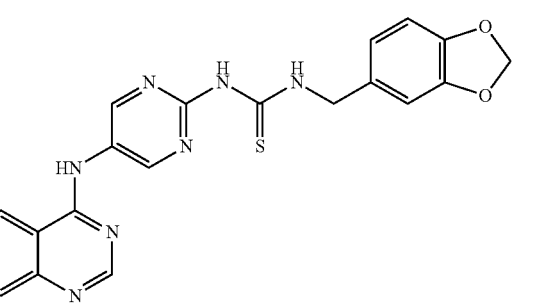 |
| 32-114 | 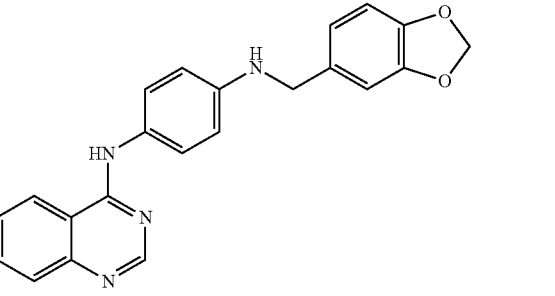 |
| 32-115 | 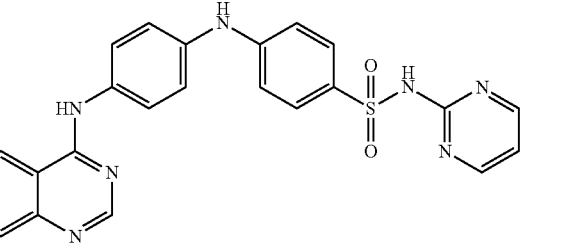 |
| 32-116 | 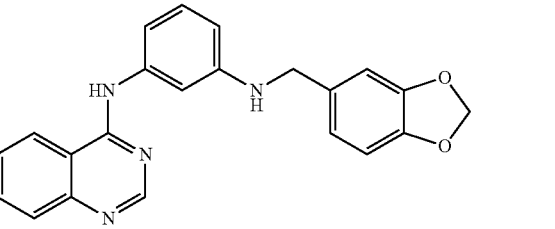 |

TABLE 3-continued

| No | Structure* |
|---|---|
| 32-117 | (structure) |

Example 33

Compound (II-2-6) Protein Kinase Inhibitory Activity

The protein serine-threonine kinases cAMP PK, MKK6 and Cdk1 were tested alongside Aurora-2 kinase to evaluate the activity of compound (II-2-6) against these protein kinases. Briefly, in this assay kinase activity is determined by quantifying the amount of ATP remaining in solution following the kinase reaction by measuring the relative light units (RLU) produced by luciferase using a luminometer. Percent activity was determined for individual compounds by comparing luminometer readings of drug-treated reactions to controls containing no drug ($RLU_{No\ Inhib}$) and no Aurora-2 enzyme ($RLU_{No\ Kinase}$) in the following equation:

$$\text{Percent Inhibition} = \frac{RLU_{No\ Kinase} - RLU_{drug}}{RLU_{No\ Kinase} - RLU_{No\ Inhib}} \times 100$$

In a 50 μl reaction, 20 ng of recombinant aurora-2 kinase (Upstate, Lake Placid, N.Y.) was incubated at 30° C. for two hours with shaking (360 rpm) with 62.50 Kemptide (Calbiochem, San Diego, Calif.), 3 μM ATP (Invitrogen, Carlsbad, Calif.) and kinase reaction buffer (40 mM Tris-HCl, 20 mM $MgCl_2$ and 0.1 μg/μl bovine serum albumin). The value of 30 ATP was determined to be the Km (concentration at which the enzyme is working at 50 μl maximum velocity) for the amount of enzyme used in this assay. This reaction was carried out in the presence of drug substances, which had been previously diluted to desired concentrations in DMSO. After incubation, 50 μl of Kinase-Glo® (Promega, Inc., Madison, Wis.) solution was added to each reaction mixture and allowed to equilibrate for 10 minutes at room temperature. Kinase-Glo solution contains luciferase enzyme and luciferin, which react with ATP to produce light. Kinase activity is determined by quantifying the amount of ATP remaining in solution following the kinase reaction by measuring the relative light units (RLU) produced by luciferase using a luminometer (Thermo Electron Corporation, Vantaa, Finland).

Figure 27:
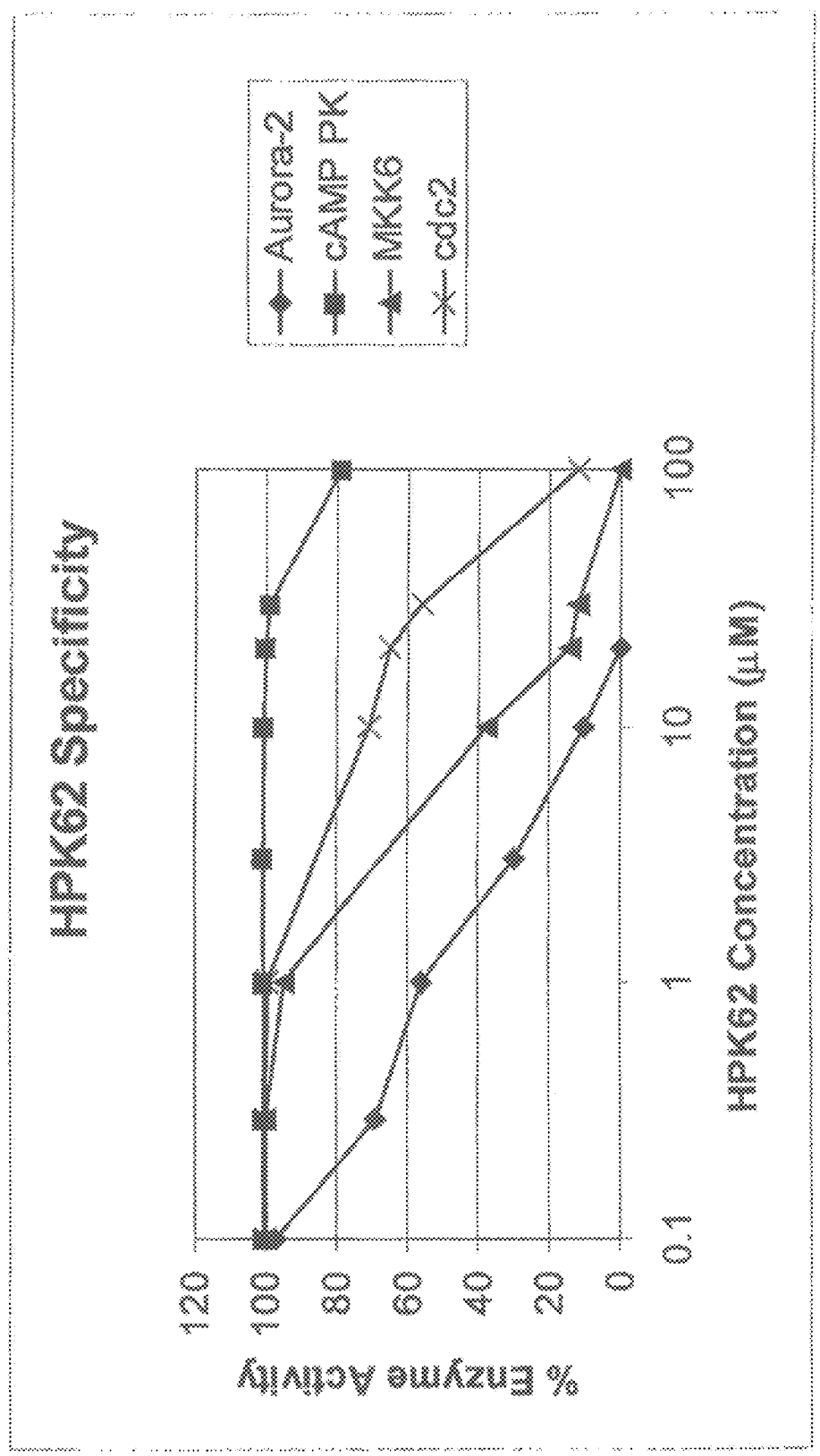
FIG. 27 shows the kinase inhibitory activity of compound (II-2-6) against multiple protein kinases.

The results of these experiments are shown in FIG. 27. Compound (II-2-6) had inhibitory activity against each of the kinases tested, with highest activity against Aurora-2 kinase.

Example 34

Synthesis and Analysis of Further Illustrative Compounds

Compound (III-1-3), also referred to herein as HPK56/MP-470, is an illustrative compound of the present invention having the following structure:

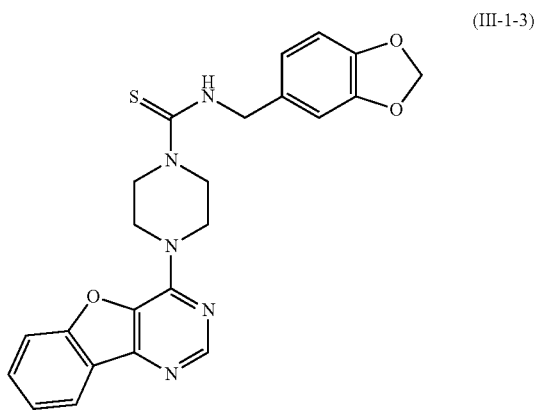 [SMILES: S=C(NCc1ccc2c(c1)OCO2)N1CCN(c2ncnc3c2oc2ccccc23)CC1]

(III-1-3)

Analogues of (III-1-3) were designed and synthesized in order to evaluate and optimize kinase selectivity, aqueous solubility, and to improve pharmacokinetic and pharmacodynamic profiles. Illustrative synthesis approaches for generating (III-1-3) analogues are depicted in the synthesis schemes below. Synthesis of $R_1$ substituted benzofuranopyrimidines was undertaken. The methyl 3-guanidinobenzofuran-2-carboxylate is prepared from methyl 3-aminobenzofuran-2-carboxylate by reacting with cyanoacetamide in presence of dioxane and dry HCl gas. The obtained guanidine is cyclized in the presence of aqueous NaOH. Similar procedures were utilized for preparing 2-substituted (III-1-3) and its analogues as depicted in the Schemes 8-10 set forth below. Introduction of —$NH_2$ at the 2 position was utilized for various sulfonic, inorganic and hydroxyacid salts. Illustrative compounds are shown in Table 4 below.

TABLE 4

| No | Structure |
|---|---|
| 34-1 | 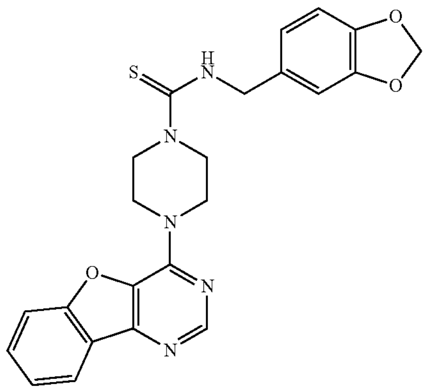 [SMILES: S=C(NCc1ccc2c(c1)OCO2)N1CCN(c2ncnc3c2oc2ccccc23)CC1] |
| 34-2 | 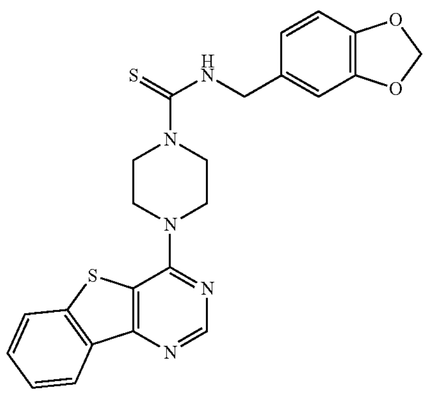 |
| 34-3 | 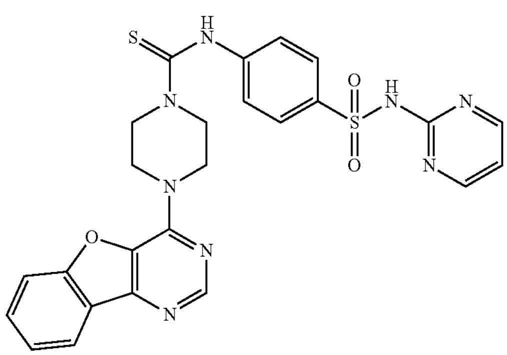 |
| 34-4 | 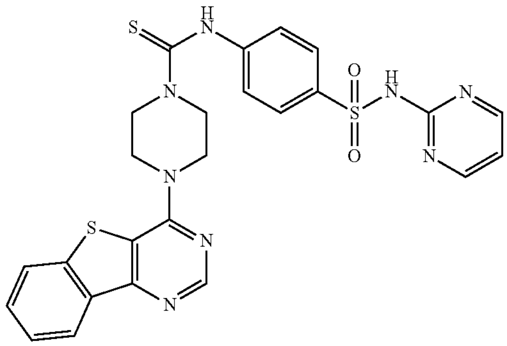 |

TABLE 4-continued

| No | Structure |
|---|---|
| 34-5 | 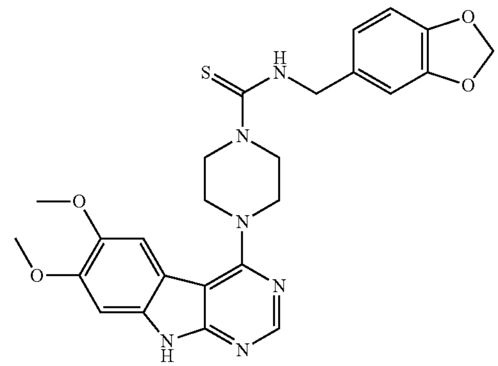 [SMILES: COc1cc2[nH]c3ncnc(N4CCN(C(=S)NCc5ccc6c(c5)OCO6)CC4)c3c2cc1OC] |
| 34-6 | 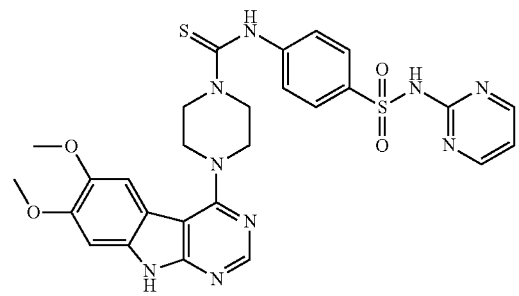 [SMILES: COc1cc2[nH]c3ncnc(N4CCN(C(=S)Nc5ccc(S(=O)(=O)Nc6ncccn6)cc5)CC4)c3c2cc1OC] |
| 34-7 | 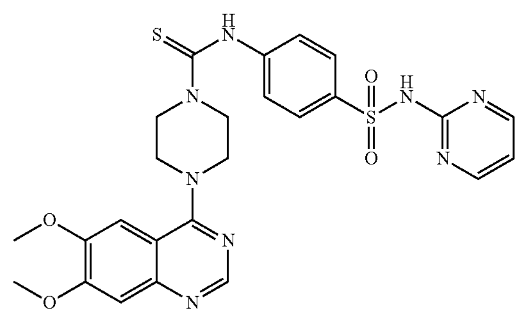 [SMILES: COc1cc2ncnc(N3CCN(C(=S)Nc4ccc(S(=O)(=O)Nc5ncccn5)cc4)CC3)c2cc1OC] |
| 34-8 | 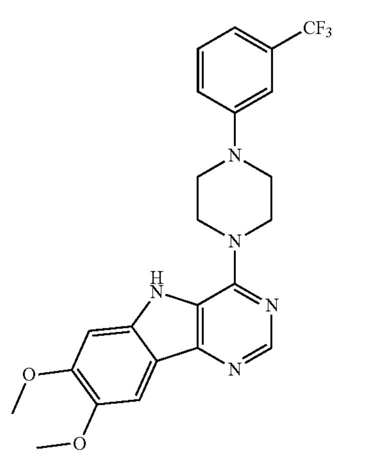 [SMILES: COc1cc2[nH]c3c(N4CCN(c5cccc(C(F)(F)F)c5)CC4)ncnc3c2cc1OC] |

TABLE 4-continued

| No | Structure |
|---|---|
| 34-9 | 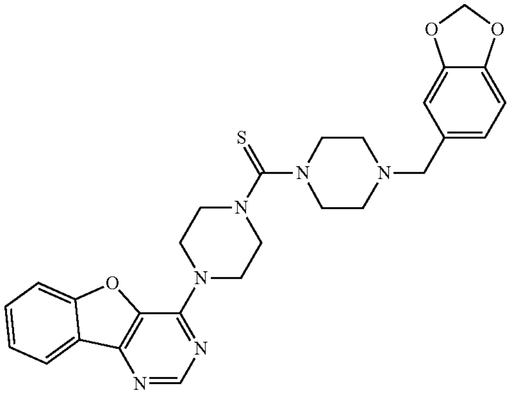 [SMILES: S=C(N1CCN(Cc2ccc3c(c2)OCO3)CC1)N1CCN(c2ncnc3c2oc2ccccc23)CC1] |
| 34-10 | 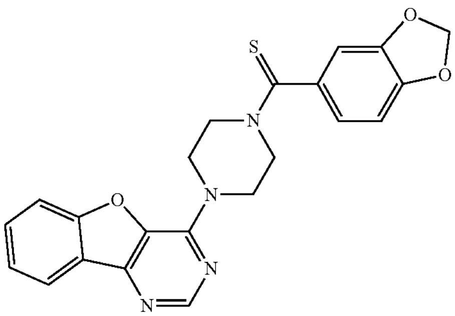 [SMILES: S=C(c1ccc2c(c1)OCO2)N1CCN(c2ncnc3c2oc2ccccc23)CC1] |
| 34-11 | 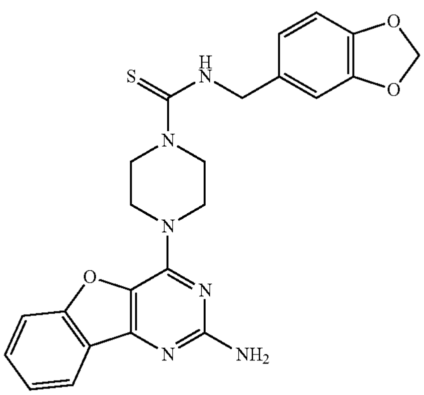 [SMILES: Nc1nc(N2CCN(C(=S)NCc3ccc4c(c3)OCO4)CC2)c2oc3ccccc3c2n1] |
| 34-12 | 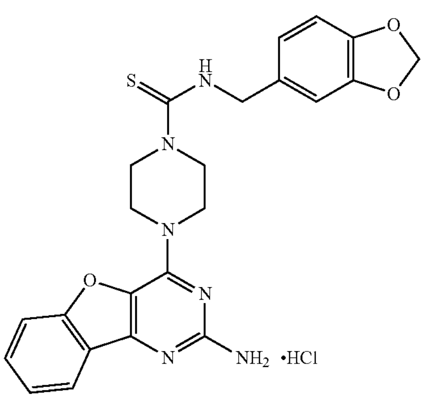 [SMILES: Nc1nc(N2CCN(C(=S)NCc3ccc4c(c3)OCO4)CC2)c2oc3ccccc3c2n1 ; Cl] |

TABLE 4-continued

| No | Structure |
|---|---|
| 34-13 | •citrate |
| 34-14 | •mesylate |
| 34-15 | •besylate |

Scheme 1
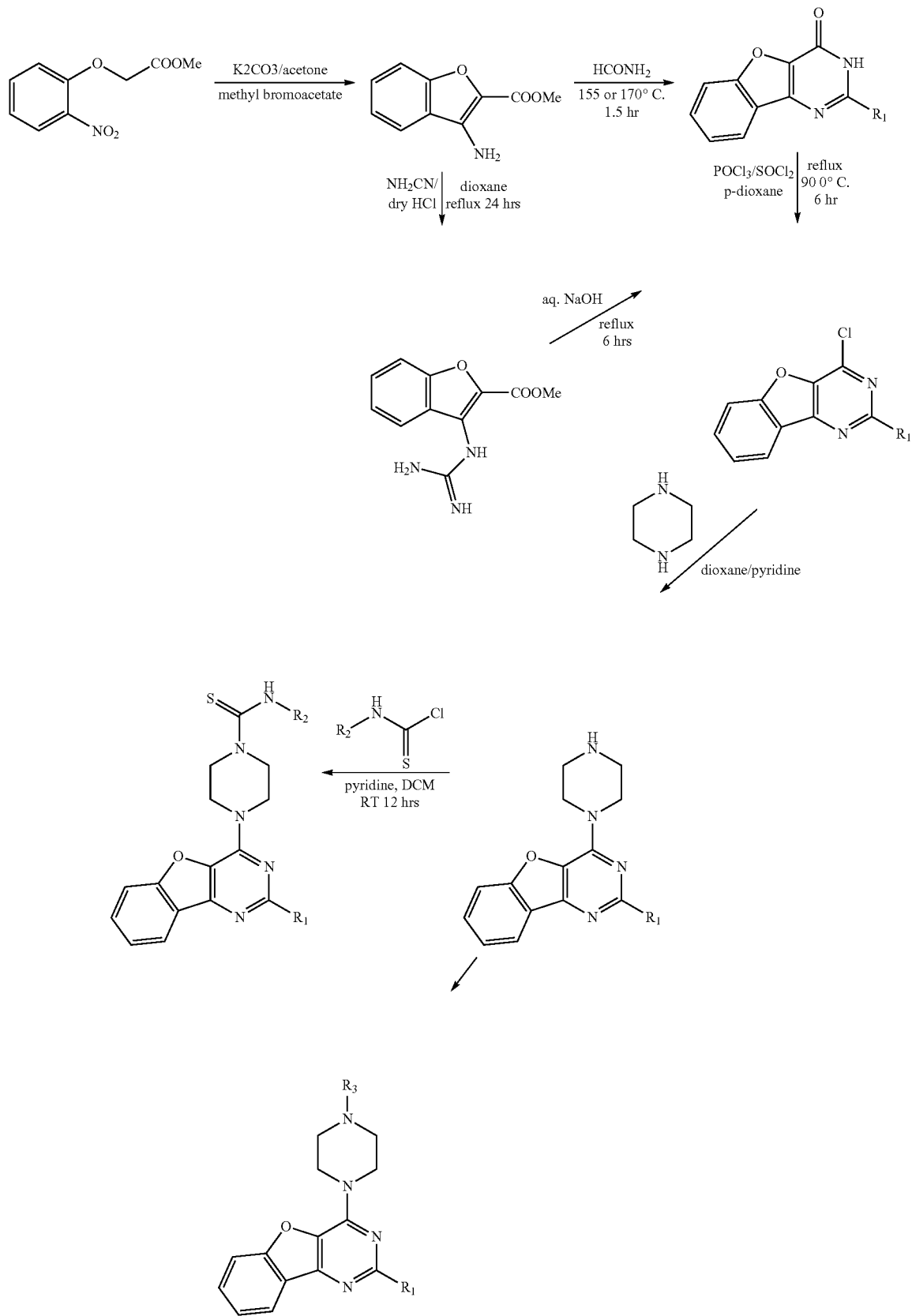

-continued

R1 = —NH2, —NH2·HCl, citrate, tartrate, mesylate, besylate

R2 = 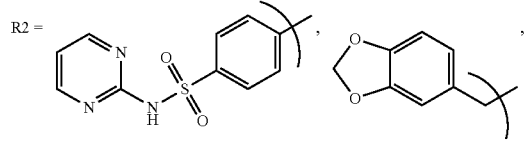

R3 = 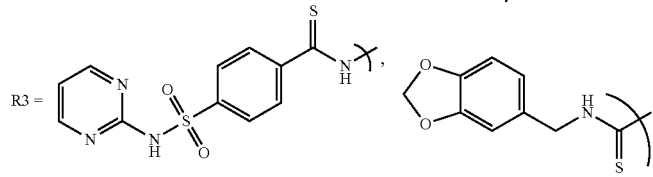

Scheme 2

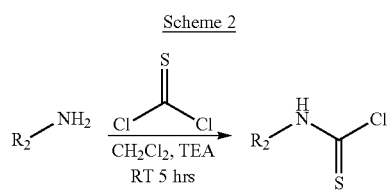

Scheme 3

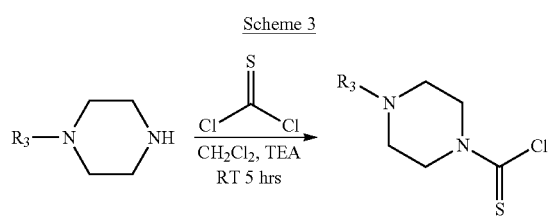

Example 35

Analysis of Compound Binding and Inhibitory Activity against c-kit Mutants

The published crystal structure of c-kit kinase (pdb code: 1PKG) and its mutated structure were used to study the mode of binding of compound (III-1-3) (HPK56/MP-470), a benzofuranopyrimidine compound, its 2-substituted analogs, and quinazoline derivatives.

(III-1-3)

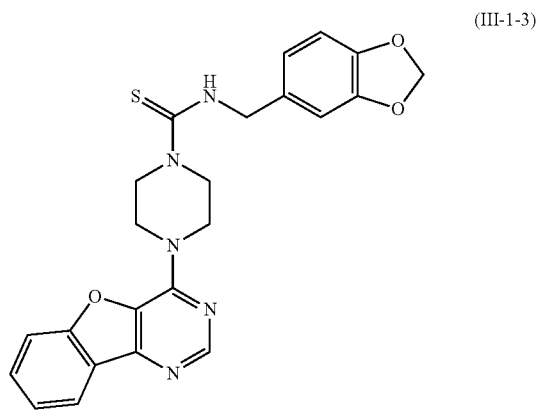 [SMILES: S=C(NCc1ccc2c(c1)OCO2)N1CCN(c2ncnc3c2oc2ccccc23)CC1]

All molecular modeling studies including docking were carried out using SCHRÖDINGER software (SCHRÖD-INGER L.L.C, New York) running on RedHat Linux. The published crystal structure of c-kit kinase (1) was used for protein preparation, generation of grids and docking using a program, Glide, which is implemented in the SCHRÖDINGER software.

The c-kit mutations in GIST tumors and their interactions with (III-1-3) and its analogues were studied on wild type c-kit, K642E (an exon 13 mutant) and D816V (an exon 17 mutant). Glide scores were generated for each compound for both wild-type and c-kit mutants. A more negative glide score is predictive of stronger binding. The determined Glide scores are shown below in Table 5. The mode of binding of (III-1-3) with these mutated c-Kit proteins predicts that (III-1-3) is more effective in binding both K642E and D816V mutations relative to wild-type c-kit.

Table 5 also shows $IC_{50}$ values in the GIST882 cell line determined for the same compounds. Briefly, cells are seeded into 96-well, tissue-culture treated, opaque white plates (Thermo Electron, Vantaa, Finland), at between 5000 and 7500 cells per well, depending on the speed of cell proliferation, in 100 µl of appropriate growth medium (determined by the ATCC). Cells are then exposed to the appropriate concentration of drug or an equal amount of DMSO (drug diluent) and allowed to grow in its presence for 96 hours. Following this, 100 µl of Cell-Titer-Glo reagent (Promega, Inc., Madison, Wis.) is added to each well. Plates are then shaken for 2 minutes at room temperature to allow for cell lysis and incubated for 10 minutes to stabilize the luminescent signal. Similar to the Kinase-Glo assay reagent, this reagent contains both luciferase enzyme and its substrate luciferin. Luciferase, activated by ATP in the cell lysate, catalyzes the conversion of luciferin to oxyluciferin, a reaction which produces light. The amount of light produced is proportionate to the amount of ATP in the cell lysate, which is itself proportional to cell number and gives an index of cellular proliferation. The $IC_{50}$ is defined as the concentration of drug that yields a 50% inhibition of cell growth, as compared to wells containing untreated cells.

TABLE 5

Activity ($IC_{50}$ µM) and Glide score results of inhibitors against WT and mutated c-kit tyrosine kinases.

| | | GIST882 | Glide score | | | |
| | | $IC_{50}$ | | | | K642E/ |
| Compound | Structure | (µM) | WT | K642E | D816V | D816V |
|---|---|---|---|---|---|---|
| HPK61 | II-2-7 | 0.45 | −9.20 | −8.79 | −8.93 | −9.10 |
| HPK62 | II-2-6 | 28.0 | −7.13 | −6.39 | −6.42 | −6.22 |

TABLE 5-continued

Activity (IC$_{50}$ µM) and Glide score results of inhibitors against WT and mutated c-kit tyrosine kinases.

| Compound | Structure | GIST882 IC$_{50}$ (µM) | WT | K642E | D816V | K642E/ D816V |
|---|---|---|---|---|---|---|
| HPK56 (MP470) | III-1-3 | 1.60 | −8.83 | −9.96 | −10.43 | −10.19 |
| HPK59 | III-1-5 | 27.5 | −7.24 | −7.01 | −6.89 | −6.37 |
| HPK57 | III-1-4 | 28.0 | −6.53 | −6.21 | −6.49 | −6.89 |
| HPK60 | 34-4 (Table 4) | 50.0 | −6.65 | −6.60 | −6.53 | −6.52 |
| HPK16 | IV-1-3 | 50.0 | −6.98 | −7.21 | −7.43 | −7.89 |

Example 36

Kinase Inhibitory Activity of Compounds (III-1-3) and (II-2-7)

Compounds (III-1-3) and (II-2-7) are illustrative compounds of the present invention having the structures shown below:

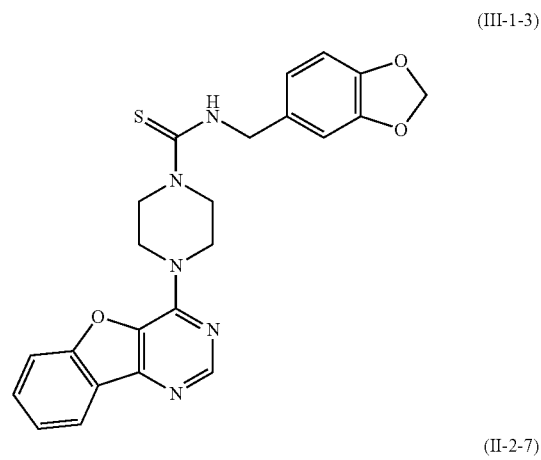

(III-1-3)

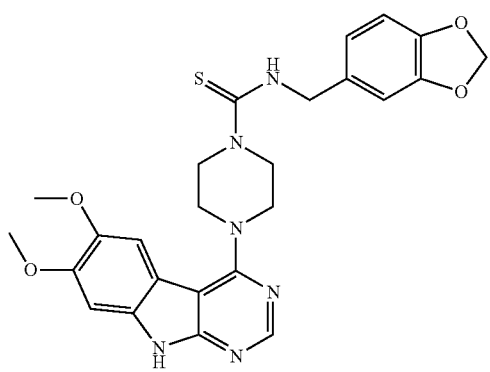

(II-2-7)

Figure 28A:
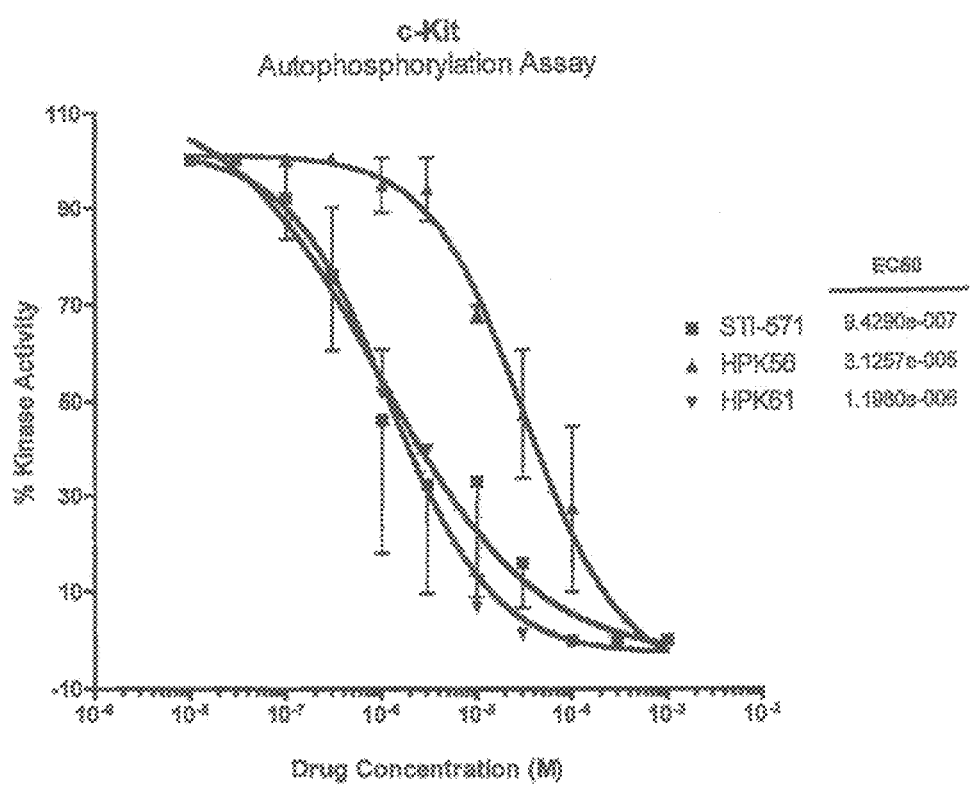
FIGS. 28A and 28B show the results of phosphorylation assays for c-kit and PDGFR-a, respectively.
Figure 28B:
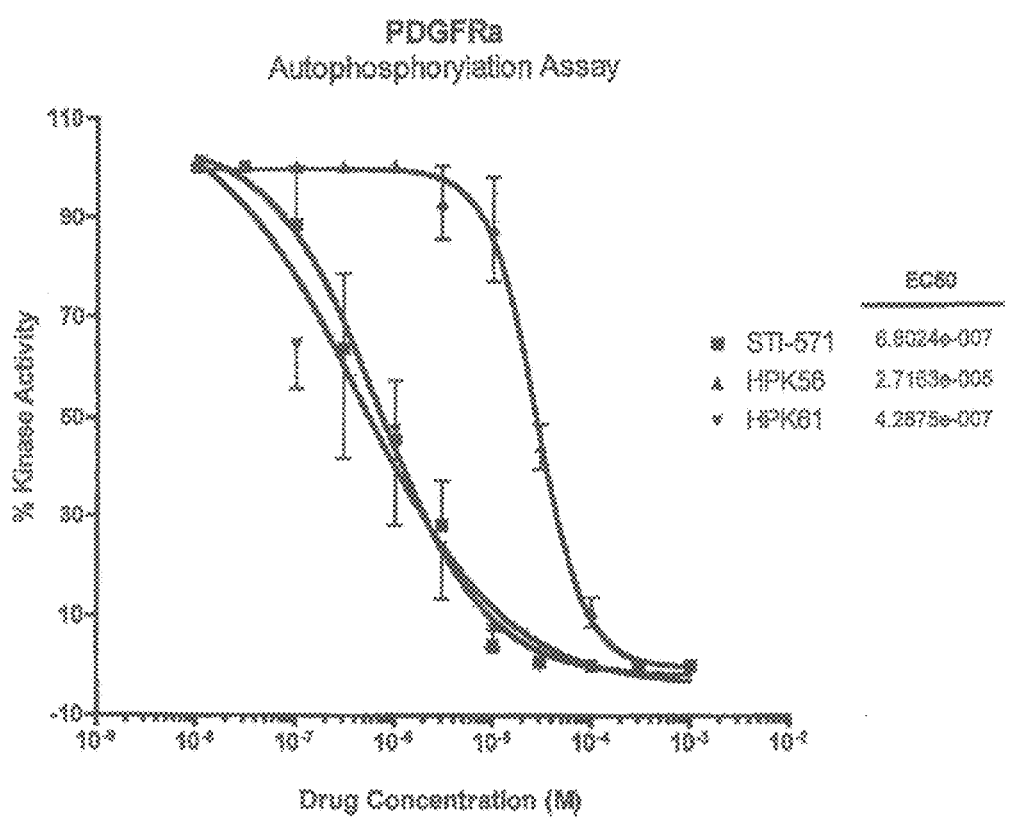

These compounds were tested for their inhibitory activity against c-Kit and the related receptor tyrosine kinase, PDGFRa. Enzymes were incubated with the appropriate concentration of inhibitor and radiolabeled γ-$^{32}$P-ATP. After 30 minutes, the reaction mixtures were electrophoresed on an acrylamide gel and autophosphorylation, quantitated by the amount of radioactivity incorporated into the enzyme, was assayed. Results from these experiments are shown in FIGS. 28A and 28B Both (III-1-3) and (II-2-7) demonstrated dose-dependent c-kit inhibitory activity against c-Kit and PDGRFa.

Example 37

Inhibitory Activity of Additional Illustrative Compounds

Figure 29:
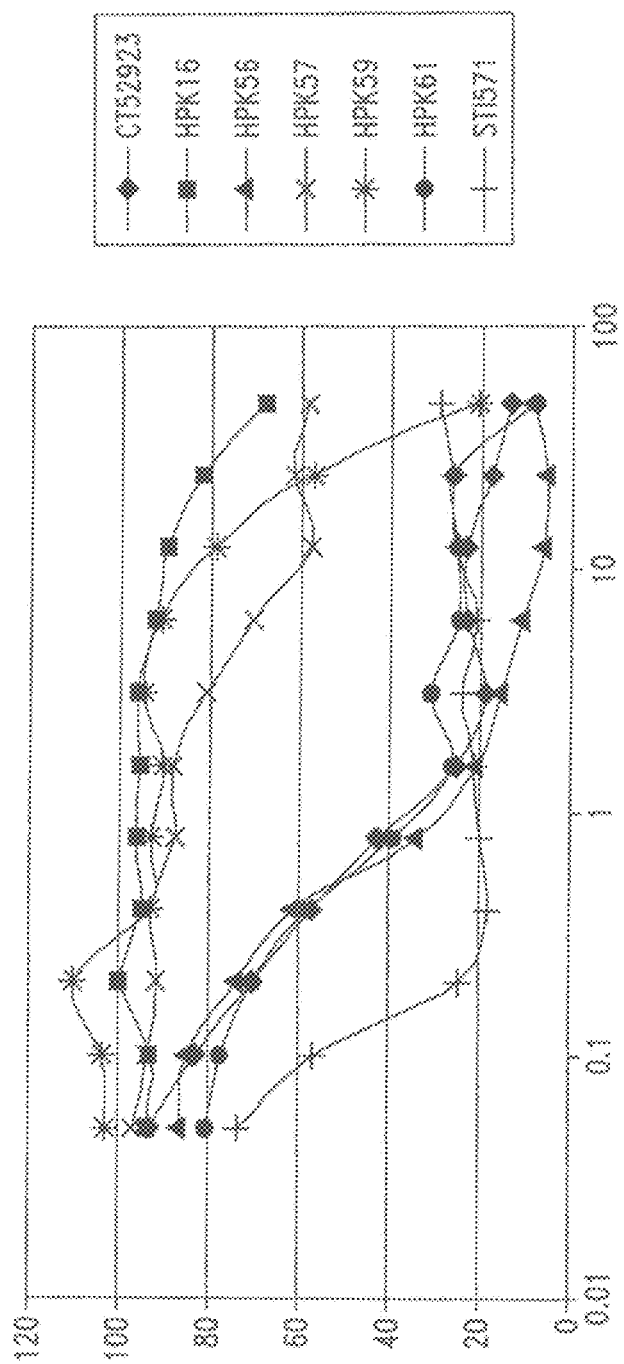
FIG. 29 shows the inhibitory activity of illustrative compounds in the GIST cell line, GIST882.

Various compounds of the invention, including (IV-1-3) (also referred to as HPK16), (III-1-3) (also referred to as HPK56), (III-1-4) (also referred to as HPK57), (III-1-5) (also referred to as HPK59), and (II-2-7) (also referred to as HPK61) were tested for activity against GIST tumor cells using the GIST882 cell line. Briefly, cells are seeded into 96-well, tissue-culture treated, opaque white plates (Thermo Electron, Vantaa, Finland), at between 5000 and 7500 cells per well, depending on the speed of cell proliferation, in 100 µl of appropriate growth medium (determined by the ATCC). Cells are then exposed to the appropriate concentration of drug or an equal amount of DMSO (drug diluent) and allowed to grow in its presence for 96 hours. Following this, 100 µl of Cell-Titer-Glo reagent (Promega, Inc., Madison, Wis.) is added to each well. Plates are then shaken for 2 minutes at room temperature to allow for cell lysis and incubated for 10 minutes to stabilize the luminescent signal. Similar to the Kinase-Glo assay reagent, this reagent contains both luciferase enzyme and its substrate luciferin. Luciferase, activated by ATP in the cell lysate, catalyzes the conversion of luciferin to oxyluciferin, a reaction which produces light. The amount of light produced is proportionate to the amount of ATP in the cell lysate, which is itself proportional to cell number and gives an index of cellular proliferation. The IC$_{50}$ is defined as the concentration of drug that yields a 50% inhibition of cell growth, as compared to wells containing untreated cells. The results of these experiments are shown in FIG. 29, demonstrating that all of the compounds tested had dose-dependent inhibitory activity, while HPK56 (III-1-3) and HPK61 (II-2-7) had the highest inhibitory activity of the inventive compounds tested.

Example 38

Synthesis of Additional Illustrative Protein Kinase Inhibitors

The following example describes the synthesis of the illustrative compounds of the present invention set forth below in Table 6, using the general synthesis Schemes 11-15 also shown below. The synthesis methods below are illustrative in nature and can be readily modified using routine and established principles of synthetic organic chemistry to produce the inventive compounds described herein.

All experiments were carried out under an inert atmosphere and at reflux and or room temperature unless otherwise stated. The purities of compounds were assessed by routine analytical HPLC. TLCs were performed on precoated silica gel plates (Merck), and the resulting chromatograms were visualized under UV light at 254 nm. Melting points were determined on a Kofler Block or with a Büchi melting point apparatus on compounds isolated as described in the experimental procedures and are uncorrected. The NMR spectra were determined in DMSO-d$_6$ solution (unless otherwise stated) on a Bruker AM 300 (300 MHz) spectrometer or on a Varian 400 (400 MHz). Chemical shifts are expressed in unit of δ (ppm), and peak multiplicities are expressed as follows: s, singlet; d, doublet; dd, doublet of doublet; t, triplet; br s, broad singlet; m, multiplet. FAB measurements have been carried out on a mass spectrometer HX-110 instrument (JEOL, Akishima, Japan) equipped with a conventional Xe gun. A mixture matrix of glycerol:thioglycerol:mNBA (meta-nitrobenzyl alcohol) 50:25:25 containing 0.1% of trifluoroacetic acid (TFA) was used. For accurate mass measurements, polyethylene glycol (PEG) was used as the internal standard. Combustion analysis (CHNS) was performed by Desert Analytics Laboratory, Tucson, Ariz.

TABLE 6

| No | Structure |
|---|---|
| 38-1 | 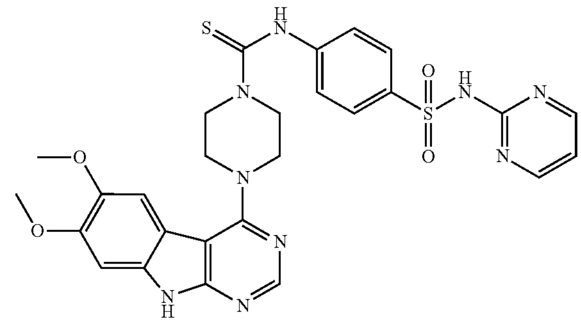 [SMILES: COc1cc2[nH]c3ncnc(N4CCN(C(=S)Nc5ccc(S(=O)(=O)Nc6ncccn6)cc5)CC4)c3c2cc1OC] |
| 38-2 | 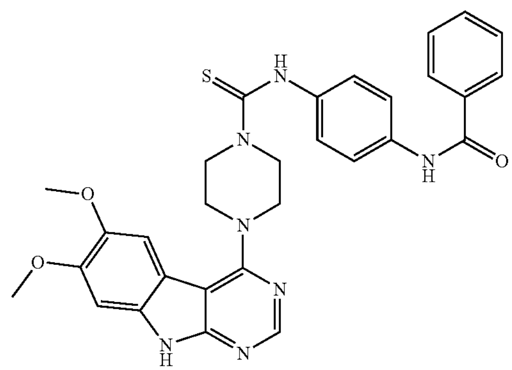 [SMILES: COc1cc2[nH]c3ncnc(N4CCN(C(=S)Nc5ccc(NC(=O)c6ccccc6)cc5)CC4)c3c2cc1OC] |
| 38-3 | 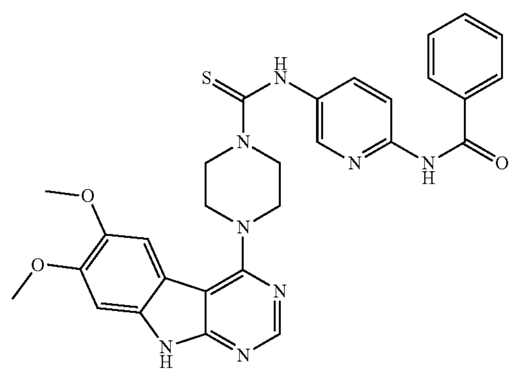 |
| 38-4 | 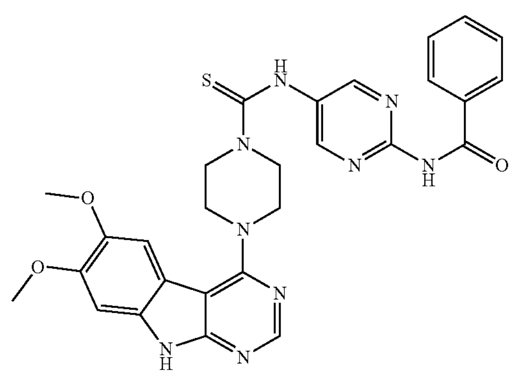 |

TABLE 6-continued
| No | Structure |
|---|---|
| 38-5 | 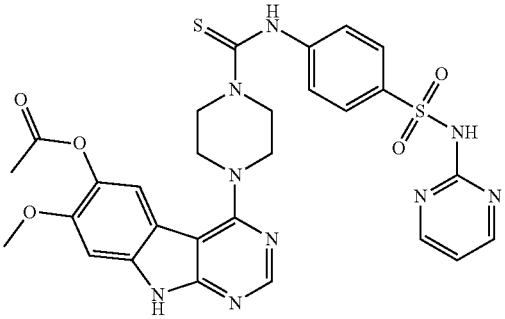 [SMILES: COc1cc2[nH]c3ncnc(N4CCN(C(=S)Nc5ccc(S(=O)(=O)Nc6ncccn6)cc5)CC4)c3c2cc1OC(C)=O] |
| 38-6 | 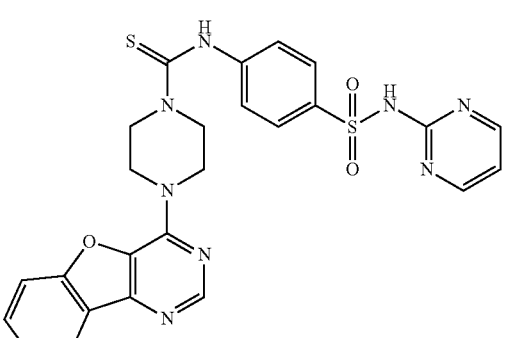 |
| 38-7 | 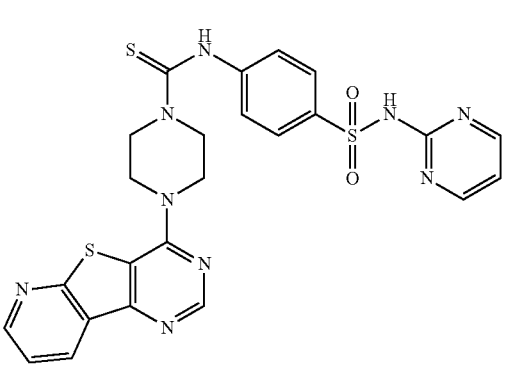 [SMILES: O=S(=O)(Nc1ncccn1)c1ccc(NC(=S)N2CCN(c3ncnc4c3sc3ncccc34)CC2)cc1] |
| 38-8 | 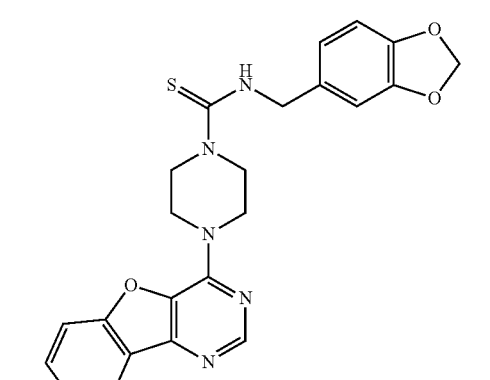 |

TABLE 6-continued
| No | Structure |
|---|---|
| 38-9 | 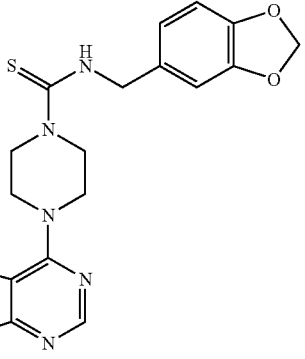 |
| 38-10 | 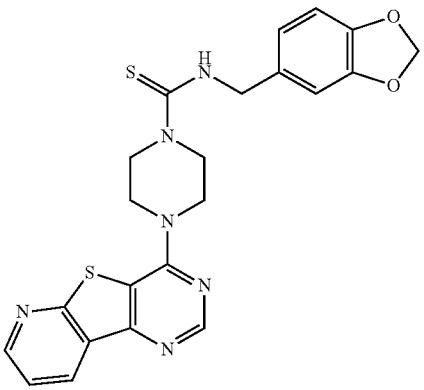 |
| 38-11 | 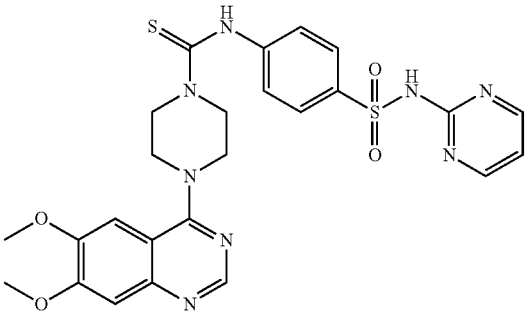 [SMILES: COc1cc2ncnc(N3CCN(C(=S)Nc4ccc(S(=O)(=O)Nc5ncccn5)cc4)CC3)c2cc1OC] |
| 38-12 | 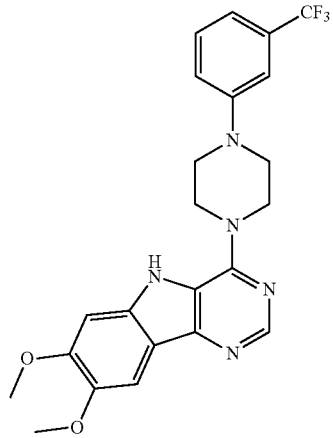 [SMILES: COc1cc2[nH]c3c(N4CCN(c5cccc(C(F)(F)F)c5)CC4)ncnc3c2cc1OC] |

TABLE 6-continued

| No | Structure |
|---|---|
| 38-13 | 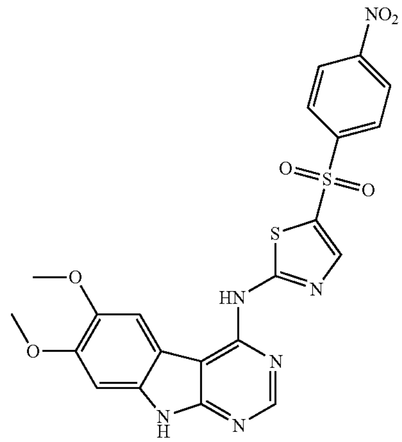 [SMILES: COc1cc2[nH]c3ncnc(Nc4ncc(S(=O)(=O)c5ccc([N+](=O)[O-])cc5)s4)c3c2cc1OC] |
| 38-14 | 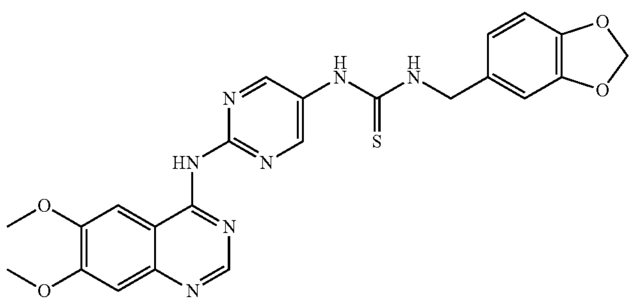 [SMILES: COc1cc2ncnc(Nc3ncc(NC(=S)NCc4ccc5c(c4)OCO5)cn3)c2cc1OC] |
| 38-15 | 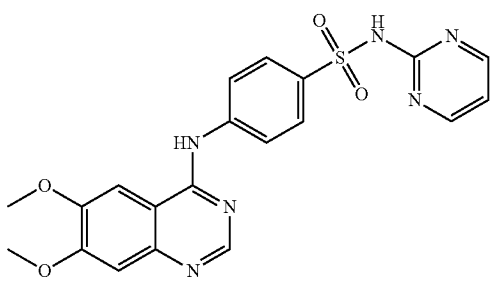 [SMILES: COc1cc2ncnc(Nc3ccc(S(=O)(=O)Nc4ncccn4)cc3)c2cc1OC] |
| 38-16 | 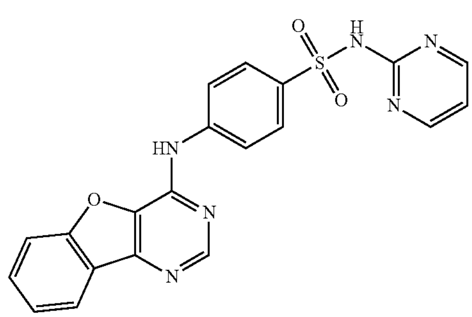 [SMILES: O=S(=O)(Nc1ncccn1)c1ccc(Nc2ncnc3c2oc2ccccc23)cc1] |

TABLE 6-continued
| No | Structure |
|---|---|
| 38-17 | 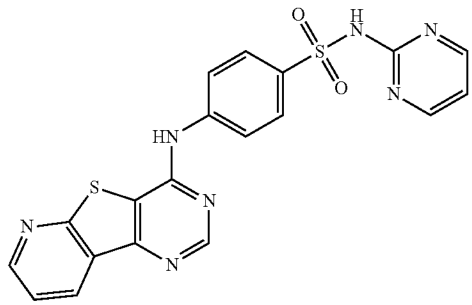 [SMILES: O=S(=O)(Nc1ncccn1)c1ccc(Nc2ncnc3c2sc2ncccc23)cc1] |
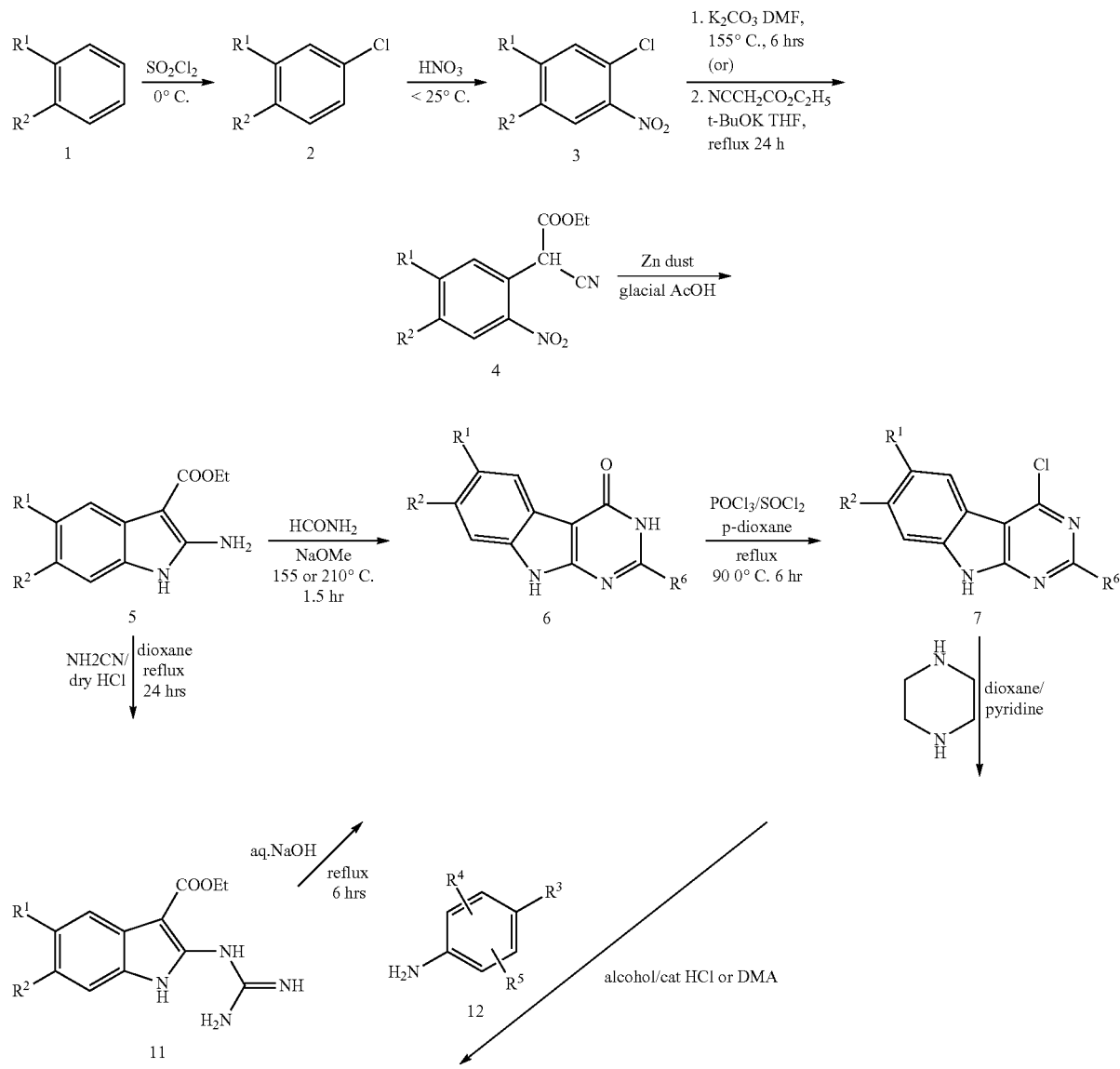
Scheme 11

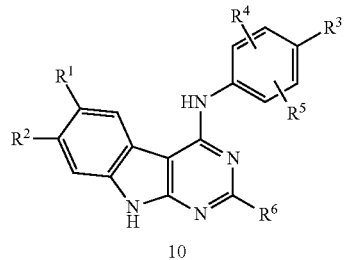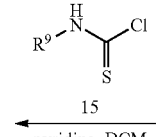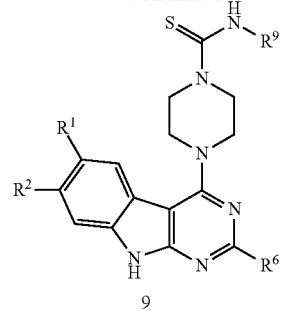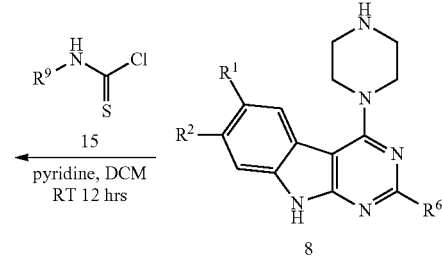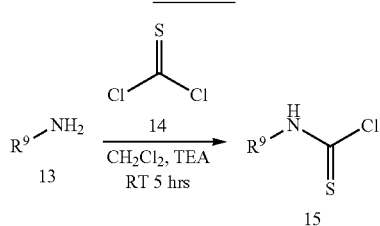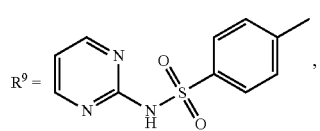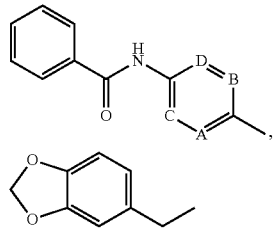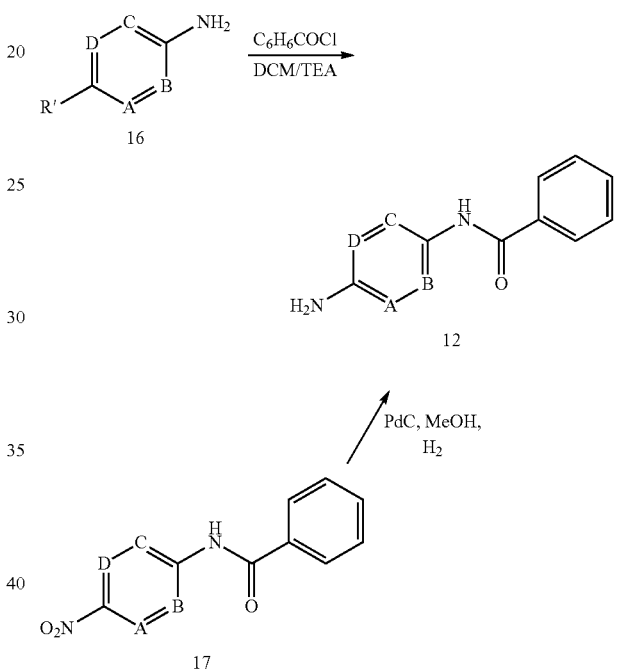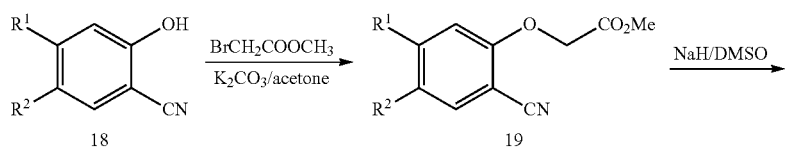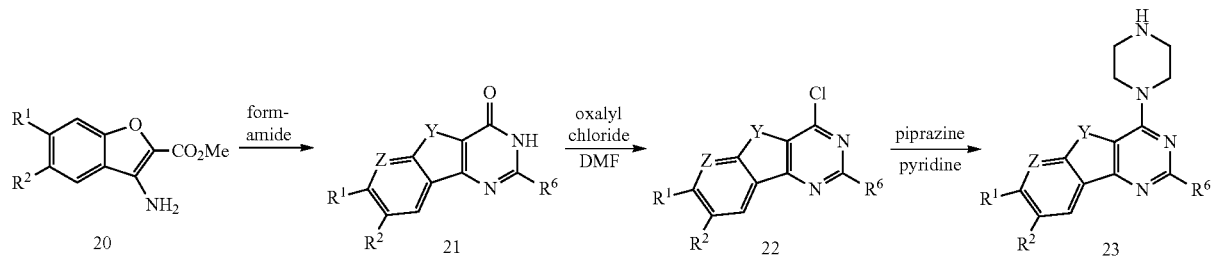

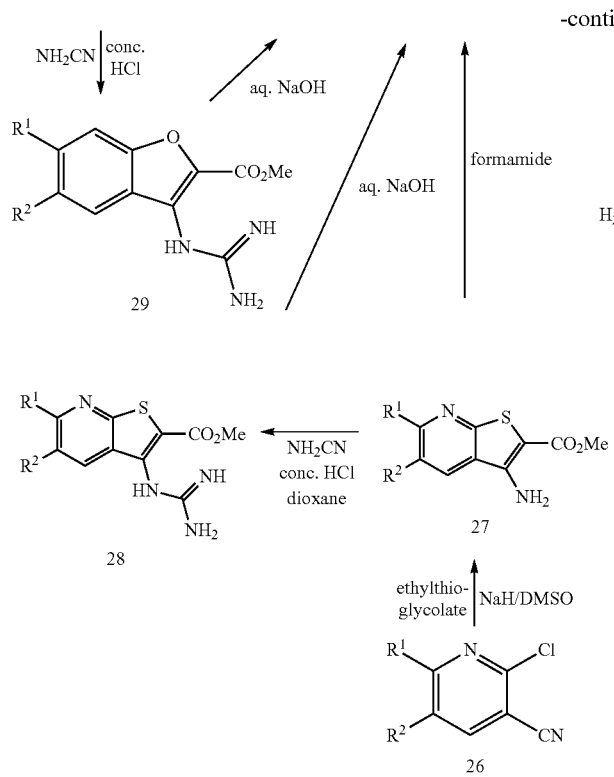

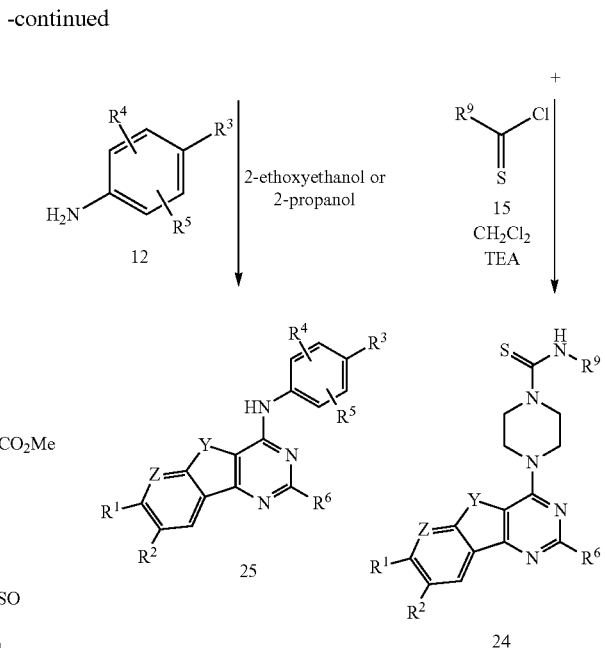

$Y = O, Z = N, H$

Scheme 15

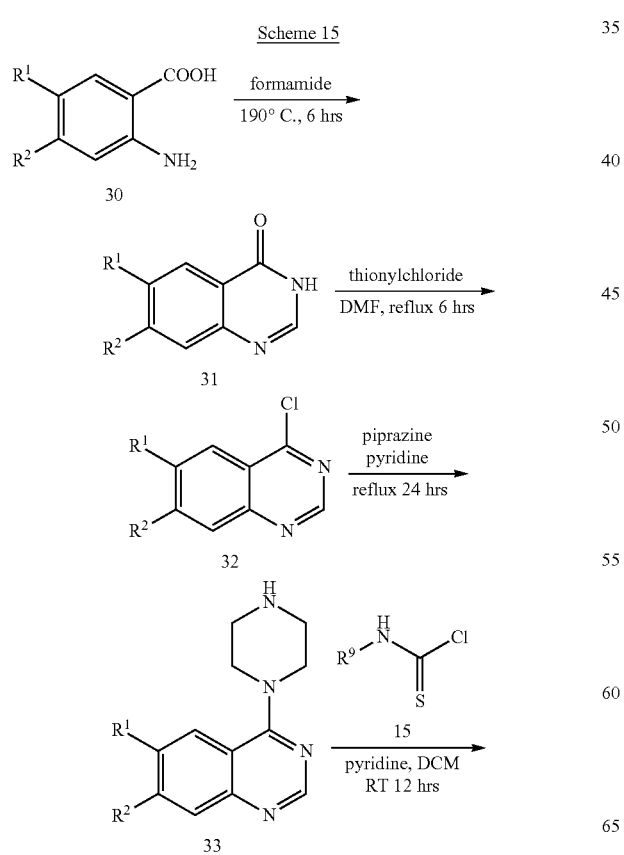

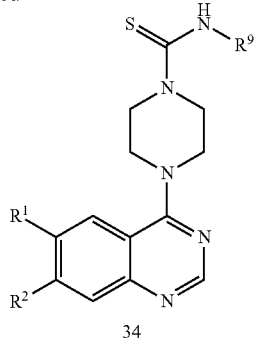

A. 4-(6,7-dimethoxy-9H-1,3,9-triaza-fluoren-4-yl)-piperazine-1-carbothioic acid [4-(pyrimidin-2-ylsulfamoyl)-phenyl]-amide (1). (see Scheme 11)

7-dimethoxy-4-(piperazin-1-yl)$_9$H-pyrimido[4,5-b]indole 8 in DCM was added dropwise to compound 10 in DCM over a period of 15 minutes followed by the addition of excess pyridine. The resulting reaction mixture was stirred at RT for 24 hours. After the completion of the reaction, MeOH was added to quench the excess of compound 10 and the solvents were evaporated. The crude product was purified by column chromatography using a DCM/5% MeOH solvent system. The obtained product 1 (Table 6) (compound 9 in Scheme 11) is a half white solid with a yield of 37.6%.

$^1$HNMR (DMSO-$d_6$, 300 MHz): δ 3.75 (s, 4H), 3.87 (s, 3H), 3.88 (s, 3H), 4.19 (s, 4H), 7.04-7.06 (m, 1H), 7.07 (s,

1H), 7.24 (s, 1H), 7.53 (d, J=8.4 Hz, 2H), 7.90 (d, J=8.4 Hz, 2H), 8.44 (s, 1H), 8.51 (d, J=4.8 HZ, 2H), 9.72 (s, 1H, —NH), 12.01 (s, 1H, —NH).

FAB HRMS [M+H]$^+$ calcd for $C_{27}H_{27}N_9O_4S_2$: 605.1627. found 606.1699

B. 7-dimethoxy-4-(piperazin-1-yl)-9H-pyrimido[4,5-b]indole

4-Chloro-6,7-dimethoxy-9,9a-dihydro-4-aH-pyrimido[4,5-b]indole 7 was dissolved in p-dioxane (50 mL), and piperazine (3.9 g) was added following the addition of pyridine (5 mL) under argon at RT. The reaction mixture was heated to reflux for 16 hours and it was cooled. The solvents were removed under vacuum and the obtained crude product was purified by flash coloumn chromatograph using a DCM/10% MeOH solvent system. The compound 8 obtained after purification yielded 66% (3.9 g) as half white solid.

C. 4-Chloro-6,7-dimethoxy-9,9a-dihydro-4-aH-pyrimido[4,5-b]indole

A suspension of 6,7-dimethoxy-3H-pyrimido[4,5-b]indol-4(9H)-one 6 (2.8 g), POCl$_3$ (20 mL) and p-dioxane 65 mL was heated at reflux for 6 hrs, then stirred at 25 0° C. for 36 hrs. The obtained mixtrure was filtered and concentrated. The crude product was purified by column chromatography using 1% MeOH/DCM to give title compound 7 73.3% (2.2 g) as pale yellow solid.

D. [4-(Pyrimidin-2-ylsulfamoyl)-phenyl]-thiophosgene chloride

Thiophosgene (0.78 mL) was slowly added to the stirred solution of sulfadiazine (1.71 g) in DCM (50 mL) following the addition of triethylamine (0.47 mL) at 0° C. After the additions, the reaction mixture was stirred at RT for 5 hrs. The reaction mixture is diluted with more DCM and is washed with water and brine and the obtained solvent was dried over Na$_2$SO$_4$. Solvent is evaporated and dried under vacuum to give compound 15 (Scheme 12) as yellowish orange solid in 64.5% yield and it was used directly in the next step.

E. N-(4-{[4-(6,7-Dimethoxy-9H-1,3,9-triaza-fluoren-4-yl)-piperazine-1-carbo-thioyl]-amino]-phenyl)-benzamide (2)

$^1$HNMR (DMSO d6, 300 MHZ) 3.73 (s, 4H), 3.87 (d, 6H, J=5.6 Hz), 4.17 (s, 4H), 7.06 (s, 1H), 7.25 (d, 2H, J=6.4 Hz), 7.29 (s, 1H), 7.55 (m, 3H), 7.70 (d, 2H, J=8.8 Hz), 7.94 (d, 2H, J=8.0 Hz), 8.42 (s, 1H), 9.44 (s, 1H, br), 10.24 (s, 1H, br), 11.98 (s, 1H, br).

FAB HRMS [M+H]$^+$ calcd for $C_{30}H_{30}N_7O_3S$: 568.6793. found 568.2131.

F. N-(5-{[4-(6,7-Dimethoxy-9H-1,3,9-triaza-fluoren-4-yl)-piperazine-1-carbo-thioyl]-amino]-pyridin-2yl)-benzamide (3)

$^1$HNMR (DMSO d6, 300 MHZ) 3.72 (s, 4H), 3.84 (d, 6H, J=7.0 Hz), 4.04 (s, 4H), 7.05 (s, 1H), 7.16 (s, 1H), 7.54 (m, 3H), 8.03 (d, 2H, J=7.4 Hz), 8.15 (s, 1H), 8.19 (d, 2H, J=8.0 Hz), 8.41 (s, 1H), 10.94 (s, 1H, br), 11.99 (s, 1H, br).

FAB HRMS [M+H]$^+$ calcd for $C_{29}H_{29}N_8O_3S$: 569.2135. found 569.0235.

G. N-(5-{[4-(6,7-Dimethoxy-9H-1,3,9-triaza-fluoren-4-yl)-piperazine-1-carbo-thioyl]-amino]-pyrimidin-2yl)-benzamide (4)

$^1$HNMR (DMSO d6, 300 MHZ) 3.80 (s, 4H), 3.86 (d, 6H, J=7.0 Hz), 4.25 (s, 4H), 7.08 (s, 1H), 7.27 (s, 1H), 7.59 (m, 3H), 7.97 (d, 2H, J=7.4Hz), 8.46 (s, 1H), 8.67 (s, 2H), 9.67 (s, 1H, br), 11.01 (s, 1H, br), 12.01 (s, 1H, br).

FAB HRMS [M+H]$^+$ calcd for $C_{28}H_{28}N_9O_3S$: 570.6548. found 570.2027.

H. Acetic acid 7-methoxy-4-{4-[4-(pyrimidin-2-ylsulfamoyl)-phenylthio-carbamoyl]-piperazin-1-yl}-9H-pyrimido[4,5-b]indol-6-yl ester (5)

$^1$HNMR (DMSO-d6, 400 MHz)

MS [+ve ESI] for $C_{28}H_{27}N_{19}O_5S_2$: found 634.7012 (M+H)$^+$.

I. 4-Benzo[4,5]furo[3,2-d]pyrimidin-4-yl-piperazine-1-carbothioic acid [4-(pyrimidin-2-ylsulfamoyl)-phenyl]-amide (6)

$^1$HNMR (DMSO-d$_6$, 300 MHZ) δ 4.17 (s, 8H), 7.04-7.08 (m, 1H), 7.49-7.52 (m, 1H), 7.56-7.59 (m, 1H), 7.70-7.75 (m, 1H), 7.84 (d, J=8.2 Hz, 1H), 7.91 (d, J=8.6 Hz, 2H), 8.12 (d, J=7.6 Hz, 2H), 8.52 (d, J=4.8 Hz, 2H), 8.58 (s, 1H), 9.82 (s, 1H, NH).

FAB HRMS [M+H]$^+$ calcd for $C_{25}H_{22}N_8O_3S_2$: 546.1256. found 547.1325.

J. 4-(9-Thia-1,5,7-triaza-fluoren-8-yl)-piperazine-1-carbothioic acid [4-(pyrimidin-2-ylsulfamoyl)-phenyl]-amide (7)

$^1$HNMR (DMSO-d$_6$, 300 MHZ) δ 4.07 (s, 8H), 6.96-6.99 (m, 1H), 7.47-7.50 (m, 1H), 7.58-7.62 (m, 1H), 7.82 (d, J=8.6 Hz, 2H), 8.43 (d, J=4.9 Hz, 2H), 8.63 (d, J=8.02 Hz, 2H), 8.70 (s, 1H), 8.80 (d, J=4.0 Hz, 1H).

FAB HRMS [M+H]$^+$ calcd for $C_{24}H_{21}N_9O_2S_3$: 563.0980. found 564.1059.

K. 4-Benzo[4,5]furo[3,2-d]pyrimidin-4-yl-piperazine-1-carbothioic acid (benzo[1,3]-dioxol-5-ylmethyl)-amide (8)

$^1$HNMR (CDCl$_3$, 300 MHZ) δ 4.09 (s, 4H), 4.27 (s, 4H), 4.82 (d, J=4.7 Hz, 2H), 5.99 (s, 2H), 6.77-6.79 (m, 1H), 6.80-6.83 (m, 1H), 6.89 (s, 1H), 7.47-7.52 (m, 1H), 7.61-7.65 (m, 1H), 7.66-7.70 (m, 1H), 8.33 (d, J=7.0 Hz, 1H).

FAB HRMS [M+H]$^+$ calcd for $C_{23}H_{21}N_5O_3S$: 447.1365. found 448.1443.

L. 4-(6,7-Dimethoxy-9H-1,3,9-triaza-fluoren-4-yl)-piperazine-1-carbothioic acid (benzo[1,3]-dioxol-5-ylmethyl)-amide (9)

$^1$HNMR (CDCl$_3$, 300 MHZ) δ 3.79 (s, 4H), 3.96 (s, 3H), 3.97 (s, 3H), 4.07 (s, 4H), 4.79 (s, 2H), 5.92 (s, 2H), 6.75 (d, J=7.9 Hz, 1H), 6.81 (d, J=7.9 Hz, 1H), 6.87 (s, 1H), 7.04 (s, 1H), 7.18 (s, 1H), 8.40 (s, 1H).

FAB HRMS [M+H]$^+$ calcd for $C_{25}H_{26}N_6O_4S$: 506.1736. found 507.1820.

M. 4-(9-Thia-1,5,7-triaza-fluoren-8-yl)-piperazine-1-carbothioic acid (benzo[1,3]-dioxol-5-ylmethyl)-amide (10)

$^1$HNMR (CDCl$_3$, 300 MHZ) δ 4.07 (s, 4H), 4.17 (s, 4H), 4.72 (d, J=4.5 Hz, 2H), 5.88 (s, 2H), 6.69 (d, 1H), 6.75 (d, 1H), 6.80 (s, 1H), 7.43-7.47 (m, 1H), 8.65 (s, 1H), 8.75 (d, J=3.8 Hz, 2H).
FAB HRMS [M+H]$^+$ calcd for C$_{22}$H$_{20}$H$_6$O$_2$S$_2$: 464.1089. found 465.1167.

N. 4-(6,7-Dimethoxy-quinazolin-4-yl)-piperazine-1-carbothioic acid [4-(pyrimidin-2-ylsulfamoyl)-phenyl]-amide (11). (Scheme 15)

To a solution of 4-(I-piperazinyl)-6,7-dimethoxyquinazoline (200 mg, 0.73 mmol) and pyridine (0.5 mL, 6.4 mmol) in dichloromethane (20 mL) was added a solution of compound 15 (Scheme 12) in dichloromethane (20 mL) and this was stirred overnight. Methanol was added to quench excess thiophosgene, and the residue after removal of solvent was purified by silica gel column chromatography eluting with 5% methanol/dichloromethane and further recrystallized from dichloromethane/hexane to give 80 mg (20%) of compound 11.
$^1$HNMR (CDCl$_3$, 300 MHZ) δ 3.85 (s, 4H), 3.98 (s, 3H), 4.02 (s, 3H), 4.11 (s, 4H), 6.98 (m, 1H), 7.08 (s, 1H), 7.32 (d, 2H), 7.88 (s, 1H), 8.00 (d, J=6.7 Hz, 2H), 8.62 (d, 2H), 8.66 (s, 1H).
FAB HRMS [M+H]$^+$ calcd for C$_{25}$H$_{26}$N$_8$O$_4$S$_2$: 566.1518. found 567.1597.

O. 6,7-dimethoxy-4-piperazin-1-yl-quinazoline

An analogous reaction to that described in Example 1, starting with 4-Chloro-6,7-dimethoxy-quinazoline (32) in presence of piprazine and pyridine at refluxing temperature gave the title compound 33 as white solid.

P. 4-Chloro-6,7-dimethoxy-quinazoline

An analogous reaction to that described in Example 1, starting with 6,7-Dimethoxy-3H-quinazolin-4-one (31) reacted with thionylchloride in presence of DMF gave compound 32.

Q. 7,8-Dimethoxy-4-[4-(3-trifluoromethyl-phenyl)-piperazin-1-yl]-5H-pyrimido[5,4-b]indole (12)

$^1$HNMR (DMSO-d6, 400 MHz)
MS [+ve ESI] for C$_{21}$H$_{16}$N$_6$O$_6$S$_2$. found 613.0572 (M+H)$^+$.

R. 1-Benzo[1,3]-dioxol-5-ylmethyl-3-[2-(6,7-dimethoxy-quinazolin-4-ylamino)-pyrimidin-5yl]-thiourea (14)

$^1$HNMR (DMSO d6, 300 MHZ) δ 3.93 (s, 3H), 3.96 (s, 3H), 4.56 (s, 2H), 6.00 (s, 2H), 6.84 (d, 1H, J=7.9 Hz), 6.89 (d, 1H, J=7.9 Hz), 6.95 (s, 1H), 7.25 (s, 1H), 7.73 (s, 1H), 8.45 (s, 1H, br), 8.62 (s, 2H), 9.5 (s, 1H, br), 10.59 (s, 1H, br).
FAB HRMS [M+H]$^+$ calcd for C$_{23}$H$_{21}$N$_7$O$_4$S: 491.1376. found 492.1454.

S. 4-(6,7-Dimethoxy-quinazolin-4-ylamino)-N-pyrimidin-2-yl-benzene sulfonamide (15)

$^1$HNMR (DMSO d6, 300 MHZ) δ 4.00 (s, 6H), 7.08 (m, 1H), 7.30 (s, 1H), 7.96 (d, 2H, J=8.7 Hz), 8.08 ((d, 2H, J=8.7 Hz), 8.15 (s, 1H), 8.53 (d, 2H), 8.85 (s, 1H).
FAB HRMS [M+H]$^+$ calcd for C$_{20}$H$_{19}$N$_6$O$_4$S: 439.1178. found 440.1180.

T. 4-(Benzo[4,5]furo[3,2-d]pyrimidin-4-yl amino-N-pyrimidin-2-yl-benzene sulfonamide (16)

$^1$HNMR (DMSO d6, 300 MHZ) 7.06 (t, 1H), 7.58 (t, 1H), 7.79 (t, 1H), 7.90 (d, 1H, J=8.4 Hz), 7.99 (d, 2H, J=8.4 Hz), 8.16 (d, 2H, J=8.9 Hz), 8.21 (d, 1H, J=7.2 Hz), 8.53 (d, 2H, J=4.9 Hz), 8.80 (s, 1H).
FAB HRMS [M+H]$^+$ calcd for C$_{20}$H$_{15}$N$_6$O$_3$S: 419.4435. found 419.0935.

U. N-pyrimidin-2-yl-4(9-thia-1,5,7-triaza-fluoren-8ylamino)-benzenesulfonamide (17)

$^1$HNMR (DMSO d6, 300 MHZ) 7.01 (t, 1H), 7.71 (t, 1H), 8.00 (d, 2H, J=8.9 Hz), 8.09 (d, 2H, J=8.9 Hz), 8.48 (d, 2H, J=5.2 Hz), 8.73 (dd, 2H, J=6.8 Hz), 8.88 (m, 2H), 10.23 (s, 1H).
FAB HRMS [M+H]$^+$ calcd for C$_{19}$H$_{14}$N$_7$O$_2$S$_2$: 436.4979. found 436.0669.

Example 39

Modulation of Rad51 by MP470 in

Western blotting for Rad51 in SF-767 cancer cells showed a large increase in Rad51 protein levels when cells were exposed to IR (XRT). Conversely, in cells pretreated with MP470, levels of Rad51 remained low and near control level even after exposure of the cells to IR (not shown).

Example 40

Treatment of Glioblastoma Cells In Vitro with MP470

Glioblastoma (GBM) is an interesting potential indication because of the involvement of multiple targets of MP470. MP470 has low micromolar activity against c-met and low nanomolar activity against mutant forms of c-Kit and PDGFR. PDGFR, c-Met and c-Kit are known and well documented gene amplifications in glioblastoma and some mutations have also been found in these genes. Due to the overexpression of these receptor tyrosine kinases and the potential for mutant forms to increase the activity of these receptors in glioblastoma, MP470 could be highly efficacious for treatment of this disease.

In addition, Rad51 overexpression is very common in glioblastoma and is thought to mediate some of the inherent resistance of these tumors to radiation and chemotherapy. Radiation treatment and alkylating agents, such as Temozolomide, are used in the treatment of GBM and both therapies are known to induce DNA damage. Cells utilize Rad51 to repair DNA damage caused by both of these agents, suggesting that MP470's ability to modulate RAD51 levels could be important in combination therapies.

To evaluate the ability of MP470 to enhance clinical therapy we used MP470 in combination with ionizing radiation on culture cancer cells. SF-767 glioblastoma multiformes cells were treated with 1 μM MP470, 800c Gy IR, or a combination of both. Cell death was measured using an MTS assay and demonstrated that either MP470 or IR alone induced cell death, but when used in combination they resulted in a synergistic effect and increased cell death by more than 2-fold over either agent alone.

Example 41

MP470 Increases the Level of Apoptosis in Treated Cancer Cells

Induction of apoptosis in cancer cells is a common mechanism of action for anti-cancer agents. To determine the role of MP470 in apoptosis, tumor cells were incubated with either compound and analyzed for apoptosis using Annexin V or TUNEL assays. Analysis of both MiaPaCa-2 and Panc-1 pancreatic cancer cells showed that both compounds were able to induce apoptosis in these cell lines. A dose dependent trend was seen in these cell lines, with higher doses inducing greater cell apoptosis. In MiaPaCa-2 cells, MP470 at 100 µM induced 81.4% apoptosis, while at 1 µM it induced 71% apoptosis. In Panc1 cells, MP470 at 10 µM induced over a 3-fold increase in apoptotic cells compared with non-treated cells.

Example 42

Inhibition of Mutant Kinases by MP470

In order to determine the specificity and potential alternative targets for MP470, kinase profile screen were performed utilizing the KinaseProfiler™ Screen (Upstate Corp) and Select Screen™ kinase profiling (Invitrogen). Between the two screens, 53 different kinases were tested, representing a broad proportion of the human kinome. MP470 was screened at a concentration of 1 µM against both wildtype and mutant kinases. Using this approach, MP470, at a concentration of 1 uM, was found to have activity against the following mutant kinases: cKit(D816V)(h), cKit(D816H)(h), cKit(V560G)(h), cKit(V654A)(h), Flt3(D835Y)(h), PDGFRα(D842V)(h), and PDGFRα(V561 D)(h).

Example 43

MP-470 Reduces Proliferation in a Prostate Tumor Cell Line

Figure 30:
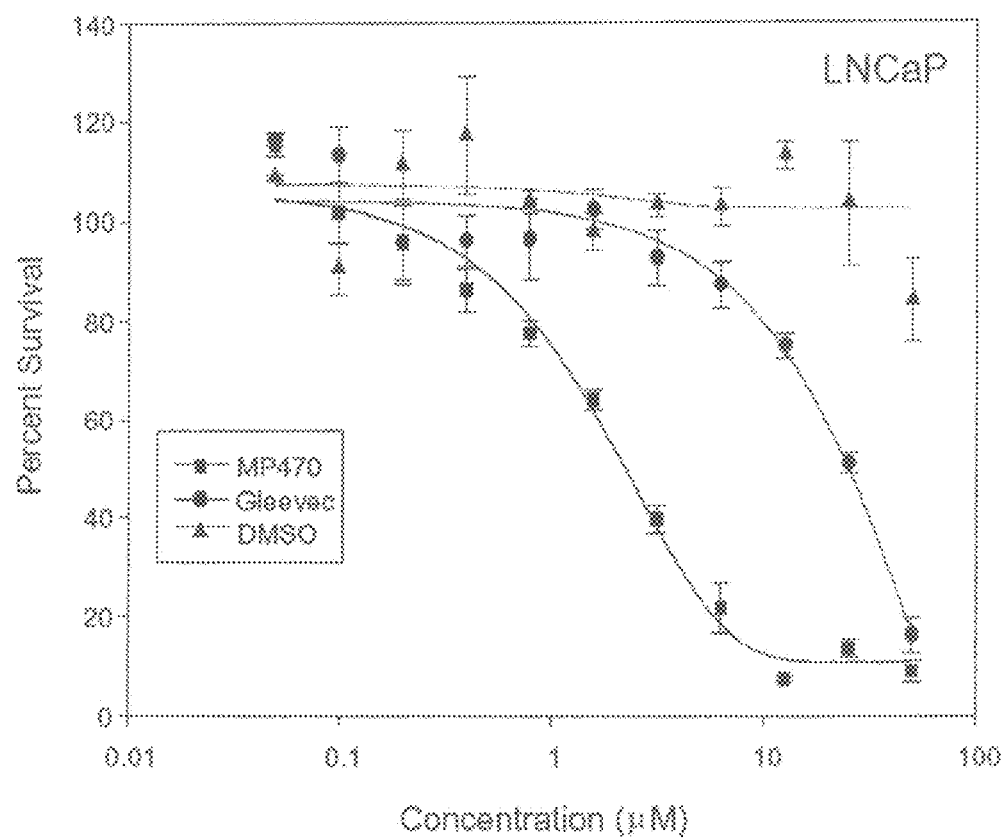
FIG. 30 shows results from MTT assays of LNCaP prostate carcinoma cells treated with MP-470 or Gleevec®.

LNCaP prostate cells in 96 well plates were exposed to a dose course of MP-470 (Compound III-1-3) or Gleevec® (imatinib mesylate). An MTT assay was performed to determine the number of viable cells in each well for each concentration of compound, and also for a set of vehicle controls (DMSO). These data are presented in FIG. 30. The concentration at which cell survival was reduced to 50% of vehicle-treated controls ($IC_{50}$) was calculated to be approximately 5 µM for MP-470, and greater than 10 µM for Gleevec® in this assay.

Example 44

Treatment Combining MP-470 and EGFR Inhibition

Induction of apoptosis by MP-470 (Compound III-1-3) was further evaluated in LNCaP prostate carcinoma cells using three different assays. First, cells were treated with MP-470 at a variety of concentrations, with or without addition of Tarceva® (erlotinib) for 48 hours. Cells were then examined for the morphological characteristics of apoptosis (membrane blebbing, nuclear fragmentation, etc.) and scored according to a binary scale (apoptotic versus non-apoptotic). These data are presented in FIG. 31A.

Figure 31:
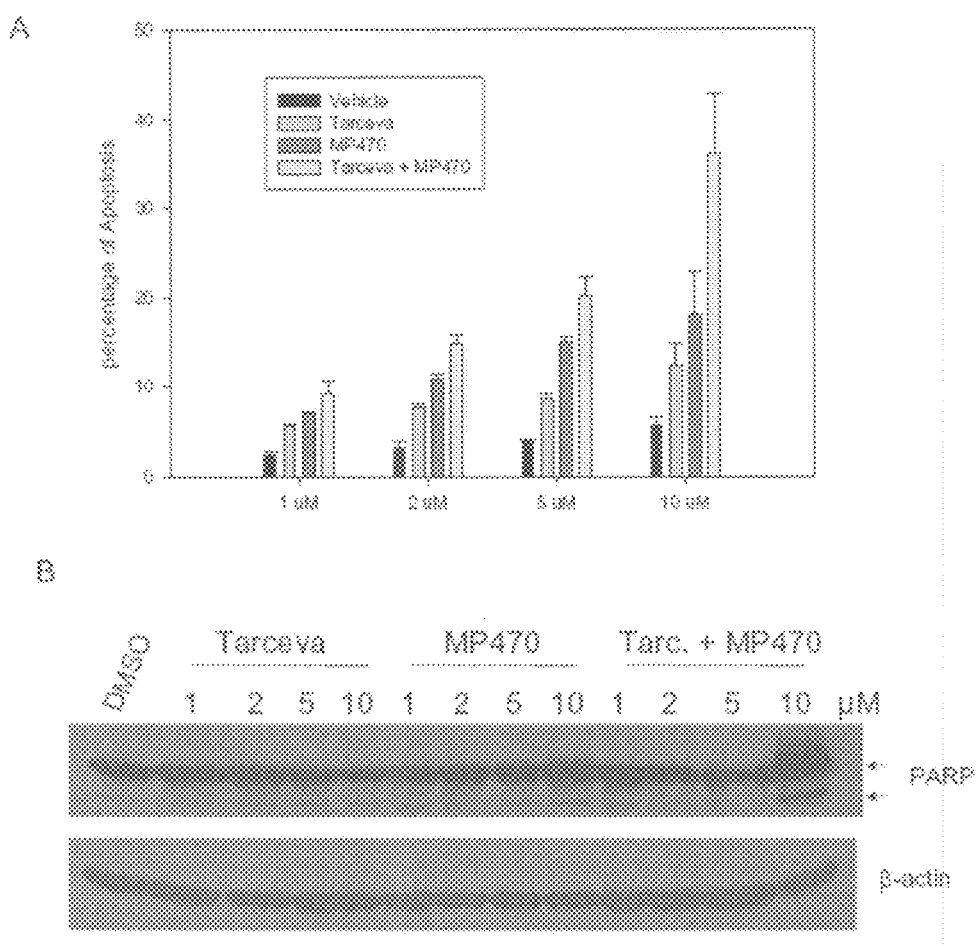
FIGS. 31A and 31B show the results of apoptosis assays for cells treated with MP-470 alone or in combination with the EGFR inhibitor Tarceva® (erlotinib).

As a more quantifiable means of determining apoptosis induction, cells were also lysed and total protein was used in an immunoblot assay for poly-[ADP ribose] polymerase (PARP) cleavage, a hallmark of apoptosis. A representative blot is shown in FIG. 31B. In each of these assays, there was a dose-dependent increase in apoptosis in response to MP-470 treatment, and this response was enhanced in the presence of EGFR inhibition by erlotinib.

Figure 32:
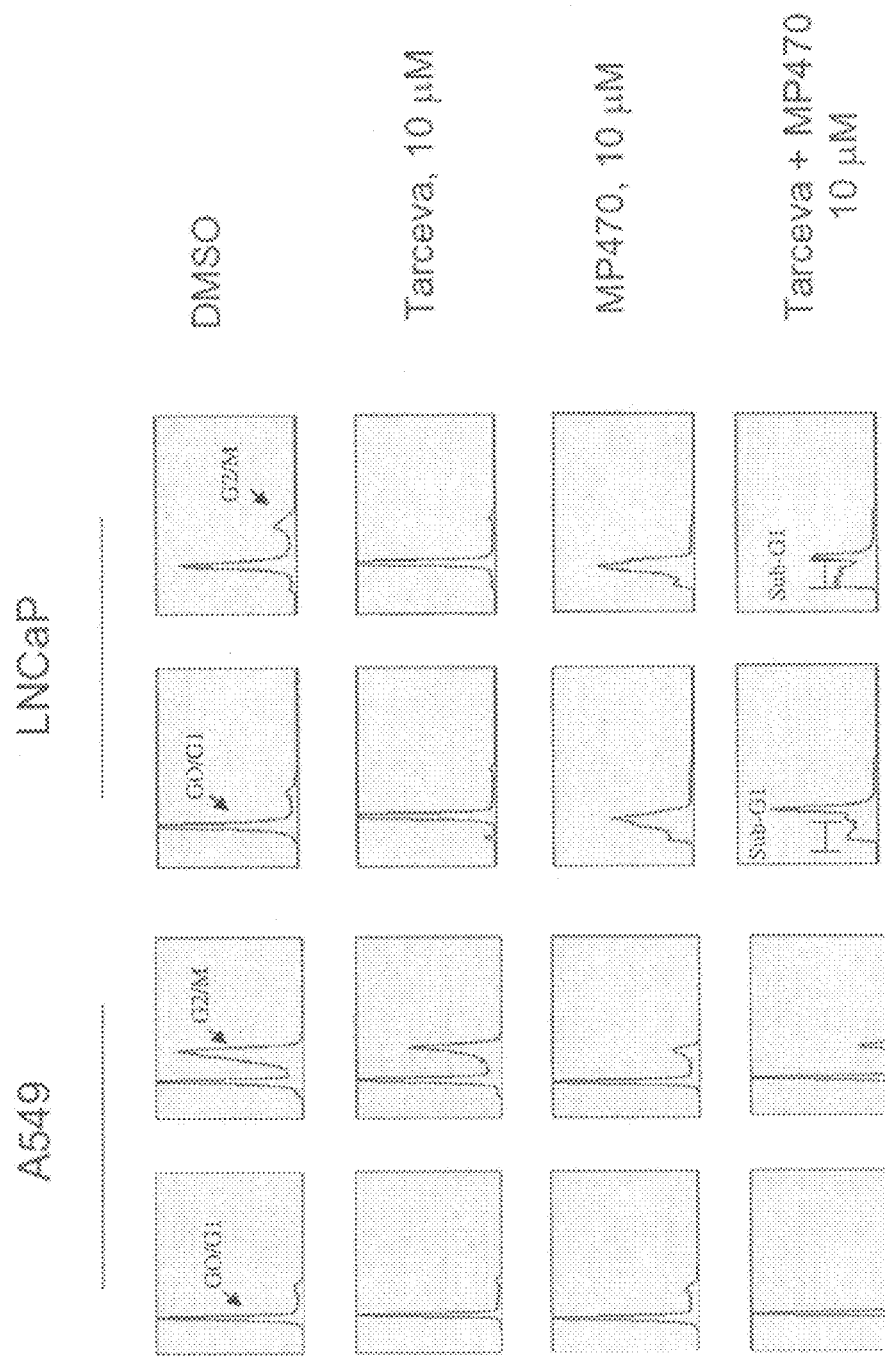
FIG. 32 shows the results of flow cytometry analysis of non-cell lung cancer and prostate cancer cells treated with MP-470 alone or in combination with Tarceva®.

In addition, A549 non-small cell lung cancer (NSCLC) cells and LNCaP prostate carcinoma cells were treated with MP-470 in the presence or absence of Tarceva® for 48 hours and subjected to flow cytometric analysis. Nocodazole was also included to induce a $G_2/M$ arrest, in an effort to determine if these compounds could overcome such a block. Representative plots from these flow cytometric analyses are shown in FIG. 32. Left-hand columns for each cell type represent cells with no additional treatment, while right-hand columns represent cells pretreated overnight with nocodazole (0.3 ug/mL) to induce $G_2/M$ arrest. MP-470 induced apoptosis and was epistatic to $G_2/M$ block, and this apoptotic response was increased in the presence of EGFR inhibition. Thus, MP-470 alone, and to a greater extent in combination with erlotinib, induced apoptosis, as represented by a sub-$G_1$ peak by flow cytometric analysis.

Example 45

MP-470 Inhibits Tyrosine Kinase Activity in Cells

Figure 33:
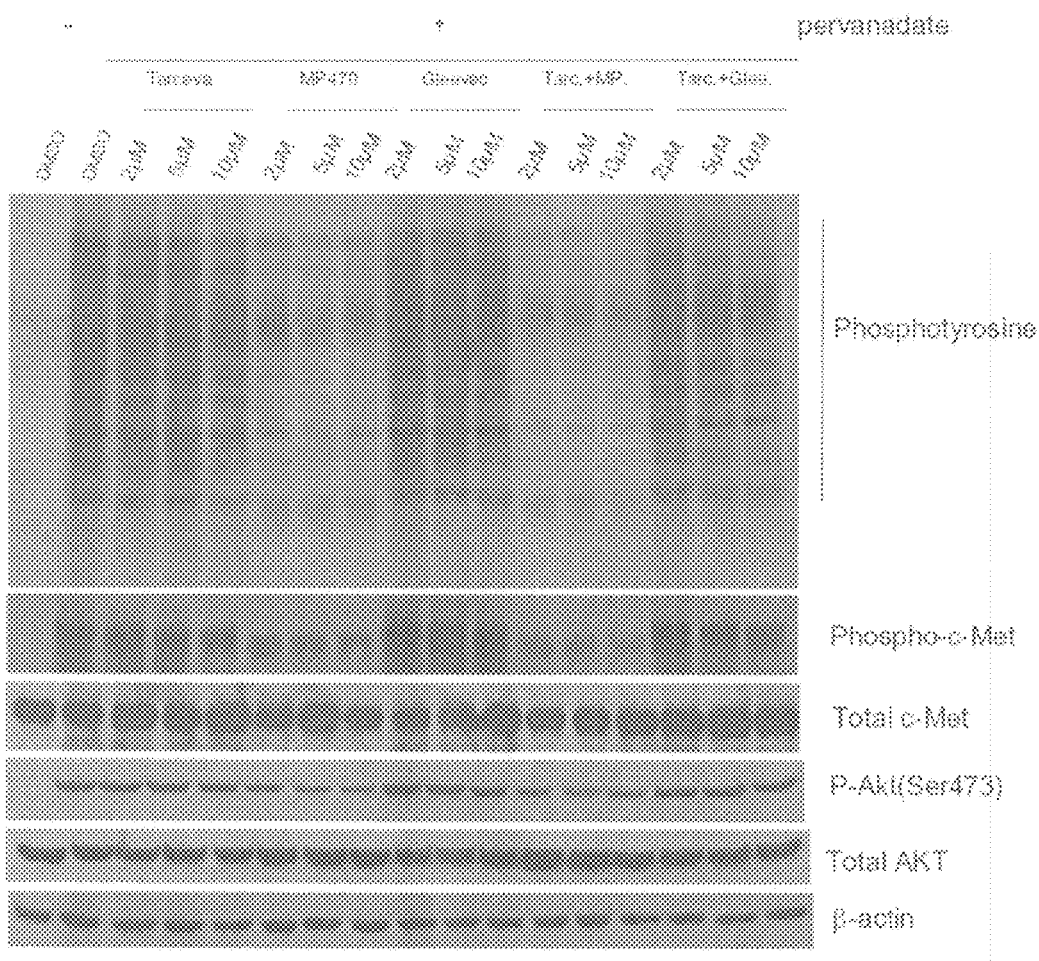
FIG. 33 shows the results of immunoblot analysis of lysates from cells treated with MP-470 alone or in combination with other tyrosine kinase inhibitors (Gleevec® and Tarceva®).

MP-470 (Compound III-1-3) has inhibitory effects on a number of receptor tyrosine kinases. In order to evaluate these effects at the cellular level, immunoblot analysis was performed on lysates from cells treated with MP470, with or without the addition of the EGFR inhibitor Tarceva®. Lysates were assayed for general tyrosine kinase activity, as well as the specific phosphorylation of c-Met and Akt. Briefly, NIH 3T3 cells were pretreated with drugs as indicated for 4 hours, then treated with pervanadate for a further 30 minutes. Immunoblot detection was carried out with antibodies for phospho-tyrosine, phospho-Met and phospho-Akt (S473), as well as total c-Met and Akt. Beta-actin was used as a loading control. Representative immunoblots are shown in FIG. 33.

These assays demonstrated that the activating autophosphorylation of c-Met is reduced by MP-470, both alone and in combination with Tarceva®, as is the phosphorylation of Akt. Neither of these effects was observed in cells treated with Tarceva® alone. Also, general tyrosine phosphorylation was reduced upon treatment with MP-470, further confirming the activity of this compound as a multitargeted tyrosine kinase inhibitor.

Figure 34:
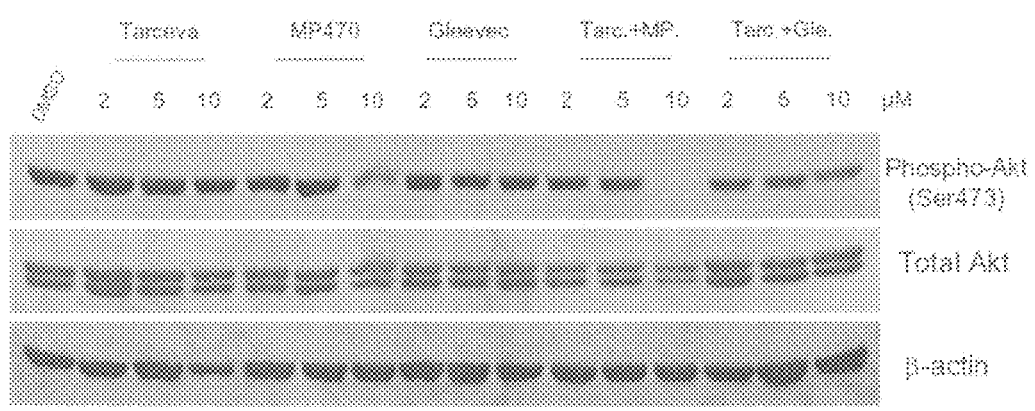
FIG. 34 shows the results of immunoblot analysis of Akt phosphorylation in response to MP-470 treatment of LNCap prostate cancer cells.

The effect of MP-470 on Akt activity was further demonstrated in a tumor cell model. LNCaP prostate carcinoma cells were treated with MP-470, in combinations with Tarceva® and Gleevec®, for 48 hours. Following incubation, cells were lysed and total protein subjected to immunoblot analysis for total Akt and phospho-Akt (S473). Phosphorylation of Akt was reduced in a dose-dependent manner in response to MP-470. This reduction appeared to be enhanced when MP-470 and Tarceva® were used in combination, though Tarceva® alone did not appear to have an effect. Representative immunoblots are shown in FIG. 34.

Example 46

MP-470 in Combination with Tarceva® Inhibits Tumor Growth In Vivo

Figure 35:
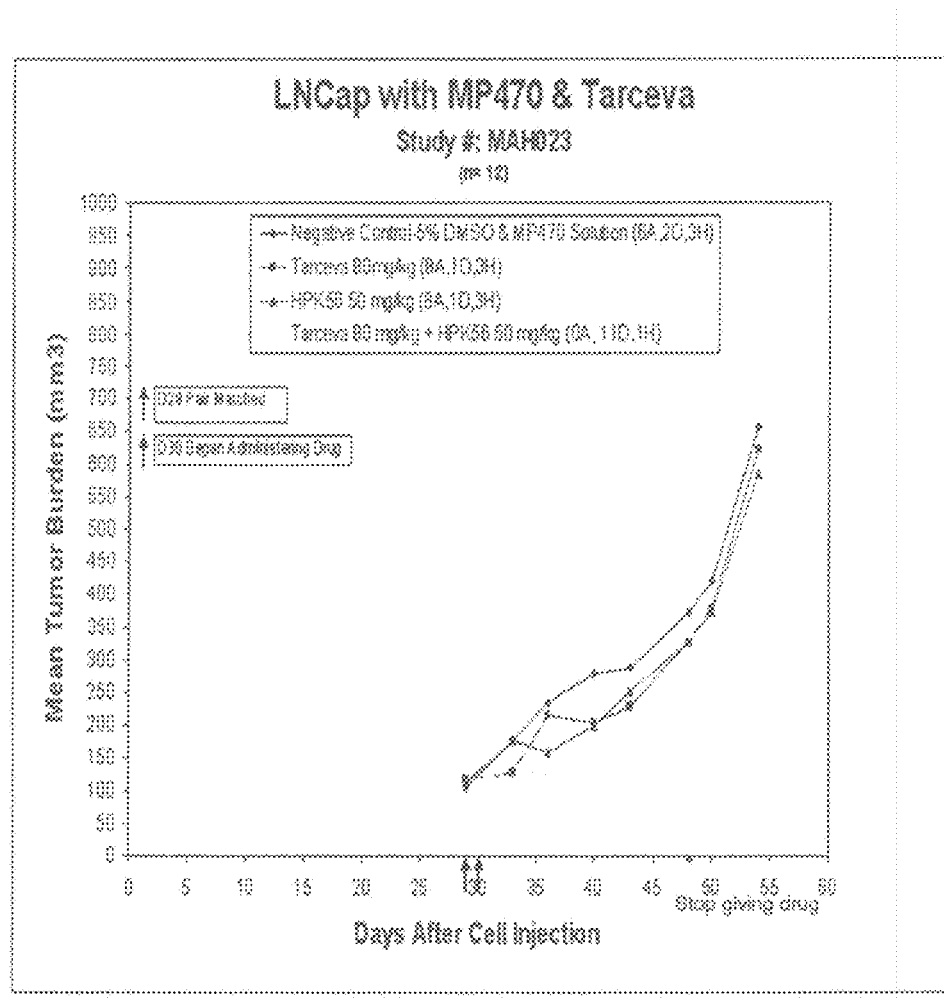
FIG. 35 shows tumor growth curves for prostate tumor xenografts treated with MP-470 (HPK56) alone or in combination with Tarceva®.

A xenograft study was carried out in order to evaluate the combined effects of MP-470 (Compound III-1-3) and Tarceva® in vivo. LNCaP cells were injected into immunocompromised mice and allowed to develop into measurable tumors, at which point treatment was initiated. Mice were allocated to one of four groups and treated with vehicle, MP-470 (referred to in FIG. 35 as HPK56), Tarceva®, or MP-470/Tarceva® in combination, as indicated. Treatment was carried out for 18 days, at which point drug administration stopped and tumors were observed for an additional week. The results of these studies are shown in graphical form in FIG. 35. The combination of these two agents effectively slowed tumor growth to nearly zero during the course of the treatment, demonstrating that the combined effects of these agents observed in vitro are carried through to in vivo efficacy.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:
1. A compound having the following structure (III-1-3):

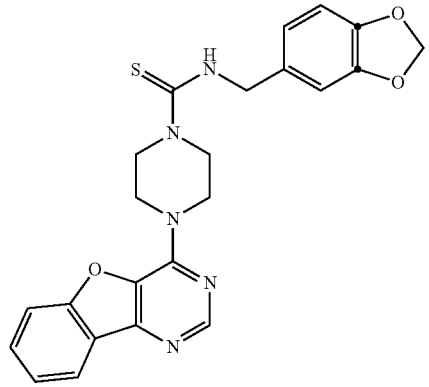

(III-1-3)

or a stereoisomer, prodrug, tautomer or pharmaceutically acceptable salt thereof.

2. A composition comprising the compound of claim 1 in combination with a pharmaceutically acceptable excipient or carrier.

3. A composition comprising the compound of claim 1 or a stereoisomer, prodrug, tautomer or pharmaceutically acceptable salt thereof, one or more other chemotherapeutic agents and a pharmaceutically acceptable excipient or carrier.

4. The composition of claim 3, wherein the chemotherapeutic agent is selected from the group consisting of mitotic inhibitors, alkylating agents, anti-metabolites, cell cycle inhibitors, enzymes, topoisomerase inhibitors, biological response modifiers, anti-hormones, antiangiogenic agents, anti-androgens, platinum coordination complexes, substituted ureas, methylhydrazine derivatives, adrenocortical suppressants, hormone and hormone antagonists, progestins, estrogens, antiestrogens, androgens, and aromatase inhibitors.

5. The composition of claim 3, wherein the chemotherapeutic agent is a DNA-damaging agent.

6. A process for the manufacture of the compound of claim 1, the process comprising reacting a compound of formula (XI):

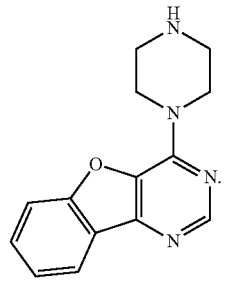

(XI)

with an appropriately activated thioamide.

7. The process of claim 6, further comprising preparing the compound of formula (XI) by reaction of a compound of formula (X):

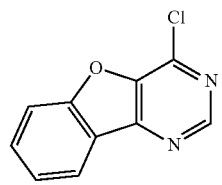

(X)

with piperazine.

8. The composition of claim 3, wherein the one or more other chemotherapeutic agents are selected from signal transduction inhibitors.

9. The composition of claim 3, wherein the one or more other chemotherapeutic agents are selected from epidermal growth factor receptor (EGFR) inhibitors.

10. The composition of claim 3, wherein the one or more other chemotherapeutic agents are selected from Tarceva® (erlotinib) and Gleevec® (imatinib mesylate).

11. The composition of claim 3, wherein the one or more other chemotherapeutic agents are selected from platinum coordination complexes, alkylating agents, epipodophyllotoxins and topoisomerase inhibitors.

12. The composition of claim 3, wherein the one or more other chemotherapeutic agents are selected from cisplatin, fluorouracil (5-FU), etoposide and irinotecan.

* * * * *

SEQUENCE LISTING

```
<160> NUMBER OF SEQ ID NOS: 11

<210> SEQ ID NO 1
<211> LENGTH: 403
<212> TYPE: PRT
<213> ORGANISM: Homo sapiens

<400> SEQUENCE: 1

Met Asp Arg Ser Lys Glu Asn Cys Ile Ser Gly Pro Val Lys Ala Thr
1               5                   10                  15

Ala Pro Val Gly Gly Pro Lys Arg Val Leu Val Thr Gln Gln Phe Pro
            20                  25                  30

Cys Gln Asn Pro Leu Pro Val Asn Ser Gly Gln Ala Gln Arg Val Leu
        35                  40                  45

Cys Pro Ser Asn Ser Ser Gln Arg Val Pro Leu Gln Ala Gln Lys Leu
    50                  55                  60

Val Ser Ser His Lys Pro Val Gln Asn Gln Lys Gln Lys Gln Leu Gln
65                  70                  75                  80

Ala Thr Ser Val Pro His Pro Val Ser Arg Pro Leu Asn Asn Thr Gln
                85                  90                  95

Lys Ser Lys Gln Pro Leu Pro Ser Ala Pro Glu Asn Asn Pro Glu Glu
            100                 105                 110

Glu Leu Ala Ser Lys Gln Lys Asn Glu Glu Ser Lys Lys Arg Gln Trp
        115                 120                 125

Ala Leu Glu Asp Phe Glu Ile Gly Arg Pro Leu Gly Lys Gly Lys Phe
    130                 135                 140

Gly Asn Val Tyr Leu Ala Arg Glu Lys Gln Ser Lys Phe Ile Leu Ala
145                 150                 155                 160

Leu Lys Val Leu Phe Lys Ala Gln Leu Glu Lys Ala Gly Val Glu His
                165                 170                 175

Gln Leu Arg Arg Glu Val Glu Ile Gln Ser His Leu Arg His Pro Asn
            180                 185                 190

Ile Leu Arg Leu Tyr Gly Tyr Phe His Asp Ala Thr Arg Val Tyr Leu
        195                 200                 205

Ile Leu Glu Tyr Ala Pro Leu Gly Thr Val Tyr Arg Glu Leu Gln Lys
    210                 215                 220

Leu Ser Lys Phe Asp Glu Gln Arg Thr Ala Thr Tyr Ile Thr Glu Leu
225                 230                 235                 240

Ala Asn Ala Leu Ser Tyr Cys His Ser Lys Arg Val Ile His Arg Asp
                245                 250                 255

Ile Lys Pro Glu Asn Leu Leu Leu Gly Ser Ala Gly Glu Leu Lys Ile
            260                 265                 270

Ala Asp Phe Gly Trp Ser Val His Ala Pro Ser Ser Arg Arg Thr Thr
        275                 280                 285

Leu Cys Gly Thr Leu Asp Tyr Leu Pro Pro Glu Met Ile Glu Gly Arg
    290                 295                 300
```

```
Met His Asp Glu Lys Val Asp Leu Trp Ser Leu Gly Val Leu Cys Tyr
305                 310                 315                 320

Glu Phe Leu Val Gly Lys Pro Pro Phe Glu Ala Asn Thr Tyr Gln Glu
                325                 330                 335

Thr Tyr Lys Arg Ile Ser Arg Val Glu Phe Thr Phe Pro Asp Phe Val
            340                 345                 350

Thr Glu Gly Ala Arg Asp Leu Ile Ser Arg Leu Leu Lys His Asn Pro
        355                 360                 365

Ser Gln Arg Pro Met Leu Arg Glu Val Leu Glu His Pro Trp Ile Thr
    370                 375                 380

Ala Asn Ser Ser Lys Pro Ser Asn Cys Gln Asn Lys Glu Ser Ala Ser
385                 390                 395                 400

Lys Gln Ser

<210> SEQ ID NO 2
<211> LENGTH: 344
<212> TYPE: PRT
<213> ORGANISM: Homo sapiens

<400> SEQUENCE: 2

Met Ala Gln Lys Glu Asn Ser Tyr Pro Trp Pro Tyr Gly Arg Gln Thr
1               5                   10                  15

Ala Pro Ser Gly Leu Ser Thr Leu Pro Gln Arg Val Leu Arg Lys Glu
                20                  25                  30

Pro Val Thr Pro Ser Ala Leu Val Leu Met Ser Arg Ser Asn Val Gln
            35                  40                  45

Pro Thr Ala Ala Pro Gly Gln Lys Val Met Glu Asn Ser Ser Gly Thr
        50                  55                  60

Pro Asp Ile Leu Thr Arg His Phe Thr Ile Asp Asp Phe Glu Ile Gly
65                  70                  75                  80

Arg Pro Leu Gly Lys Gly Lys Phe Gly Asn Val Tyr Leu Ala Arg Glu
                85                  90                  95

Lys Lys Ser His Phe Ile Val Ala Leu Lys Val Leu Phe Lys Ser Gln
                100                 105                 110

Ile Glu Lys Glu Gly Val Glu His Gln Leu Arg Arg Glu Ile Glu Ile
            115                 120                 125

Gln Ala His Leu His His Pro Asn Ile Leu Arg Leu Tyr Asn Tyr Phe
        130                 135                 140

Tyr Asp Arg Arg Arg Ile Tyr Leu Ile Leu Glu Tyr Ala Pro Arg Gly
145                 150                 155                 160

Glu Leu Tyr Lys Glu Leu Gln Lys Ser Cys Thr Phe Asp Glu Gln Arg
                165                 170                 175

Thr Ala Thr Ile Met Glu Glu Leu Ala Asp Ala Leu Met Tyr Cys His
                180                 185                 190

Gly Lys Lys Val Ile His Arg Asp Ile Lys Pro Glu Asn Leu Leu Leu
            195                 200                 205

Gly Leu Lys Gly Glu Leu Lys Ile Ala Asp Phe Gly Trp Ser Val His
        210                 215                 220

Ala Pro Ser Leu Arg Arg Lys Thr Met Cys Gly Thr Leu Asp Tyr Leu
225                 230                 235                 240

Pro Pro Glu Met Ile Glu Gly Arg Met His Asn Glu Lys Val Asp Leu
                245                 250                 255

Trp Cys Ile Gly Val Leu Cys Tyr Glu Leu Leu Val Gly Asn Pro Pro
                260                 265                 270
```

```
Phe Glu Ser Ala Ser His Asn Glu Thr Tyr Arg Arg Ile Val Lys Val
            275                 280                 285
Asp Leu Lys Phe Pro Ala Ser Val Pro Thr Gly Ala Gln Asp Leu Ile
        290                 295                 300
Ser Lys Leu Leu Arg His Asn Pro Ser Glu Arg Leu Pro Leu Ala Gln
305                 310                 315                 320
Val Ser Ala His Pro Trp Val Arg Ala Asn Ser Arg Arg Val Leu Pro
                325                 330                 335
Pro Ser Ala Leu Gln Ser Val Ala
            340

<210> SEQ ID NO 3
<211> LENGTH: 343
<212> TYPE: PRT
<213> ORGANISM: Bos taurus

<400> SEQUENCE: 3

Lys Gly Ser Glu Gln Glu Ser Val Lys Glu Phe Leu Ala Lys Ala Lys
1               5                   10                  15
Glu Asp Phe Leu Lys Lys Trp Glu Asn Pro Ala Gln Asn Thr Ala His
            20                  25                  30
Leu Asp Gln Phe Glu Arg Ile Lys Thr Leu Gly Thr Gly Ser Phe Gly
        35                  40                  45
Arg Val Met Leu Val Lys His Lys Glu Thr Gly Asn His Phe Ala Met
    50                  55                  60
Lys Ile Leu Asp Lys Gln Lys Val Val Lys Leu Lys Gln Ile Glu His
65                  70                  75                  80
Thr Leu Asn Glu Lys Arg Ile Leu Gln Ala Val Asn Phe Pro Phe Leu
                85                  90                  95
Val Lys Leu Glu Tyr Ser Phe Lys Asp Asn Ser Asn Leu Tyr Met Val
            100                 105                 110
Met Glu Tyr Val Pro Gly Gly Glu Met Phe Ser His Leu Arg Arg Ile
        115                 120                 125
Gly Arg Phe Ser Glu Pro His Ala Arg Phe Tyr Ala Ala Gln Ile Val
    130                 135                 140
Leu Thr Phe Glu Tyr Leu His Ser Leu Asp Leu Ile Tyr Arg Asp Leu
145                 150                 155                 160
Lys Pro Glu Asn Leu Leu Ile Asp Gln Gln Gly Tyr Ile Gln Val Thr
                165                 170                 175
Asp Phe Gly Phe Ala Lys Arg Val Lys Gly Arg Thr Trp Thr Leu Cys
            180                 185                 190
Gly Thr Pro Glu Tyr Leu Ala Pro Glu Ile Ile Leu Ser Lys Gly Tyr
        195                 200                 205
Asn Lys Ala Val Asp Trp Trp Ala Leu Gly Val Leu Ile Tyr Glu Met
    210                 215                 220
Ala Ala Gly Tyr Pro Pro Phe Phe Ala Asp Gln Pro Ile Gln Ile Tyr
225                 230                 235                 240
Glu Lys Ile Val Ser Gly Lys Val Arg Phe Pro Ser His Phe Ser Ser
                245                 250                 255
Asp Leu Lys Asp Leu Leu Arg Asn Leu Leu Gln Val Asp Leu Thr Lys
            260                 265                 270
Arg Phe Gly Asn Leu Lys Asp Gly Val Asn Asp Ile Lys Asn His Lys
        275                 280                 285
```

```
Trp Phe Ala Thr Thr Asp Trp Ile Ala Ile Tyr Gln Arg Lys Val Glu
        290                 295                 300

Ala Pro Phe Ile Pro Lys Phe Lys Gly Pro Gly Asp Thr Ser Asn Phe
305                 310                 315                 320

Asp Asp Tyr Glu Glu Glu Ile Arg Val Ser Ile Asn Glu Lys Cys
                325                 330                 335

Gly Lys Glu Phe Ser Glu Phe
            340

<210> SEQ ID NO 4
<211> LENGTH: 341
<212> TYPE: PRT
<213> ORGANISM: Mus musculus

<400> SEQUENCE: 4

Ser Glu Gln Glu Ser Val Lys Glu Phe Leu Ala Lys Ala Lys Glu Asp
1               5                   10                  15

Phe Leu Lys Lys Trp Glu Thr Pro Ser Gln Asn Thr Ala Gln Leu Asp
            20                  25                  30

Gln Phe Asp Arg Ile Lys Thr Leu Gly Thr Gly Ser Phe Gly Arg Val
        35                  40                  45

Met Leu Val Lys His Lys Glu Ser Gly Asn His Tyr Ala Met Lys Ile
    50                  55                  60

Leu Asp Lys Gln Lys Val Val Lys Leu Lys Gln Ile Glu His Thr Leu
65                  70                  75                  80

Asn Glu Lys Arg Ile Leu Gln Ala Val Asn Phe Pro Phe Leu Val Lys
                85                  90                  95

Leu Glu Phe Ser Phe Lys Asp Asn Ser Asn Leu Tyr Met Val Met Glu
            100                 105                 110

Tyr Val Ala Gly Gly Glu Met Phe Ser His Leu Arg Arg Ile Gly Arg
        115                 120                 125

Phe Ala Glu Pro His Ala Arg Phe Tyr Ala Ala Gln Ile Val Leu Thr
130                 135                 140

Phe Glu Tyr Leu His Ser Leu Asp Leu Ile Tyr Arg Asp Leu Lys Pro
145                 150                 155                 160

Glu Asn Leu Leu Ile Asp Gln Gln Gly Tyr Ile Gln Val Thr Asp Phe
                165                 170                 175

Gly Phe Ala Lys Arg Val Lys Gly Arg Thr Trp Thr Leu Cys Gly Thr
            180                 185                 190

Pro Glu Tyr Leu Ala Pro Glu Ile Ile Leu Ser Lys Gly Tyr Asn Lys
        195                 200                 205

Ala Val Asp Trp Trp Ala Leu Gly Val Leu Ile Tyr Glu Met Ala Ala
    210                 215                 220

Gly Tyr Pro Pro Phe Phe Ala Asp Gln Pro Ile Gln Ile Tyr Glu Lys
225                 230                 235                 240

Ile Val Ser Gly Lys Val Arg Phe Pro Ser His Phe Ser Ser Asp Leu
                245                 250                 255

Lys Asp Leu Leu Arg Asn Leu Leu Gln Val Asp Leu Thr Lys Arg Phe
            260                 265                 270

Gly Asn Leu Lys Asn Gly Val Asn Asp Ile Lys Asn His Lys Trp Phe
        275                 280                 285

Ala Thr Thr Asp Trp Ile Ala Ile Tyr Gln Arg Lys Val Glu Ala Pro
    290                 295                 300

Phe Ile Pro Lys Phe Lys Gly Pro Gly Asp Thr Ser Asn Phe Asp Asp
305                 310                 315                 320
```

Tyr Glu Glu Glu Glu Ile Arg Val Ser Ile Asn Glu Lys Cys Gly Lys
                325                 330                 335

Glu Phe Thr Glu Phe
            340

<210> SEQ ID NO 5
<211> LENGTH: 287
<212> TYPE: PRT
<213> ORGANISM: C. elegans

<400> SEQUENCE: 5

Asp Ile Trp Lys Gln Tyr Tyr Pro Gln Pro Val Glu Ile Lys His Asp
 1               5                  10                  15

His Val Leu Asp His Tyr Asp Ile His Glu Glu Leu Gly Thr Gly Ala
                20                  25                  30

Phe Gly Val Val His Arg Val Thr Glu Arg Ala Thr Gly Asn Asn Phe
            35                  40                  45

Ala Ala Lys Phe Val Met Thr Pro His Glu Ser Asp Lys Glu Thr Val
 50                  55                  60

Arg Lys Glu Ile Gln Thr Met Ser Val Leu Arg His Pro Thr Leu Val
65                  70                  75                  80

Asn Leu His Asp Ala Phe Glu Asp Asp Asn Glu Met Val Met Ile Tyr
                85                  90                  95

Glu Phe Met Ser Gly Gly Glu Leu Phe Glu Lys Val Ala Asp Glu His
            100                 105                 110

Asn Lys Met Ser Glu Asp Glu Ala Val Glu Tyr Met Arg Gln Val Cys
        115                 120                 125

Lys Gly Leu Cys His Met His Glu Asn Asn Tyr Val His Leu Asp Leu
130                 135                 140

Lys Pro Glu Asn Ile Met Phe Thr Thr Lys Arg Ser Asn Glu Leu Lys
145                 150                 155                 160

Leu Ile Asp Phe Gly Leu Thr Ala His Leu Asp Pro Lys Gln Ser Val
                165                 170                 175

Lys Val Thr Thr Gly Thr Ala Glu Phe Ala Ala Pro Glu Val Ala Glu
            180                 185                 190

Gly Lys Pro Val Gly Tyr Tyr Thr Asp Met Trp Ser Val Gly Val Leu
        195                 200                 205

Ser Tyr Ile Leu Leu Ser Gly Leu Ser Pro Phe Gly Gly Glu Asn Asp
    210                 215                 220

Asp Glu Thr Leu Arg Asn Val Lys Ser Cys Asp Trp Asn Met Asp Asp
225                 230                 235                 240

Ser Ala Phe Ser Gly Ile Ser Glu Asp Gly Lys Asp Phe Ile Arg Lys
                245                 250                 255

Leu Leu Leu Ala Asp Pro Asn Thr Arg Met Thr Ile His Gln Ala Leu
            260                 265                 270

Glu His Pro Trp Leu Thr Pro Gly Asn Ala Pro Gly Arg Asp Ser
        275                 280                 285

<210> SEQ ID NO 6
<211> LENGTH: 433
<212> TYPE: PRT
<213> ORGANISM: Homo sapiens

<400> SEQUENCE: 6

Thr Tyr Lys Tyr Leu Gln Lys Pro Met Tyr Glu Val Gln Trp Lys Val
 1               5                  10                  15

```
Val Glu Glu Ile Asn Gly Asn Asn Tyr Val Tyr Ile Asp Pro Thr Gln
        20                  25                  30

Leu Pro Tyr Asp His Lys Trp Glu Phe Pro Arg Asn Arg Leu Ser Phe
            35                  40                  45

Gly Lys Thr Leu Gly Ala Gly Ala Phe Gly Lys Val Val Glu Ala Thr
        50                  55                  60

Ala Tyr Gly Leu Ile Lys Ser Asp Ala Ala Met Thr Val Ala Val Lys
65                  70                  75                  80

Met Leu Lys Pro Ser Ala His Leu Thr Glu Arg Glu Ala Leu Met Ser
                85                  90                  95

Glu Leu Lys Val Leu Ser Tyr Leu Gly Asn His Met Asn Ile Val Asn
            100                 105                 110

Leu Leu Gly Ala Cys Thr Ile Gly Gly Pro Thr Leu Val Ile Thr Glu
            115                 120                 125

Tyr Cys Cys Tyr Gly Asp Leu Leu Asn Phe Leu Arg Arg Lys Arg Asp
130                 135                 140

Ser Phe Ile Cys Ser Lys Gln Glu Asp His Ala Glu Ala Ala Leu Tyr
145                 150                 155                 160

Lys Asn Leu Leu His Ser Lys Glu Ser Ser Cys Ser Asp Ser Thr Asn
                165                 170                 175

Glu Tyr Met Asp Met Lys Pro Gly Val Ser Tyr Val Val Pro Thr Lys
            180                 185                 190

Ala Asp Lys Arg Arg Ser Val Arg Ile Gly Ser Tyr Ile Glu Arg Asp
            195                 200                 205

Val Thr Pro Ala Ile Met Glu Asp Asp Glu Leu Ala Leu Asp Leu Glu
            210                 215                 220

Asp Leu Leu Ser Phe Ser Tyr Gln Val Ala Lys Gly Met Ala Phe Leu
225                 230                 235                 240

Ala Ser Lys Asn Cys Ile His Arg Asp Leu Ala Ala Arg Asn Ile Leu
                245                 250                 255

Leu Thr His Gly Arg Ile Thr Lys Ile Cys Asp Phe Gly Leu Ala Arg
            260                 265                 270

Asp Ile Lys Asn Asp Ser Asn Tyr Val Val Lys Gly Asn Ala Arg Leu
            275                 280                 285

Pro Val Lys Trp Met Ala Pro Glu Ser Ile Phe Asn Cys Val Tyr Thr
            290                 295                 300

Phe Glu Ser Asp Val Trp Ser Tyr Gly Ile Phe Leu Trp Glu Leu Phe
305                 310                 315                 320

Ser Leu Gly Ser Ser Pro Tyr Pro Gly Met Pro Val Asp Ser Lys Phe
                325                 330                 335

Tyr Lys Met Ile Lys Glu Gly Phe Arg Met Leu Ser Pro Glu His Ala
            340                 345                 350

Pro Ala Glu Met Tyr Asp Ile Met Lys Thr Cys Trp Asp Ala Asp Pro
            355                 360                 365

Leu Lys Arg Pro Thr Phe Lys Gln Ile Val Gln Leu Ile Glu Lys Gln
            370                 375                 380

Ile Ser Glu Ser Thr Asn His Ile Tyr Ser Asn Leu Ala Asn Cys Ser
385                 390                 395                 400

Pro Asn Arg Gln Lys Pro Val Val Asp His Ser Val Arg Ile Asn Ser
                405                 410                 415

Val Gly Ser Thr Ala Ser Ser Ser Gln Pro Leu Leu Val His Asp Asp
            420                 425                 430
```

Val

<210> SEQ ID NO 7
<211> LENGTH: 383
<212> TYPE: PRT
<213> ORGANISM: Homo sapiens

<400> SEQUENCE: 7

| | | | | | | | | | | | | | | |
|---|---|---|---|---|---|---|---|---|---|---|---|---|---|---|
| Leu | Gly | Ser | Gly | Ala | Phe | Gly | Lys | Val | Glu | Gly | Thr | Ala | Tyr | Gly |
| 1 | | | | 5 | | | | | 10 | | | | | 15 |
| Leu | Ser | Arg | Ser | Gln | Pro | Val | Met | Lys | Val | Ala | Val | Lys | Met | Leu | Lys |
| | | | 20 | | | | | 25 | | | | | 30 | | |
| Pro | Thr | Ala | Arg | Ser | Ser | Glu | Lys | Gln | Ala | Leu | Met | Ser | Glu | Leu | Lys |
| | | 35 | | | | | 40 | | | | | 45 | | | |
| Ile | Met | Thr | His | Leu | Gly | Pro | His | Leu | Asn | Ile | Val | Asn | Leu | Leu | Gly |
| 50 | | | | | 55 | | | | | 60 | | | | | |
| Ala | Cys | Thr | Lys | Ser | Gly | Pro | Ile | Tyr | Ile | Ile | Thr | Glu | Tyr | Cys | Phe |
| 65 | | | | | 70 | | | | | 75 | | | | | 80 |
| Tyr | Gly | Asp | Leu | Val | Asn | Tyr | Leu | His | Lys | Asn | Arg | Asp | Ser | Phe | Leu |
| | | | | 85 | | | | | 90 | | | | | 95 | |
| Ser | His | His | Pro | Glu | Lys | Pro | Lys | Lys | Glu | Leu | Asp | Ile | Phe | Gly | Leu |
| | | | 100 | | | | | 105 | | | | | 110 | | |
| Asn | Pro | Ala | Asp | Glu | Ser | Thr | Arg | Ser | Tyr | Val | Ile | Leu | Ser | Phe | Glu |
| | | 115 | | | | | 120 | | | | | 125 | | | |
| Asn | Asn | Gly | Asp | Tyr | Met | Asp | Met | Lys | Gln | Ala | Asp | Thr | Thr | Gln | Tyr |
| 130 | | | | | 135 | | | | | 140 | | | | | |
| Val | Pro | Met | Leu | Glu | Arg | Lys | Glu | Val | Ser | Lys | Tyr | Ser | Asp | Ile | Gln |
| 145 | | | | | 150 | | | | | 155 | | | | | 160 |
| Arg | Ser | Leu | Tyr | Asp | Arg | Pro | Ala | Ser | Tyr | Lys | Lys | Lys | Ser | Met | Leu |
| | | | | 165 | | | | | 170 | | | | | 175 | |
| Asp | Ser | Glu | Val | Lys | Asn | Leu | Leu | Ser | Asp | Asp | Asn | Ser | Glu | Gly | Leu |
| | | | 180 | | | | | 185 | | | | | 190 | | |
| Thr | Leu | Leu | Asp | Leu | Leu | Ser | Phe | Thr | Tyr | Gln | Val | Ala | Arg | Gly | Met |
| | | 195 | | | | | 200 | | | | | 205 | | | |
| Glu | Phe | Leu | Ala | Ser | Lys | Asn | Cys | Val | His | Arg | Asp | Leu | Ala | Ala | Arg |
| | 210 | | | | | 215 | | | | | 220 | | | | |
| Asn | Val | Leu | Leu | Ala | Gln | Gly | Lys | Ile | Val | Lys | Ile | Cys | Asp | Phe | Gly |
| 225 | | | | | 230 | | | | | 235 | | | | | 240 |
| Leu | Ala | Arg | Asp | Ile | Met | His | Asp | Ser | Asn | Tyr | Val | Ser | Lys | Gly | Ser |
| | | | | 245 | | | | | 250 | | | | | 255 | |
| Thr | Phe | Leu | Pro | Val | Lys | Trp | Met | Ala | Pro | Glu | Ser | Ile | Phe | Asp | Asn |
| | | | 260 | | | | | 265 | | | | | 270 | | |
| Leu | Tyr | Thr | Thr | Leu | Ser | Asp | Val | Trp | Ser | Tyr | Gly | Ile | Leu | Leu | Trp |
| | | 275 | | | | | 280 | | | | | 285 | | | |
| Glu | Ile | Phe | Ser | Leu | Gly | Gly | Thr | Pro | Tyr | Pro | Gly | Met | Met | Val | Asp |
| | 290 | | | | | 295 | | | | | 300 | | | | |
| Ser | Thr | Phe | Tyr | Asn | Lys | Ile | Lys | Ser | Gly | Tyr | Arg | Met | Ala | Lys | Pro |
| 305 | | | | | 310 | | | | | 315 | | | | | 320 |
| Asp | His | Ala | Thr | Ser | Glu | Val | Tyr | Glu | Ile | Met | Val | Lys | Cys | Trp | Asn |
| | | | | 325 | | | | | 330 | | | | | 335 | |
| Ser | Glu | Pro | Glu | Lys | Arg | Pro | Ser | Phe | Tyr | His | Leu | Ser | Glu | Ile | Val |
| | | | 340 | | | | | 345 | | | | | 350 | | |
| Glu | Asn | Leu | Leu | Pro | Gly | Gln | Tyr | Lys | Lys | Ser | Tyr | Glu | Lys | Ile | His |
| | | 355 | | | | | 360 | | | | | 365 | | | |

```
Leu Asp Phe Leu Lys Ser Asp His Pro Ala Val Ala Arg Met Arg
        370                 375                 380
```

<210> SEQ ID NO 8
<211> LENGTH: 411
<212> TYPE: PRT
<213> ORGANISM: Homo sapiens

<400> SEQUENCE: 8

```
Thr Trp Glu Leu Pro Arg Asp Gln Leu Val Leu Gly Arg Thr Leu Gly
  1               5                  10                  15

Ser Gly Ala Phe Gly Gln Val Val Glu Ala Thr Ala His Gly Leu Ser
             20                  25                  30

His Ser Gln Ala Thr Met Lys Val Ala Val Lys Met Leu Lys Ser Thr
         35                  40                  45

Ala Arg Ser Ser Glu Lys Gln Ala Leu Met Ser Glu Leu Lys Ile Met
     50                  55                  60

Ser His Leu Gly Pro His Leu Asn Val Val Asn Leu Leu Gly Ala Cys
 65                  70                  75                  80

Thr Lys Gly Gly Pro Ile Tyr Ile Ile Thr Glu Tyr Cys Arg Tyr Gly
                 85                  90                  95

Asp Leu Val Asp Tyr Leu His Arg Asn Lys His Thr Phe Leu Gln His
            100                 105                 110

His Ser Asp Lys Arg Arg Pro Pro Ser Ala Glu Leu Tyr Ser Asn Ala
        115                 120                 125

Leu Pro Val Gly Leu Pro Leu Pro Ser His Val Ser Leu Thr Gly Glu
    130                 135                 140

Ser Asp Gly Gly Tyr Met Asp Met Ser Lys Asp Glu Ser Val Asp Tyr
145                 150                 155                 160

Val Pro Met Leu Asp Met Lys Gly Asp Val Lys Tyr Ala Asp Ile Glu
                165                 170                 175

Ser Ser Asn Tyr Met Ala Pro Tyr Asp Asn Tyr Val Pro Ser Ala Pro
            180                 185                 190

Glu Arg Thr Cys Arg Ala Thr Leu Ile Asn Glu Ser Pro Val Leu Ser
        195                 200                 205

Tyr Met Asp Leu Val Gly Phe Ser Tyr Gln Val Ala Asn Gly Met Glu
    210                 215                 220

Phe Leu Ala Ser Lys Asn Cys Val His Arg Asp Leu Ala Ala Arg Asn
225                 230                 235                 240

Val Leu Ile Cys Glu Gly Lys Leu Val Lys Ile Cys Asp Phe Gly Leu
                245                 250                 255

Ala Arg Asp Ile Met Arg Asp Ser Asn Tyr Ile Ser Lys Gly Ser Thr
            260                 265                 270

Phe Leu Pro Leu Lys Trp Met Ala Pro Glu Ser Ile Phe Asn Ser Leu
        275                 280                 285

Tyr Thr Thr Leu Ser Asp Val Trp Ser Phe Gly Ile Leu Leu Trp Glu
    290                 295                 300

Ile Phe Thr Leu Gly Gly Thr Pro Tyr Pro Glu Leu Pro Met Asn Glu
305                 310                 315                 320

Gln Phe Tyr Asn Ala Ile Lys Arg Gly Tyr Arg Met Ala Gln Pro Ala
                325                 330                 335

His Ala Ser Asp Glu Ile Tyr Glu Ile Met Gln Lys Cys Trp Glu Glu
            340                 345                 350

Lys Phe Glu Ile Arg Pro Pro Phe Ser Gln Leu Val Leu Leu Leu Glu
        355                 360                 365
```

```
Arg Leu Leu Gly Glu Gly Tyr Lys Lys Tyr Gln Gln Val Asp Glu
        370                 375                 380

Glu Phe Leu Arg Ser Asp His Pro Ala Ile Leu Arg Ser Gln Ala Arg
385                 390                 395                 400

Leu Pro Gly Phe His Gly Leu Arg Ser Pro Leu
                405                 410

<210> SEQ ID NO 9
<211> LENGTH: 310
<212> TYPE: PRT
<213> ORGANISM: Homo sapiens

<400> SEQUENCE: 9

Met Val Ala Gly Val Ser Glu Tyr Glu Leu Pro Glu Asp Pro Arg Trp
1               5                   10                  15

Glu Leu Pro Arg Asp Arg Leu Val Leu Gly Lys Pro Leu Gly Glu Gly
            20                  25                  30

Ala Phe Gly Gln Val Val Leu Ala Glu Ala Ile Gly Leu Asp Lys Asp
        35                  40                  45

Lys Pro Asn Arg Val Thr Lys Val Ala Val Lys Met Leu Lys Ser Asp
50                  55                  60

Ala Thr Glu Lys Asp Leu Ser Asp Leu Ile Ser Glu Met Glu Met Met
65                  70                  75                  80

Lys Met Ile Gly Lys His Lys Asn Ile Ile Asn Leu Leu Gly Ala Cys
                85                  90                  95

Thr Gln Asp Gly Pro Leu Tyr Val Ile Val Glu Tyr Ala Ser Lys Gly
            100                 105                 110

Asn Leu Arg Glu Tyr Leu Gln Ala Arg Arg Pro Pro Gly Leu Glu Tyr
        115                 120                 125

Ser Tyr Asn Pro Ser His Asn Pro Glu Glu Gln Leu Ser Ser Lys Asp
130                 135                 140

Leu Val Ser Cys Ala Tyr Gln Val Ala Arg Gly Met Glu Tyr Leu Ala
145                 150                 155                 160

Ser Lys Lys Cys Ile His Arg Asp Leu Ala Ala Arg Asn Val Leu Val
                165                 170                 175

Thr Glu Asp Asn Val Met Lys Ile Ala Asp Phe Gly Leu Ala Arg Asp
            180                 185                 190

Ile His His Ile Asp Tyr Tyr Lys Lys Thr Thr Asn Gly Arg Leu Pro
        195                 200                 205

Val Lys Trp Met Ala Pro Glu Ala Leu Phe Asp Arg Ile Tyr Thr His
210                 215                 220

Gln Ser Asp Val Trp Ser Phe Gly Val Leu Leu Trp Glu Ile Phe Thr
225                 230                 235                 240

Leu Gly Gly Ser Pro Tyr Pro Gly Val Pro Val Glu Glu Leu Phe Lys
                245                 250                 255

Leu Leu Lys Glu Gly His Arg Met Asp Lys Pro Ser Asn Cys Thr Asn
            260                 265                 270

Glu Leu Tyr Met Met Met Arg Asp Cys Trp His Ala Val Pro Ser Gln
        275                 280                 285

Arg Pro Thr Phe Lys Gln Leu Val Glu Asp Leu Asp Arg Ile Val Ala
290                 295                 300

Leu Thr Ser Asn Gln Glu
305                 310
```

<210> SEQ ID NO 10
<211> LENGTH: 316
<212> TYPE: PRT
<213> ORGANISM: Homo sapiens
<220> FEATURE:
<221> NAME/KEY: VARIANT
<222> LOCATION: 204
<223> OTHER INFORMATION: Xaa = Any Amino Acid

<400> SEQUENCE: 10

Met Asp Pro Asp Glu Leu Pro Leu Asp Glu His Cys Glu Arg Leu Pro
1               5                   10                  15

Tyr Asp Ala Ser Lys Trp Glu Phe Pro Arg Asp Arg Leu Lys Leu Gly
            20                  25                  30

Lys Pro Leu Gly Arg Gly Ala Phe Gly Gln Val Ile Glu Ala Asp Ala
        35                  40                  45

Phe Gly Ile Asp Lys Thr Ala Thr Cys Arg Thr Val Ala Val Lys Met
    50                  55                  60

Leu Lys Glu Gly Ala Thr His Ser Glu His Arg Ala Leu Met Ser Glu
65                  70                  75                  80

Leu Lys Ile Leu Ile His Ile Gly His His Leu Asn Val Val Asn Leu
                85                  90                  95

Leu Gly Ala Cys Thr Lys Pro Gly Gly Pro Leu Met Val Ile Val Glu
            100                 105                 110

Phe Cys Lys Phe Gly Asn Leu Ser Thr Tyr Leu Arg Ser Lys Arg Asn
        115                 120                 125

Glu Phe Val Pro Tyr Lys Val Ala Pro Glu Asp Leu Tyr Lys Asp Phe
    130                 135                 140

Leu Thr Leu Glu His Leu Ile Cys Tyr Ser Phe Gln Val Ala Lys Gly
145                 150                 155                 160

Met Glu Phe Leu Ala Ser Arg Lys Cys Ile His Arg Asp Leu Ala Ala
                165                 170                 175

Arg Asn Ile Leu Leu Ser Glu Lys Asn Val Val Lys Ile Cys Asp Phe
            180                 185                 190

Gly Leu Ala Arg Asp Ile Tyr Lys Asp Pro Asp Xaa Val Arg Lys Gly
        195                 200                 205

Asp Ala Arg Leu Pro Leu Lys Trp Met Ala Pro Glu Thr Ile Phe Asp
    210                 215                 220

Arg Val Tyr Thr Ile Gln Ser Asp Val Trp Ser Phe Gly Val Leu Leu
225                 230                 235                 240

Trp Glu Ile Phe Ser Leu Gly Ala Ser Pro Tyr Pro Gly Val Lys Ile
                245                 250                 255

Asp Glu Glu Phe Cys Arg Arg Leu Lys Glu Gly Thr Arg Met Arg Ala
            260                 265                 270

Pro Asp Tyr Thr Thr Pro Glu Met Tyr Gln Thr Met Leu Asp Cys Trp
        275                 280                 285

His Gly Glu Pro Ser Gln Arg Pro Thr Phe Ser Glu Leu Val Glu His
    290                 295                 300

Leu Gly Asn Leu Leu Gln Ala Asn Ala Gln Gln Asp
305                 310                 315

<210> SEQ ID NO 11
<211> LENGTH: 293
<212> TYPE: PRT
<213> ORGANISM: Homo sapiens

<400> SEQUENCE: 11

-continued

Gly Ala Met Asp Pro Ser Ser Pro Asn Tyr Asp Lys Trp Glu Met Glu
1               5                   10                  15

Arg Thr Asp Ile Thr Met Lys His Lys Leu Gly Gly Gly Gln Tyr Gly
                20                  25                  30

Glu Val Tyr Glu Gly Val Trp Lys Lys Tyr Ser Leu Thr Val Ala Val
            35                  40                  45

Lys Thr Leu Lys Glu Asp Thr Met Glu Val Glu Glu Phe Leu Lys Glu
        50                  55                  60

Ala Ala Val Met Lys Glu Ile Lys His Pro Asn Leu Val Gln Leu Leu
65                  70                  75                  80

Gly Val Cys Thr Arg Glu Pro Pro Phe Tyr Ile Ile Thr Glu Phe Met
                85                  90                  95

Thr Tyr Gly Asn Leu Leu Asp Tyr Leu Arg Glu Cys Asn Arg Gln Glu
                100                 105                 110

Val Ser Ala Val Val Leu Leu Tyr Met Ala Thr Gln Ile Ser Ser Ala
            115                 120                 125

Met Glu Tyr Leu Glu Lys Lys Asn Phe Ile His Arg Asp Leu Ala Ala
        130                 135                 140

Arg Asn Cys Leu Val Gly Glu Asn His Leu Val Lys Val Ala Asp Phe
145                 150                 155                 160

Gly Leu Ser Arg Leu Met Thr Gly Asp Thr Tyr Thr Ala His Ala Gly
                165                 170                 175

Ala Lys Phe Pro Ile Lys Trp Thr Ala Pro Glu Ser Leu Ala Tyr Asn
                180                 185                 190

Lys Phe Ser Ile Lys Ser Asp Val Trp Ala Phe Gly Val Leu Leu Trp
            195                 200                 205

Glu Ile Ala Thr Tyr Gly Met Ser Pro Tyr Pro Gly Ile Asp Leu Ser
        210                 215                 220

Gln Val Tyr Glu Leu Leu Glu Lys Asp Tyr Arg Met Glu Arg Pro Glu
225                 230                 235                 240

Gly Cys Pro Glu Lys Val Tyr Glu Leu Met Arg Ala Cys Trp Gln Trp
                245                 250                 255

Asn Pro Ser Asp Arg Pro Ser Phe Ala Glu Ile His Gln Ala Phe Glu
                260                 265                 270

Thr Met Phe Gln Glu Ser Ser Ile Ser Asp Glu Val Glu Lys Glu Leu
            275                 280                 285

Gly Lys Arg Gly Thr
            290